US011135275B2

(12) United States Patent
Hilden et al.

(10) Patent No.: US 11,135,275 B2
(45) Date of Patent: Oct. 5, 2021

(54) COAGULATION FACTOR-TARGETING TO TREM-LIKE TRANSCRIPT 1 (TLT-1) ON ACTIVATED PLATELETS

(71) Applicant: Novo Nordisk A/S, Bagsvaerd (DK)

(72) Inventors: Ida Hilden, Frederiksberg (DK); Bernd Peschke, Slagelse (DK); Jens Breinholt, Dyssegaerd (DK); Mikael Kofod-Hansen, Broenshoej (DK)

(73) Assignee: Novo Nordisk Healthcare AG, Zurich (CH)

( * ) Notice: Subject to any disclaimer, the term of this patent is extended or adjusted under 35 U.S.C. 154(b) by 0 days.

(21) Appl. No.: 16/125,026

(22) Filed: Sep. 7, 2018

(65) Prior Publication Data

US 2019/0083587 A1 Mar. 21, 2019

Related U.S. Application Data

(63) Continuation of application No. 15/094,082, filed on Apr. 8, 2016, now abandoned, which is a continuation of application No. 13/982,360, filed as application No. PCT/EP2012/053619 on Mar. 2, 2012, now abandoned.

(60) Provisional application No. 61/449,254, filed on Mar. 4, 2011.

(30) Foreign Application Priority Data

Mar. 2, 2011 (EP) .................................... 11156682

(51) Int. Cl.

| | |
|---|---|
| *A61K 38/48* | (2006.01) |
| *A61K 47/68* | (2017.01) |
| *C07K 16/28* | (2006.01) |
| *C07K 14/47* | (2006.01) |
| *C12N 9/64* | (2006.01) |
| *C07K 14/745* | (2006.01) |
| *C12N 9/96* | (2006.01) |
| *A61K 38/00* | (2006.01) |

(52) U.S. Cl.

CPC ...... *A61K 38/4846* (2013.01); *A61K 47/6815* (2017.08); *A61K 47/6849* (2017.08); *C07K 14/4703* (2013.01); *C07K 14/745* (2013.01); *C07K 16/2803* (2013.01); *C12N 9/644* (2013.01); *C12N 9/6437* (2013.01); *C12N 9/96* (2013.01); *C12Y 304/21021* (2013.01); *C12Y 304/21022* (2013.01); *A61K 38/00* (2013.01); *C07K 2299/00* (2013.01); *C07K 2317/21* (2013.01); *C07K 2317/24* (2013.01); *C07K 2317/34* (2013.01); *C07K 2317/41* (2013.01); *C07K 2317/51* (2013.01); *C07K 2317/515* (2013.01); *C07K 2317/55* (2013.01); *C07K 2317/56* (2013.01); *C07K 2317/92* (2013.01); *C07K 2319/00* (2013.01); *C07K 2319/21* (2013.01)

(58) Field of Classification Search

CPC ................................................. A61K 38/4846

See application file for complete search history.

(56) References Cited

U.S. PATENT DOCUMENTS

| | | | |
|---|---|---|---|
| 5,877,289 A | 3/1999 | Thorpe et al. | |
| 7,553,936 B2 | 6/2009 | Mori et al. | |
| 7,887,837 B2 | 2/2011 | Takeoka | |
| 2004/0180054 A1 | 9/2004 | Kim et al. | |
| 2004/0180409 A1 | 9/2004 | McVicar et al. | |
| 2005/0147618 A1 * | 7/2005 | Rivera ................ | C12N 9/6437 424/178.1 |
| 2008/0131423 A1 | 6/2008 | Mori et al. | |
| 2008/0280831 A1 | 11/2008 | Lind et al. | |
| 2008/0300188 A1 | 12/2008 | Yang et al. | |

FOREIGN PATENT DOCUMENTS

| | | |
|---|---|---|
| WO | 2004/113521 A1 | 12/2004 |
| WO | 2006/096828 A2 | 9/2006 |
| WO | 2009/140598 A1 | 11/2009 |
| WO | 2010/015668 A1 | 2/2010 |
| WO | 2010/115866 A1 | 10/2010 |
| WO | 2011/023785 A1 | 3/2011 |

OTHER PUBLICATIONS

Karas et al, Characterization of the IgG-Fc receptor on human platelets. Blood. Dec. 1982;60(6): 1277-82.*

Lu et al, Preparation and Characterization of Monoclonal Antibody Against Protein TREM-Like Transcript-1 (TLT-1). Hybridoma vol. 25, No. 1, 2006 pp. 20-26.*

Weir et al, A new generation of high-affinity humanized PEGylated Fab' fragment anti-tumor necrosis factor-α monoclonal antibodies. Therapy. 3(4):535-545, Jul. 2006.*

Emsley J et al., Blood, "Structure and Function of Factor XI", 2010, vol. 115, pp. 2569-2577.

Gattis, J. L. et al., Journal of Biological Chemistry, "The Structure of the Extracellular Domain of Triggering Receptor Expressed on Myeloid Cells Like Transcript-1 and Evidence For a Naturally Occurring Soluble Fragment", 2006, vol. 281, No. 19, pp. 13396-13403.

Giomarelli, B. et al., Thrombosis and Haemostasis, "Inhibition of Thrombin-Induced Platelet Aggregation Using Human Single-Chain FV Antibodies Specific for TREM-Like Transcript-1", 2007, vol. 97, No. 6, pp. 955-964.

(Continued)

*Primary Examiner* — Sheridan Swope

(74) *Attorney, Agent, or Firm* — Leon Y. Lum

(57) ABSTRACT

Described are procoagulant proteins which may, for example, be fusion proteins or chemical conjugates; methods of producing procoagulant proteins; polynucleotides that encode fusion proteins and cells that expresses them. Furthermore, described are procoagulant proteins for use as a medicament. Individuals that have a coagulopathy, such as haemophilia A and B with or without inhibitors, may be treated with such procoagulant proteins.

6 Claims, 28 Drawing Sheets

Specification includes a Sequence Listing.

(56) References Cited

OTHER PUBLICATIONS

Huang X et al., Blood, "A Soluble Tissue Factor-Annexin V Chimeric Protein Has Both Procoagulant and Anticoagulant Properties", 2006, vol. 107, No. 3, pp. 980-986.

Washington A V et al., Blood, "A TREM Family Member, TLT-1, Is Found Exclusively in the Alpha-Granules of Megakaryocytes and Platelets", 2004, vol. 104, No. 4, pp. 1042-1047.

Berkner et al, Isolation and Expression of cDNAs Encoding Human Factor VII. Cold Spring Harb Symp Quant Biol 1986.vol. 51,pp. 531-541.

Halabian et ai, Expression and purification of recombinant human coagulation factor VII fused to a histidine tag using Gateway technology. Blood Transfus 2009; vol. 7 pp. 305-312.

Lu et al, Preparation and Characterization of Monoclonal Antibody Against Protein TREM-Like Transcript-1 (TL T-1). Hybridoma (Larchmt). 2006 vol. 25 No. 1 , pp. 20-26.

Monroe et al., "Platelet Activity of High-Dose Factor VIIa is Independent of Tissue Factor," Br J Haematol, 1997, vol. 39, No. 3, pp. 542-547.

Hermanson, Antibody Modification and Conjugation 1. Preparation of Antibody-Enzyme Conjugates. In: Bioconjugate Techniques, Elsevier Science 1996, pp. 456-486.

Ward et al., "Characterization of Humanized Antibodies Secreted by Aspergillus Niger," Appl Environ Microbiol, 2004, vol. 70, No. 5, pp. 2567-2576.

* cited by examiner

Fig. 1

```
      M  G  L   T  L  L   L  L  L   L  L  G   L  E  G   Q  G  I
  1  ATGGGCCTC ACCCTGCTC TTGCTGCTG CTCCTGGGA CTAGAAGGT CAGGGCATA

      V  G  S   L  P  E   V  L  Q   A  P  V   G  S  S   I  L  V
 55  GTTGGCAGC CTCCCTGAG GTGCTGCAG GCACCCGTG GGAAGCTCC ATTCTGGTG

      Q  C  H   Y  R  L   Q  D  V   K  A  Q   K  V  W   C  R  F
109  CAGTGCCAC TACAGGCTC CAGGATGTC AAAGCTCAG AAGGTGTGG TGCCGGTTC

      L  P  E   G  C  Q   P  L  V   S  S  A   V  D  R   R  A  P
163  TTGCCGGAG GGGTGCCAG CCCCTGGTG TCCTCAGCT GTGGATCGC AGAGCTCCG

      A  G  R   R  T  F   L  T  D   L  G  G   G  L  L   Q  V  E
217  GCGGGCAGG CGTACGTTT CTCACAGAC CTGGGTGGG GGCCTGCTG CAGGTGGAA

      M  V  T   L  Q  E   E  D  A   G  E  Y   G  C  M   V  D  G
271  ATGGTTACC CTGCAGGAA GAGGATGCT GGCGAGTAT GGCTGCATG GTGGATGGG

      A  R  G   P  Q  I   L  H  R   V  S  L   N  I  L   P  P  E
325  GCCAGGGGG CCCCAGATT TTGCACAGA GTCTCTCTG AACATACTG CCCCCAGAG

      E  E  E   E  T  H   K  I  G   S  L  A   E  N  A   F  S  D
379  GAAGAAGAA GAGACCCAT AAGATTGGC AGTCTGGCT GAGAACGCA TTCTCAGAC

      P  A  G   S  A  N   P  L  E   P  S  Q   D  E  K   S  I  P
433  CCTGCAGGC AGTGCCAAC CCTTTGGAA CCCAGCCAG GATGAGAAG AGCATCCCC

      L  I  W   G  A  V   L  L  V   G  L  L   V  A  A   V  V  L
487  TTGATCTGG GGTGCTGTG CTCCTGGTA GGTCTGCTG GTGGCAGCG GTGGTGCTG

      F  A  V   M  A  K   R  K  Q   G  N  R   L  G  V   C  G  R
541  TTTGCTGTG ATGGCCAAG AGGAAACAA GGGAACAGG CTTGGTGTC TGTGGCCGA

      F  L  S   S  R  V   S  G  M   N  P  S   S  V  V   H  H  V
595  TTCCTGAGC AGCAGAGTT TCAGGCATG AATCCCTCC TCAGTGGTC CACCACGTC

      S  D  S   G  P  A   A  E  L   P  L  D   V  P  H   I  R  L
649  AGTGACTCT GGACCGGCT GCTGAATTG CCTTTGGAT GTACCACAC ATTAGGCTT

      D  S  P   P  S  F   D  N  T   T  Y  T   S  L  P   L  D  S
703  GACTCACCA CCTTCATTT GACAATACC ACCTACACC AGCCTACCT CTTGATTCC

      P  S  G   K  P  S   L  P  A   P  S  S   L  P  P   L  P  P
757  CCATCAGGA AAACCTTCA CTCCCAGCT CCATCCTCA TTGCCCCCT CTACCTCCT

      K  V  L   V  C  S   K  P  V   T  Y  A   T  V  I   F  P  G
811  AAGGTCCTG GTCTGCTCC AAGCCTGTG ACATATGCC ACAGTAATC TTCCCGGGA

      G  N  K   G  G  G   T  S  C   G  P  A   Q  N  P   P  N  N
865  GGGAACAAG GGTGGAGGG ACCTCGTGT GGGCCAGCC CAGAATCCA CCTAACAAT

      Q  T  P   S  S
919  CAGACTCCA TCCAGC
```

Fig. 2

```
     HindIII          M   G  L  T   L  L  L   L  L  L   L  G  L
  1  AAGCTTGCC GCCACCATG GGCCTCACC CTGCTCTTG CTGCTGCTC CTGGGACTA
      E  G  Q   G  I  V   G  S  L   P  E  V   L  Q  A   P  V  G
 55  GAAGGTCAG GGCATAGTT GGCAGCCTC CCTGAGGTG CTGCAGGCA CCCGTGGGA
      S  S  I   L  V  Q   C  H  Y   R  L  Q   D  V  K   A  Q  K
109  AGCTCCATT CTGGTGCAG TGCCACTAC AGGCTCCAG GATGTCAAA GCTCAGAAG
      V  W  C   R  F  L   P  E  G   C  Q  P   L  V  S   S  A  V
163  GTGTGGTGC CGGTTCTTG CCGGAGGGG TGCCAGCCC CTGGTGTCC TCAGCTGTG
      D  R  R   A  P  A   G  R  R   T  F  L   T  D  L   G  G  G
217  GATCGCAGA GCTCCGGCG GGCAGGCGT ACGTTTCTC ACAGACCTG GGTGGGGGC
      L  L  Q   V  E  M   V  T  L   Q  E  E   D  A  G   E  Y  G
271  CTGCTGCAG GTGGAAATG GTTACCCTG CAGGAAGAG GATGCTGGC GAGTATGGC
      C  M  V   D  G  A   R  G  P   Q  I  L   H  R  V   S  L  N
325  TGCATGGTG GATGGGGCC AGGGGGCCC CAGATTTTG CACAGAGTC TCTCTGAAC
      I  L  P   P  E  E   E  E  E   T  H  K   I  G  S   L  A  E
379  ATACTGCCC CCAGAGGAA GAAGAAGAG ACCCATAAG ATTGGCAGT CTGGCTGAG
      N  A  F   S  D  P   A  G  S   A  N  P   L  E  P   S  Q  D
433  AACGCATTC TCAGACCCT GCAGGCAGT GCCAACCCT TTGGAACCC AGCCAGGAT

      E  K  S   I  P  H   H  H  H   H  H  *  EcoRI
487  GAGAAGAGC ATCCCCCAC CATCACCAT CACCATTAA GAATTC
```

Fig. 3A

```
      M  K  L   P  V  G   L  L  V   L  M  F   W  I  P   A  S  S
  1  ATGAAGTTG CCTGTTGGG CTGTTGGTG CTGATGTTC TGGATTCCA GCTTCCAGC

      S  D  V   V  M  T   Q  T  P   L  S  L   P  V  S   L  G  D
 55  AGTGATGTT GTGATGACC CAAACTCCA CTCTCCCTG CCTGTCAGT CTTGGAGAT

      Q  A  S   I  S  C   R  S  S   Q  S  L   V  H  R   N  G  N
109  CAAGCCTCC ATCTCTTGC AGATCTAGT CAGAGCCTT GTACACAGA AATGGAAAC

      T  Y  F   H  W  C   L  Q  K   P  G  Q   S  P  K   L  L  I
163  ACCTATTTT CATTGGTGC CTGCAGAAA CCAGGCCAG TCTCCAAAG CTCCTGATC

      Y  K  V   S  N  R   F  S  G   V  P  D   R  F  S   G  S  G
217  TACAAAGTT TCCAACCGA TTTTCTGGG GTCCCAGAC AGGTTCAGT GGCAGTGGA

      S  G  T   D  F  T   L  K  I   S  R  V   E  A  E   D  L  G
271  TCAGGGACA GATTTCACA CTCAAGATC AGCAGAGTG GAGGCTGAG GATCTGGGA

      V  Y  F   C  S  Q   S  T  H   V  P  Y   T  F  G   G  G  T
325  GTTTATTTC TGCTCTCAA AGTACACAT GTTCCGTAC ACGTTCGGA GGGGGGACC

      K  L  E   I  K  R
379  AAGCTGGAA ATAAAACGT
```

Fig. 3B

```
          1         2         3         4         5         6
123456789012345678901234567ABCDEF8901234567890123456789012345678 90   Kabat
DVVMTQTPLSLPVSLGDQASISCRSSQSLVHR-NGNTYFHWCLQKPGQSPKLLIYKVSNRFSGVPD   0012LC-V

          7         8         9         10
123456789012345678901234567890123 45AB6789012345678                  Kabat
RFSGSGSGTDFTLKISRVEAEDLGVYFCSQSTHVP--YTFGGGTKLEIKR                   0012LC-V
```

Fig. 3C

```
      M  D  F   G  L  I   F  F  I   V  A  L   L  K  G   V  Q  C
  1  ATGGATTTT GGGCTGATT TTTTTTATT GTTGCTCTT TTAAAAGGG GTCCAGTGT

      E  V  K   L  L  E   S  G  G   G  L  V   Q  P  G   G  S  L
 55  GAGGTGAAA CTTCTCGAG TCTGGAGGT GGCCTGGTG CAGCCTGGA GGATCCCTG

      K  L  S   C  A  A   S  G  F   D  F  S   R  Y  W   M  T  W
109  AAACTCTCC TGTGCAGCC TCAGGATTC GATTTTAGT AGATACTGG ATGACTTGG

      V  R  Q   A  P  G   K  G  L   E  W  I   G  E  I   N  P  D
163  GTCCGGCAG GCTCCAGGG AAAGGGCTA GAATGGATT GGAGAAATT AATCCAGAT

      S  S  T   I  N  Y   T  P  S   L  K  D   K  F  I   I  S  R
217  AGCAGTACG ATAAACTAT ACGCCATCT CTAAAGGAT AAATTCATC ATCTCCAGA

      D  N  A   K  N  T   L  Y  L   Q  M  S   E  V  R   S  E  D
271  GACAACGCC AAGAATACG CTGTACCTG CAAATGAGC GAAGTGAGA TCTGAGGAC

      T  A  L   Y  Y  C   A  S  G   V  F  T   S  W  G   Q  G  T
325  ACAGCCCTT TATTACTGT GCAAGCGGG GTGTTTACT TCCTGGGGC CAAGGGACT

      L  V  T   V  S  A
379  CTGGTCACT GTCTCTGCA
```

Fig. 3D

```
           1         2         3       4         5             6
1234567890123456789012345678901234567890123456789012ABC34567890        Kabat
EVKLLESGGGLVQPGGSLKLSCAASGFDFSRYWMT--WVRQAPGKGLEWIGEIN--PDSSTINYT      0012HC-V

           7         8         9      10                      11
12345678901234567890 12ABC345678901234567890ABCDEFGHIJK123456 7890123  Kabat
PSLKDKFIISRDNAKNTLYLQMSEVRSEDTALYYCASGVFTS--------------WGQGTLVTVSA    0012HC-V
```

Fig. 4

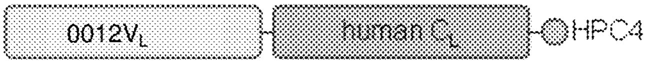

M K L P V G L L V L M F W I P A S S
1 ATGAAGTTG CCTGTTGGG CTGTTGGTG CTGATGTTC TGGATTCCA GCTTCCAGC

S D V V M T Q T P L S L P V S L G D
55 AGTGATGTT GTGATGACC CAAACTCCA CTCTCCCTG CCTGTCAGT CTTGGAGAT

Q A S I S C R S S Q S L V H R N G N
109 CAAGCCTCC ATCTCTTGC AGATCTAGT CAGAGCCTT GTACACAGA AATGGAAAC

T Y F H W C L Q K P G Q S P K L L I
163 ACCTATTTT CATTGGTGC CTGCAGAAA CCAGGCCAG TCTCCAAAG CTCCTGATC

Y K V S N R F S G V P D R F S G S G
217 TACAAAGTT TCCAACCGA TTTTCTGGG GTCCCAGAC AGGTTCAGT GGCAGTGGA

S G T D F T L K I S R V E A E D L G
271 TCAGGGACA GATTTCACA CTCAAGATC AGCAGAGTG GAGGCTGAG GATCTGGGA

V Y F C S Q S T H V P Y T F G G G T
325 GTTTATTTC TGCTCTCAA AGTACACAT GTTCCGTAC ACGTTCGGA GGGGGGACC

K L E I K R T V A A P S V F I F P P
379 AAGCTGGAA ATAAAACGT ACGGTGGCT GCACCATCT GTCTTCATC TTCCCGCCA

S D E Q L K S G T A S V V C L L N N
433 TCTGATGAG CAGTTGAAA TCTGGAACT GCCTCTGTT GTGTGCCTG CTGAATAAC

F Y P R E A K V Q W K V D N A L Q S
487 TTCTATCCC AGAGAGGCC AAAGTACAG TGGAAGGTG GATAACGCC CTCCAATCG

G N S Q E S V T E Q D S K D S T Y S
541 GGTAACTCC CAGGAGAGT GTCACAGAG CAGGACAGC AAGGACAGC ACCTACAGC

L S S T L T L S K A D Y E K H K V Y
595 CTCAGCAGC ACCCTGACG CTGAGCAAA GCAGACTAC GAGAAACAC AAAGTCTAC

A C E V T H Q G L S S P V T K S F N
649 GCCTGCGAA GTCACCCAT CAGGGCCTG AGCTCGCCC GTCACAAAG AGCTTCAAC

R G E C *E D Q V D P R L I D G K*
703 AGGGGAGAG TGT*GAGGAC CAGGTGGAC CCCAGACTG ATCGACGGC AAG*

Fig. 5

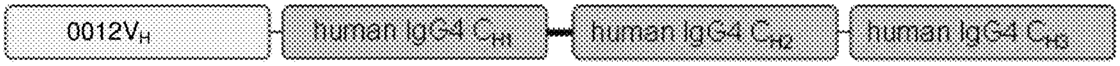

```
      M  D  F   G  L  I   F  F  I   V  A  L   L  K  G   V  Q  C
   1  ATGGATTTT GGGCTGATT TTTTTTATT GTTGCTCTT TTAAAAGGG GTCCAGTGT

      E  V  K   L  L  E   S  G  G   G  L  V   Q  P  G   G  S  L
  55  GAGGTGAAA CTTCTCGAG TCTGGAGGT GGCCTGGTG CAGCCTGGA GGATCCCTG

      K  L  S   C  A  A   S  G  F   D  F  S   R  Y  W   M  T  W
 109  AAACTCTCC TGTGCAGCC TCAGGATTC GATTTTAGT AGATACTGG ATGACTTGG

      V  R  Q   A  P  G   K  G  L   E  W  I   G  E  I   N  P  D
 163  GTCCGGCAG GCTCCAGGG AAAGGGCTA GAATGGATT GGAGAAATT AATCCAGAT

      S  S  T   I  N  Y   T  P  S   L  K  D   K  F  I   I  S  R
 217  AGCAGTACG ATAAACTAT ACGCCATCT CTAAAGGAT AAATTCATC ATCTCCAGA

      D  N  A   K  N  T   L  Y  L   Q  M  S   E  V  R   S  E  D
 271  GACAACGCC AAGAATACG CTGTACCTG CAAATGAGC GAAGTGAGA TCTGAGGAC

      T  A  L   Y  Y  C   A  S  G   V  F  T   S  W  G   Q  G  T
 325  ACAGCCCTT TATTACTGT GCAAGCGGG GTGTTTACT TCCTGGGGC CAAGGGACT

      L  V  T   V  S  A   A  S  T   K  G  P   S  V  F   P  L  A
 379  CTGGTCACT GTCTCTGCA GCTAGCACC AAGGGCCCA TCCGTCTTC CCCCTGGCG

      P  C  S   R  S  T   S  E  S   T  A  A   L  G  C   L  V  K
 433  CCCTGCTCC AGGAGCACC TCCGAGAGC ACAGCCGCC CTGGGCTGC CTGGTCAAG

      D  Y  F   P  E  P   V  T  V   S  W  N   S  G  A   L  T  S
 487  GACTACTTC CCCGAACCG GTGACGGTG TCGTGGAAC TCAGGCGCC CTGACCAGC

      G  V  H   T  F  P   A  V  L   Q  S  S   G  L  Y   S  L  S
 541  GGCGTGCAC ACCTTCCCG GCTGTCCTA CAGTCCTCA GGACTCTAC TCCCTCAGC

      S  V  V   T  V  P   S  S  S   L  G  T   K  T  Y   T  C  N
 595  AGCGTGGTG ACCGTGCCC TCCAGCAGC TTGGGCACG AAGACCTAC ACCTGCAAC

      V  D  H   K  P  S   N  T  K   V  D  K   R  V  E   S  K  Y
 649  GTAGATCAC AAGCCCAGC AACACCAAG GTGGACAAG AGAGTTGAG TCCAAATAT

      G  P  P   C  P  P   C  P  A   P  E  F   L  G  G   P  S  V
 703  GGTCCCCCA TGCCCACCA TGCCCAGCA CCTGAGTTC CTGGGGGGA CCATCAGTC

      F  L  F   P  P  K   P  K  D   T  L  M   I  S  R   T  P  E
 757  TTCCTGTTC CCCCCAAAA CCCAAGGAC ACTCTCATG ATCTCCCGG ACCCCTGAG

      V  T  C   V  V  V   D  V  S   Q  E  D   P  E  V   Q  F  N
 811  GTCACGTGC GTGGTGGTG GACGTGAGC CAGGAAGAC CCCGAGGTC CAGTTCAAC

      W  Y  V   D  G  V   E  V  H   N  A  K   T  K  P   R  E  E
 865  TGGTACGTG GATGGCGTG GAGGTGCAT AATGCCAAG ACAAAGCCG CGGGAGGAG

      Q  F  N   S  T  Y   R  V  V   S  V  L   T  V  L   H  Q  D
 919  CAGTTCAAC AGCACGTAC CGTGTGGTC AGCGTCCTC ACCGTCCTG CACCAGGAC

      W  L  N   G  K  E   Y  K  C   K  V  S   N  K  G   L  P  S
 973  TGGCTGAAC GGCAAGGAG TACAAGTGC AAGGTCTCC AACAAAGGC CTCCCGTCC

      S  I  E   K  T  I   S  K  A   K  G  Q   P  R  E   P  Q  V
1027  TCCATCGAG AAAACCATC TCCAAAGCC AAAGGGCAG CCCCGAGAG CCACAGGTG

      Y  T  L   P  P  S   Q  E  E   M  T  K   N  Q  V   S  L  T
1081  TACACCCTG CCCCCATCC CAGGAGGAG ATGACCAAG AACCAGGTC AGCCTGACC
```

Fig. 5 (cont.)

```
      C  L  V   K  G  F   Y  P  S   D  I  A   V  E  W   E  S  N
1135  TGCCTGGTC AAAGGCTTC TACCCCAGC GACATCGCC GTGGAGTGG GAGAGCAAT

      G  Q  P   E  N  N   Y  K  T   T  P  P   V  L  D   S  D  G
1189  GGGCAGCCG GAGAACAAC TACAAGACC ACGCCTCCC GTGCTGGAC TCCGACGGC

      S  F  F   L  Y  S   R  L  T   V  D  K   S  R  W   Q  E  G
1243  TCCTTCTTC CTCTACAGC AGGCTAACC GTGGACAAG AGCAGGTGG CAGGAGGGG

      N  V  F   S  C  S   V  M  H   E  A  L   H  N  H   Y  T  Q
1297  AATGTCTTC TCATGCTCC GTGATGCAT GAGGCTCTG CACAACCAC TACACACAG

      K  S  L   S  L  S   L  G  K
1351  AAGAGCCTC TCCCTGTCT CTGGGTAAA
```

White: no difference
Black: 0061 epitope

25nM FVII variants
Platelets activated with SFLLRN (30µM) and Convulxin (100ng/ml)

5nM FVII variants
Platelets activated with SFLLRN (30µM) and Convulxin (100ng/ml)

SEQUENCE LISTING

```
<160> NUMBER OF SEQ ID NOS: 259

<210> SEQ ID NO 1
<211> LENGTH: 933
<212> TYPE: DNA
<213> ORGANISM: homo Sapiens

<400> SEQUENCE: 1

atgggcctca ccctgctctt gctgctgctc ctgggactag aaggtcaggg catagttggc     60

agcctccctg aggtgctgca ggcacccgtg ggaagctcca ttctggtgca gtgccactac    120

aggctccagg atgtcaaagc tcagaaggtg tggtgccggt tcttgccgga ggggtgccag    180

cccctggtgt cctcagctgt ggatcgcaga gctccagcgg gcaggcgtac gtttctcaca    240

gacctgggtg ggggcctgct gcaggtggaa atggttaccc tgcaggaaga ggatgctggc    300

gagtatggct gcatggtgga tggggccagg gggccccaga ttttgcacag agtctctctg    360

aacatactgc ccccagagga agaagaagag acccataaga ttggcagtct ggctgagaac    420

gcattctcag accctgcagg cagtgccaac cctttggaac ccagccagga tgagaagagc    480
```

```
atccccttga tctggggtgc tgtgctcctg gtaggtctgc tggtggcagc ggtggtgctg    540

tttgctgtga tggccaagag gaaacaaggg aacaggcttg gtgtctgtgg ccgattcctg    600

agcagcagag tttcaggcat gaatccctcc tcagtggtcc accacgtcag tgactctgga    660

ccggctgctg aattgccttt ggatgtacca cacattaggc ttgactcacc accttcattt    720

gacaatacca cctacaccag cctacctctt gattccccat caggaaaacc ttcactccca    780

gctccatcct cattgccccc tctacctcct aaggtcctgg tctgctccaa gcctgtgaca    840

tatgccacag taatcttccc gggagggaac aagggtggag ggacctcgtg tgggccagcc    900

cagaatccac ctaacaatca gactccatcc agc                                 933
```

```
<210> SEQ ID NO 2
<211> LENGTH: 311
<212> TYPE: PRT
<213> ORGANISM: Homo sapiens

<400> SEQUENCE: 2

Met Gly Leu Thr Leu Leu Leu Leu Leu Leu Leu Gly Leu Glu Gly Gln
1               5                   10                  15

Gly Ile Val Gly Ser Leu Pro Glu Val Leu Gln Ala Pro Val Gly Ser
            20                  25                  30

Ser Ile Leu Val Gln Cys His Tyr Arg Leu Gln Asp Val Lys Ala Gln
        35                  40                  45

Lys Val Trp Cys Arg Phe Leu Pro Glu Gly Cys Gln Pro Leu Val Ser
    50                  55                  60

Ser Ala Val Asp Arg Arg Ala Pro Ala Gly Arg Arg Thr Phe Leu Thr
65                  70                  75                  80

Asp Leu Gly Gly Gly Leu Leu Gln Val Glu Met Val Thr Leu Gln Glu
                85                  90                  95

Glu Asp Ala Gly Glu Tyr Gly Cys Met Val Asp Gly Ala Arg Gly Pro
            100                 105                 110

Gln Ile Leu His Arg Val Ser Leu Asn Ile Leu Pro Pro Glu Glu Glu
        115                 120                 125

Glu Glu Thr His Lys Ile Gly Ser Leu Ala Glu Asn Ala Phe Ser Asp
    130                 135                 140

Pro Ala Gly Ser Ala Asn Pro Leu Glu Pro Ser Gln Asp Glu Lys Ser
145                 150                 155                 160

Ile Pro Leu Ile Trp Gly Ala Val Leu Leu Val Gly Leu Leu Val Ala
                165                 170                 175

Ala Val Val Leu Phe Ala Val Met Ala Lys Arg Lys Gln Gly Asn Arg
            180                 185                 190

Leu Gly Val Cys Gly Arg Phe Leu Ser Ser Arg Val Ser Gly Met Asn
        195                 200                 205

Pro Ser Ser Val Val His His Val Ser Asp Ser Gly Pro Ala Ala Glu
    210                 215                 220

Leu Pro Leu Asp Val Pro His Ile Arg Leu Asp Ser Pro Pro Ser Phe
225                 230                 235                 240

Asp Asn Thr Thr Tyr Thr Ser Leu Pro Leu Asp Ser Pro Ser Gly Lys
                245                 250                 255

Pro Ser Leu Pro Ala Pro Ser Ser Leu Pro Pro Leu Pro Pro Lys Val
            260                 265                 270

Leu Val Cys Ser Lys Pro Val Thr Tyr Ala Thr Val Ile Phe Pro Gly
        275                 280                 285
```

```
Gly Asn Lys Gly Gly Gly Thr Ser Cys Gly Pro Ala Gln Asn Pro Pro
    290                 295                 300

Asn Asn Gln Thr Pro Ser Ser
305                 310


<210> SEQ ID NO 3
<211> LENGTH: 528
<212> TYPE: DNA
<213> ORGANISM: Artificial sequence
<220> FEATURE:
<223> OTHER INFORMATION: /note = "extracellular domain of hTLT-1-His6"

<400> SEQUENCE: 3

aagcttgccg ccaccatggg cctcaccctg ctcttgctgc tgctcctggg actagaaggt      60

cagggcatag ttggcagcct ccctgaggtg ctgcaggcac ccgtgggaag ctccattctg     120

gtgcagtgcc actacaggct ccaggatgtc aaagctcaga aggtgtggtg ccggttcttg     180

ccggaggggt gccagcccct ggtgtcctca gctgtggatc gcagagctcc ggcgggcagg     240

cgtacgtttc tcacagacct gggtgggggc ctgctgcagg tggaaatggt taccctgcag     300

gaagaggatg ctggcgagta tggctgcatg gtggatgggg ccagggggcc ccagattttg     360

cacagagtct ctctgaacat actgcccccca gaggaagaag aagagaccca taagattggc     420

agtctggctg agaacgcatt ctcagaccct gcaggcagtg ccaacccttt ggaacccagc     480

caggatgaga agagcatccc ccaccatcac catcaccatt aagaattc                 528


<210> SEQ ID NO 4
<211> LENGTH: 168
<212> TYPE: PRT
<213> ORGANISM: Artificial sequence
<220> FEATURE:
<223> OTHER INFORMATION: /note = "extracellular domain of hTLT-1-His6"

<400> SEQUENCE: 4

Met Gly Leu Thr Leu Leu Leu Leu Leu Leu Leu Gly Leu Glu Gly Gln
1               5                   10                  15

Gly Ile Val Gly Ser Leu Pro Glu Val Leu Gln Ala Pro Val Gly Ser
            20                  25                  30

Ser Ile Leu Val Gln Cys His Tyr Arg Leu Gln Asp Val Lys Ala Gln
        35                  40                  45

Lys Val Trp Cys Arg Phe Leu Pro Glu Gly Cys Gln Pro Leu Val Ser
    50                  55                  60

Ser Ala Val Asp Arg Arg Ala Pro Ala Gly Arg Arg Thr Phe Leu Thr
65                  70                  75                  80

Asp Leu Gly Gly Gly Leu Leu Gln Val Glu Met Val Thr Leu Gln Glu
                85                  90                  95

Glu Asp Ala Gly Glu Tyr Gly Cys Met Val Asp Gly Ala Arg Gly Pro
            100                 105                 110

Gln Ile Leu His Arg Val Ser Leu Asn Ile Leu Pro Pro Glu Glu Glu
        115                 120                 125

Glu Glu Thr His Lys Ile Gly Ser Leu Ala Glu Asn Ala Phe Ser Asp
    130                 135                 140

Pro Ala Gly Ser Ala Asn Pro Leu Glu Pro Ser Gln Asp Glu Lys Ser
145                 150                 155                 160

Ile Pro His His His His His His
                165


<210> SEQ ID NO 5
```

<211> LENGTH: 106
<212> TYPE: PRT
<213> ORGANISM: Artificial sequence
<220> FEATURE:
<223> OTHER INFORMATION: /note = "hTLT-1.20-125"

<400> SEQUENCE: 5

```
Gly Ser Leu Pro Glu Val Leu Gln Ala Pro Val Gly Ser Ser Ile Leu
1               5                   10                  15

Val Gln Cys His Tyr Arg Leu Gln Asp Val Lys Ala Gln Lys Val Trp
            20                  25                  30

Cys Arg Phe Leu Pro Glu Gly Cys Gln Pro Leu Val Ser Ser Ala Val
        35                  40                  45

Asp Arg Arg Ala Pro Ala Gly Arg Arg Thr Phe Leu Thr Asp Leu Gly
    50                  55                  60

Gly Gly Leu Leu Gln Val Glu Met Val Thr Leu Gln Glu Glu Asp Ala
65                  70                  75                  80

Gly Glu Tyr Gly Cys Met Val Asp Gly Ala Arg Gly Pro Gln Ile Leu
                85                  90                  95

His Arg Val Ser Leu Asn Ile Leu Pro Pro
            100                 105
```

<210> SEQ ID NO 6
<211> LENGTH: 147
<212> TYPE: PRT
<213> ORGANISM: Artificial sequence
<220> FEATURE:
<223> OTHER INFORMATION: /note = "hTLT-1.16-162"

<400> SEQUENCE: 6

```
Gln Gly Ile Val Gly Ser Leu Pro Glu Val Leu Gln Ala Pro Val Gly
1               5                   10                  15

Ser Ser Ile Leu Val Gln Cys His Tyr Arg Leu Gln Asp Val Lys Ala
            20                  25                  30

Gln Lys Val Trp Cys Arg Phe Leu Pro Glu Gly Cys Gln Pro Leu Val
        35                  40                  45

Ser Ser Ala Val Asp Arg Arg Ala Pro Ala Gly Arg Arg Thr Phe Leu
    50                  55                  60

Thr Asp Leu Gly Gly Gly Leu Leu Gln Val Glu Met Val Thr Leu Gln
65                  70                  75                  80

Glu Glu Asp Ala Gly Glu Tyr Gly Cys Met Val Asp Gly Ala Arg Gly
                85                  90                  95

Pro Gln Ile Leu His Arg Val Ser Leu Asn Ile Leu Pro Pro Glu Glu
            100                 105                 110

Glu Glu Glu Thr His Lys Ile Gly Ser Leu Ala Glu Asn Ala Phe Ser
        115                 120                 125

Asp Pro Ala Gly Ser Ala Asn Pro Leu Glu Pro Ser Gln Asp Glu Lys
    130                 135                 140

Ser Ile Pro
145
```

<210> SEQ ID NO 7
<211> LENGTH: 37
<212> TYPE: PRT
<213> ORGANISM: Artificial sequence
<220> FEATURE:
<223> OTHER INFORMATION: /note = "hTLT-1.126-162"

<400> SEQUENCE: 7

```
Glu Glu Glu Glu Glu Thr His Lys Ile Gly Ser Leu Ala Glu Asn Ala
1               5                   10                  15

Phe Ser Asp Pro Ala Gly Ser Ala Asn Pro Leu Glu Pro Ser Gln Asp
            20                  25                  30

Glu Lys Ser Ile Pro
        35


<210> SEQ ID NO 8
<211> LENGTH: 14
<212> TYPE: PRT
<213> ORGANISM: Artificial sequence
<220> FEATURE:
<223> OTHER INFORMATION: /note = "hTLT-1.129-142"

<400> SEQUENCE: 8

Glu Glu Thr His Lys Ile Gly Ser Leu Ala Glu Asn Ala Phe
1               5                   10


<210> SEQ ID NO 9
<211> LENGTH: 396
<212> TYPE: DNA
<213> ORGANISM: Homo sapiens

<400> SEQUENCE: 9

atgaagttgc ctgttgggct gttggtgctg atgttctgga ttccagcttc cagcagtgat      60

gttgtgatga cccaaactcc actctccctg cctgtcagtc ttggagatca agcctccatc     120

tcttgcagat ctagtcagag ccttgtacac agaaatggaa acacctattt tcattggtgc     180

ctgcagaaac caggccagtc tccaaagctc ctgatctaca aagtttccaa ccgattttct     240

ggggtcccag acaggttcag tggcagtgga tcagggacag atttcacact caagatcagc     300

agagtggagg ctgaggatct gggagtttat ttctgctctc aaagtacaca tgttccgtac     360

acgttcggag gggggaccaa gctggaaata aaacgt                               396


<210> SEQ ID NO 10
<211> LENGTH: 132
<212> TYPE: PRT
<213> ORGANISM: Homo sapiens

<400> SEQUENCE: 10

Met Lys Leu Pro Val Gly Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Arg Asn Gly Asn Thr Tyr Phe His Trp Cys Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Tyr Thr Phe Gly Gly Gly Thr Lys Leu
        115                 120                 125

Glu Ile Lys Arg
    130
```

<210> SEQ ID NO 11
<211> LENGTH: 396
<212> TYPE: DNA
<213> ORGANISM: Homo sapiens

<400> SEQUENCE: 11
atggattttg ggctgatttt ttttattgtt gctcttttaa aaggggtcca gtgtgaggtg 60
aaacttctcg agtctggagg tggcctggtg cagcctggag gatccctgaa actctcctgt 120
gcagcctcag gattcgattt tagtagatac tggatgactt gggtccggca ggctccaggg 180
aaagggctag aatggattgg agaaattaat ccagatagca gtacgataaa ctatacgcca 240
tctctaaagg ataaattcat catctccaga gacaacgcca agaatacgct gtacctgcaa 300
atgagcgaag tgagatctga ggacacagcc ctttattact gtgcaagcgg ggtgtttact 360
tcctggggcc aagggactct ggtcactgtc tctgca 396

<210> SEQ ID NO 12
<211> LENGTH: 132
<212> TYPE: PRT
<213> ORGANISM: Homo sapiens

<400> SEQUENCE: 12

Met Asp Phe Gly Leu Ile Phe Phe Ile Val Ala Leu Leu Lys Gly Val
1 5 10 15

Gln Cys Glu Val Lys Leu Leu Glu Ser Gly Gly Gly Leu Val Gln Pro
20 25 30

Gly Gly Ser Leu Lys Leu Ser Cys Ala Ala Ser Gly Phe Asp Phe Ser
35 40 45

Arg Tyr Trp Met Thr Trp Val Arg Gln Ala Pro Gly Lys Gly Leu Glu
50 55 60

Trp Ile Gly Glu Ile Asn Pro Asp Ser Ser Thr Ile Asn Tyr Thr Pro
65 70 75 80

Ser Leu Lys Asp Lys Phe Ile Ile Ser Arg Asp Asn Ala Lys Asn Thr
85 90 95

Leu Tyr Leu Gln Met Ser Glu Val Arg Ser Glu Asp Thr Ala Leu Tyr
100 105 110

Tyr Cys Ala Ser Gly Val Phe Thr Ser Trp Gly Gln Gly Thr Leu Val
115 120 125

Thr Val Ser Ala
130

<210> SEQ ID NO 13
<211> LENGTH: 1377
<212> TYPE: DNA
<213> ORGANISM: Artificial sequence
<220> FEATURE:
<223> OTHER INFORMATION: /note = “mAb 0012 HC”

<400> SEQUENCE: 13
atggattttg ggctgatttt ttttattgtt gctcttttaa aaggggtcca gtgtgaggtg 60
aaacttctcg agtctggagg tggcctggtg cagcctggag gatccctgaa actctcctgt 120
gcagcctcag gattcgattt tagtagatac tggatgactt gggtccggca ggctccaggg 180
aaagggctag aatggattgg agaaattaat ccagatagca gtacgataaa ctatacgcca 240
tctctaaagg ataaattcat catctccaga gacaacgcca agaatacgct gtacctgcaa 300
atgagcgaag tgagatctga ggacacagcc ctttattact gtgcaagcgg ggtgtttact 360

-continued

```
tcctggggcc aagggactct ggtcactgtc tctgcagcta gcaccaaggg cccatccgtc    420

ttcccccctgg cgccctgctc caggagcacc tccgagagca cagccgccct gggctgcctg    480

gtcaaggact acttccccga accggtgacg gtgtcgtgga actcaggcgc cctgaccagc    540

ggcgtgcaca ccttcccggc tgtcctacag tcctcaggac tctactccct cagcagcgtg    600

gtgaccgtgc cctccagcag cttgggcacg aagacctaca cctgcaacgt agatcacaag    660

cccagcaaca ccaaggtgga caagagagtt gagtccaaat atggtccccc atgcccacca    720

tgcccagcac ctgagttcct ggggggacca tcagtcttcc tgttcccccc aaaacccaag    780

gacactctca tgatctcccg gacccctgag gtcacgtgcg tggtggtgga cgtgagccag    840

gaagaccccg aggtccagtt caactggtac gtggatggcg tggaggtgca taatgccaag    900

acaaagccgc gggaggagca gttcaacagc acgtaccgtg tggtcagcgt cctcaccgtc    960

ctgcaccagg actggctgaa cggcaaggag tacaagtgca aggtctccaa caaaggcctc   1020

ccgtcctcca tcgagaaaac catctccaaa gccaaagggc agccccgaga gccacaggtg   1080

tacaccctgc ccccatccca ggaggagatg accaagaacc aggtcagcct gacctgcctg   1140

gtcaaaggct tctaccccag cgacatcgcc gtggagtggg agagcaatgg gcagccggag   1200

aacaactaca agaccacgcc tcccgtgctg gactccgacg gctccttctt cctctacagc   1260

aggctaaccg tggacaagag caggtggcag gaggggaatg tcttctcatg ctccgtgatg   1320

catgaggctc tgcacaacca ctacacacag aagagcctct ccctgtctct gggtaaa      1377
```

<210> SEQ ID NO 14
<211> LENGTH: 714
<212> TYPE: DNA
<213> ORGANISM: Artificial sequence
<220> FEATURE:
<223> OTHER INFORMATION: /note = “mAb 0012 LC, Fab 0012 LC”

<400> SEQUENCE: 14

```
atgaagttgc ctgttgggct gttggtgctg atgttctgga ttccagcttc cagcagtgat     60

gttgtgatga cccaaactcc actctccctg cctgtcagtc ttggagatca agcctccatc    120

tcttgcagat ctagtcagag ccttgtacac agaaatggaa acacctattt tcattggtgc    180

ctgcagaaac caggccagtc tccaaagctc ctgatctaca aagtttccaa ccgattttct    240

ggggtcccag acaggttcag tggcagtgga tcagggacag atttcacact caagatcagc    300

agagtggagg ctgaggatct gggagtttat ttctgctctc aaagtacaca tgttccgtac    360

acgttcggag gggggaccaa gctggaaata aaacgtacgg tggctgcacc atctgtcttc    420

atcttcccgc catctgatga gcagttgaaa tctggaactg cctctgttgt gtgcctgctg    480

aataacttct atcccagaga ggccaaagta cagtggaagg tggataacgc cctccaatcg    540

ggtaactccc aggagagtgt cacagagcag gacagcaagg acagcaccta cagcctcagc    600

agcaccctga cgctgagcaa agcagactac gagaaacaca aagtctacgc ctgcgaagtc    660

acccatcagg gcctgagctc gcccgtcaca aagagcttca acaggggaga gtgt          714
```

<210> SEQ ID NO 15
<211> LENGTH: 1401
<212> TYPE: DNA
<213> ORGANISM: Artificial sequence
<220> FEATURE:
<223> OTHER INFORMATION: /note = “mAb 0023 HC”

<400> SEQUENCE: 15

```
atgaacttgg ggctcagctt gattttcctt gtccttgttt taaaaggtgt ccagtgtgaa     60
```

```
gtgaggctgg tggagtctgg gggaggctta gtgcagcctg gagggtccct gaaactctcc    120
tgtgcaacct ctggattcac tttcagtgac tatttcatgt attggattcg ccagactcca    180
gagaagaggc tggagtgggt cgcatacatt agtaatggtg gtgatagcag ctcttatcca    240
gacactgtaa agggccgatt caccatctcc agagacaatg ccaagaacac cctgtacctg    300
caaatgagcc gtctgaagtc tgaggacaca gccatgtatt attgtgcaac aaataaaaac    360
tgggacgatt actatgatat ggactactgg ggtcaaggaa cctcagtcac cgtctcctca    420
gctagcacca agggcccatc cgtcttcccc ctggcgccct gctccaggag cacctccgag    480
agcacagccg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgacc gtgccctcca gcagcttggg cacgaagacc    660
tacacctgca acgtagatca caagcccagc aacaccaagg tggacaagag agttgagtcc    720
aaatatggtc ccccatgccc accatgccca gcacctgagt tcctgggggg accatcagtc    780
ttcctgttcc ccccaaaacc caaggacact ctcatgatct cccggacccc tgaggtcacg    840
tgcgtggtgg tggacgtgag ccaggaagac cccgaggtcc agttcaactg gtacgtggat    900
ggcgtggagg tgcataatgc caagacaaag ccgcgggagg agcagttcaa cagcacgtac    960
cgtgtggtca gcgtcctcac cgtcctgcac caggactggc tgaacggcaa ggagtacaag   1020
tgcaaggtct ccaacaaagg cctcccgtcc tccatcgaga aaaccatctc caaagccaaa   1080
gggcagcccc gagagccaca ggtgtacacc ctgcccccat cccaggagga gatgaccaag   1140
aaccaggtca gcctgacctg cctggtcaaa ggcttctacc ccagcgacat cgccgtggag   1200
tgggagagca atgggcagcc ggagaacaac tacaagacca cgcctcccgt gctggactcc   1260
gacggctcct tcttcctcta cagcaggcta accgtggaca agagcaggtg gcaggagggg   1320
aatgtcttct catgctccgt gatgcatgag gctctgcaca accactacac acagaagagc   1380
ctctccctgt ctctgggtaa a                                             1401
```

<210> SEQ ID NO 16
<211> LENGTH: 717
<212> TYPE: DNA
<213> ORGANISM: Artificial sequence
<220> FEATURE:
<223> OTHER INFORMATION: /note = "mAb 0023 LC"

<400> SEQUENCE: 16

```
atggattcac aggcccaggt tcttatattg ctgctgctat gggtatctgg ttcctgtggg     60
gacattgtgg tgtcacagtc tccatcctcc ctggctgtgt cagcaggaga gaaggtcact    120
atgagttgca aatccagtca gagtctgctc aacagtagaa cccgaaagaa ctacttggct    180
tggtaccagc agaaaccagg gcagtctcct aaactgctga tctactgggc atccactagg    240
gaatctgggg tccctgatcg cttcacaggc agtggatctg ggacagattt cactctcacc    300
atcagcagtg tgcaggctga agacctggca gtttattact gcaagcaatc ttataatctg    360
ctcacgttcg gtgctgggac caagctggag ctgaaacgta cggtggctgc accatctgtc    420
ttcatcttcc cgccatctga tgagcagttg aaatctggaa ctgcctctgt tgtgtgcctg    480
ctgaataact tctatcccag agaggccaaa gtacagtgga aggtggataa cgccctccaa    540
tcgggtaact cccaggagag tgtcacagag caggacagca aggacagcac ctacagcctc    600
agcagcaccc tgacgctgag caaagcagac tacgagaaac acaaagtcta cgcctgcgaa    660
```

-continued gtcacccatc agggcctgag ctcgcccgtc acaaagagct tcaacagggg agagtgt 717

<210> SEQ ID NO 17
<211> LENGTH: 1401
<212> TYPE: DNA
<213> ORGANISM: Artificial sequence
<220> FEATURE:
<223> OTHER INFORMATION: /note = “mAb 0051 HC”

<400> SEQUENCE: 17
atgggttgga gctgtatcat cttctttctg gtagcaacag ctacaggtgt gcactcccag 60
gtccagctgg agcagtctgg ggctgagctg gtgaggcctg gggtctcagt gaagatttcc 120
tgcaagggtt ctggctacac attcactgat tattctatgc actgggtgaa gcagagtcat 180
gcaaagagtc tagagtggat tggagttatt agtacttact atggtgatgt taggtacaac 240
cagaagttca agggcaaggc cacaatgact gtagacaaat cctccagcac agcctatatg 300
gcacttgcca gactgacatc tgaggattct gccatctatt actgtgcaag agcccctatg 360
attacgacag gggcctggtt tgcttactgg ggccaaggga ctctggtcac tgtctctgca 420
gctagcacca agggcccatc cgtcttcccc ctggcgccct gctccaggag cacctccgag 480
agcacagccg ccctgggctg cctggtcaag gactacttcc ccgaaccggt gacggtgtcg 540
tggaactcag gcgccctgac cagcggcgtg cacaccttcc cggctgtcct acagtcctca 600
ggactctact ccctcagcag cgtggtgacc gtgccctcca gcagcttggg cacgaagacc 660
tacacctgca acgtagatca caagcccagc aacaccaagg tggacaagag agttgagtcc 720
aaatatggtc ccccatgccc accatgccca gcacctgagt tcctgggggg accatcagtc 780
ttcctgttcc ccccaaaacc caaggacact ctcatgatct cccggacccc tgaggtcacg 840
tgcgtggtgg tggacgtgag ccaggaagac cccgaggtcc agttcaactg gtacgtggat 900
ggcgtggagg tgcataatgc caagacaaag ccgcgggagg agcagttcaa cagcacgtac 960
cgtgtggtca gcgtcctcac cgtcctgcac caggactggc tgaacggcaa ggagtacaag 1020
tgcaaggtct ccaacaaagg cctcccgtcc tccatcgaga aaaccatctc caaagccaaa 1080
gggcagcccc gagagccaca ggtgtacacc ctgcccccat cccaggagga gatgaccaag 1140
aaccaggtca gcctgacctg cctggtcaaa ggcttctacc ccagcgacat cgccgtggag 1200
tgggagagca atgggcagcc ggagaacaac tacaagacca cgcctcccgt gctggactcc 1260
gacggctcct tcttcctcta cagcaggcta accgtggaca agagcaggtg gcaggagggg 1320
aatgtcttct catgctccgt gatgcatgag gctctgcaca accactacac acagaagagc 1380
ctctccctgt ctctgggtaa a 1401

<210> SEQ ID NO 18
<211> LENGTH: 702
<212> TYPE: DNA
<213> ORGANISM: Artificial sequence
<220> FEATURE:
<223> OTHER INFORMATION: /note = “mAb 0051 LC”

<400> SEQUENCE: 18
atgaagtcac agacccaggt cttcgtattt ctactgctct gtgtgtctgg tgctcatggg 60
agtattgtga tgacccagac tcccaaattc ctgcttgtat cagcaggaga cagggttacc 120
ataacctgca aggccagtca gagtgtgagt aatgatgtag cttggtacca acagaagcca 180
gggcagtctc ctaaactgct gataaactat gcatccagtc gctacactgg aatccctgat 240
cgcttcactg gcagtggata tgggacggat ttcactttca ccatcagcac tgtgcaggct 300
gaagacctgg cagtttattt ctgtcagcag gattatagct ctccgtacac gttcggaggg 360
gggaccaagc tggaaataga acgtacggtg gctgcaccat ctgtcttcat cttcccgcca 420
tctgatgagc agttgaaatc tggaactgcc tctgttgtgt gcctgctgaa taacttctat 480
cccagagagg ccaaagtaca gtggaaggtg gataacgccc tccaatcggg taactcccag 540
gagagtgtca cagagcagga cagcaaggac agcacctaca gcctcagcag caccctgacg 600
ctgagcaaag cagactacga gaaacacaaa gtctacgcct gcgaagtcac ccatcagggc 660
ctgagctcgc ccgtcacaaa gagcttcaac aggggagagt gt 702

<210> SEQ ID NO 19
<211> LENGTH: 1404
<212> TYPE: DNA
<213> ORGANISM: Artificial sequence
<220> FEATURE:
<223> OTHER INFORMATION: /note = "mAb 0052 HC"

<400> SEQUENCE: 19
atggaatgga cctgggtctt tctcttcctc ctgtcagtaa ctgcaggtgt ccattcccag 60
gtccagctgc agcagtctgg agctgagccg atgaagcctg gggcctcagt gaagatatcc 120
tgcaaggcta ctggctacac atttagtagt cactggatag agtggataaa acagaggcct 180
ggacatggcc ttgagtggat tggagagatt ttacctggaa gtggaaatac taattacaat 240
gagaaattca agggcaaggc cacattcact gcagatacat cctccaacac agcctacatg 300
caactcagca gcctgacatc tgaggactct gccgtctatt gctgtgcaag agggtactac 360
ggtcttaact acgactggta tttcgatgtc tggggcgcag ggaccacggt caccgtctcc 420
tcagctagca ccaagggccc atccgtcttc cccctggcgc cctgctccag gagcacctcc 480
gagagcacag ccgccctggg ctgcctggtc aaggactact tccccgaacc ggtgacggtg 540
tcgtggaact caggcgccct gaccagcggc gtgcacacct tcccggctgt cctacagtcc 600
tcaggactct actccctcag cagcgtggtg accgtgccct ccagcagctt gggcacgaag 660
acctacacct gcaacgtaga tcacaagccc agcaacacca aggtggacaa gagagttgag 720
tccaaatatg gtcccccatg cccaccatgc ccagcacctg agttcctggg gggaccatca 780
gtcttcctgt tccccccaaa acccaaggac actctcatga tctcccggac ccctgaggtc 840
acgtgcgtgg tggtggacgt gagccaggaa gaccccgagg tccagttcaa ctggtacgtg 900
gatggcgtgg aggtgcataa tgccaagaca aagccgcggg aggagcagtt caacagcacg 960
taccgtgtgg tcagcgtcct caccgtcctg caccaggact ggctgaacgg caaggagtac 1020
aagtgcaagg tctccaacaa aggcctcccg tcctccatcg agaaaaccat ctccaaagcc 1080
aaagggcagc cccgagagcc acaggtgtac accctgcccc catcccagga ggagatgacc 1140
aagaaccagg tcagcctgac ctgcctggtc aaaggcttct accccagcga catcgccgtg 1200
gagtgggaga gcaatgggca gccggagaac aactacaaga ccacgcctcc cgtgctggac 1260
tccgacggct ccttcttcct ctacagcagg ctaaccgtgg acaagagcag gtggcaggag 1320
gggaatgtct tctcatgctc cgtgatgcat gaggctctgc acaaccacta cacacagaag 1380
agcctctccc tgtctctggg taaa 1404

<210> SEQ ID NO 20
<211> LENGTH: 1404
<212> TYPE: DNA
<213> ORGANISM: Artificial sequence
<220> FEATURE:

<223> OTHER INFORMATION: /note = "mAb 0062 HC"

<400> SEQUENCE: 20
atggaatgga cctgggtctt tctcttcctc ctgtcagtaa ctgcaggtgt ccattcccag 60
gtccagctgc agcagtctgg agctgagccg atgaagcctg gggcctcagt gaagatatcc 120
tgcaaggcta ctggctacac atttagtagt cactggatag agtggataaa acagaggcct 180
ggacatggcc ttgagtggat tggagagatt ttacctggaa gtggaaatac taattacaat 240
gagaaattca agggcaaggc cacattcact gcagatacat cctccaacac agcctacatg 300
caactcagca gcctgacatc tgaggactct gccgtctatt actgtgcaag agggtactac 360
ggtcttaact acgactggta tttcgatgtc tggggcgcag ggaccacggt caccgtctcc 420
tcagctagca ccaagggccc atccgtcttc cccctggcgc cctgctccag gagcacctcc 480
gagagcacag ccgccctggg ctgcctggtc aaggactact tccccgaacc ggtgacggtg 540
tcgtggaact caggcgccct gaccagcggc gtgcacacct tcccggctgt cctacagtcc 600
tcaggactct actccctcag cagcgtggtg accgtgccct ccagcagctt gggcacgaag 660
acctacacct gcaacgtaga tcacaagccc agcaacacca aggtggacaa gagagttgag 720
tccaaatatg gtcccccatg cccaccatgc ccagcacctg agttcctggg gggaccatca 780
gtcttcctgt tccccccaaa acccaaggac actctcatga tctcccggac ccctgaggtc 840
acgtgcgtgg tggtggacgt gagccaggaa gaccccgagg tccagttcaa ctggtacgtg 900
gatggcgtgg aggtgcataa tgccaagaca aagccgcggg aggagcagtt caacagcacg 960
taccgtgtgg tcagcgtcct caccgtcctg caccaggact ggctgaacgg caaggagtac 1020
aagtgcaagg tctccaacaa aggcctcccg tcctccatcg agaaaaccat ctccaaagcc 1080
aaagggcagc cccgagagcc acaggtgtac accctgcccc catcccagga ggagatgacc 1140
aagaaccagg tcagcctgac ctgcctggtc aaaggcttct accccagcga catcgccgtg 1200
gagtgggaga gcaatgggca gccggagaac aactacaaga ccacgcctcc cgtgctggac 1260
tccgacggct ccttcttcct ctacagcagg ctaaccgtgg acaagagcag gtggcaggag 1320
gggaatgtct tctcatgctc cgtgatgcat gaggctctgc acaaccacta cacacagaag 1380
agcctctccc tgtctctggg taaa 1404

<210> SEQ ID NO 21
<211> LENGTH: 702
<212> TYPE: DNA
<213> ORGANISM: Artificial sequence
<220> FEATURE:
<223> OTHER INFORMATION: /note = "mAb 0052 LC, mAb 0062 LC"

<400> SEQUENCE: 21
atgatgtcct ctgctcagtt ccttggtctc ctgttgctct gttttcaagg taccagatgt 60
gatatccaga tgacacagac tacatcctcc ctgtctgcct ctctgggaga cagagtcacc 120
attagttgca gggcaagtca ggacattagc aattatttaa actggtatca gcagaaacca 180
gatggaactg ttaaactcct tatcttctac acatcaagat tacactcagg agtcccgtca 240
aggttcagtg gcagtgggtc tgggacagat tattctctca ccattagcaa cctggaaccg 300
gaagatattg ccacttacta ttgccaacag gatactaagc ttccgtacac gttcggaggg 360
gggaccaaac tggagatgaa acgtacggtg gctgcaccat ctgtcttcat cttcccgcca 420
tctgatgagc agttgaaatc tggaactgcc tctgttgtgt gcctgctgaa taacttctat 480
cccagagagg ccaaagtaca gtggaaggtg gataacgccc tccaatcggg taactcccag 540
gagagtgtca cagagcagga cagcaaggac agcacctaca gcctcagcag caccctgacg 600
ctgagcaaag cagactacga gaaacacaaa gtctacgcct gcgaagtcac ccatcagggc 660
ctgagctcgc ccgtcacaaa gagcttcaac aggggagagt gt 702

<210> SEQ ID NO 22
<211> LENGTH: 1377
<212> TYPE: DNA
<213> ORGANISM: Artificial sequence
<220> FEATURE:
<223> OTHER INFORMATION: /note = “mAb 0061 HC”

<400> SEQUENCE: 22
atggattttg ggctgatttt ttttattgtt gctcttttaa aaggggtcca gtgtgaggtg 60
aaacttctcg agtctggagg tggcctggtg cagcctggag gatccctgaa actctcctgt 120
gcagcctcag gattcgattt tagtagatac tggatgactt gggtccggca ggctccaggg 180
aaagggctag aatggattgg agaaattaat ccagatagca gtacgataaa ctataaccca 240
tctctaaagg ataaattcat catctccaga gacaacgcca agaatacgct gtacctgcaa 300
atgagcgaag tgagatctga ggacacagcc ctttattact gtgcaagcgg ggtgtttact 360
tcctggggcc aagggactct ggtcactgtc tctgcagcta gcaccaaggg cccatccgtc 420
ttccccctgg cgccctgctc caggagcacc tccgagagca cagccgccct gggctgcctg 480
gtcaaggact acttccccga accggtgacg gtgtcgtgga actcaggcgc cctgaccagc 540
ggcgtgcaca ccttcccggc tgtcctacag tcctcaggac tctactccct cagcagcgtg 600
gtgaccgtgc cctccagcag cttgggcacg aagacctaca cctgcaacgt agatcacaag 660
cccagcaaca ccaaggtgga caagagagtt gagtccaaat atggtccccc atgcccacca 720
tgcccagcac ctgagttcct ggggggacca tcagtcttcc tgttcccccc aaaacccaag 780
gacactctca tgatctcccg gacccctgag gtcacgtgcg tggtggtgga cgtgagccag 840
gaagaccccg aggtccagtt caactggtac gtggatggcg tggaggtgca taatgccaag 900
acaaagccgc gggaggagca gttcaacagc acgtaccgtg tggtcagcgt cctcaccgtc 960
ctgcaccagg actggctgaa cggcaaggag tacaagtgca aggtctccaa caaaggcctc 1020
ccgtcctcca tcgagaaaac catctccaaa gccaaagggc agccccgaga gccacaggtg 1080
tacaccctgc ccccatccca ggaggagatg accaagaacc aggtcagcct gacctgcctg 1140
gtcaaaggct tctaccccag cgacatcgcc gtggagtggg agagcaatgg gcagccggag 1200
aacaactaca agaccacgcc tcccgtgctg gactccgacg gctccttctt cctctacagc 1260
aggctaaccg tggacaagag caggtggcag gaggggaatg tcttctcatg ctccgtgatg 1320
catgaggctc tgcacaacca ctacacacag aagagcctct ccctgtctct gggtaaa 1377

<210> SEQ ID NO 23
<211> LENGTH: 1377
<212> TYPE: DNA
<213> ORGANISM: Artificial sequence
<220> FEATURE:
<223> OTHER INFORMATION: /note = “mAb 0082 HC”

<400> SEQUENCE: 23
atggattttg ggctgatttt ttttattgtt gctcttttaa aaggggtcca gtgtgaggtg 60
aaacttctcg agtctggagg tggcctggtg cagcctggag gatccctgaa actctcctgt 120
gcagcctcag gattcgattt tagtagatac tggatgactt gggtccggca ggctccaggg 180
aaagggctag aatggattgg agaaattaat ccagatagca gtacgataaa ctatgcgcca 240
tctctaaagg ataaattcat catctccaga gacaacgcca agaatacgct gtacctgcaa 300
atgagcgaag tgagatctga ggacacagcc ctttattact gtgcaagcgg ggtgtttact 360
tcctggggcc aagggactct ggtcactgtc tctgcagcta gcaccaaggg cccatccgtc 420 ttcccccctgg cgccctgctc caggagcacc tccgagagca cagccgccct gggctgcctg 480
gtcaaggact acttccccga accggtgacg gtgtcgtgga actcaggcgc cctgaccagc 540
ggcgtgcaca ccttcccggc tgtcctacag tcctcaggac tctactccct cagcagcgtg 600
gtgaccgtgc cctccagcag cttgggcacg aagacctaca cctgcaacgt agatcacaag 660
cccagcaaca ccaaggtgga caagagagtt gagtccaaat atggtccccc atgcccacca 720
tgcccagcac ctgagttcct ggggggacca tcagtcttcc tgttcccccc aaaacccaag 780
gacactctca tgatctcccg gacccctgag gtcacgtgcg tggtggtgga cgtgagccag 840
gaagaccccg aggtccagtt caactggtac gtggatggcg tggaggtgca taatgccaag 900
acaaagccgc gggaggagca gttcaacagc acgtaccgtg tggtcagcgt cctcaccgtc 960
ctgcaccagg actggctgaa cggcaaggag tacaagtgca aggtctccaa caaaggcctc 1020
ccgtcctcca tcgagaaaac catctccaaa gccaaagggc agccccgaga gccacaggtg 1080
tacaccctgc ccccatccca ggaggagatg accaagaacc aggtcagcct gacctgcctg 1140
gtcaaaggct tctaccccag cgacatcgcc gtggagtggg agagcaatgg gcagccggag 1200
aacaactaca agaccacgcc tcccgtgctg gactccgacg gctccttctt cctctacagc 1260
aggctaaccg tggacaagag caggtggcag gaggggaatg tcttctcatg ctccgtgatg 1320
catgaggctc tgcacaacca ctacacacag aagagcctct ccctgtctct gggtaaa 1377

<210> SEQ ID NO 24
<211> LENGTH: 714
<212> TYPE: DNA
<213> ORGANISM: Artificial sequence
<220> FEATURE:
<223> OTHER INFORMATION: /note = “mAb 0061 LC, Fab 0061 LC, mAb 0082 LC, Fab 0082 LC”

<400> SEQUENCE: 24
atgaagttgc ctgttgggct gttggtgctg atgttctgga ttccagcttc cagcagtgat 60
gttgtgatga cccaaactcc actctccctg cctgtcagtc ttggagatca agcctccatc 120
tcttgcagat ctagtcagag ccttgtacac agaaatggaa acacctattt tcattgggcc 180
ctgcagaaac caggccagtc tccaaagctc ctgatctaca aagtttccaa ccgattttct 240
ggggtcccag acaggttcag tggcagtgga tcagggacag atttcacact caagatcagc 300
agagtggagg ctgaggatct gggagtttat ttctgctctc aaagtacaca tgttccgtac 360
acgttcggag gggggaccaa gctggaaata aaacgtacgg tggctgcacc atctgtcttc 420
atcttcccgc catctgatga gcagttgaaa tctggaactg cctctgttgt gtgcctgctg 480
aataacttct atcccagaga ggccaaagta cagtggaagg tggataacgc cctccaatcg 540
ggtaactccc aggagagtgt cacagagcag gacagcaagg acagcaccta cagcctcagc 600
agcaccctga cgctgagcaa agcagactac gagaaacaca aagtctacgc ctgcgaagtc 660
acccatcagg gcctgagctc gcccgtcaca aagagcttca acaggggaga gtgt 714

<210> SEQ ID NO 25
<211> LENGTH: 699
<212> TYPE: DNA

<213> ORGANISM: Artificial sequence
<220> FEATURE:
<223> OTHER INFORMATION: /note = "Fab 0012 VH-CH1"

<400> SEQUENCE: 25
atggattttg ggctgatttt ttttattgtt gctcttttaa aaggggtcca gtgtgaggtg 60
aaacttctcg agtctggagg tggcctggtg cagcctggag gatccctgaa actctcctgt 120
gcagcctcag gattcgattt tagtagatac tggatgactt gggtccggca ggctccaggg 180
aaagggctag aatggattgg agaaattaat ccagatagca gtacgataaa ctatacgcca 240
tctctaaagg ataaattcat catctccaga gacaacgcca agaatacgct gtacctgcaa 300
atgagcgaag tgagatctga ggacacagcc ctttattact gtgcaagcgg ggtgtttact 360
tcctggggcc aagggactct ggtcactgtc tctgcagcta gcaccaaggg cccatccgtc 420 ttcccctgg cgccctgctc caggagcacc tccgagagca cagccgccct gggctgcctg 480
gtcaaggact acttccccga accggtgacg gtgtcgtgga actcaggcgc cctgaccagc 540
ggcgtgcaca ccttcccggc tgtcctacag tcctcaggac tctactccct cagcagcgtg 600
gtgaccgtgc cctccagcag cttgggcacg aagacctaca cctgcaacgt agatcacaag 660
cccagcaaca ccaaggtgga caagagagtt gagtccaaa 699

<210> SEQ ID NO 26
<211> LENGTH: 723
<212> TYPE: DNA
<213> ORGANISM: Artificial sequence
<220> FEATURE:
<223> OTHER INFORMATION: /note = "Fab 0023 VH-CH1"

<400> SEQUENCE: 26
atgaacttgg ggctcagctt gattttcctt gtccttgttt taaaaggtgt ccagtgtgaa 60
gtgaggctgg tggagtctgg gggaggctta gtgcagcctg gagggtccct gaaactctcc 120
tgtgcaacct ctggattcac tttcagtgac tatttcatgt attggattcg ccagactcca 180
gagaagaggc tggagtgggt cgcatacatt agtaatggtg gtgatagcag ctcttatcca 240
gacactgtaa agggccgatt caccatctcc agagacaatg ccaagaacac cctgtacctg 300
caaatgagcc gtctgaagtc tgaggacaca gccatgtatt attgtgcaac aaataaaaac 360
tgggacgatt actatgatat ggactactgg ggtcaaggaa cctcagtcac cgtctcctca 420
gctagcacca agggcccatc cgtcttcccc ctggcgccct gctccaggag cacctccgag 480
agcacagccg ccctgggctg cctggtcaag gactacttcc ccgaaccggt gacggtgtcg 540
tggaactcag gcgccctgac cagcggcgtg cacaccttcc cggctgtcct acagtcctca 600
ggactctact ccctcagcag cgtggtgacc gtgccctcca gcagcttggg cacgaagacc 660
tacacctgca acgtagatca caagcccagc aacaccaagg tggacaagag agttgagtcc 720
aaa 723

<210> SEQ ID NO 27
<211> LENGTH: 723
<212> TYPE: DNA
<213> ORGANISM: Artificial sequence
<220> FEATURE:
<223> OTHER INFORMATION: /note = "Fab 0051 VH-CH1"

<400> SEQUENCE: 27
atgggttgga gctgtatcat cttctttctg gtagcaacag ctacaggtgt gcactcccag 60
gtccagctgg agcagtctgg ggctgagctg gtgaggcctg ggtctcagt gaagatttcc 120

```
tgcaagggtt ctggctacac attcactgat tattctatgc actgggtgaa gcagagtcat    180

gcaaagagtc tagagtggat tggagttatt agtacttact atggtgatgt taggtacaac    240

cagaagttca agggcaaggc cacaatgact gtagacaaat cctccagcac agcctatatg    300

gcacttgcca gactgacatc tgaggattct gccatctatt actgtgcaag agcccctatg    360

attacgacag gggcctggtt tgcttactgg ggccaaggga ctctggtcac tgtctctgca    420

gctagcacca agggcccatc cgtcttcccc ctggcgccct gctccaggag cacctccgag    480

agcacagccg ccctgggctg cctggtcaag gactacttcc ccgaaccggt gacggtgtcg    540

tggaactcag gcgccctgac cagcggcgtg cacaccttcc cggctgtcct acagtcctca    600

ggactctact ccctcagcag cgtggtgacc gtgccctcca gcagcttggg cacgaagacc    660

tacacctgca acgtagatca caagcccagc aacaccaagg tggacaagag agttgagtcc    720

aaa                                                                  723
```

<210> SEQ ID NO 28
<211> LENGTH: 726
<212> TYPE: DNA
<213> ORGANISM: Artificial sequence
<220> FEATURE:
<223> OTHER INFORMATION: /note = “Fab 0052 VH-CH1”

<400> SEQUENCE: 28

```
atggaatgga cctgggtctt tctcttcctc ctgtcagtaa ctgcaggtgt ccattcccag     60

gtccagctgc agcagtctgg agctgagccg atgaagcctg gggcctcagt gaagatatcc    120

tgcaaggcta ctggctacac atttagtagt cactggatag agtggataaa acagaggcct    180

ggacatggcc ttgagtggat tggagagatt ttacctggaa gtggaaatac taattacaat    240

gagaaattca agggcaaggc cacattcact gcagatacat cctccaacac agcctacatg    300

caactcagca gcctgacatc tgaggactct gccgtctatt gctgtgcaag agggtactac    360

ggtcttaact acgactggta tttcgatgtc tggggcgcag ggaccacggt caccgtctcc    420

tcagctagca ccaagggccc atccgtcttc cccctggcgc cctgctccag gagcacctcc    480

gagagcacag ccgccctggg ctgcctggtc aaggactact tccccgaacc ggtgacggtg    540

tcgtggaact caggcgccct gaccagcggc gtgcacacct tcccggctgt cctacagtcc    600

tcaggactct actccctcag cagcgtggtg accgtgccct ccagcagctt gggcacgaag    660

acctacacct gcaacgtaga tcacaagccc agcaacacca aggtggacaa gagagttgag    720

tccaaa                                                               726
```

<210> SEQ ID NO 29
<211> LENGTH: 699
<212> TYPE: DNA
<213> ORGANISM: Artificial sequence
<220> FEATURE:
<223> OTHER INFORMATION: /note = “Fab 0061 VH-CH1”

<400> SEQUENCE: 29

```
atggattttg ggctgatttt ttttattgtt gctcttttaa aaggggtcca gtgtgaggtg     60

aaacttctcg agtctggagg tggcctggtg cagcctggag gatccctgaa actctcctgt    120

gcagcctcag gattcgattt tagtagatac tggatgactt gggtccggca ggctccaggg    180

aaagggctag aatggattgg agaaattaat ccagatagca gtacgataaa ctataaccca    240

tctctaaagg ataaattcat catctccaga gacaacgcca agaatacgct gtacctgcaa    300
```

-continued

```
atgagcgaag tgagatctga ggacacagcc ctttattact gtgcaagcgg ggtgtttact    360

tcctggggcc aagggactct ggtcactgtc tctgcagcta gcaccaaggg cccatccgtc    420

ttcccccctgg cgccctgctc caggagcacc tccgagagca cagccgccct gggctgcctg    480

gtcaaggact acttccccga accggtgacg gtgtcgtgga actcaggcgc cctgaccagc    540

ggcgtgcaca ccttcccggc tgtcctacag tcctcaggac tctactccct cagcagcgtg    600

gtgaccgtgc cctccagcag cttgggcacg aagacctaca cctgcaacgt agatcacaag    660

cccagcaaca ccaaggtgga caagagagtt gagtccaaa                         699
```

<210> SEQ ID NO 30
<211> LENGTH: 699
<212> TYPE: DNA
<213> ORGANISM: Artificial sequence
<220> FEATURE:
<223> OTHER INFORMATION: /note = “Fab 0082 VH-CH1”

<400> SEQUENCE: 30

```
atggattttg ggctgatttt ttttattgtt gctcttttaa aaggggtcca gtgtgaggtg     60

aaacttctcg agtctggagg tggcctggtg cagcctggag gatccctgaa actctcctgt    120

gcagcctcag gattcgattt tagtagatac tggatgactt gggtccggca ggctccaggg    180

aaagggctag aatggattgg agaaattaat ccagatagca gtacgataaa ctatgcgcca    240

tctctaaagg ataaattcat catctccaga gacaacgcca agaatacgct gtacctgcaa    300

atgagcgaag tgagatctga ggacacagcc ctttattact gtgcaagcgg ggtgtttact    360

tcctggggcc aagggactct ggtcactgtc tctgcagcta gcaccaaggg cccatccgtc    420

ttcccccctgg cgccctgctc caggagcacc tccgagagca cagccgccct gggctgcctg    480

gtcaaggact acttccccga accggtgacg gtgtcgtgga actcaggcgc cctgaccagc    540

ggcgtgcaca ccttcccggc tgtcctacag tcctcaggac tctactccct cagcagcgtg    600

gtgaccgtgc cctccagcag cttgggcacg aagacctaca cctgcaacgt agatcacaag    660

cccagcaaca ccaaggtgga caagagagtt gagtccaaa                         699
```

<210> SEQ ID NO 31
<211> LENGTH: 741
<212> TYPE: DNA
<213> ORGANISM: Artificial sequence
<220> FEATURE:
<223> OTHER INFORMATION: /note = “hIgG4 hinge-CH2-CH3”

<400> SEQUENCE: 31

```
atggattttg ggctgatttt ttttattgtt gctcttttaa aaggggtcca gtgtgagtcc     60

aaatatggtc ccccatgccc accatgccca gcacctgagt tcctgggggg accatcagtc    120

ttcctgttcc ccccaaaacc caaggacact ctcatgatct cccggacccc tgaggtcacg    180

tgcgtggtgg tggacgtgag ccaggaagac cccgaggtcc agttcaactg gtacgtggat    240

ggcgtggagg tgcataatgc caagacaaag ccgcgggagg agcagttcaa cagcacgtac    300

cgtgtggtca gcgtcctcac cgtcctgcac caggactggc tgaacggcaa ggagtacaag    360

tgcaaggtct ccaacaaagg cctcccgtcc tccatcgaga aaaccatctc caaagccaaa    420

gggcagcccc gagagccaca ggtgtacacc ctgcccccat cccaggagga gatgaccaag    480

aaccaggtca gcctgacctg cctggtcaaa ggcttctacc ccagcgacat cgccgtggag    540

tgggagagca atgggcagcc ggagaacaac tacaagacca cgcctcccgt gctggactcc    600

gacggctcct tcttcctcta cagcaggcta accgtggaca agagcaggtg gcaggagggg    660
```

```
aatgtcttct catgctccgt gatgcatgag gctctgcaca accactacac acagaagagc    720

ctctccctgt ctctgggtaa a                                              741


<210> SEQ ID NO 32
<211> LENGTH: 459
<212> TYPE: PRT
<213> ORGANISM: Artificial sequence
<220> FEATURE:
<223> OTHER INFORMATION: /note = "mAb 0012, HC (mouse VH-human IgG4 CH1-
      CH2-CH3)"

<400> SEQUENCE: 32

Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
        35                  40                  45

Arg Tyr Trp Met Thr Trp Val Arg Gln Ala Pro Gly Lys Gly Leu Glu
    50                  55                  60

Trp Ile Gly Glu Ile Asn Pro Asp Ser Ser Thr Ile Asn Tyr Thr Pro
65                  70                  75                  80

Ser Leu Lys Asp Lys Phe Ile Ile Ser Arg Asp Asn Ala Lys Asn Thr
                85                  90                  95

Leu Tyr Leu Gln Met Ser Glu Val Arg Ser Glu Asp Thr Ala Leu Tyr
            100                 105                 110

Tyr Cys Ala Ser Gly Val Phe Thr Ser Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220

Lys Val Asp Lys Arg Val Glu Ser Lys Tyr Gly Pro Pro Cys Pro Pro
225                 230                 235                 240

Cys Pro Ala Pro Glu Phe Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Glu Asp Pro Glu Val Gln Phe Asn
        275                 280                 285

Trp Tyr Val Asp Gly Val Glu Val His Asn Ala Lys Thr Lys Pro Arg
    290                 295                 300

Glu Glu Gln Phe Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335
```

```
Asn Lys Gly Leu Pro Ser Ser Ile Glu Lys Thr Ile Ser Lys Ala Lys
            340                 345                 350

Gly Gln Pro Arg Glu Pro Gln Val Tyr Thr Leu Pro Pro Ser Gln Glu
        355                 360                 365

Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Arg Leu Thr Val Asp Lys Ser Arg Trp Gln Glu Gly
            420                 425                 430

Asn Val Phe Ser Cys Ser Val Met His Glu Ala Leu His Asn His Tyr
        435                 440                 445

Thr Gln Lys Ser Leu Ser Leu Ser Leu Gly Lys
    450                 455


<210> SEQ ID NO 33
<211> LENGTH: 238
<212> TYPE: PRT
<213> ORGANISM: Artificial sequence
<220> FEATURE:
<223> OTHER INFORMATION: /note = "mAb 0012, LC (mouse VL - human Kappa
      CL); Fab 0012, LC (mouse VL - human Kappa CL)"

<400> SEQUENCE: 33

Met Lys Leu Pro Val Gly Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Arg Asn Gly Asn Thr Tyr Phe His Trp Cys Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Tyr Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 34
<211> LENGTH: 467
<212> TYPE: PRT
<213> ORGANISM: Artificial sequence
<220> FEATURE:
<223> OTHER INFORMATION: /note = "mAb 0023, HC (mouse VH-human IgG4 CH1-CH2-CH3)"

<400> SEQUENCE: 34

```
Met Asn Leu Gly Leu Ser Leu Ile Phe Leu Val Leu Val Leu Lys Gly
1               5                   10                  15

Val Gln Cys Glu Val Arg Leu Val Glu Ser Gly Gly Gly Leu Val Gln
            20                  25                  30

Pro Gly Gly Ser Leu Lys Leu Ser Cys Ala Thr Ser Gly Phe Thr Phe
        35                  40                  45

Ser Asp Tyr Phe Met Tyr Trp Ile Arg Gln Thr Pro Glu Lys Arg Leu
    50                  55                  60

Glu Trp Val Ala Tyr Ile Ser Asn Gly Gly Asp Ser Ser Ser Tyr Pro
65                  70                  75                  80

Asp Thr Val Lys Gly Arg Phe Thr Ile Ser Arg Asp Asn Ala Lys Asn
                85                  90                  95

Thr Leu Tyr Leu Gln Met Ser Arg Leu Lys Ser Glu Asp Thr Ala Met
            100                 105                 110

Tyr Tyr Cys Ala Thr Asn Lys Asn Trp Asp Asp Tyr Tyr Asp Met Asp
        115                 120                 125

Tyr Trp Gly Gln Gly Thr Ser Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
```

```
        355                 360                 365

Tyr Thr Leu Pro Pro Ser Gln Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
        435                 440                 445

His Glu Ala Leu His Asn His Tyr Thr Gln Lys Ser Leu Ser Leu Ser
    450                 455                 460

Leu Gly Lys
465


<210> SEQ ID NO 35
<211> LENGTH: 239
<212> TYPE: PRT
<213> ORGANISM: Artificial sequence
<220> FEATURE:
<223> OTHER INFORMATION: /note = "mAb 0023, LC (mouse VL - human Kappa
      CL); Fab 0023, LC (mouse VL - human Kappa CL)"

<400> SEQUENCE: 35

Met Asp Ser Gln Ala Gln Val Leu Ile Leu Leu Leu Leu Trp Val Ser
1               5                   10                  15

Gly Ser Cys Gly Asp Ile Val Val Ser Gln Ser Pro Ser Ser Leu Ala
            20                  25                  30

Val Ser Ala Gly Glu Lys Val Thr Met Ser Cys Lys Ser Ser Gln Ser
        35                  40                  45

Leu Leu Asn Ser Arg Thr Arg Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Lys Gln Ser Tyr Asn Leu Leu Thr Phe Gly Ala Gly Thr Lys
        115                 120                 125

Leu Glu Leu Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 36
<211> LENGTH: 467
<212> TYPE: PRT
<213> ORGANISM: Artificial sequence
<220> FEATURE:
<223> OTHER INFORMATION: /note = "mAb 0051, HC (mouse VH-human IgG4 CH1-CH2-CH3)"

<400> SEQUENCE: 36

```
Met Gly Trp Ser Cys Ile Ile Phe Phe Leu Val Ala Thr Ala Thr Gly
1               5                   10                  15

Val His Ser Gln Val Gln Leu Glu Gln Ser Gly Ala Glu Leu Val Arg
            20                  25                  30

Pro Gly Val Ser Val Lys Ile Ser Cys Lys Gly Ser Gly Tyr Thr Phe
        35                  40                  45

Thr Asp Tyr Ser Met His Trp Val Lys Gln Ser His Ala Lys Ser Leu
    50                  55                  60

Glu Trp Ile Gly Val Ile Ser Thr Tyr Tyr Gly Asp Val Arg Tyr Asn
65                  70                  75                  80

Gln Lys Phe Lys Gly Lys Ala Thr Met Thr Val Asp Lys Ser Ser Ser
                85                  90                  95

Thr Ala Tyr Met Ala Leu Ala Arg Leu Thr Ser Glu Asp Ser Ala Ile
            100                 105                 110

Tyr Tyr Cys Ala Arg Ala Pro Met Ile Thr Thr Gly Ala Trp Phe Ala
        115                 120                 125

Tyr Trp Gly Gln Gly Thr Leu Val Thr Val Ser Ala Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
        355                 360                 365
```

```
Tyr Thr Leu Pro Pro Ser Gln Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
        435                 440                 445

His Glu Ala Leu His Asn His Tyr Thr Gln Lys Ser Leu Ser Leu Ser
    450                 455                 460

Leu Gly Lys
465


<210> SEQ ID NO 37
<211> LENGTH: 234
<212> TYPE: PRT
<213> ORGANISM: Artificial sequence
<220> FEATURE:
<223> OTHER INFORMATION: /note = "mAb 0051, LC (mouse VL - human Kappa
      CL); Fab 0051, LC (mouse VL - human Kappa CL)"

<400> SEQUENCE: 37

Met Lys Ser Gln Thr Gln Val Phe Val Phe Leu Leu Leu Cys Val Ser
1               5                   10                  15

Gly Ala His Gly Ser Ile Val Met Thr Gln Thr Pro Lys Phe Leu Leu
            20                  25                  30

Val Ser Ala Gly Asp Arg Val Thr Ile Thr Cys Lys Ala Ser Gln Ser
        35                  40                  45

Val Ser Asn Asp Val Ala Trp Tyr Gln Gln Lys Pro Gly Gln Ser Pro
    50                  55                  60

Lys Leu Leu Ile Asn Tyr Ala Ser Ser Arg Tyr Thr Gly Ile Pro Asp
65                  70                  75                  80

Arg Phe Thr Gly Ser Gly Tyr Gly Thr Asp Phe Thr Phe Thr Ile Ser
                85                  90                  95

Thr Val Gln Ala Glu Asp Leu Ala Val Tyr Phe Cys Gln Gln Asp Tyr
            100                 105                 110

Ser Ser Pro Tyr Thr Phe Gly Gly Gly Thr Lys Leu Glu Ile Glu Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

```
<210> SEQ ID NO 38
<211> LENGTH: 468
<212> TYPE: PRT
<213> ORGANISM: Artificial sequence
<220> FEATURE:
<223> OTHER INFORMATION: /note = "mAb 0052, HC (mouse VH-human IgG4 CH1-
      CH2-CH3)"

<400> SEQUENCE: 38

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Pro Met Lys
            20                  25                  30

Pro Gly Ala Ser Val Lys Ile Ser Cys Lys Ala Thr Gly Tyr Thr Phe
        35                  40                  45

Ser Ser His Trp Ile Glu Trp Ile Lys Gln Arg Pro Gly His Gly Leu
    50                  55                  60

Glu Trp Ile Gly Glu Ile Leu Pro Gly Ser Gly Asn Thr Asn Tyr Asn
65                  70                  75                  80

Glu Lys Phe Lys Gly Lys Ala Thr Phe Thr Ala Asp Thr Ser Ser Asn
                85                  90                  95

Thr Ala Tyr Met Gln Leu Ser Ser Leu Thr Ser Glu Asp Ser Ala Val
            100                 105                 110

Tyr Cys Cys Ala Arg Gly Tyr Tyr Gly Leu Asn Tyr Asp Trp Tyr Phe
        115                 120                 125

Asp Val Trp Gly Ala Gly Thr Thr Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Lys Thr Tyr Thr Cys
    210                 215                 220

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

Gln Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
            340                 345                 350

Ile Glu Lys Thr Ile Ser Lys Ala Lys Gly Gln Pro Arg Glu Pro Gln
        355                 360                 365
```

-continued

```
Val Tyr Thr Leu Pro Pro Ser Gln Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
            420                 425                 430

Val Asp Lys Ser Arg Trp Gln Glu Gly Asn Val Phe Ser Cys Ser Val
        435                 440                 445

Met His Glu Ala Leu His Asn His Tyr Thr Gln Lys Ser Leu Ser Leu
    450                 455                 460

Ser Leu Gly Lys
465


<210> SEQ ID NO 39
<211> LENGTH: 234
<212> TYPE: PRT
<213> ORGANISM: Artificial sequence
<220> FEATURE:
<223> OTHER INFORMATION: /note = "mAb 0052, LC (mouse VL - human Kappa
      CL); mAb 0062, LC (mouse VL - human Kappa CL); Fab 0052, LC (mouse
      VL - human Kappa CL)"

<400> SEQUENCE: 39

Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Asn Trp Tyr Gln Gln Lys Pro Asp Gly Thr Val
    50                  55                  60

Lys Leu Leu Ile Phe Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Pro Glu Asp Ile Ala Thr Tyr Tyr Cys Gln Gln Asp Thr
            100                 105                 110

Lys Leu Pro Tyr Thr Phe Gly Gly Gly Thr Lys Leu Glu Met Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 40
<211> LENGTH: 459
<212> TYPE: PRT
<213> ORGANISM: Artificial sequence
<220> FEATURE:
<223> OTHER INFORMATION: /note = "mAb 0061, HC (mouse VH-human IgG4 CH1-CH2-CH3)"

<400> SEQUENCE: 40

```
Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
        35                  40                  45

Arg Tyr Trp Met Thr Trp Val Arg Gln Ala Pro Gly Lys Gly Leu Glu
    50                  55                  60

Trp Ile Gly Glu Ile Asn Pro Asp Ser Ser Thr Ile Asn Tyr Asn Pro
65                  70                  75                  80

Ser Leu Lys Asp Lys Phe Ile Ile Ser Arg Asp Asn Ala Lys Asn Thr
                85                  90                  95

Leu Tyr Leu Gln Met Ser Glu Val Arg Ser Glu Asp Thr Ala Leu Tyr
            100                 105                 110

Tyr Cys Ala Ser Gly Val Phe Thr Ser Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220

Lys Val Asp Lys Arg Val Glu Ser Lys Tyr Gly Pro Pro Cys Pro Pro
225                 230                 235                 240

Cys Pro Ala Pro Glu Phe Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Glu Asp Pro Glu Val Gln Phe Asn
        275                 280                 285

Trp Tyr Val Asp Gly Val Glu Val His Asn Ala Lys Thr Lys Pro Arg
    290                 295                 300

Glu Glu Gln Phe Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Gly Leu Pro Ser Ser Ile Glu Lys Thr Ile Ser Lys Ala Lys
            340                 345                 350

Gly Gln Pro Arg Glu Pro Gln Val Tyr Thr Leu Pro Pro Ser Gln Glu
        355                 360                 365
```

```
Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Arg Leu Thr Val Asp Lys Ser Arg Trp Gln Glu Gly
            420                 425                 430

Asn Val Phe Ser Cys Ser Val Met His Glu Ala Leu His Asn His Tyr
        435                 440                 445

Thr Gln Lys Ser Leu Ser Leu Ser Leu Gly Lys
    450                 455


<210> SEQ ID NO 41
<211> LENGTH: 238
<212> TYPE: PRT
<213> ORGANISM: Artificial sequence
<220> FEATURE:
<223> OTHER INFORMATION: /note = "mAb 0061, LC (mouse VL - human Kappa
      CL); Fab 0061, LC (mouse VL - human Kappa CL); mAb 0082, LC (mouse
      VL - human Kappa CL); Fab 0082, LC (mouse VL - human Kappa CL)"

<400> SEQUENCE: 41

Met Lys Leu Pro Val Gly Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Arg Asn Gly Asn Thr Tyr Phe His Trp Ala Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Tyr Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235


<210> SEQ ID NO 42
<211> LENGTH: 468
<212> TYPE: PRT
```

```
<213> ORGANISM: Artificial sequence
<220> FEATURE:
<223> OTHER INFORMATION: /note = "mAb 0062, HC (mouse VH-human IgG4 CH1-
      CH2-CH3)"

<400> SEQUENCE: 42

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Pro Met Lys
            20                  25                  30

Pro Gly Ala Ser Val Lys Ile Ser Cys Lys Ala Thr Gly Tyr Thr Phe
        35                  40                  45

Ser Ser His Trp Ile Glu Trp Ile Lys Gln Arg Pro Gly His Gly Leu
    50                  55                  60

Glu Trp Ile Gly Glu Ile Leu Pro Gly Ser Gly Asn Thr Asn Tyr Asn
65                  70                  75                  80

Glu Lys Phe Lys Gly Lys Ala Thr Phe Thr Ala Asp Thr Ser Ser Asn
                85                  90                  95

Thr Ala Tyr Met Gln Leu Ser Ser Leu Thr Ser Glu Asp Ser Ala Val
            100                 105                 110

Tyr Tyr Cys Ala Arg Gly Tyr Tyr Gly Leu Asn Tyr Asp Trp Tyr Phe
        115                 120                 125

Asp Val Trp Gly Ala Gly Thr Thr Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Lys Thr Tyr Thr Cys
    210                 215                 220

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

Gln Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Gln Glu Glu Met Thr Lys Asn Gln Val
    370                 375                 380
```

```
Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
            420                 425                 430

Val Asp Lys Ser Arg Trp Gln Glu Gly Asn Val Phe Ser Cys Ser Val
        435                 440                 445

Met His Glu Ala Leu His Asn His Tyr Thr Gln Lys Ser Leu Ser Leu
    450                 455                 460

Ser Leu Gly Lys
465


<210> SEQ ID NO 43
<211> LENGTH: 459
<212> TYPE: PRT
<213> ORGANISM: Artificial sequence
<220> FEATURE:
<223> OTHER INFORMATION: /note = "mAb 0082, HC (mouse VH-human IgG4 CH1-
      CH2-CH3)"

<400> SEQUENCE: 43

Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
        35                  40                  45

Arg Tyr Trp Met Thr Trp Val Arg Gln Ala Pro Gly Lys Gly Leu Glu
    50                  55                  60

Trp Ile Gly Glu Ile Asn Pro Asp Ser Ser Thr Ile Asn Tyr Ala Pro
65                  70                  75                  80

Ser Leu Lys Asp Lys Phe Ile Ile Ser Arg Asp Asn Ala Lys Asn Thr
                85                  90                  95

Leu Tyr Leu Gln Met Ser Glu Val Arg Ser Glu Asp Thr Ala Leu Tyr
            100                 105                 110

Tyr Cys Ala Ser Gly Val Phe Thr Ser Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220

Lys Val Asp Lys Arg Val Glu Ser Lys Tyr Gly Pro Pro Cys Pro Pro
225                 230                 235                 240

Cys Pro Ala Pro Glu Phe Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270
```

Cys Val Val Val Asp Val Ser Gln Glu Asp Pro Glu Val Gln Phe Asn
275 280 285

Trp Tyr Val Asp Gly Val Glu Val His Asn Ala Lys Thr Lys Pro Arg
290 295 300

Glu Glu Gln Phe Asn Ser Thr Tyr Arg Val Val Ser Val Leu Thr Val
305 310 315 320

Leu His Gln Asp Trp Leu Asn Gly Lys Glu Tyr Lys Cys Lys Val Ser
325 330 335

Asn Lys Gly Leu Pro Ser Ser Ile Glu Lys Thr Ile Ser Lys Ala Lys
340 345 350

Gly Gln Pro Arg Glu Pro Gln Val Tyr Thr Leu Pro Pro Ser Gln Glu
355 360 365

Glu Met Thr Lys Asn Gln Val Ser Leu Thr Cys Leu Val Lys Gly Phe
370 375 380

Tyr Pro Ser Asp Ile Ala Val Glu Trp Glu Ser Asn Gly Gln Pro Glu
385 390 395 400

Asn Asn Tyr Lys Thr Thr Pro Pro Val Leu Asp Ser Asp Gly Ser Phe
405 410 415

Phe Leu Tyr Ser Arg Leu Thr Val Asp Lys Ser Arg Trp Gln Glu Gly
420 425 430

Asn Val Phe Ser Cys Ser Val Met His Glu Ala Leu His Asn His Tyr
435 440 445

Thr Gln Lys Ser Leu Ser Leu Ser Leu Gly Lys
450 455

<210> SEQ ID NO 44
<211> LENGTH: 233
<212> TYPE: PRT
<213> ORGANISM: Artificial sequence
<220> FEATURE:
<223> OTHER INFORMATION: /note = “Fab 0012, mouse VH - human IgG4 CH1”

<400> SEQUENCE: 44

Met Asp Phe Gly Leu Ile Phe Phe Ile Val Ala Leu Leu Lys Gly Val
1 5 10 15

Gln Cys Glu Val Lys Leu Leu Glu Ser Gly Gly Gly Leu Val Gln Pro
20 25 30

Gly Gly Ser Leu Lys Leu Ser Cys Ala Ala Ser Gly Phe Asp Phe Ser
35 40 45

Arg Tyr Trp Met Thr Trp Val Arg Gln Ala Pro Gly Lys Gly Leu Glu
50 55 60

Trp Ile Gly Glu Ile Asn Pro Asp Ser Ser Thr Ile Asn Tyr Thr Pro
65 70 75 80

Ser Leu Lys Asp Lys Phe Ile Ile Ser Arg Asp Asn Ala Lys Asn Thr
85 90 95

Leu Tyr Leu Gln Met Ser Glu Val Arg Ser Glu Asp Thr Ala Leu Tyr
100 105 110

Tyr Cys Ala Ser Gly Val Phe Thr Ser Trp Gly Gln Gly Thr Leu Val
115 120 125

Thr Val Ser Ala Ala Ser Thr Lys Gly Pro Ser Val Phe Pro Leu Ala
130 135 140

Pro Cys Ser Arg Ser Thr Ser Glu Ser Thr Ala Ala Leu Gly Cys Leu
145 150 155 160

Val Lys Asp Tyr Phe Pro Glu Pro Val Thr Val Ser Trp Asn Ser Gly
165 170 175

```
Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220

Lys Val Asp Lys Arg Val Glu Ser Lys
225                 230
```

<210> SEQ ID NO 45
<211> LENGTH: 241
<212> TYPE: PRT
<213> ORGANISM: Artificial sequence
<220> FEATURE:
<223> OTHER INFORMATION: /note = "Fab 0023, mouse VH - human IgG4 CH1"

<400> SEQUENCE: 45

```
Met Asn Leu Gly Leu Ser Leu Ile Phe Leu Val Leu Val Leu Lys Gly
1               5                   10                  15

Val Gln Cys Glu Val Arg Leu Val Glu Ser Gly Gly Gly Leu Val Gln
            20                  25                  30

Pro Gly Gly Ser Leu Lys Leu Ser Cys Ala Thr Ser Gly Phe Thr Phe
        35                  40                  45

Ser Asp Tyr Phe Met Tyr Trp Ile Arg Gln Thr Pro Glu Lys Arg Leu
    50                  55                  60

Glu Trp Val Ala Tyr Ile Ser Asn Gly Gly Asp Ser Ser Ser Tyr Pro
65                  70                  75                  80

Asp Thr Val Lys Gly Arg Phe Thr Ile Ser Arg Asp Asn Ala Lys Asn
                85                  90                  95

Thr Leu Tyr Leu Gln Met Ser Arg Leu Lys Ser Glu Asp Thr Ala Met
            100                 105                 110

Tyr Tyr Cys Ala Thr Asn Lys Asn Trp Asp Asp Tyr Tyr Asp Met Asp
        115                 120                 125

Tyr Trp Gly Gln Gly Thr Ser Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys
```

<210> SEQ ID NO 46
<211> LENGTH: 241
<212> TYPE: PRT
<213> ORGANISM: Artificial sequence
<220> FEATURE:
<223> OTHER INFORMATION: /note = "Fab 0051, mouse VH - human IgG4 CH1"

<400> SEQUENCE: 46

```
Met Gly Trp Ser Cys Ile Ile Phe Phe Leu Val Ala Thr Ala Thr Gly
1               5                   10                  15

Val His Ser Gln Val Gln Leu Glu Gln Ser Gly Ala Glu Leu Val Arg
            20                  25                  30

Pro Gly Val Ser Val Lys Ile Ser Cys Lys Gly Ser Gly Tyr Thr Phe
        35                  40                  45

Thr Asp Tyr Ser Met His Trp Val Lys Gln Ser His Ala Lys Ser Leu
    50                  55                  60

Glu Trp Ile Gly Val Ile Ser Thr Tyr Tyr Gly Asp Val Arg Tyr Asn
65                  70                  75                  80

Gln Lys Phe Lys Gly Lys Ala Thr Met Thr Val Asp Lys Ser Ser Ser
                85                  90                  95

Thr Ala Tyr Met Ala Leu Ala Arg Leu Thr Ser Glu Asp Ser Ala Ile
            100                 105                 110

Tyr Tyr Cys Ala Arg Ala Pro Met Ile Thr Thr Gly Ala Trp Phe Ala
        115                 120                 125

Tyr Trp Gly Gln Gly Thr Leu Val Thr Val Ser Ala Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys


<210> SEQ ID NO 47
<211> LENGTH: 242
<212> TYPE: PRT
<213> ORGANISM: Artificial sequence
<220> FEATURE:
<223> OTHER INFORMATION: /note = "Fab 0052, mouse VH - human IgG4 CH1"

<400> SEQUENCE: 47

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Pro Met Lys
            20                  25                  30

Pro Gly Ala Ser Val Lys Ile Ser Cys Lys Ala Thr Gly Tyr Thr Phe
        35                  40                  45

Ser Ser His Trp Ile Glu Trp Ile Lys Gln Arg Pro Gly His Gly Leu
    50                  55                  60

Glu Trp Ile Gly Glu Ile Leu Pro Gly Ser Gly Asn Thr Asn Tyr Asn
65                  70                  75                  80

Glu Lys Phe Lys Gly Lys Ala Thr Phe Thr Ala Asp Thr Ser Ser Asn
                85                  90                  95

Thr Ala Tyr Met Gln Leu Ser Ser Leu Thr Ser Glu Asp Ser Ala Val
            100                 105                 110
```

```
Tyr Cys Cys Ala Arg Gly Tyr Tyr Gly Leu Asn Tyr Asp Trp Tyr Phe
        115                 120                 125

Asp Val Trp Gly Ala Gly Thr Thr Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Lys Thr Tyr Thr Cys
    210                 215                 220

Asn Val Asp His Lys Pro Ser Asn Thr Lys Val Asp Lys Arg Val Glu
225                 230                 235                 240

Ser Lys


<210> SEQ ID NO 48
<211> LENGTH: 233
<212> TYPE: PRT
<213> ORGANISM: Artificial sequence
<220> FEATURE:
<223> OTHER INFORMATION: /note = "Fab 0082, mouse VH - human IgG4 CH1"

<400> SEQUENCE: 48

Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
        35                  40                  45

Arg Tyr Trp Met Thr Trp Val Arg Gln Ala Pro Gly Lys Gly Leu Glu
    50                  55                  60

Trp Ile Gly Glu Ile Asn Pro Asp Ser Ser Thr Ile Asn Tyr Ala Pro
65                  70                  75                  80

Ser Leu Lys Asp Lys Phe Ile Ile Ser Arg Asp Asn Ala Lys Asn Thr
                85                  90                  95

Leu Tyr Leu Gln Met Ser Glu Val Arg Ser Glu Asp Thr Ala Leu Tyr
            100                 105                 110

Tyr Cys Ala Ser Gly Val Phe Thr Ser Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220

Lys Val Asp Lys Arg Val Glu Ser Lys
```

225 230

<210> SEQ ID NO 49
<211> LENGTH: 7
<212> TYPE: PRT
<213> ORGANISM: Artificial sequence
<220> FEATURE:
<223> OTHER INFORMATION: /note = "linker, L2"

<400> SEQUENCE: 49

Gly Ser Gly Gly Gly Gly Ser
1 5

<210> SEQ ID NO 50
<211> LENGTH: 12
<212> TYPE: PRT
<213> ORGANISM: Artificial sequence
<220> FEATURE:
<223> OTHER INFORMATION: /note = "linker, L3"

<400> SEQUENCE: 50

Gly Ser Gly Gly Gly Gly Ser Gly Gly Gly Gly Ser
1 5 10

<210> SEQ ID NO 51
<211> LENGTH: 17
<212> TYPE: PRT
<213> ORGANISM: Artificial sequence
<220> FEATURE:
<223> OTHER INFORMATION: /note = "linker, L4a"

<400> SEQUENCE: 51

Gly Ser Gly Gly Gly Gly Ser Gly Gly Gly Gly Ser Gly Gly Gly Gly
1 5 10 15

Ser

<210> SEQ ID NO 52
<211> LENGTH: 17
<212> TYPE: PRT
<213> ORGANISM: Artificial sequence
<220> FEATURE:
<223> OTHER INFORMATION: /note = "linker, L4b"

<400> SEQUENCE: 52

Gly Gly Gly Gly Ser Gly Gly Gly Gly Ser Gly Gly Gly Gly Ser Gly
1 5 10 15

Ser

<210> SEQ ID NO 53
<211> LENGTH: 22
<212> TYPE: PRT
<213> ORGANISM: Artificial sequence
<220> FEATURE:
<223> OTHER INFORMATION: /note = "linker, L5"

<400> SEQUENCE: 53

Gly Gly Gly Gly Ser Gly Ser Gly Gly Gly Gly Ser Gly Gly Gly Gly
1 5 10 15

Ser Gly Gly Gly Gly Ser
20

<210> SEQ ID NO 54
<211> LENGTH: 27
<212> TYPE: PRT
<213> ORGANISM: Artificial sequence
<220> FEATURE:
<223> OTHER INFORMATION: /note = "linker, L6"

<400> SEQUENCE: 54

Gly Gly Gly Gly Ser Gly Gly Gly Gly Ser Gly Ser Gly Gly Gly Gly
1 5 10 15

Ser Gly Gly Gly Gly Ser Gly Gly Gly Gly Ser
20 25

<210> SEQ ID NO 55
<211> LENGTH: 32
<212> TYPE: PRT
<213> ORGANISM: Artificial sequence
<220> FEATURE:
<223> OTHER INFORMATION: /note = "linker, L7"

<400> SEQUENCE: 55

Gly Gly Gly Gly Ser Gly Gly Gly Gly Ser Gly Gly Gly Gly Ser Gly
1 5 10 15

Ser Gly Gly Gly Gly Ser Gly Gly Gly Gly Ser Gly Gly Gly Gly Ser
20 25 30

<210> SEQ ID NO 56
<211> LENGTH: 37
<212> TYPE: PRT
<213> ORGANISM: Artificial sequence
<220> FEATURE:
<223> OTHER INFORMATION: /note = "linker, L8"

<400> SEQUENCE: 56

Gly Gly Gly Gly Ser Gly Gly Gly Gly Ser Gly Gly Gly Gly Ser Gly
1 5 10 15

Gly Gly Gly Ser Gly Ser Gly Gly Gly Gly Ser Gly Gly Gly Gly Ser
20 25 30

Gly Gly Gly Gly Ser
35

<210> SEQ ID NO 57
<211> LENGTH: 42
<212> TYPE: PRT
<213> ORGANISM: Artificial sequence
<220> FEATURE:
<223> OTHER INFORMATION: /note = "linker, L9"

<400> SEQUENCE: 57

Gly Gly Gly Gly Ser Gly Gly Gly Gly Ser Gly Gly Gly Gly Ser Gly
1 5 10 15

Gly Gly Gly Ser Gly Gly Gly Gly Ser Gly Ser Gly Gly Gly Gly Ser
20 25 30

Gly Gly Gly Gly Ser Gly Gly Gly Gly Ser
35 40

<210> SEQ ID NO 58
<211> LENGTH: 16
<212> TYPE: PRT
<213> ORGANISM: Artificial sequence
<220> FEATURE:
<223> OTHER INFORMATION: /note = "linker, L10"

<400> SEQUENCE: 58

Tyr Gly Pro Pro Ser Pro Ser Ser Pro Ala Pro Glu Phe Leu Gly Gly
1 5 10 15

<210> SEQ ID NO 59
<211> LENGTH: 12
<212> TYPE: PRT
<213> ORGANISM: Artificial sequence
<220> FEATURE:
<223> OTHER INFORMATION: /note = "Purification tag, HPC4 tag"

<400> SEQUENCE: 59

Glu Asp Gln Val Asp Pro Arg Leu Ile Asp Gly Lys
1 5 10

<210> SEQ ID NO 60
<211> LENGTH: 28
<212> TYPE: DNA
<213> ORGANISM: Artificial sequence
<220> FEATURE:
<223> OTHER INFORMATION: /note = "primer no. 50"

<400> SEQUENCE: 60
caacacttac ttgtcctggt tcctgcag 28

<210> SEQ ID NO 61
<211> LENGTH: 28
<212> TYPE: DNA
<213> ORGANISM: Artificial sequence
<220> FEATURE:
<223> OTHER INFORMATION: /note = "primer no. 51"

<400> SEQUENCE: 61
ctgcaggaac caggacaagt aagtgttg 28

<210> SEQ ID NO 62
<211> LENGTH: 36
<212> TYPE: DNA
<213> ORGANISM: Artificial sequence
<220> FEATURE:
<223> OTHER INFORMATION: /note = "primer no. 69"

<400> SEQUENCE: 62
gctctagact aacactcatt cctgttgaag ctcttg 36

<210> SEQ ID NO 63
<211> LENGTH: 39
<212> TYPE: DNA
<213> ORGANISM: Artificial sequence
<220> FEATURE:
<223> OTHER INFORMATION: /note = "primer no. 98"

<400> SEQUENCE: 63
tttaaagaat tcctaacact ctcccctgtt gaagctctt 39

<210> SEQ ID NO 64
<211> LENGTH: 39
<212> TYPE: DNA
<213> ORGANISM: Artificial sequence
<220> FEATURE:
<223> OTHER INFORMATION: /note = "primer no. 100"

<400> SEQUENCE: 64
tttaaagaat tctcatttac ccagagacag ggagaggct 39

<210> SEQ ID NO 65
<211> LENGTH: 21
<212> TYPE: DNA
<213> ORGANISM: Artificial sequence
<220> FEATURE:
<223> OTHER INFORMATION: /note = "primer no. 312"

<400> SEQUENCE: 65
gtctaccaca acacacgtga c 21

<210> SEQ ID NO 66
<211> LENGTH: 27
<212> TYPE: DNA
<213> ORGANISM: Artificial sequence
<220> FEATURE:
<223> OTHER INFORMATION: /note = "primer no. 339"

<400> SEQUENCE: 66
actggatggt gggaagatgg atacagt 27

<210> SEQ ID NO 67
<211> LENGTH: 27
<212> TYPE: DNA
<213> ORGANISM: Artificial sequence
<220> FEATURE:
<223> OTHER INFORMATION: /note = "primer no. 341"

<400> SEQUENCE: 67
agatccaggg gctagcggat agacaga 27

<210> SEQ ID NO 68
<211> LENGTH: 30
<212> TYPE: DNA
<213> ORGANISM: Artificial sequence
<220> FEATURE:
<223> OTHER INFORMATION: /note = "primer no. 348"

<400> SEQUENCE: 68
ggagctggtg gtggcatctc aggacctttg 30

<210> SEQ ID NO 69
<211> LENGTH: 30
<212> TYPE: DNA
<213> ORGANISM: Artificial sequence
<220> FEATURE:
<223> OTHER INFORMATION: /note = "primer no. 347"

<400> SEQUENCE: 69
cctgtaggac cagagggctc caaggacact 30

<210> SEQ ID NO 70
<211> LENGTH: 48
<212> TYPE: DNA
<213> ORGANISM: Artificial sequence
<220> FEATURE:
<223> OTHER INFORMATION: /note = "primer no. 448"

<400> SEQUENCE: 70
tttaaaaagc ttgccgccac catggagacc cctgcctggc cccgggtc 48

<210> SEQ ID NO 71
<211> LENGTH: 48
<212> TYPE: DNA
<213> ORGANISM: Artificial sequence
<220> FEATURE:
<223> OTHER INFORMATION: /note = "primer no. 449"

<400> SEQUENCE: 71
tttaaagaat tcctattctc taaattcccc tttctcctgg cccataca 48

<210> SEQ ID NO 72

<211> LENGTH: 75
<212> TYPE: DNA
<213> ORGANISM: Artificial sequence
<220> FEATURE:
<223> OTHER INFORMATION: /note = "primer no. 466"

<400> SEQUENCE: 72
ggaggtggcg ggtctggtgg cgggggatca ggcgggggag gttcctcagg cactacaaat 60
actgtggcag catat 75

<210> SEQ ID NO 73
<211> LENGTH: 75
<212> TYPE: DNA
<213> ORGANISM: Artificial sequence
<220> FEATURE:
<223> OTHER INFORMATION: /note = "primer no. 467"

<400> SEQUENCE: 73
ggaacctccc ccgcctgatc ccccgccacc agacccgcca cctccttctc taaattcccc 60
tttctcctgg cccat 75

<210> SEQ ID NO 74
<211> LENGTH: 65
<212> TYPE: DNA
<213> ORGANISM: Artificial sequence
<220> FEATURE:
<223> OTHER INFORMATION: /note = "primer no. 483"

<400> SEQUENCE: 74
aaatttaagc ttactagtcc tgcaggttta aacgaatttg gatccggagg tggcgggtct 60
ggtgg 65

<210> SEQ ID NO 75
<211> LENGTH: 48
<212> TYPE: DNA
<213> ORGANISM: Artificial sequence
<220> FEATURE:
<223> OTHER INFORMATION: /note = "primer no. 484"

<400> SEQUENCE: 75
gaatttagcg gccgcgaatt cggatccgga acctcccccg cctgatcc 48

<210> SEQ ID NO 76
<211> LENGTH: 81
<212> TYPE: DNA
<213> ORGANISM: Artificial sequence
<220> FEATURE:
<223> OTHER INFORMATION: /note = "primer no. 485"

<400> SEQUENCE: 76
aaatttgaat tcttacttgc cgtcgatcag tctggggtcc acctggtcct cacactctcc 60
cctgttgaag ctctttgtga c 81

<210> SEQ ID NO 77
<211> LENGTH: 30
<212> TYPE: DNA
<213> ORGANISM: Artificial sequence
<220> FEATURE:
<223> OTHER INFORMATION: /note = "primer no. 486"

<400> SEQUENCE: 77
acggatctct agcaagcttc gtacggtggc 30

<210> SEQ ID NO 78
<211> LENGTH: 81
<212> TYPE: DNA
<213> ORGANISM: Artificial sequence
<220> FEATURE:
<223> OTHER INFORMATION: /note = "primer no. 487"

<400> SEQUENCE: 78
aaatttgaat tcttacttgc cgtcgatcag tctggggtcc acctggtcct ctttggactc 60
aactctcttg tccaccttgg t 81

<210> SEQ ID NO 79
<211> LENGTH: 45
<212> TYPE: DNA
<213> ORGANISM: Artificial sequence
<220> FEATURE:
<223> OTHER INFORMATION: /note = "primer no. 488"

<400> SEQUENCE: 79
aaatttgaat tcttatttgg actcaactct cttgtccacc ttggt 45

<210> SEQ ID NO 80
<211> LENGTH: 30
<212> TYPE: DNA
<213> ORGANISM: Artificial sequence
<220> FEATURE:
<223> OTHER INFORMATION: /note = "primer no. 489"

<400> SEQUENCE: 80
acggatctct agcaagcttg ctagcaccaa 30

<210> SEQ ID NO 81
<211> LENGTH: 54
<212> TYPE: DNA
<213> ORGANISM: Artificial sequence
<220> FEATURE:
<223> OTHER INFORMATION: /note = "primer no. 490"

<400> SEQUENCE: 81
aaatttaagc ttgccgccac catggatttt gggctgattt tttttattgt tgct 54

<210> SEQ ID NO 82
<211> LENGTH: 45
<212> TYPE: DNA
<213> ORGANISM: Artificial sequence
<220> FEATURE:
<223> OTHER INFORMATION: /note = "primer no. 491"

<400> SEQUENCE: 82
aaatttgcta gctgcagaga cagtgaccag agtcccttgg cccca 45

<210> SEQ ID NO 83
<211> LENGTH: 51
<212> TYPE: DNA
<213> ORGANISM: Artificial sequence
<220> FEATURE:
<223> OTHER INFORMATION: /note = "primer no. 492"

<400> SEQUENCE: 83
aaatttaagc ttgccgccac catgaagtca cagacccagg tcttcgtatt t 51

<210> SEQ ID NO 84
<211> LENGTH: 51
<212> TYPE: DNA
<213> ORGANISM: Artificial sequence
<220> FEATURE:

<223> OTHER INFORMATION: /note = "primer no. 493"

<400> SEQUENCE: 84
aaatttaagc ttgccgccac catgaagttg cctgttgggc tgttggtgct g 51

<210> SEQ ID NO 85
<211> LENGTH: 38
<212> TYPE: DNA
<213> ORGANISM: Artificial sequence
<220> FEATURE:
<223> OTHER INFORMATION: /note = "primer no. 494"

<400> SEQUENCE: 85
aaatttcgta cgttctattt ccagcttggt cccccctc 38

<210> SEQ ID NO 86
<211> LENGTH: 42
<212> TYPE: DNA
<213> ORGANISM: Artificial sequence
<220> FEATURE:
<223> OTHER INFORMATION: /note = "primer no. 495"

<400> SEQUENCE: 86
aaatttcgta cgttttattt ccagcttggt cccccctccg aa 42

<210> SEQ ID NO 87
<211> LENGTH: 69
<212> TYPE: DNA
<213> ORGANISM: Artificial sequence
<220> FEATURE:
<223> OTHER INFORMATION: /note = "primer no. 512"

<400> SEQUENCE: 87
aaatttggat ccgaggtgaa acttctcgag tctggaggtg gcctggtgca gcctggaggt 60
tccctgaaa 69

<210> SEQ ID NO 88
<211> LENGTH: 36
<212> TYPE: DNA
<213> ORGANISM: Artificial sequence
<220> FEATURE:
<223> OTHER INFORMATION: /note = "primer no. 513"

<400> SEQUENCE: 88
tttaaaggat tctttaccca gagacaggga gaggct 36

<210> SEQ ID NO 89
<211> LENGTH: 42
<212> TYPE: DNA
<213> ORGANISM: Artificial sequence
<220> FEATURE:
<223> OTHER INFORMATION: /note = "primer no. 514"

<400> SEQUENCE: 89
aaatttggat cctttggact caactctctt gtccaccttg gt 42

<210> SEQ ID NO 90
<211> LENGTH: 54
<212> TYPE: DNA
<213> ORGANISM: Artificial sequence
<220> FEATURE:
<223> OTHER INFORMATION: /note = "primer no. 546"

<400> SEQUENCE: 90
aaatttaagc ttgccgccac catgaacttg gggctcagct tgattttcct tgtc 54

<210> SEQ ID NO 91
<211> LENGTH: 42
<212> TYPE: DNA
<213> ORGANISM: Artificial sequence
<220> FEATURE:
<223> OTHER INFORMATION: /note = “primer no. 547”

<400> SEQUENCE: 91
aaatttgcta gctgaggaga cggtgactga ggttccttga cc 42

<210> SEQ ID NO 92
<211> LENGTH: 54
<212> TYPE: DNA
<213> ORGANISM: Artificial sequence
<220> FEATURE:
<223> OTHER INFORMATION: /note = “primer no. 548”

<400> SEQUENCE: 92
aaatttaagc ttgccgccac catggattca caggcccagg ttcttatatt gctg 54

<210> SEQ ID NO 93
<211> LENGTH: 42
<212> TYPE: DNA
<213> ORGANISM: Artificial sequence
<220> FEATURE:
<223> OTHER INFORMATION: /note = “primer no. 549”

<400> SEQUENCE: 93
aaatttcgta cgtttcagct ccagcttggt cccagcaccg aa 42

<210> SEQ ID NO 94
<211> LENGTH: 48
<212> TYPE: DNA
<213> ORGANISM: Artificial sequence
<220> FEATURE:
<223> OTHER INFORMATION: /note = “primer no. 551”

<400> SEQUENCE: 94
aaatttaaat ttggatccga tgttgtgatg acccaaactc cactctcc 48

<210> SEQ ID NO 95
<211> LENGTH: 42
<212> TYPE: DNA
<213> ORGANISM: Artificial sequence
<220> FEATURE:
<223> OTHER INFORMATION: /note = “primer no. 552”

<400> SEQUENCE: 95
aaatttaaat ttggatccac actctcccct gttgaagctc tt 42

<210> SEQ ID NO 96
<211> LENGTH: 54
<212> TYPE: DNA
<213> ORGANISM: Artificial sequence
<220> FEATURE:
<223> OTHER INFORMATION: /note = “primer no. 572”

<400> SEQUENCE: 96
aaatttaagc ttgccgccac catggatttt gggctgattt tttttattgt tgct 54

<210> SEQ ID NO 97
<211> LENGTH: 49
<212> TYPE: DNA
<213> ORGANISM: Artificial sequence
<220> FEATURE:

<223> OTHER INFORMATION: /note = “primer no. 574”

<400> SEQUENCE: 97
aaatttaagc ttgccgccac catgaagttg cctgttgggc tgttggtgc 49

<210> SEQ ID NO 98
<211> LENGTH: 84
<212> TYPE: DNA
<213> ORGANISM: Artificial sequence
<220> FEATURE:
<223> OTHER INFORMATION: /note = “primer no. 583”

<400> SEQUENCE: 98
aaatttggat ccggaacctc ccccgcctga tcccccgcca ccagacccgc cacctccaca 60
ctctcccctg ttgaagctct ttgt 84

<210> SEQ ID NO 99
<211> LENGTH: 99
<212> TYPE: DNA
<213> ORGANISM: Artificial sequence
<220> FEATURE:
<223> OTHER INFORMATION: /note = “primer no. 584”

<400> SEQUENCE: 99
aaatttggat ccagacccgc cacctccgga acctcccccg cctgatcccc cgccaccaga 60
cccgccacct ccacactctc ccctgttgaa gctctttgt 99

<210> SEQ ID NO 100
<211> LENGTH: 69
<212> TYPE: DNA
<213> ORGANISM: Artificial sequence
<220> FEATURE:
<223> OTHER INFORMATION: /note = “primer no. 585”

<400> SEQUENCE: 100
aaatttggat cctgatcccc cgccaccaga cccgccacct ccacactctc ccctgttgaa 60
gctctttgt 69

<210> SEQ ID NO 101
<211> LENGTH: 69
<212> TYPE: DNA
<213> ORGANISM: Artificial sequence
<220> FEATURE:
<223> OTHER INFORMATION: /note = “primer no. 586”

<400> SEQUENCE: 101
aaatttggat ccggtggcgg gggatcaggc gggggaggtt cctcaggcac tacaaatact 60
gtggcagca 69

<210> SEQ ID NO 102
<211> LENGTH: 87
<212> TYPE: DNA
<213> ORGANISM: Artificial sequence
<220> FEATURE:
<223> OTHER INFORMATION: /note = “primer no. 587”

<400> SEQUENCE: 102
aaatttggat ccggaacctc ccccgcctga tcccccgcca ccagacccgc cacctccttt 60
acccagagac agggagaggc tcttctg 87

<210> SEQ ID NO 103
<211> LENGTH: 102

<212> TYPE: DNA
<213> ORGANISM: Artificial sequence
<220> FEATURE:
<223> OTHER INFORMATION: /note = "primer no. 588"

<400> SEQUENCE: 103
aaatttggat ccagacccgc cacctccgga acctccccg cctgatcccc cgccaccaga 60
cccgccacct cctttaccca gagacaggga gaggctcttc tg 102

<210> SEQ ID NO 104
<211> LENGTH: 72
<212> TYPE: DNA
<213> ORGANISM: Artificial sequence
<220> FEATURE:
<223> OTHER INFORMATION: /note = "primer no. 589"

<400> SEQUENCE: 104
aaatttggat cctgatcccc cgccaccaga cccgccacct cctttaccca gagacaggga 60
gaggctcttc tg 72

<210> SEQ ID NO 105
<211> LENGTH: 54
<212> TYPE: DNA
<213> ORGANISM: Artificial sequence
<220> FEATURE:
<223> OTHER INFORMATION: /note = "primer no. 590"

<400> SEQUENCE: 105
aaatttggat ccagacccgc cacctccaca ctctcccctg ttgaagctct ttgt 54

<210> SEQ ID NO 106
<211> LENGTH: 114
<212> TYPE: DNA
<213> ORGANISM: Artificial sequence
<220> FEATURE:
<223> OTHER INFORMATION: /note = "primer no. 591"

<400> SEQUENCE: 106
aaatttggat ccagacccgc cacctccaga cccgccacct ccggaacctc ccccgcctga 60
tcccccgcca ccagacccgc cacctccaca ctctcccctg ttgaagctct ttgt 114

<210> SEQ ID NO 107
<211> LENGTH: 57
<212> TYPE: DNA
<213> ORGANISM: Artificial sequence
<220> FEATURE:
<223> OTHER INFORMATION: /note = "primer no. 592"

<400> SEQUENCE: 107
aaatttggat cctgatcccc cgccaccttt acccagagac agggagaggc tcttctg 57

<210> SEQ ID NO 108
<211> LENGTH: 117
<212> TYPE: DNA
<213> ORGANISM: Artificial sequence
<220> FEATURE:
<223> OTHER INFORMATION: /note = "primer no. 593"

<400> SEQUENCE: 108
aaatttggat ccagacccgc cacctccaga cccgccacct ccggaacctc ccccgcctga 60
tcccccgcca ccagacccgc cacctccttt acccagagac agggagaggc tcttctg 117

<210> SEQ ID NO 109

<211> LENGTH: 45
<212> TYPE: DNA
<213> ORGANISM: Artificial sequence
<220> FEATURE:
<223> OTHER INFORMATION: /note = "primer no. 598"

<400> SEQUENCE: 109
ggaaacacct attttcattg ggccctgcag aaaccaggcc agtct 45

<210> SEQ ID NO 110
<211> LENGTH: 45
<212> TYPE: DNA
<213> ORGANISM: Artificial sequence
<220> FEATURE:
<223> OTHER INFORMATION: /note = "primer no. 599"

<400> SEQUENCE: 110
agactggcct ggtttctgca gggcccaatg aaaataggtg tttcc 45

<210> SEQ ID NO 111
<211> LENGTH: 36
<212> TYPE: DNA
<213> ORGANISM: Artificial sequence
<220> FEATURE:
<223> OTHER INFORMATION: /note = "primer no. 610"

<400> SEQUENCE: 111
gctctagact aacactcatt cctgttgaag ctcttg 36

<210> SEQ ID NO 112
<211> LENGTH: 38
<212> TYPE: DNA
<213> ORGANISM: Artificial sequence
<220> FEATURE:
<223> OTHER INFORMATION: /note = "primer no. 613"

<400> SEQUENCE: 112
aaaaatctag aatagacaga tgggggtgtc gttttggc 38

<210> SEQ ID NO 113
<211> LENGTH: 34
<212> TYPE: DNA
<213> ORGANISM: Artificial sequence
<220> FEATURE:
<223> OTHER INFORMATION: /note = "primer no. 614"

<400> SEQUENCE: 113
aaaaatctag acttgaccag gcatcctaga gtca 34

<210> SEQ ID NO 114
<211> LENGTH: 35
<212> TYPE: DNA
<213> ORGANISM: Artificial sequence
<220> FEATURE:
<223> OTHER INFORMATION: /note = "primer no. 615"

<400> SEQUENCE: 114
aaaaatctag aaggggccag tggatagact gatgg 35

<210> SEQ ID NO 115
<211> LENGTH: 35
<212> TYPE: DNA
<213> ORGANISM: Artificial sequence
<220> FEATURE:
<223> OTHER INFORMATION: /note = "primer no. 616"

<400> SEQUENCE: 115
aaaaatctag aagggaccaa gggatagaca gatgg 35

<210> SEQ ID NO 116
<211> LENGTH: 50
<212> TYPE: DNA
<213> ORGANISM: Artificial sequence
<220> FEATURE:
<223> OTHER INFORMATION: /note = “primer no. 617”

<400> SEQUENCE: 116
aaatttaagc ttgccgccac catggaatgg acctgggtct ttctcttcct 50

<210> SEQ ID NO 117
<211> LENGTH: 39
<212> TYPE: DNA
<213> ORGANISM: Artificial sequence
<220> FEATURE:
<223> OTHER INFORMATION: /note = “primer no. 618”

<400> SEQUENCE: 117
aaatttgcta gctgaggaga cggtgaccgt ggtccctgc 39

<210> SEQ ID NO 118
<211> LENGTH: 48
<212> TYPE: DNA
<213> ORGANISM: Artificial sequence
<220> FEATURE:
<223> OTHER INFORMATION: /note = “primer no. 619”

<400> SEQUENCE: 118
aaatttaagc ttgccgccac catgatgtcc tctgctcagt tccttggt 48

<210> SEQ ID NO 119
<211> LENGTH: 39
<212> TYPE: DNA
<213> ORGANISM: Artificial sequence
<220> FEATURE:
<223> OTHER INFORMATION: /note = “primer no. 620”

<400> SEQUENCE: 119
aaatttcgta cgtttcatct ccagtttggt cccccctcc 39

<210> SEQ ID NO 120
<211> LENGTH: 50
<212> TYPE: DNA
<213> ORGANISM: Artificial sequence
<220> FEATURE:
<223> OTHER INFORMATION: /note = “primer no. 627”

<400> SEQUENCE: 120
aaatttaagc ttgccgccac catgggttgg agctgtatca tcttctttct 50

<210> SEQ ID NO 121
<211> LENGTH: 39
<212> TYPE: DNA
<213> ORGANISM: Artificial sequence
<220> FEATURE:
<223> OTHER INFORMATION: /note = “primer no. 628”

<400> SEQUENCE: 121
aaatttgcta gctgcagaga cagtgaccag agtcccttg 39

<210> SEQ ID NO 122
<211> LENGTH: 45
<212> TYPE: DNA

<213> ORGANISM: Artificial sequence
<220> FEATURE:
<223> OTHER INFORMATION: /note = “primer no. 682”

<400> SEQUENCE: 122
gatagcagta cgataaacta taacccatct ctaaaggata aattc 45

<210> SEQ ID NO 123
<211> LENGTH: 45
<212> TYPE: DNA
<213> ORGANISM: Artificial sequence
<220> FEATURE:
<223> OTHER INFORMATION: /note = “primer no. 683”

<400> SEQUENCE: 123
gaatttatcc tttagagatg ggttatagtt tatcgtactg ctatc 45

<210> SEQ ID NO 124
<211> LENGTH: 45
<212> TYPE: DNA
<213> ORGANISM: Artificial sequence
<220> FEATURE:
<223> OTHER INFORMATION: /note = “primer no. 684”

<400> SEQUENCE: 124
tctgaggact ctgccgtcta ttactgtgca agagggtact acggt 45

<210> SEQ ID NO 125
<211> LENGTH: 45
<212> TYPE: DNA
<213> ORGANISM: Artificial sequence
<220> FEATURE:
<223> OTHER INFORMATION: /note = “primer no. 685”

<400> SEQUENCE: 125
accgtagtac cctcttgcac agtaatagac ggcagagtcc tcaga 45

<210> SEQ ID NO 126
<211> LENGTH: 81
<212> TYPE: DNA
<213> ORGANISM: Artificial sequence
<220> FEATURE:
<223> OTHER INFORMATION: /note = “primer no. 686”

<400> SEQUENCE: 126
tgctgccaca gtatttgtag tgcctgatcc ccccaggaac tcaggtgctg gggatgatgg 60
ggatggggga ccatatttgg a 81

<210> SEQ ID NO 127
<211> LENGTH: 51
<212> TYPE: DNA
<213> ORGANISM: Artificial sequence
<220> FEATURE:
<223> OTHER INFORMATION: /note = “primer no. 687”

<400> SEQUENCE: 127
ccagcacctg agttcctggg gggatcaggc actacaaata ctgtggcagc a 51

<210> SEQ ID NO 128
<211> LENGTH: 45
<212> TYPE: DNA
<213> ORGANISM: Artificial sequence
<220> FEATURE:
<223> OTHER INFORMATION: /note = “primer no. 688”

<400> SEQUENCE: 128
gatagcagta cgataaacta tgcgccatct ctaaaggata aattc 45

<210> SEQ ID NO 129
<211> LENGTH: 45
<212> TYPE: DNA
<213> ORGANISM: Artificial sequence
<220> FEATURE:
<223> OTHER INFORMATION: /note = "primer no. 689"

<400> SEQUENCE: 129
gaatttatcc tttagagatg gcgcatagtt tatcgtactg ctatc 45

<210> SEQ ID NO 130
<211> LENGTH: 54
<212> TYPE: DNA
<213> ORGANISM: Artificial sequence
<220> FEATURE:
<223> OTHER INFORMATION: /note = "primer no. 699"

<400> SEQUENCE: 130
aaatttggat ccggcggggg aggttcctca ggcactacaa atactgtggc agca 54

<210> SEQ ID NO 131
<211> LENGTH: 39
<212> TYPE: DNA
<213> ORGANISM: Artificial sequence
<220> FEATURE:
<223> OTHER INFORMATION: /note = "primer no. 700"

<400> SEQUENCE: 131
aaatttggat cctcaggcac tacaaatact gtggcagca 39

<210> SEQ ID NO 132
<211> LENGTH: 57
<212> TYPE: DNA
<213> ORGANISM: Artificial sequence
<220> FEATURE:
<223> OTHER INFORMATION: /note = "primer no. 701"

<400> SEQUENCE: 132
accaaggtgg acaagagagt tgagtccaaa tcaggcacta caaatactgt ggcagca 57

<210> SEQ ID NO 133
<211> LENGTH: 60
<212> TYPE: DNA
<213> ORGANISM: Artificial sequence
<220> FEATURE:
<223> OTHER INFORMATION: /note = "primer no. 702"

<400> SEQUENCE: 133
tgctgccaca gtatttgtag tgcctgattt ggactcaact ctcttgtcca ccttggtgtt 60

<210> SEQ ID NO 134
<211> LENGTH: 57
<212> TYPE: DNA
<213> ORGANISM: Artificial sequence
<220> FEATURE:
<223> OTHER INFORMATION: /note = "primer no. 703"

<400> SEQUENCE: 134
gtcacaaaga gcttcaacag gggagagtgt tcaggcacta caaatactgt ggcagca 57

<210> SEQ ID NO 135
<211> LENGTH: 57
<212> TYPE: DNA

<213> ORGANISM: Artificial sequence
<220> FEATURE:
<223> OTHER INFORMATION: /note = "primer no. 704"

<400> SEQUENCE: 135
tgctgccaca gtatttgtag tgcctgaaca ctctcccctg ttgaagctct ttgtgac 57

<210> SEQ ID NO 136
<211> LENGTH: 60
<212> TYPE: DNA
<213> ORGANISM: Artificial sequence
<220> FEATURE:
<223> OTHER INFORMATION: /note = "primer no. 800"

<400> SEQUENCE: 136
cagaagagcc tctccctgtc tctgggtaaa tcaggcacta caaatactgt ggcagcatat 60

<210> SEQ ID NO 137
<211> LENGTH: 60
<212> TYPE: DNA
<213> ORGANISM: Artificial sequence
<220> FEATURE:
<223> OTHER INFORMATION: /note = "primer no. 801"

<400> SEQUENCE: 137
atatgctgcc acagtatttg tagtgcctga tttacccaga gacagggaga ggctcttctg 60

<210> SEQ ID NO 138
<211> LENGTH: 49
<212> TYPE: DNA
<213> ORGANISM: Artificial sequence
<220> FEATURE:
<223> OTHER INFORMATION: /note = "primer no. 842"

<400> SEQUENCE: 138
aaatttaagc ttgccgccac catgaggtgc ctagctgagt tcctggggc 49

<210> SEQ ID NO 139
<211> LENGTH: 45
<212> TYPE: DNA
<213> ORGANISM: Artificial sequence
<220> FEATURE:
<223> OTHER INFORMATION: /note = "primer no. 843"

<400> SEQUENCE: 139
aaatttcgta cgttttattt ccaactttgt ccccgagccg aacgt 45

<210> SEQ ID NO 140
<211> LENGTH: 49
<212> TYPE: DNA
<213> ORGANISM: Artificial sequence
<220> FEATURE:
<223> OTHER INFORMATION: /note = "primer no. 844"

<400> SEQUENCE: 140
aaatttaagc ttgccgccac catggaatgg agcggggtct ttatctttc 49

<210> SEQ ID NO 141
<211> LENGTH: 39
<212> TYPE: DNA
<213> ORGANISM: Artificial sequence
<220> FEATURE:
<223> OTHER INFORMATION: /note = "primer no. 845"

<400> SEQUENCE: 141
aaatttgcta gctgaggaga cggtgactga ggttccttg 39

<210> SEQ ID NO 142
<211> LENGTH: 55
<212> TYPE: DNA
<213> ORGANISM: Artificial sequence
<220> FEATURE:
<223> OTHER INFORMATION: /note = “primer 1000”

<400> SEQUENCE: 142
ctgtctctgg gtaaacacca tcaccaccac cactgagaat tccccgacct cgacc 55

<210> SEQ ID NO 143
<211> LENGTH: 55
<212> TYPE: DNA
<213> ORGANISM: Artificial sequence
<220> FEATURE:
<223> OTHER INFORMATION: /note = “primer no. 1001”

<400> SEQUENCE: 143
gaggtcgggg aattctcagt ggtggtggtg atggtgttta cccagagaca gggag 55

<210> SEQ ID NO 144
<211> LENGTH: 48
<212> TYPE: DNA
<213> ORGANISM: Artificial sequence
<220> FEATURE:
<223> OTHER INFORMATION: /note = “primer no. 1002”

<400> SEQUENCE: 144
ctcttttaaa aggggtccag tgtgagtcca aatatggtcc cccatgcc 48

<210> SEQ ID NO 145
<211> LENGTH: 50
<212> TYPE: DNA
<213> ORGANISM: Artificial sequence
<220> FEATURE:
<223> OTHER INFORMATION: /note = “primer no. 1003”

<400> SEQUENCE: 145
catgggggac catatttgga ctcacactgg accccttta aaagagcaac 50

<210> SEQ ID NO 146
<211> LENGTH: 233
<212> TYPE: PRT
<213> ORGANISM: Artificial sequence
<220> FEATURE:
<223> OTHER INFORMATION: /note = “0061VH-CH1”

<400> SEQUENCE: 146

```
Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
        35                  40                  45

Arg Tyr Trp Met Thr Trp Val Arg Gln Ala Pro Gly Lys Gly Leu Glu
    50                  55                  60

Trp Ile Gly Glu Ile Asn Pro Asp Ser Ser Thr Ile Asn Tyr Asn Pro
65                  70                  75                  80

Ser Leu Lys Asp Lys Phe Ile Ile Ser Arg Asp Asn Ala Lys Asn Thr
                85                  90                  95

Leu Tyr Leu Gln Met Ser Glu Val Arg Ser Glu Asp Thr Ala Leu Tyr
            100                 105                 110
```

```
Tyr Cys Ala Ser Gly Val Phe Thr Ser Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220

Lys Val Asp Lys Arg Val Glu Ser Lys
225                 230


<210> SEQ ID NO 147
<211> LENGTH: 247
<212> TYPE: PRT
<213> ORGANISM: Artificial sequence
<220> FEATURE:
<223> OTHER INFORMATION: /note = "hIgG4-hinge-CH2-CH3"

<400> SEQUENCE: 147

Met Asp Phe Gly Leu Ile Phe Phe Ile Val Ala Leu Leu Lys Gly Val
1               5                   10                  15

Gln Cys Glu Ser Lys Tyr Gly Pro Pro Cys Pro Pro Cys Pro Ala Pro
            20                  25                  30

Glu Phe Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser Gln Glu Asp Pro Glu Val Gln Phe Asn Trp Tyr Val Asp
65                  70                  75                  80

Gly Val Glu Val His Asn Ala Lys Thr Lys Pro Arg Glu Glu Gln Phe
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Gly Leu
        115                 120                 125

Pro Ser Ser Ile Glu Lys Thr Ile Ser Lys Ala Lys Gly Gln Pro Arg
    130                 135                 140

Glu Pro Gln Val Tyr Thr Leu Pro Pro Ser Gln Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Arg Leu Thr Val Asp Lys Ser Arg Trp Gln Glu Gly Asn Val Phe Ser
    210                 215                 220

Cys Ser Val Met His Glu Ala Leu His Asn His Tyr Thr Gln Lys Ser
225                 230                 235                 240
```

```
Leu Ser Leu Ser Leu Gly Lys
                245


<210> SEQ ID NO 148
<211> LENGTH: 6
<212> TYPE: PRT
<213> ORGANISM: Artificial sequence
<220> FEATURE:
<223> OTHER INFORMATION: /note = "His6 tag"

<400> SEQUENCE: 148

His His His His His His
1               5


<210> SEQ ID NO 149
<211> LENGTH: 172
<212> TYPE: PRT
<213> ORGANISM: Artificial sequence
<220> FEATURE:
<223> OTHER INFORMATION: /note = "hTLT-1.18-188"

<400> SEQUENCE: 149

Met Ile Val Gly Ser Leu Pro Glu Val Leu Gln Ala Pro Val Gly Ser
1               5                   10                  15

Ser Ile Leu Val Gln Cys His Tyr Arg Leu Gln Asp Val Lys Ala Gln
            20                  25                  30

Lys Val Trp Cys Arg Phe Leu Pro Glu Gly Cys Gln Pro Leu Val Ser
        35                  40                  45

Ser Ala Val Asp Arg Arg Ala Pro Ala Gly Arg Arg Thr Phe Leu Thr
    50                  55                  60

Asp Leu Gly Gly Gly Leu Leu Gln Val Glu Met Val Thr Leu Gln Glu
65                  70                  75                  80

Glu Asp Ala Gly Glu Tyr Gly Cys Met Val Asp Gly Ala Arg Gly Pro
                85                  90                  95

Gln Ile Leu His Arg Val Ser Leu Asn Ile Leu Pro Pro Glu Glu Glu
            100                 105                 110

Glu Glu Thr His Lys Ile Gly Ser Leu Ala Glu Asn Ala Phe Ser Asp
        115                 120                 125

Pro Ala Gly Ser Ala Asn Pro Leu Glu Pro Ser Gln Asp Glu Lys Ser
    130                 135                 140

Ile Pro Leu Ile Trp Gly Ala Val Leu Leu Val Gly Leu Leu Val Ala
145                 150                 155                 160

Ala Val Val Leu Phe Ala Val Met Ala Lys Arg Lys
                165                 170


<210> SEQ ID NO 150
<211> LENGTH: 32
<212> TYPE: DNA
<213> ORGANISM: Artificial sequence
<220> FEATURE:
<223> OTHER INFORMATION: /note = "primer no. 1004"

<400> SEQUENCE: 150

ggaattccat atgatagttg gcagcctccc tg                                  32


<210> SEQ ID NO 151
<211> LENGTH: 39
<212> TYPE: DNA
<213> ORGANISM: Artificial sequence
<220> FEATURE:
<223> OTHER INFORMATION: /note = "primer no. 1005"
```

<400> SEQUENCE: 151
ataagaatgc ggccgcctat ttcctcttgg ccatcacag 39

<210> SEQ ID NO 152
<211> LENGTH: 215
<212> TYPE: PRT
<213> ORGANISM: Artificial sequence
<220> FEATURE:
<223> OTHER INFORMATION: /note = "Fab 0100 HC"

<400> SEQUENCE: 152

```
Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Thr Trp Val Arg Gln Ala Pro Gly Lys Gly Leu Glu Trp Ile
        35                  40                  45

Gly Glu Ile Asn Pro Asp Ser Ser Thr Ile Asn Tyr Asn Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Glu Val Arg Ser Glu Asp Thr Ala Leu Tyr Tyr Cys
                85                  90                  95

Ala Ser Gly Val Phe Thr Ser Trp Gly Gln Gly Thr Leu Val Thr Val
            100                 105                 110

Ser Ala Ala Ser Thr Lys Gly Pro Ser Val Phe Pro Leu Ala Pro Cys
        115                 120                 125

Ser Arg Ser Thr Ser Glu Ser Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Lys Thr Tyr Thr Cys Asn Val Asp His Lys Pro Ser Asn Thr Lys Val
        195                 200                 205

Asp Lys Arg Val Glu Ser Lys
    210                 215
```

<210> SEQ ID NO 153
<211> LENGTH: 219
<212> TYPE: PRT
<213> ORGANISM: Artificial sequence
<220> FEATURE:
<223> OTHER INFORMATION: /note = "Fab 0100 LC"

<400> SEQUENCE: 153

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Arg
            20                  25                  30

Asn Gly Asn Thr Tyr Phe His Trp Ala Leu Gln Lys Pro Gly Gln Ser
        35                  40                  45

Pro Lys Leu Leu Ile Tyr Lys Val Ser Asn Arg Phe Ser Gly Val Pro
    50                  55                  60
```

-continued

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Phe Cys Ser Gln Ser
85 90 95

Thr His Val Pro Tyr Thr Phe Gly Gly Gly Thr Lys Leu Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 154
<211> LENGTH: 6588
<212> TYPE: DNA
<213> ORGANISM: Homo sapiens

<400> SEQUENCE: 154
gcgcagctgc gccagtttta tgtggcggcg cagggcatta gctggagcta tcgcccggaa 60
ccgaccaaca gcagcctgaa cctgagcgtg accagcttta aaaaaattgt gtatcgcgaa 120
tatgaaccgt attttaaaaa agaaaaaccg cagagcacca ttagcggcct gctgggcccg 180
accctgtatg cggaagtggg cgatattatt aaagtgcatt ttaaaaacaa agcggataaa 240
ccgctgagca ttcatccgca gggcattcgc tatagcaaac tgagcgaagg cgcgagctat 300
ctggatcata cctttccggc ggaaaaaatg gatgatgcgg tggcgccggg ccgcgaatat 360
acctatgaat ggagcattag cgaagatagc ggcccgaccc atgatgatcc gccgtgcctg 420
acccatattt attatagcca tgaaaacctg attgaagatt ttaacagcgg cctgattggc 480
ccgctgctga tttgcaaaaa aggcaccctg accgaaggcg gcacccagaa aacctttgat 540
aaacagattg tgctgctgtt tgcggtgttt gatgaaagca aaagctggag ccagagcagc 600
agcctgatgt ataccgtgaa cggctatgtg aacggcacca tgccggatat taccgtgtgc 660
gcgcatgatc atattagctg gcatctgctg ggcatgagca gcggcccgga actgtttagc 720
attcatttta acggccaggt gctggaacag aaccatcata aagtgagcgc gattaccctg 780
gtgagcgcga ccagcaccac cgcgaacatg accgtgggcc cggaaggcaa atggattatt 840
agcagcctga ccccgaaaca tctgcaggcg ggcatgcagg cgtatattga tattaaaaac 900
tgcccgaaaa aaacccgcaa cctgaaaaaa attacccgcg aacagcgccg ccatatgaaa 960
cgctgggaat attttattgc ggcggaagaa gtgatttggg attatgcgcc ggtgattccg 1020
gcgaacatgg ataaaaaata tcgcagccag catctggata actttagcaa ccagattggc 1080
aaacattata aaaaagtgat gtatacccag tatgaagatg aaagctttac caaacatacc 1140
gtgaacccga acatgaaaga agatggcatt ctgggcccga ttattcgcgc gcaggtgcgc 1200
gataccctga aaattgtgtt taaaaacatg gcgagccgcc cgtatagcat ttatccgcat 1260
ggcgtgacct ttagcccgta tgaagatgaa gtgaacagca gctttaccag cggccgcaac 1320
aacaccatga ttcgcgcggt gcagccgggc gaaacctata cctataaatg gaacattctg 1380
gaatttgatg aaccgaccga aaacgatgcg cagtgcctga cccgcccgta ttatagcgat 1440
gtggatatta tgcgcgatat tgcgagcggc ctgattggcc tgctgctgat ttgcaaaagc 1500
cgcagcctgg atcgccgcgg cattcagcgc gcggcggata ttgaacagca ggcggtgttt 1560
gcggtgtttg atgaaaacaa aagctggtat ctggaagata acattaacaa attttgcgaa 1620
aacccggatg aagtgaaacg cgatgatccg aaattttatg aaagcaacat tatgagcacc 1680
attaacggct atgtgccgga aagcattacc accctgggct tttgctttga tgataccgtg 1740
cagtggcatt tttgcagcgt gggcacccag aacgaaattc tgaccattca ttttaccggc 1800
catagcttta tttatggcaa acgccatgaa gataccctga ccctgtttcc gatgcgcggc 1860
gaaagcgtga ccgtgaccat ggataacgtg ggcacctgga tgctgaccag catgaacagc 1920
agcccgcgca gcaaaaaact gcgcctgaaa tttcgcgatg tgaaatgcat tccggatgat 1980
gatgaagata gctatgaaat ttttgaaccg ccggaaagca ccgtgatggc gacccgcaaa 2040
atgcatgatc gcctggaacc ggaagatgaa gaaagcgatg cggattatga ttatcagaac 2100
cgcctggcgg cggcgctggg cattcgcagc tttcgcaaca gcagcctgaa ccaggaagaa 2160
gaagaattta acctgaccgc gctggcgctg gaaaacggca ccgaatttgt gagcagcaac 2220
accgatatta ttgtgggcag caactatagc agcccgagca acattagcaa atttaccgtg 2280
aacaacctgg cggaaccgca gaaagcgccg agccatcagc aggcgaccac cgcgggcagc 2340
ccgctgcgcc atctgattgg caaaaacagc gtgctgaaca gcagcaccgc ggaacatagc 2400
agcccgtata gcgaagatcc gattgaagat ccgctgcagc cggatgtgac cggcattcgc 2460
ctgctgagcc tgggcgcggg cgaatttaaa agccaggaac atgcgaaaca taaaggcccg 2520
aaagtggaac gcgatcaggc ggcgaaacat cgctttagct ggatgaaact gctggcgcat 2580
aaagtgggcc gccatctgag ccaggatacc ggcagcccga gcggcatgcg cccgtgggaa 2640
gatctgccga gccaggatac cggcagcccg agccgcatgc gcccgtggaa agatccgccg 2700
agcgatctgc tgctgctgaa acagagcaac agcagcaaaa ttctggtggg ccgctggcat 2760
ctggcgagcg aaaaaggcag ctatgaaatt attcaggata ccgatgaaga taccgcggtg 2820
aacaactggc tgattagccc gcagaacgcg agccgcgcgt ggggcgaaag caccccgctg 2880
gcgaacaaac cgggcaaaca gagcggccat ccgaaatttc cgcgcgtgcg ccataaaagc 3000
ctgcaggtgc gccaggatgg cggcaaaagc cgcctgaaaa aaagccagtt tctgattaaa 3000
acccgcaaaa aaaaaaaaga aaaacatacc catcatgcgc cgctgagccc gcgcaccttt 3060
catccgctgc gcagcgaagc gtataacacc tttagcgaac gccgcctgaa acatagcctg 3120
gtgctgcata aaagcaacga aaccagcctg ccgaccgatc tgaaccagac cctgccgagc 3180
atggattttg gctggattgc gagcctgccg gatcataacc agaacagcag caacgatacc 3240
ggccaggcga gctgcccgcc gggcctgtat cagaccgtgc cgccggaaga acattatcag 3300
acctttccga ttcaggatcc ggatcagatg catagcacca gcgatccgag ccatcgcagc 3360
agcagcccgg aactgagcga aatgctggaa tatgatcgca gccataaaag ctttccgacc 3420
gatattagcc agatgagccc gagcagcgaa catgaagtgt ggcagaccgt gattagcccg 3480
gatctgagcc aggtgaccct gagcccggaa ctgagccaga ccaacctgag cccggatctg 3540
agccatacca ccctgagccc ggaactgatt cagcgcaacc tgagcccggc gctgggccag 3600
atgccgatta gcccggatct gagccatacc accctgagcc cggatctgag ccataccacc 3660
ctgagcctgg atctgagcca gaccaacctg agcccggaac tgagccagac caacctgagc 3720
ccggcgctgg gccagatgcc gctgagcccg gatctgagcc ataccaccct gagcctggat 3780
tttagccaga ccaacctgag cccggaactg agccatatga ccctgagccc ggaactgagc 3840
cagaccaacc tgagcccggc gctgggccag atgccgatta gcccggatct gagccatacc 3900
accctgagcc tggattttag ccagaccaac ctgagcccgg aactgagcca gaccaacctg 3960
agcccggcgc tgggccagat gccgctgagc ccggatccga gccataccac cctgagcctg 4020
gatctgagcc agaccaacct gagcccggaa ctgagccaga ccaacctgag cccggatctg 4080
agcgaaatgc cgctgtttgc ggatctgagc cagattccgc tgaccccgga tctggatcag 4140
atgaccctga gcccggatct gggcgaaacc gatctgagcc cgaactttgg ccagatgagc 4200
ctgagcccgg atctgagcca ggtgaccctg agcccggata ttagcgatac caccctgctg 4260
ccggatctga gccagattag cccgccgccg gatctggatc agatttttta tccgagcgaa 4320
agcagccaga gcctgctgct gcaggaattt aacgaaagct ttccgtatcc ggatctgggc 4380
cagatgccga gcccgagcag cccgaccctg aacgatacct ttctgagcaa agaatttaac 4440
ccgctggtga ttgtgggcct gagcaaagat ggcaccgatt atattgaaat tattccgaaa 4500
gaagaagtgc agagcagcga agatgattat gcggaaattg attatgtgcc gtatgatgat 4560
ccgtataaaa ccgatgtgcg caccaacatt aacagcagcc gcgatccgga taacattgcg 4620
gcgtggtatc tgcgcagcaa caacggcaac cgccgcaact attatattgc ggcggaagaa 4680
attagctggg attatagcga atttgtgcag cgcgaaaccg atattgaaga tagcgatgat 4740
attccggaag ataccaccta taaaaaagtg gtgtttcgca aatatctgga tagcaccttt 4800
accaaacgcg atccgcgcgg cgaatatgaa gaacatctgg gcattctggg cccgattatt 4860
cgcgcggaag tggatgatgt gattcaggtg cgctttaaaa acctggcgag ccgcccgtat 4920
agcctgcatg cgcatggcct gagctatgaa aaaagcagcg aaggcaaaac ctatgaagat 4980
gatagcccgg aatggtttaa agaagataac gcggtgcagc cgaacagcag ctatacctat 5040
gtgtggcatg cgaccgaacg cagcggcccg gaaagcccgg gcagcgcgtg ccgcgcgtgg 5100
gcgtattata gcgcggtgaa cccggaaaaa gatattcata gcggcctgat tggcccgctg 5160
ctgatttgcc agaaaggcat tctgcataaa gatagcaaca tgccgatgga tatgcgcgaa 5220
tttgtgctgc tgtttatgac ctttgatgaa aaaaaaagct ggtattatga aaaaaaaagc 5280
cgcagcagct ggcgcctgac cagcagcgaa atgaaaaaaa gccatgaatt tcatgcgatt 5340
aacggcatga tttatagcct gccgggcctg aaaatgtatg aacaggaatg ggtgcgcctg 5400
catctgctga acattggcgg cagccaggat attcatgtgg tgcattttca tggccagacc 5460
ctgctggaaa acggcaacaa acagcatcag ctgggcgtgt ggccgctgct gccgggcagc 5520
tttaaaaccc tggaaatgaa agcgagcaaa ccgggctggt ggctgctgaa caccgaagtg 5580
ggcgaaaacc agcgcgcggg catgcagacc ccgtttctga ttatggatcg cgattgccgc 5640
atgccgatgg gcctgagcac cggcattatt agcgatagcc agattaaagc gagcgaattt 5700
ctgggctatt gggaaccgcg cctggcgcgc ctgaacaacg gcggcagcta taacgcgtgg 5760
agcgtggaaa aactggcggc ggaatttgcg agcaaaccgt ggattcaggt ggatatgcag 5820
aaagaagtga ttattaccgg cattcagacc cagggcgcga aacattatct gaaaagctgc 5880
tataccaccg aattttatgt ggcgtatagc agcaaccaga ttaactggca gatttttaaa 5940
ggcaacagca cccgcaacgt gatgtatttt aacggcaaca gcgatgcgag caccattaaa 6000

```
gaaaaccagt ttgatccgcc gattgtggcg cgctatattc gcattagccc gacccgcgcg   6060

tataaccgcc cgaccctgcg cctggaactg cagggctgcg aagtgaacgg ctgcagcacc   6120

ccgctgggca tggaaaacgg caaaattgaa aacaaacaga ttaccgcgag cagctttaaa   6180

aaaagctggt ggggcgatta ttgggaaccg tttcgcgcgc gcctgaacgc gcagggccgc   6240

gtgaacgcgt ggcaggcgaa agcgaacaac aacaaacagt ggctggaaat tgatctgctg   6300

aaaattaaaa aaattaccgc gattattacc cagggctgca aaagcctgag cagcgaaatg   6360

tatgtgaaaa gctataccat tcattatagc gaacagggcg tggaatggaa accgtatcgc   6420

ctgaaaagca gcatggtgga taaaattttt gaaggcaaca ccaacaccaa aggccatgtg   6480

aaaaactttt ttaacccgcc gattattagc cgctttattc gcgtgattcc gaaaacctgg   6540

aaccagagca ttgcgctgcg cctggaactg tttggctgcg atatttat                6588


<210> SEQ ID NO 155
<211> LENGTH: 2196
<212> TYPE: PRT
<213> ORGANISM: Homo sapiens

<400> SEQUENCE: 155

Ala Gln Leu Arg Gln Phe Tyr Val Ala Ala Gln Gly Ile Ser Trp Ser
1               5                   10                  15

Tyr Arg Pro Glu Pro Thr Asn Ser Ser Leu Asn Leu Ser Val Thr Ser
            20                  25                  30

Phe Lys Lys Ile Val Tyr Arg Glu Tyr Glu Pro Tyr Phe Lys Lys Glu
        35                  40                  45

Lys Pro Gln Ser Thr Ile Ser Gly Leu Leu Gly Pro Thr Leu Tyr Ala
    50                  55                  60

Glu Val Gly Asp Ile Ile Lys Val His Phe Lys Asn Lys Ala Asp Lys
65                  70                  75                  80

Pro Leu Ser Ile His Pro Gln Gly Ile Arg Tyr Ser Lys Leu Ser Glu
                85                  90                  95

Gly Ala Ser Tyr Leu Asp His Thr Phe Pro Ala Glu Lys Met Asp Asp
            100                 105                 110

Ala Val Ala Pro Gly Arg Glu Tyr Thr Tyr Glu Trp Ser Ile Ser Glu
        115                 120                 125

Asp Ser Gly Pro Thr His Asp Asp Pro Pro Cys Leu Thr His Ile Tyr
    130                 135                 140

Tyr Ser His Glu Asn Leu Ile Glu Asp Phe Asn Ser Gly Leu Ile Gly
145                 150                 155                 160

Pro Leu Leu Ile Cys Lys Lys Gly Thr Leu Thr Glu Gly Gly Thr Gln
                165                 170                 175

Lys Thr Phe Asp Lys Gln Ile Val Leu Leu Phe Ala Val Phe Asp Glu
            180                 185                 190

Ser Lys Ser Trp Ser Gln Ser Ser Ser Leu Met Tyr Thr Val Asn Gly
        195                 200                 205

Tyr Val Asn Gly Thr Met Pro Asp Ile Thr Val Cys Ala His Asp His
    210                 215                 220

Ile Ser Trp His Leu Leu Gly Met Ser Ser Gly Pro Glu Leu Phe Ser
225                 230                 235                 240

Ile His Phe Asn Gly Gln Val Leu Glu Gln Asn His His Lys Val Ser
                245                 250                 255

Ala Ile Thr Leu Val Ser Ala Thr Ser Thr Thr Ala Asn Met Thr Val
            260                 265                 270
```

-continued

```
Gly Pro Glu Gly Lys Trp Ile Ile Ser Ser Leu Thr Pro Lys His Leu
        275                 280                 285

Gln Ala Gly Met Gln Ala Tyr Ile Asp Ile Lys Asn Cys Pro Lys Lys
    290                 295                 300

Thr Arg Asn Leu Lys Lys Ile Thr Arg Glu Gln Arg Arg His Met Lys
305                 310                 315                 320

Arg Trp Glu Tyr Phe Ile Ala Ala Glu Glu Val Ile Trp Asp Tyr Ala
                325                 330                 335

Pro Val Ile Pro Ala Asn Met Asp Lys Lys Tyr Arg Ser Gln His Leu
            340                 345                 350

Asp Asn Phe Ser Asn Gln Ile Gly Lys His Tyr Lys Lys Val Met Tyr
        355                 360                 365

Thr Gln Tyr Glu Asp Glu Ser Phe Thr Lys His Thr Val Asn Pro Asn
    370                 375                 380

Met Lys Glu Asp Gly Ile Leu Gly Pro Ile Ile Arg Ala Gln Val Arg
385                 390                 395                 400

Asp Thr Leu Lys Ile Val Phe Lys Asn Met Ala Ser Arg Pro Tyr Ser
                405                 410                 415

Ile Tyr Pro His Gly Val Thr Phe Ser Pro Tyr Glu Asp Glu Val Asn
            420                 425                 430

Ser Ser Phe Thr Ser Gly Arg Asn Asn Thr Met Ile Arg Ala Val Gln
        435                 440                 445

Pro Gly Glu Thr Tyr Thr Tyr Lys Trp Asn Ile Leu Glu Phe Asp Glu
    450                 455                 460

Pro Thr Glu Asn Asp Ala Gln Cys Leu Thr Arg Pro Tyr Tyr Ser Asp
465                 470                 475                 480

Val Asp Ile Met Arg Asp Ile Ala Ser Gly Leu Ile Gly Leu Leu Leu
                485                 490                 495

Ile Cys Lys Ser Arg Ser Leu Asp Arg Arg Gly Ile Gln Arg Ala Ala
            500                 505                 510

Asp Ile Glu Gln Gln Ala Val Phe Ala Val Phe Asp Glu Asn Lys Ser
        515                 520                 525

Trp Tyr Leu Glu Asp Asn Ile Asn Lys Phe Cys Glu Asn Pro Asp Glu
    530                 535                 540

Val Lys Arg Asp Asp Pro Lys Phe Tyr Glu Ser Asn Ile Met Ser Thr
545                 550                 555                 560

Ile Asn Gly Tyr Val Pro Glu Ser Ile Thr Thr Leu Gly Phe Cys Phe
                565                 570                 575

Asp Asp Thr Val Gln Trp His Phe Cys Ser Val Gly Thr Gln Asn Glu
            580                 585                 590

Ile Leu Thr Ile His Phe Thr Gly His Ser Phe Ile Tyr Gly Lys Arg
        595                 600                 605

His Glu Asp Thr Leu Thr Leu Phe Pro Met Arg Gly Glu Ser Val Thr
    610                 615                 620

Val Thr Met Asp Asn Val Gly Thr Trp Met Leu Thr Ser Met Asn Ser
625                 630                 635                 640

Ser Pro Arg Ser Lys Lys Leu Arg Leu Lys Phe Arg Asp Val Lys Cys
                645                 650                 655

Ile Pro Asp Asp Asp Glu Asp Ser Tyr Glu Ile Phe Glu Pro Pro Glu
            660                 665                 670

Ser Thr Val Met Ala Thr Arg Lys Met His Asp Arg Leu Glu Pro Glu
        675                 680                 685
```

-continued

```
Asp Glu Glu Ser Asp Ala Asp Tyr Asp Tyr Gln Asn Arg Leu Ala Ala
    690                 695                 700

Ala Leu Gly Ile Arg Ser Phe Arg Asn Ser Ser Leu Asn Gln Glu Glu
705                 710                 715                 720

Glu Glu Phe Asn Leu Thr Ala Leu Ala Leu Glu Asn Gly Thr Glu Phe
                725                 730                 735

Val Ser Ser Asn Thr Asp Ile Ile Val Gly Ser Asn Tyr Ser Ser Pro
            740                 745                 750

Ser Asn Ile Ser Lys Phe Thr Val Asn Asn Leu Ala Glu Pro Gln Lys
        755                 760                 765

Ala Pro Ser His Gln Gln Ala Thr Thr Ala Gly Ser Pro Leu Arg His
    770                 775                 780

Leu Ile Gly Lys Asn Ser Val Leu Asn Ser Ser Thr Ala Glu His Ser
785                 790                 795                 800

Ser Pro Tyr Ser Glu Asp Pro Ile Glu Asp Pro Leu Gln Pro Asp Val
                805                 810                 815

Thr Gly Ile Arg Leu Leu Ser Leu Gly Ala Gly Glu Phe Lys Ser Gln
            820                 825                 830

Glu His Ala Lys His Lys Gly Pro Lys Val Glu Arg Asp Gln Ala Ala
        835                 840                 845

Lys His Arg Phe Ser Trp Met Lys Leu Leu Ala His Lys Val Gly Arg
    850                 855                 860

His Leu Ser Gln Asp Thr Gly Ser Pro Ser Gly Met Arg Pro Trp Glu
865                 870                 875                 880

Asp Leu Pro Ser Gln Asp Thr Gly Ser Pro Ser Arg Met Arg Pro Trp
                885                 890                 895

Lys Asp Pro Pro Ser Asp Leu Leu Leu Leu Lys Gln Ser Asn Ser Ser
            900                 905                 910

Lys Ile Leu Val Gly Arg Trp His Leu Ala Ser Glu Lys Gly Ser Tyr
        915                 920                 925

Glu Ile Ile Gln Asp Thr Asp Glu Asp Thr Ala Val Asn Asn Trp Leu
    930                 935                 940

Ile Ser Pro Gln Asn Ala Ser Arg Ala Trp Gly Glu Ser Thr Pro Leu
945                 950                 955                 960

Ala Asn Lys Pro Gly Lys Gln Ser Gly His Pro Lys Phe Pro Arg Val
                965                 970                 975

Arg His Lys Ser Leu Gln Val Arg Gln Asp Gly Gly Lys Ser Arg Leu
            980                 985                 990

Lys Lys Ser Gln Phe Leu Ile Lys  Thr Arg Lys Lys Lys  Lys Glu Lys
        995                 1000                1005

His Thr  His His Ala Pro Leu  Ser Pro Arg Thr Phe  His Pro Leu
    1010                1015                1020

Arg Ser  Glu Ala Tyr Asn Thr  Phe Ser Glu Arg Arg  Leu Lys His
    1025                1030                1035

Ser Leu  Val Leu His Lys Ser  Asn Glu Thr Ser Leu  Pro Thr Asp
    1040                1045                1050

Leu Asn  Gln Thr Leu Pro Ser  Met Asp Phe Gly Trp  Ile Ala Ser
    1055                1060                1065

Leu Pro  Asp His Asn Gln Asn  Ser Ser Asn Asp Thr  Gly Gln Ala
    1070                1075                1080

Ser Cys  Pro Pro Gly Leu Tyr  Gln Thr Val Pro Pro  Glu Glu His
    1085                1090                1095

Tyr Gln  Thr Phe Pro Ile Gln  Asp Pro Asp Gln Met  His Ser Thr
```

```
    1100                1105                1110

Ser Asp  Pro Ser His Arg Ser  Ser Ser Pro Glu Leu  Ser Glu Met
    1115                1120                1125

Leu Glu  Tyr Asp Arg Ser His  Lys Ser Phe Pro Thr  Asp Ile Ser
    1130                1135                1140

Gln Met  Ser Pro Ser Ser Glu  His Glu Val Trp Gln  Thr Val Ile
    1145                1150                1155

Ser Pro  Asp Leu Ser Gln Val  Thr Leu Ser Pro Glu  Leu Ser Gln
    1160                1165                1170

Thr Asn  Leu Ser Pro Asp Leu  Ser His Thr Thr Leu  Ser Pro Glu
    1175                1180                1185

Leu Ile  Gln Arg Asn Leu Ser  Pro Ala Leu Gly Gln  Met Pro Ile
    1190                1195                1200

Ser Pro  Asp Leu Ser His Thr  Thr Leu Ser Pro Asp  Leu Ser His
    1205                1210                1215

Thr Thr  Leu Ser Leu Asp Leu  Ser Gln Thr Asn Leu  Ser Pro Glu
    1220                1225                1230

Leu Ser  Gln Thr Asn Leu Ser  Pro Ala Leu Gly Gln  Met Pro Leu
    1235                1240                1245

Ser Pro  Asp Leu Ser His Thr  Thr Leu Ser Leu Asp  Phe Ser Gln
    1250                1255                1260

Thr Asn  Leu Ser Pro Glu Leu  Ser His Met Thr Leu  Ser Pro Glu
    1265                1270                1275

Leu Ser  Gln Thr Asn Leu Ser  Pro Ala Leu Gly Gln  Met Pro Ile
    1280                1285                1290

Ser Pro  Asp Leu Ser His Thr  Thr Leu Ser Leu Asp  Phe Ser Gln
    1295                1300                1305

Thr Asn  Leu Ser Pro Glu Leu  Ser Gln Thr Asn Leu  Ser Pro Ala
    1310                1315                1320

Leu Gly  Gln Met Pro Leu Ser  Pro Asp Pro Ser His  Thr Thr Leu
    1325                1330                1335

Ser Leu  Asp Leu Ser Gln Thr  Asn Leu Ser Pro Glu  Leu Ser Gln
    1340                1345                1350

Thr Asn  Leu Ser Pro Asp Leu  Ser Glu Met Pro Leu  Phe Ala Asp
    1355                1360                1365

Leu Ser  Gln Ile Pro Leu Thr  Pro Asp Leu Asp Gln  Met Thr Leu
    1370                1375                1380

Ser Pro  Asp Leu Gly Glu Thr  Asp Leu Ser Pro Asn  Phe Gly Gln
    1385                1390                1395

Met Ser  Leu Ser Pro Asp Leu  Ser Gln Val Thr Leu  Ser Pro Asp
    1400                1405                1410

Ile Ser  Asp Thr Thr Leu Leu  Pro Asp Leu Ser Gln  Ile Ser Pro
    1415                1420                1425

Pro Pro  Asp Leu Asp Gln Ile  Phe Tyr Pro Ser Glu  Ser Ser Gln
    1430                1435                1440

Ser Leu  Leu Leu Gln Glu Phe  Asn Glu Ser Phe Pro  Tyr Pro Asp
    1445                1450                1455

Leu Gly  Gln Met Pro Ser Pro  Ser Ser Pro Thr Leu  Asn Asp Thr
    1460                1465                1470

Phe Leu  Ser Lys Glu Phe Asn  Pro Leu Val Ile Val  Gly Leu Ser
    1475                1480                1485

Lys Asp  Gly Thr Asp Tyr Ile  Glu Ile Ile Pro Lys  Glu Glu Val
    1490                1495                1500
```

```
Gln Ser  Ser Glu Asp Asp Tyr  Ala Glu Ile Asp Tyr  Val Pro Tyr
    1505                 1510                 1515

Asp Asp  Pro Tyr Lys Thr Asp  Val Arg Thr Asn Ile  Asn Ser Ser
    1520                 1525                 1530

Arg Asp  Pro Asp Asn Ile Ala  Ala Trp Tyr Leu Arg  Ser Asn Asn
    1535                 1540                 1545

Gly Asn  Arg Arg Asn Tyr Tyr  Ile Ala Ala Glu Glu  Ile Ser Trp
    1550                 1555                 1560

Asp Tyr  Ser Glu Phe Val Gln  Arg Glu Thr Asp Ile  Glu Asp Ser
    1565                 1570                 1575

Asp Asp  Ile Pro Glu Asp Thr  Thr Tyr Lys Lys Val  Val Phe Arg
    1580                 1585                 1590

Lys Tyr  Leu Asp Ser Thr Phe  Thr Lys Arg Asp Pro  Arg Gly Glu
    1595                 1600                 1605

Tyr Glu  Glu His Leu Gly Ile  Leu Gly Pro Ile Ile  Arg Ala Glu
    1610                 1615                 1620

Val Asp  Asp Val Ile Gln Val  Arg Phe Lys Asn Leu  Ala Ser Arg
    1625                 1630                 1635

Pro Tyr  Ser Leu His Ala His  Gly Leu Ser Tyr Glu  Lys Ser Ser
    1640                 1645                 1650

Glu Gly  Lys Thr Tyr Glu Asp  Asp Ser Pro Glu Trp  Phe Lys Glu
    1655                 1660                 1665

Asp Asn  Ala Val Gln Pro Asn  Ser Ser Tyr Thr Tyr  Val Trp His
    1670                 1675                 1680

Ala Thr  Glu Arg Ser Gly Pro  Glu Ser Pro Gly Ser  Ala Cys Arg
    1685                 1690                 1695

Ala Trp  Ala Tyr Tyr Ser Ala  Val Asn Pro Glu Lys  Asp Ile His
    1700                 1705                 1710

Ser Gly  Leu Ile Gly Pro Leu  Leu Ile Cys Gln Lys  Gly Ile Leu
    1715                 1720                 1725

His Lys  Asp Ser Asn Met Pro  Met Asp Met Arg Glu  Phe Val Leu
    1730                 1735                 1740

Leu Phe  Met Thr Phe Asp Glu  Lys Lys Ser Trp Tyr  Tyr Glu Lys
    1745                 1750                 1755

Lys Ser  Arg Ser Ser Trp Arg  Leu Thr Ser Ser Glu  Met Lys Lys
    1760                 1765                 1770

Ser His  Glu Phe His Ala Ile  Asn Gly Met Ile Tyr  Ser Leu Pro
    1775                 1780                 1785

Gly Leu  Lys Met Tyr Glu Gln  Glu Trp Val Arg Leu  His Leu Leu
    1790                 1795                 1800

Asn Ile  Gly Gly Ser Gln Asp  Ile His Val Val His  Phe His Gly
    1805                 1810                 1815

Gln Thr  Leu Leu Glu Asn Gly  Asn Lys Gln His Gln  Leu Gly Val
    1820                 1825                 1830

Trp Pro  Leu Leu Pro Gly Ser  Phe Lys Thr Leu Glu  Met Lys Ala
    1835                 1840                 1845

Ser Lys  Pro Gly Trp Trp Leu  Leu Asn Thr Glu Val  Gly Glu Asn
    1850                 1855                 1860

Gln Arg  Ala Gly Met Gln Thr  Pro Phe Leu Ile Met  Asp Arg Asp
    1865                 1870                 1875

Cys Arg  Met Pro Met Gly Leu  Ser Thr Gly Ile Ile  Ser Asp Ser
    1880                 1885                 1890
```

-continued

```
Gln Ile  Lys Ala Ser Glu Phe  Leu Gly Tyr Trp Glu  Pro Arg Leu
    1895                 1900                 1905

Ala Arg  Leu Asn Asn Gly Gly  Ser Tyr Asn Ala Trp  Ser Val Glu
    1910                 1915                 1920

Lys Leu  Ala Ala Glu Phe Ala  Ser Lys Pro Trp Ile  Gln Val Asp
    1925                 1930                 1935

Met Gln  Lys Glu Val Ile Ile  Thr Gly Ile Gln Thr  Gln Gly Ala
    1940                 1945                 1950

Lys His  Tyr Leu Lys Ser Cys  Tyr Thr Thr Glu Phe  Tyr Val Ala
    1955                 1960                 1965

Tyr Ser  Ser Asn Gln Ile Asn  Trp Gln Ile Phe Lys  Gly Asn Ser
    1970                 1975                 1980

Thr Arg  Asn Val Met Tyr Phe  Asn Gly Asn Ser Asp  Ala Ser Thr
    1985                 1990                 1995

Ile Lys  Glu Asn Gln Phe Asp  Pro Pro Ile Val Ala  Arg Tyr Ile
    2000                 2005                 2010

Arg Ile  Ser Pro Thr Arg Ala  Tyr Asn Arg Pro Thr  Leu Arg Leu
    2015                 2020                 2025

Glu Leu  Gln Gly Cys Glu Val  Asn Gly Cys Ser Thr  Pro Leu Gly
    2030                 2035                 2040

Met Glu  Asn Gly Lys Ile Glu  Asn Lys Gln Ile Thr  Ala Ser Ser
    2045                 2050                 2055

Phe Lys  Lys Ser Trp Trp Gly  Asp Tyr Trp Glu Pro  Phe Arg Ala
    2060                 2065                 2070

Arg Leu  Asn Ala Gln Gly Arg  Val Asn Ala Trp Gln  Ala Lys Ala
    2075                 2080                 2085

Asn Asn  Asn Lys Gln Trp Leu  Glu Ile Asp Leu Leu  Lys Ile Lys
    2090                 2095                 2100

Lys Ile  Thr Ala Ile Ile Thr  Gln Gly Cys Lys Ser  Leu Ser Ser
    2105                 2110                 2115

Glu Met  Tyr Val Lys Ser Tyr  Thr Ile His Tyr Ser  Glu Gln Gly
    2120                 2125                 2130

Val Glu  Trp Lys Pro Tyr Arg  Leu Lys Ser Ser Met  Val Asp Lys
    2135                 2140                 2145

Ile Phe  Glu Gly Asn Thr Asn  Thr Lys Gly His Val  Lys Asn Phe
    2150                 2155                 2160

Phe Asn  Pro Pro Ile Ile Ser  Arg Phe Ile Arg Val  Ile Pro Lys
    2165                 2170                 2175

Thr Trp  Asn Gln Ser Ile Ala  Leu Arg Leu Glu Leu  Phe Gly Cys
    2180                 2185                 2190

Asp Ile  Tyr
    2195
```

<210> SEQ ID NO 156
<211> LENGTH: 1218
<212> TYPE: DNA
<213> ORGANISM: Homo sapiens

<400> SEQUENCE: 156

```
gcgaacgcgt ttctggaaga actgcgcccg ggcagcctgg aacgcgaatg caaagaagaa     60

cagtgcagct ttgaagaagc gcgcgaaatt tttaaagatg cggaacgcac caaactgttt    120

tggattagct atagcgatgg cgatcagtgc gcgagcagcc cgtgccagaa cggcggcagc    180

tgcaaagatc agctgcagag ctatatttgc ttttgcctgc cggcgtttga aggccgcaac    240
```

```
tgcgaaaccc ataaagatga tcagctgatt tgcgtgaacg aaaacggcgg ctgcgaacag    300

tattgcagcg atcataccgg caccaaacgc agctgccgct gccatgaagg ctatagcctg    360

ctggcggatg gcgtgagctg caccccgacc gtggaatatc cgtgcggcaa aattccgatt    420

ctggaaaaac gcaacgcgag caaaccgcag ggccgcattg tgggcggcaa agtgtgcccg    480

aaaggcgaat gcccgtggca ggtgctgctg ctggtgaacg gcgcgcagct gtgcggcggc    540

accctgatta acaccatttg ggtggtgagc gcggcgcatt gctttgataa aattaaaaac    600

tggcgcaacc tgattgcggt gctgggcgaa catgatctga gcgaacatga tggcgatgaa    660

cagagccgcc gcgtggcgca ggtgattatt ccgagcacct atgtgccggg caccaccaac    720

catgatattg cgctgctgcg cctgcatcag ccggtggtgc tgaccgatca tgtggtgccg    780

ctgtgcctgc cggaacgcac ctttagcgaa cgcaccctgg cgtttgtgcg ctttagcctg    840

gtgagcggct ggggccagct gctggatcgc ggcgcgaccg cgctggaact gatggtgctg    900

aacgtgccgc gcctgatgac ccaggattgc ctgcagcaga gccgcaaagt gggcgatagc    960

ccgaacatta ccgaatatat gttttgcgcg ggctatagcg atggcagcaa agatagctgc   1020

aaaggcgata gcggcggccc gcatgcgacc cattatcgcg gcacctggta tctgaccggc   1080

attgtgagct ggggccaggg ctgcgcgacc gtgggccatt ttggcgtgta tacccgcgtg   1140

agccagtata ttgaatggct gcagaaactg atgcgcagcg aaccgcgccc gggcgtgctg   1200

ctgcgcgcgc cgtttccg                                                 1218
```

```
<210> SEQ ID NO 157
<211> LENGTH: 406
<212> TYPE: PRT
<213> ORGANISM: Homo sapiens

<400> SEQUENCE: 157

Ala Asn Ala Phe Leu Glu Glu Leu Arg Pro Gly Ser Leu Glu Arg Glu
1               5                   10                  15

Cys Lys Glu Glu Gln Cys Ser Phe Glu Glu Ala Arg Glu Ile Phe Lys
            20                  25                  30

Asp Ala Glu Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
    130                 135                 140

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
```

```
        195                 200                 205

Gly Glu His Asp Leu Ser Glu His Asp Gly Asp Glu Gln Ser Arg Arg
    210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
            260                 265                 270

Leu Ala Phe Val Arg Phe Ser Leu Val Ser Gly Trp Gly Gln Leu Leu
        275                 280                 285

Asp Arg Gly Ala Thr Ala Leu Glu Leu Met Val Leu Asn Val Pro Arg
    290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
            340                 345                 350

Arg Gly Thr Trp Tyr Leu Thr Gly Ile Val Ser Trp Gly Gln Gly Cys
        355                 360                 365

Ala Thr Val Gly His Phe Gly Val Tyr Thr Arg Val Ser Gln Tyr Ile
    370                 375                 380

Glu Trp Leu Gln Lys Leu Met Arg Ser Glu Pro Arg Pro Gly Val Leu
385                 390                 395                 400

Leu Arg Ala Pro Phe Pro
                405


<210> SEQ ID NO 158
<211> LENGTH: 6996
<212> TYPE: DNA
<213> ORGANISM: Homo sapiens

<400> SEQUENCE: 158

gcgacccgcc gctattatct gggcgcggtg gaactgagct gggattatat gcagagcgat      60

ctgggcgaac tgccggtgga tgcgcgcttt ccgccgcgcg tgccgaaaag ctttccgttt     120

aacaccagcg tggtgtataa aaaaaccctg tttgtggaat ttaccgatca tctgtttaac     180

attgcgaaac cgcgcccgcc gtggatgggc ctgctgggcc cgaccattca ggcggaagtg     240

tatgataccg tggtgattac cctgaaaaac atggcgagcc atccggtgag cctgcatgcg     300

gtgggcgtga gctattggaa agcgagcgaa ggcgcggaat atgatgatca gaccagccag     360

cgcgaaaaag aagatgataa agtgtttccg ggcggcagcc atacctatgt gtggcaggtg     420

ctgaaagaaa acggcccgat ggcgagcgat ccgctgtgcc tgacctatag ctatctgagc     480

catgtggatc tggtgaaaga tctgaacagc ggcctgattg gcgcgctgct ggtgtgccgc     540

gaaggcagcc tggcgaaaga aaaaacccag accctgcata aatttattct gctgtttgcg     600

gtgtttgatg aaggcaaaag ctggcatagc gaaaccaaaa acagcctgat gcaggatcgc     660

gatgcggcga gcgcgcgcgc gtggccgaaa atgcataccg tgaacggcta tgtgaaccgc     720

agcctgccgg gcctgattgg ctgccatcgc aaaagcgtgt attggcatgt gattggcatg     780

ggcaccaccc cggaagtgca tagcattttt ctggaaggcc ataccttttct ggtgcgcaac    840

catcgccagg cgagcctgga aattagcccg attaccttttc tgaccgcgca gaccctgctg   900
```

-continued

```
atggatctgg gccagtttct gctgttttgc catattagca gccatcagca tgatggcatg    960
gaagcgtatg tgaaagtgga tagctgcccg gaagaaccgc agctgcgcat gaaaaacaac   1020
gaagaagcgg aagattatga tgatgatctg accgatagcg aaatggatgt ggtgcgcttt   1080
gatgatgata acagcccgag ctttattcag attcgcagcg tggcgaaaaa acatccgaaa   1140
acctgggtgc attatattgc ggcggaagaa gaagattggg attatgcgcc gctggtgctg   1200
gcgccggatg atcgcagcta taaaagccag tatctgaaca acggcccgca gcgcattggc   1260
cgcaaatata aaaaagtgcg ctttatggcg tataccgatg aaacctttaa aacccgcgaa   1320
gcgattcagc atgaaagcgg cattctgggc ccgctgctgt atggcgaagt gggcgatacc   1380
ctgctgatta tttttaaaaa ccaggcgagc cgcccgtata acatttatcc gcatggcatt   1440
accgatgtgc gcccgctgta tagccgccgc ctgccgaaag gcgtgaaaca tctgaaagat   1500
tttccgattc tgccgggcga aatttttaaa tataaatgga ccgtgaccgt ggaagatggc   1560
ccgaccaaaa gcgatccgcg ctgcctgacc cgctattata gcagctttgt gaacatggaa   1620
cgcgatctgg cgagcggcct gattggcccg ctgctgattt gctataaaga aagcgtggat   1680
cagcgcggca accagattat gagcgataaa cgcaacgtga ttctgtttag cgtgtttgat   1740
gaaaaccgca gctggtatct gaccgaaaac attcagcgct ttctgccgaa cccggcgggc   1800
gtgcagctgg aagatccgga atttcaggcg agcaacatta tgcatagcat taacggctat   1860
gtgtttgata gcctgcagct gagcgtgtgc ctgcatgaag tggcgtattg gtatattctg   1920
agcattggcg cgcagaccga ttttctgagc gtgtttttta gcggctatac ctttaaacat   1980
aaaatggtgt atgaagatac cctgaccctg tttccgttta gcggcgaaac cgtgtttatg   2040
agcatggaaa acccgggcct gtggattctg ggctgccata acagcgattt tcgcaaccgc   2100
ggcatgaccg cgctgctgaa agtgagcagc tgcgataaaa acaccggcga ttattatgaa   2160
gatagctatg aagatattag cgcgtatctg ctgagcaaaa acaacgcgat tgaaccgcgc   2220
agctttagcc agaacagccg ccatccgagc acccgccaga aacagtttaa cgcgaccacc   2280
attccggaaa acgatattga aaaaaccgat ccgtggtttg cgcatcgcac cccgatgccg   2340
aaaattcaga acgtgagcag cagcgatctg ctgatgctgc tgcgccagag cccgaccccg   2400
catggcctga gcctgagcga tctgcaggaa gcgaaatatg aaacctttag cgatgatccg   2460
agcccgggcg cgattgatag caacaacagc ctgagcgaaa tgacccattt tcgcccgcag   2520
ctgcatcata gcggcgatat ggtgtttacc ccggaaagcg gcctgcagct gcgcctgaac   2580
gaaaaactgg gcaccaccgc ggcgaccgaa ctgaaaaaac tggattttaa agtgagcagc   2640
accagcaaca acctgattag caccattccg agcgataacc tggcggcggg caccgataac   2700
accagcagcc tgggcccgcc gagcatgccg gtgcattatg atagccagct ggataccacc   2760
ctgtttggca aaaaaagcag cccgctgacc gaaagcggcg gcccgctgag cctgagcgaa   2820
gaaaacaacg atagcaaact gctggaaagc ggcctgatga acagccagga aagcagctgg   2880
ggcaaaaacg tgagcagcac cgaaagcggc cgcctgttta aaggcaaacg cgcgcatggc   2940
ccggcgctgc tgaccaaaga taacgcgctg tttaaagtga gcattagcct gctgaaaacc   3000
aacaaaacca gcaacaacag cgcgaccaac cgcaaaaccc atattgatgg cccgagcctg   3060
ctgattgaaa acagcccgag cgtgtggcag aacattctgg aaagcgatac cgaatttaaa   3120
aaagtgaccc cgctgattca tgatcgcatg ctgatggata aaaacgcgac cgcgctgcgc   3180
ctgaaccata tgagcaacaa aaccaccagc agcaaaaaca tggaaatggt gcagcagaaa   3240
aaagaaggcc cgattccgcc ggatgcgcag aacccggata tgagcttttt taaaatgctg   3300
```

-continued

```
tttctgccgg aaagcgcgcg ctggattcag cgcacccatg gcaaaaacag cctgaacagc   3360
ggccagggcc cgagcccgaa acagctggtg agcctgggcc cggaaaaaag cgtggaaggc   3420
cagaactttc tgagcgaaaa aaacaaagtg gtggtgggca aaggcgaatt taccaaagat   3480
gtgggcctga aagaaatggt gtttccgagc agccgcaacc tgtttctgac caacctggat   3540
aacctgcatg aaaacaacac ccataaccag gaaaaaaaaa ttcaggaaga aattgaaaaa   3600
aaagaaaccc tgattcagga aaacgtggtg ctgccgcaga ttcataccgt gaccggcacc   3660
aaaaacttta tgaaaaacct gtttctgctg agcacccgcc agaacgtgga aggcagctat   3720
gatggcgcgt atgcgccggt gctgcaggat tttcgcagcc tgaacgatag caccaaccgc   3780
accaaaaaac ataccgcgca ttttagcaaa aaaggcgaag aagaaaacct ggaaggcctg   3840
ggcaaccaga ccaaacagat tgtggaaaaa tatgcgtgca ccacccgcat tagcccgaac   3900
accagccagc agaactttgt gacccagcgc agcaaacgcg cgctgaaaca gtttcgcctg   3960
ccgctggaag aaaccgaact ggaaaaacgc attattgtgg atgataccag cacccagtgg   4020
agcaaaaaca tgaaacatct gaccccgagc accctgaccc agattgatta taacgaaaaa   4080
gaaaaaggcg cgattaccca gagcccgctg agcgattgcc tgacccgcag ccatagcatt   4140
ccgcaggcga accgcagccc gctgccgatt gcgaaagtga gcagctttcc gagcattcgc   4200
ccgatttatc tgacccgcgt gctgtttcag gataacagca gccatctgcc ggcggcgagc   4260
tatcgcaaaa aagatagcgg cgtgcaggaa agcagccatt ttctgcaggg cgcgaaaaaa   4320
aacaacctga gcctggcgat tctgaccctg gaaatgaccg gcgatcagcg cgaagtgggc   4380
agcctgggca ccagcgcgac caacagcgtg acctataaaa aagtggaaaa caccgtgctg   4440
ccgaaaccgg atctgccgaa aaccagcggc aaagtggaac tgctgccgaa agtgcatatt   4500
tatcagaaag atctgtttcc gaccgaaacc agcaacggca gcccgggcca tctggatctg   4560
gtggaaggca gcctgctgca gggcaccgaa ggcgcgatta aatggaacga agcgaaccgc   4620
ccgggcaaag tgccgtttct gcgcgtggcg accgaaagca gcgcgaaaac cccgagcaaa   4680
ctgctggatc cgctggcgtg ggataaccat tatggcaccc agattccgaa agaagaatgg   4740
aaaagccagg aaaaaagccc ggaaaaaacc gcgtttaaaa aaaaagatac cattctgagc   4800
ctgaacgcgt gcgaaagcaa ccatgcgatt gcggcgatta acgaaggcca gaacaaaccg   4860
gaaattgaag tgacctgggc gaaacagggc cgcaccgaac gcctgtgcag ccagaacccg   4920
ccggtgctga aacgccatca gcgcgaaatt acccgcacca ccctgcagag cgatcaggaa   4980
gaaattgatt atgatgatac cattagcgtg gaaatgaaaa aagaagattt tgatatttat   5040
gatgaagatg aaaaccagag cccgcgcagc tttcagaaaa aaacccgcca ttattttatt   5100
gcggcggtgg aacgcctgtg ggattatggc atgagcagca gcccgcatgt gctgcgcaac   5160
cgcgcgcaga gcggcagcgt gccgcagttt aaaaaagtgg tgtttcagga atttaccgat   5220
ggcagcttta cccagccgct gtatcgcggc gaactgaacg aacatctggg cctgctgggc   5280
ccgtatattc gcgcggaagt ggaagataac attatggtga cctttcgcaa ccaggcgagc   5340
cgcccgtata gcttttatag cagcctgatt agctatgaag aagatcagcg ccagggcgcg   5400
gaaccgcgca aaaactttgt gaaaccgaac gaaaccaaaa cctatttttg gaaagtgcag   5460
catcatatgg cgccgaccaa agatgaattt gattgcaaag cgtgggcgta ttttagcgat   5520
gtggatctgg aaaaagatgt gcatagcggc ctgattggcc cgctgctggt gtgccatacc   5580
aacaccctga acccggcgca tggccgccag gtgaccgtgc aggaatttgc gctgtttttt   5640
```

```
accattttttg atgaaaccaa aagctggtat tttaccgaaa acatggaacg caactgccgc   5700

gcgccgtgca acattcagat ggaagatccg acctttaaag aaaactatcg ctttcatgcg   5760

attaacggct atattatgga taccctgccg ggcctggtga tggcgcagga tcagcgcatt   5820

cgctggtatc tgctgagcat gggcagcaac gaaaacattc atagcattca ttttagcggc   5880

catgtgttta ccgtgcgcaa aaaagaagaa tataaaatgg cgctgtataa cctgtatccg   5940

ggcgtgtttg aaaccgtgga aatgctgccg agcaaagcgg gcatttggcg cgtggaatgc   6000

ctgattggcg aacatctgca tgcgggcatg agcaccctgt ttctggtgta tagcaacaaa   6060

tgccagaccc cgctgggcat ggcgagcggc catattcgcg attttcagat taccgcgagc   6120

ggccagtatg gccagtgggc gccgaaactg gcgcgcctgc attatagcgg cagcattaac   6180

gcgtggagca ccaaagaacc gtttagctgg attaaagtgg atctgctggc gccgatgatt   6240

attcatggca ttaaaaccca gggcgcgcgc cagaaattta gcagcctgta tattagccag   6300

tttattatta tgtatagcct ggatggcaaa aaatggcaga cctatcgcgg caacagcacc   6360

ggcaccctga tggtgttttt tggcaacgtg gatagcagcg gcattaaaca taacattttt   6420

aacccgccga ttattgcgcg ctatattcgc ctgcatccga cccattatag cattcgcagc   6480

accctgcgca tggaactgat gggctgcgat ctgaacagct gcagcatgcc gctgggcatg   6540

gaaagcaaag cgattagcga tgcgcagatt accgcgagca gctattttac caacatgttt   6600

gcgacctgga gcccgagcaa agcgcgcctg catctgcagg gccgcagcaa cgcgtggcgc   6660

ccgcaggtga acaacccgaa agaatggctg caggtggatt ttcagaaaac catgaaagtg   6720

accggcgtga ccacccaggg cgtgaaaagc ctgctgacca gcatgtatgt gaaagaattt   6780

ctgattagca gcagccagga tggccatcag tggaccctgt tttttcagaa cggcaaagtg   6840

aaagtgtttc agggcaacca ggatagcttt accccggtgg tgaacagcct ggatccgccg   6900

ctgctgaccc gctatctgcg cattcatccg cagagctggg tgcatcagat tgcgctgcgc   6960

atggaagtgc tgggctgcga agcgcaggat ctgtat                             6996
```

```
<210> SEQ ID NO 159
<211> LENGTH: 2332
<212> TYPE: PRT
<213> ORGANISM: Homo sapiens

<400> SEQUENCE: 159

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
```

-continued

```
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560
```

```
Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
    770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
        835                 840                 845

Phe Thr Pro Glu Ser Gly Leu Gln Leu Arg Leu Asn Glu Lys Leu Gly
    850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
        915                 920                 925

Leu Thr Glu Ser Gly Gly Pro Leu Ser Leu Ser Glu Glu Asn Asn Asp
    930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975
```

```
Arg Ala His Gly Pro Ala Leu Leu Thr Lys Asp Asn Ala Leu Phe Lys
            980                 985                 990

Val Ser Ile Ser Leu Leu Lys Thr  Asn Lys Thr Ser Asn  Asn Ser Ala
        995                 1000                 1005

Thr Asn  Arg Lys Thr His Ile  Asp Gly Pro Ser Leu  Leu Ile Glu
    1010                 1015                 1020

Asn Ser  Pro Ser Val Trp Gln  Asn Ile Leu Glu Ser  Asp Thr Glu
    1025                 1030                 1035

Phe Lys  Lys Val Thr Pro Leu  Ile His Asp Arg Met  Leu Met Asp
    1040                 1045                 1050

Lys Asn  Ala Thr Ala Leu Arg  Leu Asn His Met Ser  Asn Lys Thr
    1055                 1060                 1065

Thr Ser  Ser Lys Asn Met Glu  Met Val Gln Gln Lys  Lys Glu Gly
    1070                 1075                 1080

Pro Ile  Pro Pro Asp Ala Gln  Asn Pro Asp Met Ser  Phe Phe Lys
    1085                 1090                 1095

Met Leu  Phe Leu Pro Glu Ser  Ala Arg Trp Ile Gln  Arg Thr His
    1100                 1105                 1110

Gly Lys  Asn Ser Leu Asn Ser  Gly Gln Gly Pro Ser  Pro Lys Gln
    1115                 1120                 1125

Leu Val  Ser Leu Gly Pro Glu  Lys Ser Val Glu Gly  Gln Asn Phe
    1130                 1135                 1140

Leu Ser  Glu Lys Asn Lys Val  Val Val Gly Lys Gly  Glu Phe Thr
    1145                 1150                 1155

Lys Asp  Val Gly Leu Lys Glu  Met Val Phe Pro Ser  Ser Arg Asn
    1160                 1165                 1170

Leu Phe  Leu Thr Asn Leu Asp  Asn Leu His Glu Asn  Asn Thr His
    1175                 1180                 1185

Asn Gln  Glu Lys Lys Ile Gln  Glu Glu Ile Glu Lys  Lys Glu Thr
    1190                 1195                 1200

Leu Ile  Gln Glu Asn Val Val  Leu Pro Gln Ile His  Thr Val Thr
    1205                 1210                 1215

Gly Thr  Lys Asn Phe Met Lys  Asn Leu Phe Leu Leu  Ser Thr Arg
    1220                 1225                 1230

Gln Asn  Val Glu Gly Ser Tyr  Asp Gly Ala Tyr Ala  Pro Val Leu
    1235                 1240                 1245

Gln Asp  Phe Arg Ser Leu Asn  Asp Ser Thr Asn Arg  Thr Lys Lys
    1250                 1255                 1260

His Thr  Ala His Phe Ser Lys  Lys Gly Glu Glu Glu  Asn Leu Glu
    1265                 1270                 1275

Gly Leu  Gly Asn Gln Thr Lys  Gln Ile Val Glu Lys  Tyr Ala Cys
    1280                 1285                 1290

Thr Thr  Arg Ile Ser Pro Asn  Thr Ser Gln Gln Asn  Phe Val Thr
    1295                 1300                 1305

Gln Arg  Ser Lys Arg Ala Leu  Lys Gln Phe Arg Leu  Pro Leu Glu
    1310                 1315                 1320

Glu Thr  Glu Leu Glu Lys Arg  Ile Ile Val Asp Asp  Thr Ser Thr
    1325                 1330                 1335

Gln Trp  Ser Lys Asn Met Lys  His Leu Thr Pro Ser  Thr Leu Thr
    1340                 1345                 1350

Gln Ile  Asp Tyr Asn Glu Lys  Glu Lys Gly Ala Ile  Thr Gln Ser
    1355                 1360                 1365

Pro Leu  Ser Asp Cys Leu Thr  Arg Ser His Ser Ile  Pro Gln Ala
```

-continued 1370 1375 1380

Asn Arg Ser Pro Leu Pro Ile Ala Lys Val Ser Ser Phe Pro Ser
1385 1390 1395

Ile Arg Pro Ile Tyr Leu Thr Arg Val Leu Phe Gln Asp Asn Ser
1400 1405 1410

Ser His Leu Pro Ala Ala Ser Tyr Arg Lys Lys Asp Ser Gly Val
1415 1420 1425

Gln Glu Ser Ser His Phe Leu Gln Gly Ala Lys Lys Asn Asn Leu
1430 1435 1440

Ser Leu Ala Ile Leu Thr Leu Glu Met Thr Gly Asp Gln Arg Glu
1445 1450 1455

Val Gly Ser Leu Gly Thr Ser Ala Thr Asn Ser Val Thr Tyr Lys
1460 1465 1470

Lys Val Glu Asn Thr Val Leu Pro Lys Pro Asp Leu Pro Lys Thr
1475 1480 1485

Ser Gly Lys Val Glu Leu Leu Pro Lys Val His Ile Tyr Gln Lys
1490 1495 1500

Asp Leu Phe Pro Thr Glu Thr Ser Asn Gly Ser Pro Gly His Leu
1505 1510 1515

Asp Leu Val Glu Gly Ser Leu Leu Gln Gly Thr Glu Gly Ala Ile
1520 1525 1530

Lys Trp Asn Glu Ala Asn Arg Pro Gly Lys Val Pro Phe Leu Arg
1535 1540 1545

Val Ala Thr Glu Ser Ser Ala Lys Thr Pro Ser Lys Leu Leu Asp
1550 1555 1560

Pro Leu Ala Trp Asp Asn His Tyr Gly Thr Gln Ile Pro Lys Glu
1565 1570 1575

Glu Trp Lys Ser Gln Glu Lys Ser Pro Glu Lys Thr Ala Phe Lys
1580 1585 1590

Lys Lys Asp Thr Ile Leu Ser Leu Asn Ala Cys Glu Ser Asn His
1595 1600 1605

Ala Ile Ala Ala Ile Asn Glu Gly Gln Asn Lys Pro Glu Ile Glu
1610 1615 1620

Val Thr Trp Ala Lys Gln Gly Arg Thr Glu Arg Leu Cys Ser Gln
1625 1630 1635

Asn Pro Pro Val Leu Lys Arg His Gln Arg Glu Ile Thr Arg Thr
1640 1645 1650

Thr Leu Gln Ser Asp Gln Glu Glu Ile Asp Tyr Asp Asp Thr Ile
1655 1660 1665

Ser Val Glu Met Lys Lys Glu Asp Phe Asp Ile Tyr Asp Glu Asp
1670 1675 1680

Glu Asn Gln Ser Pro Arg Ser Phe Gln Lys Lys Thr Arg His Tyr
1685 1690 1695

Phe Ile Ala Ala Val Glu Arg Leu Trp Asp Tyr Gly Met Ser Ser
1700 1705 1710

Ser Pro His Val Leu Arg Asn Arg Ala Gln Ser Gly Ser Val Pro
1715 1720 1725

Gln Phe Lys Lys Val Val Phe Gln Glu Phe Thr Asp Gly Ser Phe
1730 1735 1740

Thr Gln Pro Leu Tyr Arg Gly Glu Leu Asn Glu His Leu Gly Leu
1745 1750 1755

Leu Gly Pro Tyr Ile Arg Ala Glu Val Glu Asp Asn Ile Met Val
1760 1765 1770

```
Thr Phe  Arg Asn Gln Ala Ser  Arg Pro Tyr Ser Phe  Tyr Ser Ser
    1775                 1780                 1785

Leu Ile  Ser Tyr Glu Glu Asp  Gln Arg Gln Gly Ala  Glu Pro Arg
    1790                 1795                 1800

Lys Asn  Phe Val Lys Pro Asn  Glu Thr Lys Thr Tyr  Phe Trp Lys
    1805                 1810                 1815

Val Gln  His His Met Ala Pro  Thr Lys Asp Glu Phe  Asp Cys Lys
    1820                 1825                 1830

Ala Trp  Ala Tyr Phe Ser Asp  Val Asp Leu Glu Lys  Asp Val His
    1835                 1840                 1845

Ser Gly  Leu Ile Gly Pro Leu  Leu Val Cys His Thr  Asn Thr Leu
    1850                 1855                 1860

Asn Pro  Ala His Gly Arg Gln  Val Thr Val Gln Glu  Phe Ala Leu
    1865                 1870                 1875

Phe Phe  Thr Ile Phe Asp Glu  Thr Lys Ser Trp Tyr  Phe Thr Glu
    1880                 1885                 1890

Asn Met  Glu Arg Asn Cys Arg  Ala Pro Cys Asn Ile  Gln Met Glu
    1895                 1900                 1905

Asp Pro  Thr Phe Lys Glu Asn  Tyr Arg Phe His Ala  Ile Asn Gly
    1910                 1915                 1920

Tyr Ile  Met Asp Thr Leu Pro  Gly Leu Val Met Ala  Gln Asp Gln
    1925                 1930                 1935

Arg Ile  Arg Trp Tyr Leu Leu  Ser Met Gly Ser Asn  Glu Asn Ile
    1940                 1945                 1950

His Ser  Ile His Phe Ser Gly  His Val Phe Thr Val  Arg Lys Lys
    1955                 1960                 1965

Glu Glu  Tyr Lys Met Ala Leu  Tyr Asn Leu Tyr Pro  Gly Val Phe
    1970                 1975                 1980

Glu Thr  Val Glu Met Leu Pro  Ser Lys Ala Gly Ile  Trp Arg Val
    1985                 1990                 1995

Glu Cys  Leu Ile Gly Glu His  Leu His Ala Gly Met  Ser Thr Leu
    2000                 2005                 2010

Phe Leu  Val Tyr Ser Asn Lys  Cys Gln Thr Pro Leu  Gly Met Ala
    2015                 2020                 2025

Ser Gly  His Ile Arg Asp Phe  Gln Ile Thr Ala Ser  Gly Gln Tyr
    2030                 2035                 2040

Gly Gln  Trp Ala Pro Lys Leu  Ala Arg Leu His Tyr  Ser Gly Ser
    2045                 2050                 2055

Ile Asn  Ala Trp Ser Thr Lys  Glu Pro Phe Ser Trp  Ile Lys Val
    2060                 2065                 2070

Asp Leu  Leu Ala Pro Met Ile  Ile His Gly Ile Lys  Thr Gln Gly
    2075                 2080                 2085

Ala Arg  Gln Lys Phe Ser Ser  Leu Tyr Ile Ser Gln  Phe Ile Ile
    2090                 2095                 2100

Met Tyr  Ser Leu Asp Gly Lys  Lys Trp Gln Thr Tyr  Arg Gly Asn
    2105                 2110                 2115

Ser Thr  Gly Thr Leu Met Val  Phe Phe Gly Asn Val  Asp Ser Ser
    2120                 2125                 2130

Gly Ile  Lys His Asn Ile Phe  Asn Pro Pro Ile Ile  Ala Arg Tyr
    2135                 2140                 2145

Ile Arg  Leu His Pro Thr His  Tyr Ser Ile Arg Ser  Thr Leu Arg
    2150                 2155                 2160
```

Met Glu Leu Met Gly Cys Asp Leu Asn Ser Cys Ser Met Pro Leu
2165 2170 2175

Gly Met Glu Ser Lys Ala Ile Ser Asp Ala Gln Ile Thr Ala Ser
2180 2185 2190

Ser Tyr Phe Thr Asn Met Phe Ala Thr Trp Ser Pro Ser Lys Ala
2195 2200 2205

Arg Leu His Leu Gln Gly Arg Ser Asn Ala Trp Arg Pro Gln Val
2210 2215 2220

Asn Asn Pro Lys Glu Trp Leu Gln Val Asp Phe Gln Lys Thr Met
2225 2230 2235

Lys Val Thr Gly Val Thr Thr Gln Gly Val Lys Ser Leu Leu Thr
2240 2245 2250

Ser Met Tyr Val Lys Glu Phe Leu Ile Ser Ser Ser Gln Asp Gly
2255 2260 2265

His Gln Trp Thr Leu Phe Phe Gln Asn Gly Lys Val Lys Val Phe
2270 2275 2280

Gln Gly Asn Gln Asp Ser Phe Thr Pro Val Val Asn Ser Leu Asp
2285 2290 2295

Pro Pro Leu Leu Thr Arg Tyr Leu Arg Ile His Pro Gln Ser Trp
2300 2305 2310

Val His Gln Ile Ala Leu Arg Met Glu Val Leu Gly Cys Glu Ala
2315 2320 2325

Gln Asp Leu Tyr
2330

<210> SEQ ID NO 160
<211> LENGTH: 1245
<212> TYPE: DNA
<213> ORGANISM: Homo sapiens

<400> SEQUENCE: 160
tataattcag gtaaattgga agagtttgtt caagggaacc ttgagagaga atgtatggaa 60
gaaaagtgta gttttgaaga agcacgagaa gtttttgaaa acactgaaag aacaactgaa 120
ttttggaagc agtatgttga tggagatcag tgtgagtcca atccatgttt aaatggcggc 180
agttgcaagg atgacattaa ttcctatgaa tgttggtgtc cctttggatt tgaaggaaag 240
aactgtgaat tagatgtaac atgtaacatt aagaatggca gatgcgagca gttttgtaaa 300
aatagtgctg ataacaaggt ggtttgctcc tgtactgagg gatatcgact tgcagaaaac 360
cagaagtcct gtgaaccagc agtgccattt ccatgtggaa gagtttctgt ttcacaaact 420
tctaagctca cccgtgctga ggctgttttt cctgatgtgg actatgtaaa ttctactgaa 480
gctgaaacca ttttggataa catcactcaa agcacccaat catttaatga cttcactcgg 540
gttgttggtg gagaagatgc caaaccaggt caattccctt ggcaggttgt tttgaatggt 600
aaagttgatg cattctgtgg aggctctatc gttaatgaaa aatggattgt aactgctgcc 660
cactgtgttg aaactggtgt taaaattaca gttgtcgcag gtgaacataa tattgaggag 720
acagaacata cagagcaaaa gcgaaatgtg attcgaatta ttcctcacca caactacaat 780
gcagctatta ataagtacaa ccatgacatt gcccttctgg aactggacga accettagtg 840 ctaaacagct acgttacacc tatttgcatt gctgacaagg aatacacgaa catcttcctc 900
aaatttggat ctggctatgt aagtggctgg ggaagagtct tccacaaagg gagatcagct 960
ttagttcttc agtaccttag agttccactt gttgaccgag ccacatgtct tcgatctaca 1020
aagttcacca tctataacaa catgttctgt gctggcttcc atgaaggagg tagagattca 1080

```
tgtcaaggag atagtggggg accccatgtt actgaagtgg aagggaccag tttcttaact   1140

ggaattatta gctggggtga agagtgtgca atgaaaggca aatatggaat atataccaag   1200

gtatcccggt atgtcaactg gattaaggaa aaaacaaagc tcact                   1245


<210> SEQ ID NO 161
<211> LENGTH: 415
<212> TYPE: PRT
<213> ORGANISM: Homo sapiens

<400> SEQUENCE: 161

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Ala Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Glu Pro Leu Val Leu Asn Ser Tyr Val Thr Pro Ile
        275                 280                 285

Cys Ile Ala Asp Lys Glu Tyr Thr Asn Ile Phe Leu Lys Phe Gly Ser
    290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
```

340 345 350

Phe His Glu Gly Gly Arg Asp Ser Cys Gln Gly Asp Ser Gly Gly Pro
355 360 365

His Val Thr Glu Val Glu Gly Thr Ser Phe Leu Thr Gly Ile Ile Ser
370 375 380

Trp Gly Glu Glu Cys Ala Met Lys Gly Lys Tyr Gly Ile Tyr Thr Lys
385 390 395 400

Val Ser Arg Tyr Val Asn Trp Ile Lys Glu Lys Thr Lys Leu Thr
405 410 415

<210> SEQ ID NO 162
<211> LENGTH: 1344
<212> TYPE: DNA
<213> ORGANISM: Homo sapiens

<400> SEQUENCE: 162
gcgaacagct ttctggaaga aatgaaaaaa ggccatctgg aacgcgaatg catggaagaa 60
acctgcagct atgaagaagc gcgcgaagtg tttgaagata gcgataaaac caacgaattt 120
tggaacaaat ataaagatgg cgatcagtgc gaaaccagcc cgtgccagaa ccagggcaaa 180
tgcaaagatg gcctgggcga atatacctgc acctgcctgg aaggctttga aggcaaaaac 240
tgcgaactgt ttacccgcaa actgtgcagc ctggataacg gcgattgcga tcagttttgc 300
catgaagaac agaacagcgt ggtgtgcagc tgcgcgcgcg gctataccct ggcggataac 360
ggcaaagcgt gcattccgac cggcccgtat ccgtgcggca aacagaccct ggaacgccgc 420
aaacgcagcg tggcgcaggc gaccagcagc agcggcgaag cgccggatag cattacctgg 480
aaaccgtatg atgcggcgga tctggatccg accgaaaacc cgtttgatct gctggatttt 540
aaccagaccc agccggaacg cggcgataac aacctgaccc gcattgtggg cggccaggaa 600
tgcaaagatg gcgaatgccc gtggcaggcg ctgctgatta acgaagaaaa cgaaggcttt 660
tgcggcggca ccattctgag cgaattttat attctgaccg cggcgcattg cctgtatcag 720
gcgaaacgct ttaaagtgcg cgtgggcgat cgcaacaccg aacaggaaga aggcggcgaa 780
gcggtgcatg aagtggaagt ggtgattaaa cataaccgct ttaccaaaga aacctatgat 840
tttgatattg cggtgctgcg cctgaaaacc ccgattacct ttcgcatgaa cgtggcgccg 900
gcgtgcctgc cggaacgcga ttgggcggaa agcaccctga tgacccagaa aaccggcatt 960
gtgagcggct ttggccgcac ccatgaaaaa ggccgccaga gcacccgcct gaaaatgctg 1020
gaagtgccgt atgtggatcg caacagctgc aaactgagca gcagctttat tattacccag 1080
aacatgtttt gcgcgggcta tgataccaaa caggaagatg cgtgccaggg cgatagcggc 1140
ggcccgcatg tgacccgctt taaagatacc tattttgtga ccggcattgt gagctggggc 1200
gaaggctgcg cgcgcaaagg caaatatggc atttatacca aagtgaccgc gtttctgaaa 1260
tggattgatc gcagcatgaa aacccgcggc ctgccgaaag cgaaaagcca tgcgccggaa 1320
gtgattacca gcagcccgct gaaa 1344

<210> SEQ ID NO 163
<211> LENGTH: 448
<212> TYPE: PRT
<213> ORGANISM: Homo sapiens

<400> SEQUENCE: 163

Ala Asn Ser Phe Leu Glu Glu Met Lys Lys Gly His Leu Glu Arg Glu
1 5 10 15

-continued

```
Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
    130                 135                 140

Ala Gln Ala Thr Ser Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Asp Asn Asn Leu
            180                 185                 190

Thr Arg Ile Val Gly Gly Gln Glu Cys Lys Asp Gly Glu Cys Pro Trp
        195                 200                 205

Gln Ala Leu Leu Ile Asn Glu Glu Asn Glu Gly Phe Cys Gly Gly Thr
    210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
            260                 265                 270

Arg Phe Thr Lys Glu Thr Tyr Asp Phe Asp Ile Ala Val Leu Arg Leu
        275                 280                 285

Lys Thr Pro Ile Thr Phe Arg Met Asn Val Ala Pro Ala Cys Leu Pro
    290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
            340                 345                 350

Ser Ser Ser Phe Ile Ile Thr Gln Asn Met Phe Cys Ala Gly Tyr Asp
        355                 360                 365

Thr Lys Gln Glu Asp Ala Cys Gln Gly Asp Ser Gly Gly Pro His Val
    370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
            420                 425                 430

Lys Ala Lys Ser His Ala Pro Glu Val Ile Thr Ser Ser Pro Leu Lys
```

435 440 445

<210> SEQ ID NO 164
<211> LENGTH: 1821
<212> TYPE: DNA
<213> ORGANISM: Homo sapiens

<400> SEQUENCE: 164
gaatgcgtga cccagctgct gaaagatacc tgctttgaag gcggcgatat taccaccgtg 60
tttaccccga gcgcgaaata ttgccaggtg gtgtgcacct atcatccgcg ctgcctgctg 120
tttaccttta ccgcggaaag cccgagcgaa gatccgaccc gctggtttac ctgcgtgctg 180
aaagatagcg tgaccgaaac cctgccgcgc gtgaaccgca ccgcggcgat tagcggctat 240
agctttaaac agtgcagcca tcagattagc gcgtgcaaca aagatattta tgtggatctg 300
gatatgaaag gcattaacta taacagcagc gtggcgaaaa gcgcgcagga atgccaggaa 360
cgctgcaccg atgatgtgca ttgccatttt tttacctatg cgacccgcca gtttccgagc 420
ctggaacatc gcaacatttg cctgctgaaa catacccaga ccggcacccc gacccgcatt 480
accaaactgg ataaagtggt gagcggcttt agcctgaaaa gctgcgcgct gagcaacctg 540
gcgtgcattc gcgatatttt tccgaacacc gtgtttgcgg atagcaacat tgatagcgtg 600
atggcgccgg atgcgtttgt gtgcggccgc atttgcaccc atcatccggg ctgcctgttt 660
tttacctttt ttagccagga atggccgaaa gaaagccagc gcaacctgtg cctgctgaaa 720
accagcgaaa gcggcctgcc gagcacccgc attaaaaaaa gcaaagcgct gagcggcttt 780
agcctgcaga gctgccgcca tagcattccg gtgttttgcc atagcagctt ttatcatgat 840
accgattttc tgggcgaaga actggatatt gtggcggcga aaagccatga agcgtgccag 900
aaactgtgca ccaacgcggt gcgctgccag tttttttacct ataccccggc gcaggcgagc 960
tgcaacgaag gcaaaggcaa atgctatctg aaactgagca gcaacggcag cccgaccaaa 1020
attctgcatg gccgcggcgg cattagcggc tataccctgc gcctgtgcaa aatggataac 1080
gaatgcacca ccaaaattaa accgcgcatt gtgggcggca ccgcgagcgt gcgcggcgaa 1140
tggccgtggc aggtgaccct gcataccacc agcccgaccc agcgccatct gtgcggcggc 1200
agcattattg gcaaccagtg gattctgacc gcggcgcatt gcttttatgg cgtggaaagc 1260
ccgaaaattc tgcgcgtgta tagcggcatt ctgaaccaga gcgaaattaa agaagatacc 1320
agcttttttg gcgtgcagga aattattatt catgatcagt ataaaatggc ggaaagcggc 1380
tatgatattg cgctgctgaa actggaaacc accgtgaact ataccgatag ccagcgcccg 1440
atttgcctgc cgagcaaagg cgatcgcaac gtgatttata ccgattgctg ggtgaccggc 1500
tggggctatc gcaaactgcg cgataaaatt cagaacaccc tgcagaaagc gaaaattccg 1560
ctggtgacca acgaagaatg ccagaaacgc tatcgcggcc ataaaattac ccataaaatg 1620
atttgcgcgg gctatcgcga aggcggcaaa gatgcgtgca aaggcgatag cggcggcccg 1680
ctgagctgca aacataacga agtgtggcat ctggtgggca ttaccagctg gggcgaaggc 1740
tgcgcgcagc gcgaacgccc gggcgtgtat accaacgtgg tggaatatgt ggattggatt 1800
ctggaaaaaa cccaggcggt g 1821

<210> SEQ ID NO 165
<211> LENGTH: 607
<212> TYPE: PRT
<213> ORGANISM: Homo sapiens

<400> SEQUENCE: 165

-continued

```
Glu Cys Val Thr Gln Leu Leu Lys Asp Thr Cys Phe Glu Gly Gly Asp
1               5                   10                  15

Ile Thr Thr Val Phe Thr Pro Ser Ala Lys Tyr Cys Gln Val Val Cys
            20                  25                  30

Thr Tyr His Pro Arg Cys Leu Leu Phe Thr Phe Thr Ala Glu Ser Pro
        35                  40                  45

Ser Glu Asp Pro Thr Arg Trp Phe Thr Cys Val Leu Lys Asp Ser Val
    50                  55                  60

Thr Glu Thr Leu Pro Arg Val Asn Arg Thr Ala Ala Ile Ser Gly Tyr
65                  70                  75                  80

Ser Phe Lys Gln Cys Ser His Gln Ile Ser Ala Cys Asn Lys Asp Ile
                85                  90                  95

Tyr Val Asp Leu Asp Met Lys Gly Ile Asn Tyr Asn Ser Ser Val Ala
            100                 105                 110

Lys Ser Ala Gln Glu Cys Gln Glu Arg Cys Thr Asp Asp Val His Cys
        115                 120                 125

His Phe Phe Thr Tyr Ala Thr Arg Gln Phe Pro Ser Leu Glu His Arg
    130                 135                 140

Asn Ile Cys Leu Leu Lys His Thr Gln Thr Gly Thr Pro Thr Arg Ile
145                 150                 155                 160

Thr Lys Leu Asp Lys Val Val Ser Gly Phe Ser Leu Lys Ser Cys Ala
                165                 170                 175

Leu Ser Asn Leu Ala Cys Ile Arg Asp Ile Phe Pro Asn Thr Val Phe
            180                 185                 190

Ala Asp Ser Asn Ile Asp Ser Val Met Ala Pro Asp Ala Phe Val Cys
        195                 200                 205

Gly Arg Ile Cys Thr His His Pro Gly Cys Leu Phe Phe Thr Phe Phe
    210                 215                 220

Ser Gln Glu Trp Pro Lys Glu Ser Gln Arg Asn Leu Cys Leu Leu Lys
225                 230                 235                 240

Thr Ser Glu Ser Gly Leu Pro Ser Thr Arg Ile Lys Lys Ser Lys Ala
                245                 250                 255

Leu Ser Gly Phe Ser Leu Gln Ser Cys Arg His Ser Ile Pro Val Phe
            260                 265                 270

Cys His Ser Ser Phe Tyr His Asp Thr Asp Phe Leu Gly Glu Glu Leu
        275                 280                 285

Asp Ile Val Ala Ala Lys Ser His Glu Ala Cys Gln Lys Leu Cys Thr
    290                 295                 300

Asn Ala Val Arg Cys Gln Phe Phe Thr Tyr Thr Pro Ala Gln Ala Ser
305                 310                 315                 320

Cys Asn Glu Gly Lys Gly Lys Cys Tyr Leu Lys Leu Ser Ser Asn Gly
                325                 330                 335

Ser Pro Thr Lys Ile Leu His Gly Arg Gly Gly Ile Ser Gly Tyr Thr
            340                 345                 350

Leu Arg Leu Cys Lys Met Asp Asn Glu Cys Thr Thr Lys Ile Lys Pro
        355                 360                 365

Arg Ile Val Gly Gly Thr Ala Ser Val Arg Gly Glu Trp Pro Trp Gln
    370                 375                 380

Val Thr Leu His Thr Thr Ser Pro Thr Gln Arg His Leu Cys Gly Gly
385                 390                 395                 400

Ser Ile Ile Gly Asn Gln Trp Ile Leu Thr Ala Ala His Cys Phe Tyr
                405                 410                 415
```

```
Gly Val Glu Ser Pro Lys Ile Leu Arg Val Tyr Ser Gly Ile Leu Asn
            420                 425                 430

Gln Ser Glu Ile Lys Glu Asp Thr Ser Phe Phe Gly Val Gln Glu Ile
        435                 440                 445

Ile Ile His Asp Gln Tyr Lys Met Ala Glu Ser Gly Tyr Asp Ile Ala
    450                 455                 460

Leu Leu Lys Leu Glu Thr Thr Val Asn Tyr Thr Asp Ser Gln Arg Pro
465                 470                 475                 480

Ile Cys Leu Pro Ser Lys Gly Asp Arg Asn Val Ile Tyr Thr Asp Cys
                485                 490                 495

Trp Val Thr Gly Trp Gly Tyr Arg Lys Leu Arg Asp Lys Ile Gln Asn
            500                 505                 510

Thr Leu Gln Lys Ala Lys Ile Pro Leu Val Thr Asn Glu Glu Cys Gln
        515                 520                 525

Lys Arg Tyr Arg Gly His Lys Ile Thr His Lys Met Ile Cys Ala Gly
    530                 535                 540

Tyr Arg Glu Gly Gly Lys Asp Ala Cys Lys Gly Asp Ser Gly Gly Pro
545                 550                 555                 560

Leu Ser Cys Lys His Asn Glu Val Trp His Leu Val Gly Ile Thr Ser
                565                 570                 575

Trp Gly Glu Gly Cys Ala Gln Arg Glu Arg Pro Gly Val Tyr Thr Asn
            580                 585                 590

Val Val Glu Tyr Val Asp Trp Ile Leu Glu Lys Thr Gln Ala Val
        595                 600                 605
```

```
<210> SEQ ID NO 166
<211> LENGTH: 750
<212> TYPE: DNA
<213> ORGANISM: Artificial sequence
<220> FEATURE:
<223> OTHER INFORMATION: 0012LC.C36A-HPC4

<400> SEQUENCE: 166

atgaagttgc ctgttgggct gttggtgctg atgttctgga ttccagcttc cagcagtgat     60

gttgtgatga cccaaactcc actctccctg cctgtcagtc ttggagatca agcctccatc    120

tcttgcagat ctagtcagag ccttgtacac agaaatggaa acacctattt tcattgggcc    180

ctgcagaaac caggccagtc tccaaagctc ctgatctaca aagtttccaa ccgattttct    240

ggggtcccag acaggttcag tggcagtgga tcagggacag atttcacact caagatcagc    300

agagtggagg ctgaggatct gggagtttat ttctgctctc aaagtacaca tgttccgtac    360

acgttcggag gggggaccaa gctggaaata aaacgtacgg tggctgcacc atctgtcttc    420

atcttcccgc catctgatga gcagttgaaa tctggaactg cctctgttgt gtgcctgctg    480

aataacttct atcccagaga ggccaaagta cagtggaagg tggataacgc cctccaatcg    540

ggtaactccc aggagagtgt cacagagcag gacagcaagg acagcaccta cagcctcagc    600

agcaccctga cgctgagcaa agcagactac gagaaacaca aagtctacgc ctgcgaagtc    660

acccatcagg gcctgagctc gcccgtcaca aagagcttca acaggggaga gtgtgaggac    720

caggtggacc ccagactgat cgacggcaag                                     750

<210> SEQ ID NO 167
<211> LENGTH: 250
<212> TYPE: PRT
<213> ORGANISM: Artificial sequence
<220> FEATURE:
<223> OTHER INFORMATION: 0012LC.C36A-HPC4
```

<400> SEQUENCE: 167

```
Met Lys Leu Pro Val Gly Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Arg Asn Gly Asn Thr Tyr Phe His Trp Ala Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Tyr Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys Glu Asp
225                 230                 235                 240

Gln Val Asp Pro Arg Leu Ile Asp Gly Lys
                245                 250
```

<210> SEQ ID NO 168
<211> LENGTH: 735
<212> TYPE: DNA
<213> ORGANISM: Artificial sequence
<220> FEATURE:
<223> OTHER INFORMATION: 0012VH-CH1-HPC4

<400> SEQUENCE: 168

```
atggatttg ggctgatttt ttttattgtt gctcttttaa aaggggtcca gtgtgaggtg      60

aaacttctcg agtctggagg tggcctggtg cagcctggag gatccctgaa actctcctgt     120

gcagcctcag gattcgattt tagtagatac tggatgactt gggtccggca ggctccaggg     180

aaagggctag aatggattgg agaaattaat ccagatagca gtacgataaa ctatacgcca     240

tctctaaagg ataaattcat catctccaga gacaacgcca agaatacgct gtacctgcaa     300

atgagcgaag tgagatctga ggacacagcc ctttattact gtgcaagcgg ggtgtttact     360

tcctggggcc aagggactct ggtcactgtc tctgcagcta gcaccaaggg cccatccgtc     420

ttccccctgg cgccctgctc caggagcacc tccgagagca cagccgccct gggctgcctg     480

gtcaaggact acttccccga accggtgacg gtgtcgtgga actcaggcgc cctgaccagc     540
```

ggcgtgcaca ccttcccggc tgtcctacag tcctcaggac tctactccct cagcagcgtg 600
gtgaccgtgc cctccagcag cttgggcacg aagacctaca cctgcaacgt agatcacaag 660
cccagcaaca ccaaggtgga caagagagtt gagtccaaag aggaccaggt ggaccccaga 720
ctgatcgacg gcaag 735

<210> SEQ ID NO 169
<211> LENGTH: 245
<212> TYPE: PRT
<213> ORGANISM: Artificial sequence
<220> FEATURE:
<223> OTHER INFORMATION: 0012VH-CH1-HPC4

<400> SEQUENCE: 169

Met Asp Phe Gly Leu Ile Phe Phe Ile Val Ala Leu Leu Lys Gly Val
1 5 10 15

Gln Cys Glu Val Lys Leu Leu Glu Ser Gly Gly Gly Leu Val Gln Pro
20 25 30

Gly Gly Ser Leu Lys Leu Ser Cys Ala Ala Ser Gly Phe Asp Phe Ser
35 40 45

Arg Tyr Trp Met Thr Trp Val Arg Gln Ala Pro Gly Lys Gly Leu Glu
50 55 60

Trp Ile Gly Glu Ile Asn Pro Asp Ser Ser Thr Ile Asn Tyr Thr Pro
65 70 75 80

Ser Leu Lys Asp Lys Phe Ile Ile Ser Arg Asp Asn Ala Lys Asn Thr
85 90 95

Leu Tyr Leu Gln Met Ser Glu Val Arg Ser Glu Asp Thr Ala Leu Tyr
100 105 110

Tyr Cys Ala Ser Gly Val Phe Thr Ser Trp Gly Gln Gly Thr Leu Val
115 120 125

Thr Val Ser Ala Ala Ser Thr Lys Gly Pro Ser Val Phe Pro Leu Ala
130 135 140

Pro Cys Ser Arg Ser Thr Ser Glu Ser Thr Ala Ala Leu Gly Cys Leu
145 150 155 160

Val Lys Asp Tyr Phe Pro Glu Pro Val Thr Val Ser Trp Asn Ser Gly
165 170 175

Ala Leu Thr Ser Gly Val His Thr Phe Pro Ala Val Leu Gln Ser Ser
180 185 190

Gly Leu Tyr Ser Leu Ser Ser Val Val Thr Val Pro Ser Ser Ser Leu
195 200 205

Gly Thr Lys Thr Tyr Thr Cys Asn Val Asp His Lys Pro Ser Asn Thr
210 215 220

Lys Val Asp Lys Arg Val Glu Ser Lys Glu Asp Gln Val Asp Pro Arg
225 230 235 240

Leu Ile Asp Gly Lys
245

<210> SEQ ID NO 170
<211> LENGTH: 714
<212> TYPE: DNA
<213> ORGANISM: Artificial sequence
<220> FEATURE:
<223> OTHER INFORMATION: 0012VH.T60N-CH1-YGPPC

<400> SEQUENCE: 170
atggattttg ggctgatttt ttttattgtt gctcttttaa aaggggtcca gtgtgaggtg 60
aaacttctcg agtctggagg tggcctggtg cagcctggag gatccctgaa actctcctgt 120

```
gcagcctcag gattcgattt tagtagatac tggatgactt gggtccggca ggctccaggg    180

aaagggctag aatggattgg agaaattaat ccagatagca gtacgataaa ctataaccca    240

tctctaaagg ataaattcat catctccaga gacaacgcca agaatacgct gtacctgcaa    300

atgagcgaag tgagatctga ggacacagcc ctttattact gtgcaagcgg ggtgtttact    360

tcctggggcc aagggactct ggtcactgtc tctgcagcta gcaccaaggg cccatccgtc    420

ttcccectgg cgccctgctc caggagcacc tccgagagca cagccgccct gggctgcctg    480

gtcaaggact acttccccga accggtgacg gtgtcgtgga actcaggcgc cctgaccagc    540

ggcgtgcaca ccttcccggc tgtcctacag tcctcaggac tctactccct cagcagcgtg    600

gtgaccgtgc cctccagcag cttgggcacg aagacctaca cctgcaacgt agatcacaag    660

cccagcaaca ccaaggtgga caagagagtt gagtccaaat atggtccccc atgc          714
```

<210> SEQ ID NO 171
<211> LENGTH: 238
<212> TYPE: PRT
<213> ORGANISM: Artificial Sequence
<220> FEATURE:
<223> OTHER INFORMATION: 0012VH.T60N-CH1-YGPPC

<400> SEQUENCE: 171

```
Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
        35                  40                  45

Arg Tyr Trp Met Thr Trp Val Arg Gln Ala Pro Gly Lys Gly Leu Glu
    50                  55                  60

Trp Ile Gly Glu Ile Asn Pro Asp Ser Ser Thr Ile Asn Tyr Asn Pro
65                  70                  75                  80

Ser Leu Lys Asp Lys Phe Ile Ile Ser Arg Asp Asn Ala Lys Asn Thr
                85                  90                  95

Leu Tyr Leu Gln Met Ser Glu Val Arg Ser Glu Asp Thr Ala Leu Tyr
            100                 105                 110

Tyr Cys Ala Ser Gly Val Phe Thr Ser Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220

Lys Val Asp Lys Arg Val Glu Ser Lys Tyr Gly Pro Pro Cys
225                 230                 235
```

<210> SEQ ID NO 172
<211> LENGTH: 2091

```
<212> TYPE: DNA
<213> ORGANISM: Artificial Sequence
<220> FEATURE:
<223> OTHER INFORMATION: FIX-L4b-0012LC

<400> SEQUENCE: 172

atgcagcgcg tgaacatgat catggcagaa tcaccaggcc tcatcaccat ctgcctttta     60

ggatatctac tcagtgctga atgtacagtt tttcttgatc atgaaaacgc caacaaaatt    120

ctgaatcggc caaagaggta taattcaggt aaattggaag agtttgttca agggaacctt    180

gagagagaat gtatggaaga aaagtgtagt tttgaagaag cacgagaagt tttgaaaac     240

actgaaagaa caactgaatt ttggaagcag tatgttgatg gagatcagtg tgagtccaat    300

ccatgtttaa atggcggcag ttgcaaggat gacattaatt cctatgaatg ttggtgtccc    360

tttggatttg aaggaaagaa ctgtgaatta gatgtaacat gtaacattaa gaatggcaga    420

tgcgagcagt tttgtaaaaa tagtgctgat aacaaggtgg tttgctcctg tactgaggga    480

tatcgacttg cagaaaacca gaagtcctgt gaaccagcag tgccatttcc atgtggaaga    540

gtttctgttt cacaaacttc taagctcacc cgtgctgagg ctgtttttcc tgatgtggac    600

tatgtaaatt ctactgaagc tgaaaccatt ttggataaca tcactcaaag cacccaatca    660

tttaatgact tcactcgggt tgttggtgga gaagatgcca aaccaggtca attcccttgg    720

caggttgttt tgaatggtaa agttgatgca ttctgtggag gctctatcgt taatgaaaaa    780

tggattgtaa ctgctgccca ctgtgttgaa actggtgtta aaattacagt tgtcgcaggt    840

gaacataata ttgaggagac agaacataca gagcaaaagc gaaatgtgat tcgaattatt    900

cctcaccaca actacaatgc agctattaat aagtacaacc atgacattgc ccttctggaa    960

ctggacgaac ccttagtgct aaacagctac gttacaccta tttgcattgc tgacaaggaa   1020

tacacgaaca tcttcctcaa atttggatct ggctatgtaa gtggctgggg aagagtcttc   1080

cacaaaggga gatcagcttt agttcttcag taccttagag ttccacttgt tgaccgagcc   1140

acatgtcttc gatctacaaa gttcaccatc tataacaaca tgttctgtgc tggcttccat   1200

gaaggaggta gagattcatg tcaaggagat agtgggggac cccatgttac tgaagtggaa   1260

gggaccagtt tcttaactgg aattattagc tggggtgaag agtgtgcaat gaaaggcaaa   1320

tatggaatat ataccaaggt atcccggtat gtcaactgga ttaaggaaaa aacaaagctc   1380

actggaggtg gcgggtctgg tggcggggga tcaggcgggg gaggttccgg atccgatgtt   1440

gtgatgaccc aaactccact ctccctgcct gtcagtcttg gagatcaagc ctccatctct   1500

tgcagatcta gtcagagcct tgtacacaga aatggaaaca cctattttca ttggtgcctg   1560

cagaaaccag gccagtctcc aaagctcctg atctacaaag tttccaaccg attttctggg   1620

gtcccagaca ggttcagtgg cagtggatca gggacagatt tcacactcaa gatcagcaga   1680

gtggaggctg aggatctggg agtttatttc tgctctcaaa gtacacatgt tccgtacacg   1740

ttcggagggg ggaccaagct ggaaataaaa cgtacggtgg ctgcaccatc tgtcttcatc   1800

ttcccgccat ctgatgagca gttgaaatct ggaactgcct ctgttgtgtg cctgctgaat   1860

aacttctatc ccagagaggc caaagtacag tggaaggtgg ataacgccct ccaatcgggt   1920

aactcccagg agagtgtcac agagcaggac agcaaggaca gcacctacag cctcagcagc   1980

accctgacgc tgagcaaagc agactacgag aaacacaaag tctacgcctg cgaagtcacc   2040

catcagggcc tgagctcgcc cgtcacaaag agcttcaaca ggggagagtg t            2091

<210> SEQ ID NO 173
```

```
<211> LENGTH: 697
<212> TYPE: PRT
<213> ORGANISM: Artificial Sequence
<220> FEATURE:
<223> OTHER INFORMATION: FIX-L4b-0012LC

<400> SEQUENCE: 173

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Ala Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380
```

```
Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr Gly Gly Gly
    450                 455                 460

Gly Ser Gly Gly Gly Gly Ser Gly Gly Gly Gly Ser Gly Ser Asp Val
465                 470                 475                 480

Val Met Thr Gln Thr Pro Leu Ser Leu Pro Val Ser Leu Gly Asp Gln
                485                 490                 495

Ala Ser Ile Ser Cys Arg Ser Ser Gln Ser Leu Val His Arg Asn Gly
            500                 505                 510

Asn Thr Tyr Phe His Trp Cys Leu Gln Lys Pro Gly Gln Ser Pro Lys
        515                 520                 525

Leu Leu Ile Tyr Lys Val Ser Asn Arg Phe Ser Gly Val Pro Asp Arg
    530                 535                 540

Phe Ser Gly Ser Gly Ser Gly Thr Asp Phe Thr Leu Lys Ile Ser Arg
545                 550                 555                 560

Val Glu Ala Glu Asp Leu Gly Val Tyr Phe Cys Ser Gln Ser Thr His
                565                 570                 575

Val Pro Tyr Thr Phe Gly Gly Gly Thr Lys Leu Glu Ile Lys Arg Thr
            580                 585                 590

Val Ala Ala Pro Ser Val Phe Ile Phe Pro Pro Ser Asp Glu Gln Leu
        595                 600                 605

Lys Ser Gly Thr Ala Ser Val Val Cys Leu Leu Asn Asn Phe Tyr Pro
    610                 615                 620

Arg Glu Ala Lys Val Gln Trp Lys Val Asp Asn Ala Leu Gln Ser Gly
625                 630                 635                 640

Asn Ser Gln Glu Ser Val Thr Glu Gln Asp Ser Lys Asp Ser Thr Tyr
                645                 650                 655

Ser Leu Ser Ser Thr Leu Thr Leu Ser Lys Ala Asp Tyr Glu Lys His
            660                 665                 670

Lys Val Tyr Ala Cys Glu Val Thr His Gln Gly Leu Ser Ser Pro Val
        675                 680                 685

Thr Lys Ser Phe Asn Arg Gly Glu Cys
    690                 695
```

<210> SEQ ID NO 174
<211> LENGTH: 246
<212> TYPE: PRT
<213> ORGANISM: Artificial Sequence
<220> FEATURE:
<223> OTHER INFORMATION: 0003Fab LC=0062LC-HPC4

<400> SEQUENCE: 174

```
Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45
```

```
Ile Ser Asn Tyr Leu Asn Trp Tyr Gln Gln Lys Pro Asp Gly Thr Val
    50                  55                  60

Lys Leu Leu Ile Phe Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Pro Glu Asp Ile Ala Thr Tyr Tyr Cys Gln Gln Asp Thr
            100                 105                 110

Lys Leu Pro Tyr Thr Phe Gly Gly Gly Thr Lys Leu Glu Met Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys Glu Asp Gln Val Asp Pro
225                 230                 235                 240

Arg Leu Ile Asp Gly Lys
                245
```

<210> SEQ ID NO 175
<211> LENGTH: 247
<212> TYPE: PRT
<213> ORGANISM: Artificial Sequence
<220> FEATURE:
<223> OTHER INFORMATION: 0003Fab VH-CH1-YGPPC=0062VH-CH1-YGPPC

<400> SEQUENCE: 175

```
Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Pro Met Lys
            20                  25                  30

Pro Gly Ala Ser Val Lys Ile Ser Cys Lys Ala Thr Gly Tyr Thr Phe
        35                  40                  45

Ser Ser His Trp Ile Glu Trp Ile Lys Gln Arg Pro Gly His Gly Leu
    50                  55                  60

Glu Trp Ile Gly Glu Ile Leu Pro Gly Ser Gly Asn Thr Asn Tyr Asn
65                  70                  75                  80

Glu Lys Phe Lys Gly Lys Ala Thr Phe Thr Ala Asp Thr Ser Ser Asn
                85                  90                  95

Thr Ala Tyr Met Gln Leu Ser Ser Leu Thr Ser Glu Asp Ser Ala Val
            100                 105                 110

Tyr Tyr Cys Ala Arg Gly Tyr Tyr Gly Leu Asn Tyr Asp Trp Tyr Phe
        115                 120                 125

Asp Val Trp Gly Ala Gly Thr Thr Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160
```

```
Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Lys Thr Tyr Thr Cys
    210                 215                 220

Asn Val Asp His Lys Pro Ser Asn Thr Lys Val Asp Lys Arg Val Glu
225                 230                 235                 240

Ser Lys Tyr Gly Pro Pro Cys
                245


<210> SEQ ID NO 176
<211> LENGTH: 246
<212> TYPE: PRT
<213> ORGANISM: Artificial Sequence
<220> FEATURE:
<223> OTHER INFORMATION: 0051VH-CH1-YGPPC (part of 0074Fab)

<400> SEQUENCE: 176

Met Gly Trp Ser Cys Ile Ile Phe Phe Leu Val Ala Thr Ala Thr Gly
1               5                   10                  15

Val His Ser Gln Val Gln Leu Glu Gln Ser Gly Ala Glu Leu Val Arg
            20                  25                  30

Pro Gly Val Ser Val Lys Ile Ser Cys Lys Gly Ser Gly Tyr Thr Phe
        35                  40                  45

Thr Asp Tyr Ser Met His Trp Val Lys Gln Ser His Ala Lys Ser Leu
    50                  55                  60

Glu Trp Ile Gly Val Ile Ser Thr Tyr Tyr Gly Asp Val Arg Tyr Asn
65                  70                  75                  80

Gln Lys Phe Lys Gly Lys Ala Thr Met Thr Val Asp Lys Ser Ser Ser
                85                  90                  95

Thr Ala Tyr Met Ala Leu Ala Arg Leu Thr Ser Glu Asp Ser Ala Ile
            100                 105                 110

Tyr Tyr Cys Ala Arg Ala Pro Met Ile Thr Thr Gly Ala Trp Phe Ala
        115                 120                 125

Tyr Trp Gly Gln Gly Thr Leu Val Thr Val Ser Ala Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys
                245


<210> SEQ ID NO 177
```

<211> LENGTH: 246
<212> TYPE: PRT
<213> ORGANISM: Artificial Sequence
<220> FEATURE:
<223> OTHER INFORMATION: 0051LC-HPC4 (part of 0074Fab)

<400> SEQUENCE: 177

```
Met Lys Ser Gln Thr Gln Val Phe Val Phe Leu Leu Leu Cys Val Ser
1               5                   10                  15

Gly Ala His Gly Ser Ile Val Met Thr Gln Thr Pro Lys Phe Leu Leu
            20                  25                  30

Val Ser Ala Gly Asp Arg Val Thr Ile Thr Cys Lys Ala Ser Gln Ser
        35                  40                  45

Val Ser Asn Asp Val Ala Trp Tyr Gln Gln Lys Pro Gly Gln Ser Pro
    50                  55                  60

Lys Leu Leu Ile Asn Tyr Ala Ser Ser Arg Tyr Thr Gly Ile Pro Asp
65                  70                  75                  80

Arg Phe Thr Gly Ser Gly Tyr Gly Thr Asp Phe Thr Phe Thr Ile Ser
                85                  90                  95

Thr Val Gln Ala Glu Asp Leu Ala Val Tyr Phe Cys Gln Gln Asp Tyr
            100                 105                 110

Ser Ser Pro Tyr Thr Phe Gly Gly Gly Thr Lys Leu Glu Ile Glu Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys Glu Asp Gln Val Asp Pro
225                 230                 235                 240

Arg Leu Ile Asp Gly Lys
                245
```

<210> SEQ ID NO 178
<211> LENGTH: 246
<212> TYPE: PRT
<213> ORGANISM: Artificial Sequence
<220> FEATURE:
<223> OTHER INFORMATION: 0023VH-CH1-YGPPC (part of 0004Fab)

<400> SEQUENCE: 178

```
Met Asn Leu Gly Leu Ser Leu Ile Phe Leu Val Leu Val Leu Lys Gly
1               5                   10                  15

Val Gln Cys Glu Val Arg Leu Val Glu Ser Gly Gly Gly Leu Val Gln
            20                  25                  30

Pro Gly Gly Ser Leu Lys Leu Ser Cys Ala Thr Ser Gly Phe Thr Phe
        35                  40                  45

Ser Asp Tyr Phe Met Tyr Trp Ile Arg Gln Thr Pro Glu Lys Arg Leu
    50                  55                  60

Glu Trp Val Ala Tyr Ile Ser Asn Gly Gly Asp Ser Ser Ser Tyr Pro
```

```
65                  70                  75                  80

Asp Thr Val Lys Gly Arg Phe Thr Ile Ser Arg Asp Asn Ala Lys Asn
                85                  90                  95

Thr Leu Tyr Leu Gln Met Ser Arg Leu Lys Ser Glu Asp Thr Ala Met
            100                 105                 110

Tyr Tyr Cys Ala Thr Asn Lys Asn Trp Asp Asp Tyr Tyr Asp Met Asp
        115                 120                 125

Tyr Trp Gly Gln Gly Thr Ser Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys
                245


<210> SEQ ID NO 179
<211> LENGTH: 251
<212> TYPE: PRT
<213> ORGANISM: Artificial Sequence
<220> FEATURE:
<223> OTHER INFORMATION: 0023LC-HPC4 (part of 0004Fab)

<400> SEQUENCE: 179

Met Asp Ser Gln Ala Gln Val Leu Ile Leu Leu Leu Leu Trp Val Ser
1               5                   10                  15

Gly Ser Cys Gly Asp Ile Val Val Ser Gln Ser Pro Ser Ser Leu Ala
            20                  25                  30

Val Ser Ala Gly Glu Lys Val Thr Met Ser Cys Lys Ser Ser Gln Ser
        35                  40                  45

Leu Leu Asn Ser Arg Thr Arg Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Lys Gln Ser Tyr Asn Leu Leu Thr Phe Gly Ala Gly Thr Lys
        115                 120                 125

Leu Glu Leu Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
```

-continued

```
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys Glu
225                 230                 235                 240

Asp Gln Val Asp Pro Arg Leu Ile Asp Gly Lys
                245                 250


<210> SEQ ID NO 180
<211> LENGTH: 696
<212> TYPE: PRT
<213> ORGANISM: Artificial Sequence
<220> FEATURE:
<223> OTHER INFORMATION: human FVII-L4b-0062VH-CH1-HPC4

<400> SEQUENCE: 180

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
```

```
    290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
        355                 360                 365

Gly Tyr Ser Asp Gly Ser Lys Asp Ser Cys Lys Gly Asp Ser Gly Gly
    370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro Gly Gly Gly Gly
        435                 440                 445

Ser Gly Gly Gly Gly Ser Gly Gly Gly Gly Ser Gly Ser Gln Val Gln
    450                 455                 460

Leu Gln Gln Ser Gly Ala Glu Pro Met Lys Pro Gly Ala Ser Val Lys
465                 470                 475                 480

Ile Ser Cys Lys Ala Thr Gly Tyr Thr Phe Ser Ser His Trp Ile Glu
                485                 490                 495

Trp Ile Lys Gln Arg Pro Gly His Gly Leu Glu Trp Ile Gly Glu Ile
            500                 505                 510

Leu Pro Gly Ser Gly Asn Thr Asn Tyr Asn Glu Lys Phe Lys Gly Lys
        515                 520                 525

Ala Thr Phe Thr Ala Asp Thr Ser Ser Asn Thr Ala Tyr Met Gln Leu
    530                 535                 540

Ser Ser Leu Thr Ser Glu Asp Ser Ala Val Tyr Tyr Cys Ala Arg Gly
545                 550                 555                 560

Tyr Tyr Gly Leu Asn Tyr Asp Trp Tyr Phe Asp Val Trp Gly Ala Gly
                565                 570                 575

Thr Thr Val Thr Val Ser Ser Ala Ser Thr Lys Gly Pro Ser Val Phe
            580                 585                 590

Pro Leu Ala Pro Cys Ser Arg Ser Thr Ser Glu Ser Thr Ala Ala Leu
        595                 600                 605

Gly Cys Leu Val Lys Asp Tyr Phe Pro Glu Pro Val Thr Val Ser Trp
    610                 615                 620

Asn Ser Gly Ala Leu Thr Ser Gly Val His Thr Phe Pro Ala Val Leu
625                 630                 635                 640

Gln Ser Ser Gly Leu Tyr Ser Leu Ser Ser Val Val Thr Val Pro Ser
                645                 650                 655

Ser Ser Leu Gly Thr Lys Thr Tyr Thr Cys Asn Val Asp His Lys Pro
            660                 665                 670

Ser Asn Thr Lys Val Asp Lys Arg Val Glu Ser Lys Glu Asp Gln Val
        675                 680                 685

Asp Pro Arg Leu Ile Asp Gly Lys
    690                 695

<210> SEQ ID NO 181
```

<211> LENGTH: 407
<212> TYPE: PRT
<213> ORGANISM: Artificial Sequence
<220> FEATURE:
<223> OTHER INFORMATION: human FVII-407C (C-terminal cysteine)

<400> SEQUENCE: 181

```
Ala Asn Ala Phe Leu Glu Glu Leu Arg Pro Gly Ser Leu Glu Arg Glu
1               5                   10                  15

Cys Lys Glu Glu Gln Cys Ser Phe Glu Glu Ala Arg Glu Ile Phe Lys
            20                  25                  30

Asp Ala Glu Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
    130                 135                 140

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
        195                 200                 205

Gly Glu His Asp Leu Ser Glu His Asp Gly Asp Glu Gln Ser Arg Arg
    210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
            260                 265                 270

Leu Ala Phe Val Arg Phe Ser Leu Val Ser Gly Trp Gly Gln Leu Leu
        275                 280                 285

Asp Arg Gly Ala Thr Ala Leu Glu Leu Met Val Leu Asn Val Pro Arg
    290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
            340                 345                 350

Arg Gly Thr Trp Tyr Leu Thr Gly Ile Val Ser Trp Gly Gln Gly Cys
        355                 360                 365

Ala Thr Val Gly His Phe Gly Val Tyr Thr Arg Val Ser Gln Tyr Ile
    370                 375                 380
```

```
Glu Trp Leu Gln Lys Leu Met Arg Ser Glu Pro Arg Pro Gly Val Leu
385                 390                 395                 400

Leu Arg Ala Pro Phe Pro Cys
                405
```

<210> SEQ ID NO 182
<211> LENGTH: 697
<212> TYPE: PRT
<213> ORGANISM: Artificial Sequence
<220> FEATURE:
<223> OTHER INFORMATION: human FIX-L4b-0061LC

<400> SEQUENCE: 182

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Ala Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335
```

```
Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr Gly Gly Gly
    450                 455                 460

Gly Ser Gly Gly Gly Gly Ser Gly Gly Gly Gly Ser Gly Ser Asp Val
465                 470                 475                 480

Val Met Thr Gln Thr Pro Leu Ser Leu Pro Val Ser Leu Gly Asp Gln
                485                 490                 495

Ala Ser Ile Ser Cys Arg Ser Ser Gln Ser Leu Val His Arg Asn Gly
            500                 505                 510

Asn Thr Tyr Phe His Trp Ala Leu Gln Lys Pro Gly Gln Ser Pro Lys
        515                 520                 525

Leu Leu Ile Tyr Lys Val Ser Asn Arg Phe Ser Gly Val Pro Asp Arg
    530                 535                 540

Phe Ser Gly Ser Gly Ser Gly Thr Asp Phe Thr Leu Lys Ile Ser Arg
545                 550                 555                 560

Val Glu Ala Glu Asp Leu Gly Val Tyr Phe Cys Ser Gln Ser Thr His
                565                 570                 575

Val Pro Tyr Thr Phe Gly Gly Gly Thr Lys Leu Glu Ile Lys Arg Thr
            580                 585                 590

Val Ala Ala Pro Ser Val Phe Ile Phe Pro Pro Ser Asp Glu Gln Leu
        595                 600                 605

Lys Ser Gly Thr Ala Ser Val Val Cys Leu Leu Asn Asn Phe Tyr Pro
    610                 615                 620

Arg Glu Ala Lys Val Gln Trp Lys Val Asp Asn Ala Leu Gln Ser Gly
625                 630                 635                 640

Asn Ser Gln Glu Ser Val Thr Glu Gln Asp Ser Lys Asp Ser Thr Tyr
                645                 650                 655

Ser Leu Ser Ser Thr Leu Thr Leu Ser Lys Ala Asp Tyr Glu Lys His
            660                 665                 670

Lys Val Tyr Ala Cys Glu Val Thr His Gln Gly Leu Ser Ser Pro Val
        675                 680                 685

Thr Lys Ser Phe Asn Arg Gly Glu Cys
    690                 695
```

<210> SEQ ID NO 183
<211> LENGTH: 113
<212> TYPE: PRT
<213> ORGANISM: Artificial Sequence
<220> FEATURE:
<223> OTHER INFORMATION: Synthetic

<400> SEQUENCE: 183

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Arg
            20                  25                  30

Asn Gly Asn Thr Tyr Phe His Trp Cys Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

Arg


<210> SEQ ID NO 184
<211> LENGTH: 114
<212> TYPE: PRT
<213> ORGANISM: Artificial Sequence
<220> FEATURE:
<223> OTHER INFORMATION: Synthetic

<400> SEQUENCE: 184

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Thr Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Glu Val Arg Ser Glu Asp Thr Ala Leu Tyr Tyr Cys
                85                  90                  95

Ala Ser Gly Val Phe Thr Ser Trp Gly Gln Gly Thr Leu Val Thr Val
            100                 105                 110

Ser Ala


<210> SEQ ID NO 185
<211> LENGTH: 250
<212> TYPE: PRT
<213> ORGANISM: Artificial Sequence
<220> FEATURE:
<223> OTHER INFORMATION: Synthetic

<400> SEQUENCE: 185

Met Lys Leu Pro Val Gly Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Arg Asn Gly Asn Thr Tyr Phe His Trp Cys Leu Gln Lys Pro
    50                  55                  60
```

-continued

```
Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Tyr Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys Glu Asp
225                 230                 235                 240

Gln Val Asp Pro Arg Leu Ile Asp Gly Lys
                245                 250
```

<210> SEQ ID NO 186
<211> LENGTH: 750
<212> TYPE: DNA
<213> ORGANISM: Homo sapiens

<400> SEQUENCE: 186

```
atgaagttgc ctgttgggct gttggtgctg atgttctgga ttccagcttc cagcagtgat     60

gttgtgatga cccaaactcc actctccctg cctgtcagtc ttggagatca agcctccatc    120

tcttgcagat ctagtcagag ccttgtacac agaaatggaa acacctattt tcattggtgc    180

ctgcagaaac caggccagtc tccaaagctc ctgatctaca aagtttccaa ccgattttct    240

ggggtcccag acaggttcag tggcagtgga tcagggacag atttcacact caagatcagc    300

agagtggagg ctgaggatct gggagtttat ttctgctctc aaagtacaca tgttccgtac    360

acgttcggag gggggaccaa gctggaaata aaacgtacgg tggctgcacc atctgtcttc    420

atcttcccgc catctgatga gcagttgaaa tctggaactg cctctgttgt gtgcctgctg    480

aataacttct atcccagaga ggccaaagta cagtggaagg tggataacgc cctccaatcg    540

ggtaactccc aggagagtgt cacagagcag gacagcaagg acagcaccta cagcctcagc    600

agcaccctga cgctgagcaa agcagactac gagaaacaca aagtctacgc ctgcgaagtc    660

acccatcagg gcctgagctc gcccgtcaca aagagcttca acaggggaga gtgtgaggac    720

caggtggacc ccagactgat cgacggcaag                                      750
```

<210> SEQ ID NO 187
<211> LENGTH: 153
<212> TYPE: PRT
<213> ORGANISM: Artificial Sequence
<220> FEATURE:
<223> OTHER INFORMATION: Synthetic

<400> SEQUENCE: 187

-continued

```
Gln Gly Ile Val Gly Ser Leu Pro Glu Val Leu Gln Ala Pro Val Gly
1               5                   10                  15

Ser Ser Ile Leu Val Gln Cys His Tyr Arg Leu Gln Asp Val Lys Ala
            20                  25                  30

Gln Lys Val Trp Cys Arg Phe Leu Pro Glu Gly Cys Gln Pro Leu Val
        35                  40                  45

Ser Ser Ala Val Asp Arg Arg Ala Pro Ala Gly Arg Arg Thr Phe Leu
    50                  55                  60

Thr Asp Leu Gly Gly Gly Leu Leu Gln Val Glu Met Val Thr Leu Gln
65                  70                  75                  80

Glu Glu Asp Ala Gly Glu Tyr Gly Cys Met Val Asp Gly Ala Arg Gly
                85                  90                  95

Pro Gln Ile Leu His Arg Val Ser Leu Asn Ile Leu Pro Pro Glu Glu
            100                 105                 110

Glu Glu Glu Thr His Lys Ile Gly Ser Leu Ala Glu Asn Ala Phe Ser
        115                 120                 125

Asp Pro Ala Gly Ser Ala Asn Pro Leu Glu Pro Ser Gln Asp Glu Lys
    130                 135                 140

Ser Ile Pro His His His His His His
145                 150
```

<210> SEQ ID NO 188
<211> LENGTH: 37
<212> TYPE: PRT
<213> ORGANISM: Artificial Sequence
<220> FEATURE:
<223> OTHER INFORMATION: Synthetic

<400> SEQUENCE: 188

```
Glu Glu Glu Glu Glu Thr His Lys Ile Gly Ser Leu Ala Glu Asn Ala
1               5                   10                  15

Phe Ser Asp Pro Ala Gly Ser Ala Asn Pro Leu Glu Pro Ser Gln Asp
            20                  25                  30

Glu Lys Ser Ile Pro
        35
```

<210> SEQ ID NO 189
<211> LENGTH: 7
<212> TYPE: PRT
<213> ORGANISM: Artificial Sequence
<220> FEATURE:
<223> OTHER INFORMATION: Synthetic

<400> SEQUENCE: 189

```
Gly Ser Gly Gly Gly Gly Ser
1               5
```

<210> SEQ ID NO 190
<211> LENGTH: 12
<212> TYPE: PRT
<213> ORGANISM: Artificial Sequence
<220> FEATURE:
<223> OTHER INFORMATION: Synthetic

<400> SEQUENCE: 190

```
Gly Ser Gly Gly Gly Gly Ser Gly Gly Gly Gly Ser
1               5                   10
```

<210> SEQ ID NO 191
<211> LENGTH: 17

```
<212> TYPE: PRT
<213> ORGANISM: Artificial Sequence
<220> FEATURE:
<223> OTHER INFORMATION: Synthetic

<400> SEQUENCE: 191

Gly Ser Gly Gly Gly Gly Ser Gly Gly Gly Gly Ser Gly Gly Gly Gly
1               5                   10                  15

Ser


<210> SEQ ID NO 192
<211> LENGTH: 17
<212> TYPE: PRT
<213> ORGANISM: Artificial Sequence
<220> FEATURE:
<223> OTHER INFORMATION: Synthetic

<400> SEQUENCE: 192

Gly Gly Gly Gly Ser Gly Gly Gly Gly Ser Gly Gly Gly Gly Ser Gly
1               5                   10                  15

Ser


<210> SEQ ID NO 193
<211> LENGTH: 22
<212> TYPE: PRT
<213> ORGANISM: Artificial Sequence
<220> FEATURE:
<223> OTHER INFORMATION: Synthetic

<400> SEQUENCE: 193

Gly Gly Gly Gly Ser Gly Ser Gly Gly Gly Gly Ser Gly Gly Gly Gly
1               5                   10                  15

Ser Gly Gly Gly Gly Ser
            20


<210> SEQ ID NO 194
<211> LENGTH: 27
<212> TYPE: PRT
<213> ORGANISM: Artificial Sequence
<220> FEATURE:
<223> OTHER INFORMATION: Synthetic

<400> SEQUENCE: 194

Gly Gly Gly Gly Ser Gly Gly Gly Gly Ser Gly Ser Gly Gly Gly Gly
1               5                   10                  15

Ser Gly Gly Gly Gly Ser Gly Gly Gly Gly Ser
            20                  25


<210> SEQ ID NO 195
<211> LENGTH: 32
<212> TYPE: PRT
<213> ORGANISM: Artificial Sequence
<220> FEATURE:
<223> OTHER INFORMATION: Synthetic

<400> SEQUENCE: 195

Gly Gly Gly Gly Ser Gly Gly Gly Gly Ser Gly Gly Gly Gly Ser Gly
1               5                   10                  15

Ser Gly Gly Gly Gly Ser Gly Gly Gly Gly Ser Gly Gly Gly Gly Ser
            20                  25                  30


<210> SEQ ID NO 196
<211> LENGTH: 37
<212> TYPE: PRT
```

-continued

```
<213> ORGANISM: Artificial Sequence
<220> FEATURE:
<223> OTHER INFORMATION: Synthetic

<400> SEQUENCE: 196

Gly Gly Gly Gly Ser Gly Gly Gly Gly Ser Gly Gly Gly Gly Ser Gly
1               5                   10                  15

Gly Gly Gly Ser Gly Ser Gly Gly Gly Gly Ser Gly Gly Gly Gly Ser
            20                  25                  30

Gly Gly Gly Gly Ser
        35


<210> SEQ ID NO 197
<211> LENGTH: 42
<212> TYPE: PRT
<213> ORGANISM: Artificial Sequence
<220> FEATURE:
<223> OTHER INFORMATION: Synthetic

<400> SEQUENCE: 197

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Ser Gly Gly Gly Gly Ser
            20                  25                  30

Gly Gly Gly Gly Ser Gly Gly Gly Gly Ser
        35                  40


<210> SEQ ID NO 198
<211> LENGTH: 16
<212> TYPE: PRT
<213> ORGANISM: Artificial Sequence
<220> FEATURE:
<223> OTHER INFORMATION: Synthetic

<400> SEQUENCE: 198

Tyr Gly Pro Pro Ser Pro Ser Ser Pro Ala Pro Glu Phe Leu Gly Gly
1               5                   10                  15


<210> SEQ ID NO 199
<211> LENGTH: 27
<212> TYPE: DNA
<213> ORGANISM: Homo sapiens

<400> SEQUENCE: 199

actggatggt gggaagatgg atacagt                                         27


<210> SEQ ID NO 200
<211> LENGTH: 27
<212> TYPE: DNA
<213> ORGANISM: Homo sapiens

<400> SEQUENCE: 200

agatccaggg gctagcggat agacaga                                         27


<210> SEQ ID NO 201
<211> LENGTH: 30
<212> TYPE: DNA
<213> ORGANISM: Homo sapiens

<400> SEQUENCE: 201

cctgtaggac cagagggctc caaggacact                                      30


<210> SEQ ID NO 202
```

<211> LENGTH: 30
<212> TYPE: DNA
<213> ORGANISM: Homo sapiens

<400> SEQUENCE: 202
ggagctggtg gtggcatctc aggacctttg 30

<210> SEQ ID NO 203
<211> LENGTH: 48
<212> TYPE: DNA
<213> ORGANISM: Homo sapiens

<400> SEQUENCE: 203
tttaaaaagc ttgccgccac catggagacc cctgcctggc cccgggtc 48

<210> SEQ ID NO 204
<211> LENGTH: 75
<212> TYPE: DNA
<213> ORGANISM: Homo sapiens

<400> SEQUENCE: 204
ggaacctccc ccgcctgatc ccccgccacc agacccgcca cctccttctc taaattcccc 60
tttctcctgg cccat 75

<210> SEQ ID NO 205
<211> LENGTH: 48
<212> TYPE: DNA
<213> ORGANISM: Homo sapiens

<400> SEQUENCE: 205
gaatttagcg gccgcgaatt cggatccgga acctcccccg cctgatcc 48

<210> SEQ ID NO 206
<211> LENGTH: 81
<212> TYPE: DNA
<213> ORGANISM: Homo sapiens

<400> SEQUENCE: 206
aaatttgaat tcttacttgc cgtcgatcag tctggggtcc acctggtcct cacactctcc 60
cctgttgaag ctctttgtga c 81

<210> SEQ ID NO 207
<211> LENGTH: 30
<212> TYPE: DNA
<213> ORGANISM: Homo sapiens

<400> SEQUENCE: 207
acggatctct agcaagcttc gtacggtggc 30

<210> SEQ ID NO 208
<211> LENGTH: 81
<212> TYPE: DNA
<213> ORGANISM: Homo sapiens

<400> SEQUENCE: 208
aaatttgaat tcttacttgc cgtcgatcag tctggggtcc acctggtcct ctttggactc 60
aactctcttg tccaccttgg t 81

<210> SEQ ID NO 209
<211> LENGTH: 45
<212> TYPE: DNA
<213> ORGANISM: Homo sapiens

<400> SEQUENCE: 209
aaatttgaat tcttatttgg actcaactct cttgtccacc ttggt 45

<210> SEQ ID NO 210
<211> LENGTH: 30
<212> TYPE: DNA
<213> ORGANISM: Homo sapiens

<400> SEQUENCE: 210
acggatctct agcaagcttg ctagcaccaa 30

<210> SEQ ID NO 211
<211> LENGTH: 54
<212> TYPE: DNA
<213> ORGANISM: Homo sapiens

<400> SEQUENCE: 211
aaatttaagc ttgccgccac catggatttt gggctgattt tttttattgt tgct 54

<210> SEQ ID NO 212
<211> LENGTH: 45
<212> TYPE: DNA
<213> ORGANISM: Homo sapiens

<400> SEQUENCE: 212
aaatttgcta gctgcagaga cagtgaccag agtcccttgg cccca 45

<210> SEQ ID NO 213
<211> LENGTH: 51
<212> TYPE: DNA
<213> ORGANISM: Homo sapiens

<400> SEQUENCE: 213
aaatttaagc ttgccgccac catgaagtca cagacccagg tcttcgtatt t 51

<210> SEQ ID NO 214
<211> LENGTH: 51
<212> TYPE: DNA
<213> ORGANISM: Homo sapiens

<400> SEQUENCE: 214
aaatttaagc ttgccgccac catgaagttg cctgttgggc tgttggtgct g 51

<210> SEQ ID NO 215
<211> LENGTH: 38
<212> TYPE: DNA
<213> ORGANISM: Homo sapiens

<400> SEQUENCE: 215
aaatttcgta cgttctattt ccagcttggt cccccctc 38

<210> SEQ ID NO 216
<211> LENGTH: 42
<212> TYPE: DNA
<213> ORGANISM: Homo sapiens

<400> SEQUENCE: 216
aaatttcgta cgttttattt ccagcttggt cccccctccg aa 42

<210> SEQ ID NO 217
<211> LENGTH: 54
<212> TYPE: DNA

<213> ORGANISM: Homo sapiens

<400> SEQUENCE: 217
aaatttaagc ttgccgccac catgaacttg gggctcagct tgattttcct tgtc 54

<210> SEQ ID NO 218
<211> LENGTH: 42
<212> TYPE: DNA
<213> ORGANISM: Homo sapiens

<400> SEQUENCE: 218
aaatttgcta gctgaggaga cggtgactga ggttccttga cc 42

<210> SEQ ID NO 219
<211> LENGTH: 54
<212> TYPE: DNA
<213> ORGANISM: Homo sapiens

<400> SEQUENCE: 219
aaatttaagc ttgccgccac catggattca caggcccagg ttcttatatt gctg 54

<210> SEQ ID NO 220
<211> LENGTH: 42
<212> TYPE: DNA
<213> ORGANISM: Homo sapiens

<400> SEQUENCE: 220
aaatttcgta cgtttcagct ccagcttggt cccagcaccg aa 42

<210> SEQ ID NO 221
<211> LENGTH: 48
<212> TYPE: DNA
<213> ORGANISM: Homo sapiens

<400> SEQUENCE: 221
aaatttaaat ttggatccga tgttgtgatg acccaaactc cactctcc 48

<210> SEQ ID NO 222
<211> LENGTH: 54
<212> TYPE: DNA
<213> ORGANISM: Homo sapiens

<400> SEQUENCE: 222
aaatttaagc ttgccgccac catggatttt gggctgattt tttttattgt tgct 54

<210> SEQ ID NO 223
<211> LENGTH: 51
<212> TYPE: DNA
<213> ORGANISM: Homo sapiens

<400> SEQUENCE: 223
aaatttaagc ttgccgccac catgaacttg gggctcagct tgattttcct t 51

<210> SEQ ID NO 224
<211> LENGTH: 45
<212> TYPE: DNA
<213> ORGANISM: Homo sapiens

<400> SEQUENCE: 224
ggaaacacct attttcattg ggccctgcag aaaccaggcc agtct 45

<210> SEQ ID NO 225
<211> LENGTH: 45

<212> TYPE: DNA
<213> ORGANISM: Homo sapiens

<400> SEQUENCE: 225
agactggcct ggtttctgca gggcccaatg aaaataggtg tttcc 45

<210> SEQ ID NO 226
<211> LENGTH: 36
<212> TYPE: DNA
<213> ORGANISM: Homo sapiens

<400> SEQUENCE: 226
gctctagact aacactcatt cctgttgaag ctcttg 36

<210> SEQ ID NO 227
<211> LENGTH: 38
<212> TYPE: DNA
<213> ORGANISM: Homo sapiens

<400> SEQUENCE: 227
aaaaatctag aatagacaga tgggggtgtc gttttggc 38

<210> SEQ ID NO 228
<211> LENGTH: 34
<212> TYPE: DNA
<213> ORGANISM: Homo sapiens

<400> SEQUENCE: 228
aaaaatctag acttgaccag gcatcctaga gtca 34

<210> SEQ ID NO 229
<211> LENGTH: 35
<212> TYPE: DNA
<213> ORGANISM: Homo sapiens

<400> SEQUENCE: 229
aaaaatctag aaggggccag tggatagact gatgg 35

<210> SEQ ID NO 230
<211> LENGTH: 35
<212> TYPE: DNA
<213> ORGANISM: Homo sapiens

<400> SEQUENCE: 230
aaaaatctag aagggaccaa gggatagaca gatgg 35

<210> SEQ ID NO 231
<211> LENGTH: 50
<212> TYPE: DNA
<213> ORGANISM: Homo sapiens

<400> SEQUENCE: 231
aaatttaagc ttgccgccac catggaatgg acctgggtct ttctcttcct 50

<210> SEQ ID NO 232
<211> LENGTH: 39
<212> TYPE: DNA
<213> ORGANISM: Homo sapiens

<400> SEQUENCE: 232
aaatttgcta gctgaggaga cggtgaccgt ggtccctgc 39

<210> SEQ ID NO 233

<211> LENGTH: 48
<212> TYPE: DNA
<213> ORGANISM: Homo sapiens

<400> SEQUENCE: 233
aaatttaagc ttgccgccac catgatgtcc tctgctcagt tccttggt 48

<210> SEQ ID NO 234
<211> LENGTH: 39
<212> TYPE: DNA
<213> ORGANISM: Homo sapiens

<400> SEQUENCE: 234
aaatttcgta cgtttcatct ccagtttggt cccccctcc 39

<210> SEQ ID NO 235
<211> LENGTH: 50
<212> TYPE: DNA
<213> ORGANISM: Homo sapiens

<400> SEQUENCE: 235
aaatttaagc ttgccgccac catgggttgg agctgtatca tcttctttct 50

<210> SEQ ID NO 236
<211> LENGTH: 39
<212> TYPE: DNA
<213> ORGANISM: Homo sapiens

<400> SEQUENCE: 236
aaatttgcta gctgcagaga cagtgaccag agtcccttg 39

<210> SEQ ID NO 237
<211> LENGTH: 45
<212> TYPE: DNA
<213> ORGANISM: Homo sapiens

<400> SEQUENCE: 237
gatagcagta cgataaacta taacccatct ctaaaggata aattc 45

<210> SEQ ID NO 238
<211> LENGTH: 45
<212> TYPE: DNA
<213> ORGANISM: Homo sapiens

<400> SEQUENCE: 238
gaatttatcc tttagagatg ggttatagtt tatcgtactg ctatc 45

<210> SEQ ID NO 239
<211> LENGTH: 45
<212> TYPE: DNA
<213> ORGANISM: Homo sapiens

<400> SEQUENCE: 239
tctgaggact ctgccgtcta ttactgtgca agagggtact acggt 45

<210> SEQ ID NO 240
<211> LENGTH: 45
<212> TYPE: DNA
<213> ORGANISM: Homo sapiens

<400> SEQUENCE: 240
accgtagtac cctcttgcac agtaatagac ggcagagtcc tcaga 45

<210> SEQ ID NO 241
<211> LENGTH: 45
<212> TYPE: DNA
<213> ORGANISM: Homo sapiens

<400> SEQUENCE: 241
gatagcagta cgataaacta tgcgccatct ctaaaggata aattc 45

<210> SEQ ID NO 242
<211> LENGTH: 45
<212> TYPE: DNA
<213> ORGANISM: Homo sapiens

<400> SEQUENCE: 242
gaatttatcc tttagagatg gcgcatagtt tatcgtactg ctatc 45

<210> SEQ ID NO 243
<211> LENGTH: 48
<212> TYPE: DNA
<213> ORGANISM: Homo sapiens

<400> SEQUENCE: 243
tttaaagaat tctcagcatg ggggaccata tttggactca actctctt 48

<210> SEQ ID NO 244
<211> LENGTH: 48
<212> TYPE: DNA
<213> ORGANISM: Homo sapiens

<400> SEQUENCE: 244
tttaaaaagc ttgccgccac catggtctcc caggccctca ggctcctc 48

<210> SEQ ID NO 245
<211> LENGTH: 87
<212> TYPE: DNA
<213> ORGANISM: Homo sapiens

<400> SEQUENCE: 245
tttaaaggat ccggaacctc ccccgcctga tcccccgcca ccagacccgc cacctccggg 60
aaatggggct cgcaggagga ctcctgg 87

<210> SEQ ID NO 246
<211> LENGTH: 49
<212> TYPE: DNA
<213> ORGANISM: Homo sapiens

<400> SEQUENCE: 246
tttaaaaagc ttgccgccac catgcagcgc gtgaacatga tcatggcag 49

<210> SEQ ID NO 247
<211> LENGTH: 93
<212> TYPE: DNA
<213> ORGANISM: Homo sapiens

<400> SEQUENCE: 247
tttaaaggat ccggaacctc ccccgcctga tcccccgcca ccagacccgc cacctccagt 60
gagctttgtt ttttccttaa tccagttgac ata 93

<210> SEQ ID NO 248
<211> LENGTH: 42
<212> TYPE: DNA
<213> ORGANISM: Homo sapiens

<400> SEQUENCE: 248
aaatttggat ccgatgttgt gatgacccaa actccactct cc 42

<210> SEQ ID NO 249
<211> LENGTH: 42
<212> TYPE: DNA
<213> ORGANISM: Homo sapiens

<400> SEQUENCE: 249
aaatttgaat tcctaacact ctcccctgtt gaagctcttt gt 42

<210> SEQ ID NO 250
<211> LENGTH: 28
<212> TYPE: DNA
<213> ORGANISM: Homo sapiens

<400> SEQUENCE: 250
aaatgatttg ccctcccata tgtccttc 28

<210> SEQ ID NO 251
<211> LENGTH: 39
<212> TYPE: DNA
<213> ORGANISM: Homo sapiens

<400> SEQUENCE: 251
aaatttggat cccaggtcca gctgcagcag tctggagct 39

<210> SEQ ID NO 252
<211> LENGTH: 12
<212> TYPE: PRT
<213> ORGANISM: Artificial Sequence
<220> FEATURE:
<223> OTHER INFORMATION: Synthetic

<400> SEQUENCE: 252

Val Gln Cys His Tyr Arg Leu Gln Asp Val Lys Ala
1 5 10

<210> SEQ ID NO 253
<211> LENGTH: 6
<212> TYPE: PRT
<213> ORGANISM: Artificial Sequence
<220> FEATURE:
<223> OTHER INFORMATION: Synthetic

<400> SEQUENCE: 253

Leu Gly Gly Gly Leu Leu
1 5

<210> SEQ ID NO 254
<211> LENGTH: 8
<212> TYPE: PRT
<213> ORGANISM: Artificial Sequence
<220> FEATURE:
<223> OTHER INFORMATION: Synthetic

<400> SEQUENCE: 254

Gly Ala Arg Gly Pro Gln Ile Leu
1 5

<210> SEQ ID NO 255
<211> LENGTH: 12
<212> TYPE: PRT
<213> ORGANISM: Artificial Sequence
<220> FEATURE:

```
<223> OTHER INFORMATION: Synthetic

<400> SEQUENCE: 255

Leu Pro Glu Gly Cys Gln Pro Leu Val Ser Ser Ala
1               5                   10


<210> SEQ ID NO 256
<211> LENGTH: 11
<212> TYPE: PRT
<213> ORGANISM: Artificial Sequence
<220> FEATURE:
<223> OTHER INFORMATION: Synthetic

<400> SEQUENCE: 256

Arg Gly Pro Gln Ile Leu His Arg Val Ser Leu
1               5                   10


<210> SEQ ID NO 257
<211> LENGTH: 16
<212> TYPE: PRT
<213> ORGANISM: Artificial Sequence
<220> FEATURE:
<223> OTHER INFORMATION: Synthetic

<400> SEQUENCE: 257

Glu Thr His Lys Ile Gly Ser Leu Ala Glu Asn Ala Phe Ser Asp Pro
1               5                   10                  15


<210> SEQ ID NO 258
<211> LENGTH: 44
<212> TYPE: PRT
<213> ORGANISM: Artificial Sequence
<220> FEATURE:
<223> OTHER INFORMATION: Synthetic

<400> SEQUENCE: 258

Leu Asn Ile Leu Pro Pro Glu Glu Glu Glu Glu Thr His Lys Ile Gly
1               5                   10                  15

Ser Leu Ala Glu Asn Ala Phe Ser Asp Pro Ala Gly Ser Ala Asn Pro
            20                  25                  30

Leu Glu Pro Ser Gln Asp Glu Lys Ser Ile Pro Leu
        35                  40


<210> SEQ ID NO 259
<211> LENGTH: 21
<212> TYPE: PRT
<213> ORGANISM: Artificial Sequence
<220> FEATURE:
<223> OTHER INFORMATION: Synthetic

<400> SEQUENCE: 259

Ser Phe Ser Gln Asn Ser Arg His Pro Ser Gln Asn Pro Pro Val Leu
1               5                   10                  15

Lys Arg His Gln Arg
            20
```

COAGULATION FACTOR-TARGETING TO TREM-LIKE TRANSCRIPT 1 (TLT-1) ON ACTIVATED PLATELETS

CROSS-REFERENCE TO RELATED APPLICATIONS

This application is a continuation of U.S. application Ser. No. 15/094,082, filed Apr. 8, 2016 which is a Continuation of U.S. application Ser. No. 13/982,360 filed Jul. 29, 2013 which is a 35 U.S.C. § 371 National Stage application of International Application PCT/EP2012/053619 (WO 2012/117091 A1), filed Mar. 2, 2012, which claimed priority of European Patent Application 11156682.4, filed Mar. 2, 2011; this application claims priority under 35 U.S.C. § 119 of U.S. Provisional Application 61/449,254, filed Mar. 4, 2011; the contents of all above-mentioned applications are incorporated herein by reference.

FIELD OF THE INVENTION

The current invention relates to procoagulant proteins, polynucleotides that encode procoagulant fusion proteins, cells that express procoagulant fusion proteins, a process for preparing procoagulant proteins and uses of said procoagulant proteins.

INCORPORATION-BY-REFERENCE OF THE SEQUENCE LISTING

The instant application contains a Sequence Listing which has been submitted in ASCII format via EFS-Web and is hereby incorporated by reference in its entirety. Said ASCII copy, created on Sep. 5, 2018, is named 8314US04_SeqeneceListing_ST25.txt and is 267 kilobytes in size.

BACKGROUND OF THE INVENTION

Normal resting platelets freely flow throughout the blood circulation when the endothelium is intact. When the single-layered endothelial barrier is damaged, resting platelets adhere to subendothelial structures by means of glycoprotein (GP) receptors. For example, GPIaIIa and GPVI bind collagen; GPIcIIa binds fibronectin; GPIcIIa binds laminin and GPIb-V-IX binds von Willebrand Factor (vWF) polymers. Adhesion to the extravascular tissue components exposed following a vessel injury in conjunction with the influence of factors produced locally at the site of injury, e.g. the serine protease thrombin, lead to activation of the platelets. In the complex process of activation, platelets change shape and expose certain phospholipids on their surface. Also, receptors already present on the platelet surface in the resting state become activated upon platelet activation. Additionally, platelet activation leads to the release and surface exposure of molecules which in the resting state are stored intracellularly in alpha and dense granules and thus not present on the surface of platelets in the resting state. GPIIbIIIa is an example of a platelet receptor present on the surface of both resting and activated platelets. GPIIbIIIa exists on resting platelets in a closed and inactive conformation and during platelet activation assumes an open and active conformation capable of binding its ligands, including fibrinogen and fibrin. An example of a receptor stored intracellularly in alpha granules in resting platelets, but released and exposed on the surface of the activated platelet is TREM-like transcript 1 (TLT-1) (Washington et al., Blood, 104, 1042-1047 (2004), Gattis et al., Journal of Biological Chemistry, 281, 13396-13403 (2006)) to which the present application relates.

The blood coagulation cascade is initiated when tissue factor (TF) bearing cells in the subendothelium are exposed to components circulating in the blood. Exposure of TF to circulating coagulation factor VIIa (FVIIa) triggers the formation of small amounts of thrombin, which serves as a procoagulant signal leading to further recruitment and activation of platelets adhered to the site of injury. The coagulation is further propagated and amplified on the surface of the activated platelets, eventually leading to a burst of thrombin generation, which in turn lead to activation and polymerization of fibrinogen to fibrin fibers, cross-linking and stabilizing the haemostatic clot. A feature attributed to several of the components of the coagulation cascade is their ability to specifically associate with the phospholipid membrane of activated platelets. To this end, FVIIa as well as e.g. coagulation factors IX and X (FIX and FX, respectively) and their corresponding activated forms (FVIIa, FIXa and FXa, respectively), possess a γ-carboxyglutamic acid rich region (Gla domain) which enables them to be directed and bind to the surface of activated platelets. Coagulation factor VIII (FVIII) is associated with activated platelets by binding via its light chain. The mechanism of coagulation factor XI (FXI) binding to platelets is more controversial but growing evidence suggests that platelets affect FXI and FXIa and that binding of FXI to platelets requires residues in the FXI A3 domain (Emsley et al., 2010, Blood, Vol. 115, p. 2569).

Membrane binding strongly enhances the activity of coagulation factors such as FVIIa. However, their interactions with platelet membranes are of varying affinity. For example, the binding constant ($K_D$) for FVIIa to the platelet surface is in the low micromolar range. Improved platelet binding and localisation of the coagulation factors to the activated platelet surface may enhance their activity. A means of doing so is thus desirable.

In subjects with a coagulopathy, such as human beings with haemophilia A, B or C, various steps of the coagulation cascade are rendered dysfunctional due to, for example, the absence or insufficient presence of a functional coagulation factor. Such dysfunction of one part of coagulation results in insufficient blood coagulation leading to spontaneous bleeds e.g. in joints and potentially life-threatening bleeding.

An object of the current invention is to provide a compound that is suitable for use as a procoagulant drug in such subjects. A second object of the current invention is to provide procoagulant molecules that have increased activity, compared to the coagulation factors from which they derive. A third object of the current invention is to provide molecules that up-regulate blood coagulation in a physiologically suitable microenvironment. A fourth object of the current invention is to provide procoagulant molecules that have longer half lives than the coagulation factor from which they derive. A fifth object of the current invention is to provide procoagulant molecules that do not give rise to a drop in platelet count. A further object of the current invention is to direct a coagulation factor to the surface of activated platelets. One particular object of the invention is to enhance the generation of FIXa and/or FXa on the surface of the activated platelet. Thus, the object is to enable the initiation of blood coagulation on the surface of activated platelets that are located intravascularly or extravascularly.

WO06/096828 discloses chimeric proteins that comprise soluble tissue factor (sTF) and a phosphatidyl serine (PS) binding domain, such as Annexin V. PS is exposed on the surface of activated cells, such as monocytes, endothelial cells and cells undergoing apoptosis, as well as on activated and resting platelets. The chimeric proteins are both procoagulant and anti-coagulant; the latter due to the fact that, in higher doses, constructs compete with coagulation factors in binding to PS on activated platelets. Thus, the chimeric proteins of WO06/096828 have a different set of properties than the procoagulant proteins described herein.

SUMMARY OF THE INVENTION

The procoagulant proteins of the present invention are specifically targeted to activated platelets, present at sites of injury. Proteins of the present invention are based upon the identification of particular receptors and component epitopes that appear on platelet membranes when platelets are no longer resting but are activated or in the process of being activated. Thus, the invention relates to a method of enhancing coagulation on the surface of activated platelets.

Procoagulant proteins of the invention comprise (i) at least one coagulation factor, covalently attached to (ii) an antibody or a fragment thereof that is capable of binding (iii) a receptor, and/or a fragment or variant thereof, which is exposed on the surface of activated platelets and is exposed to a lesser degree (and in some assays not detectably exposed) on the surface of resting platelets. TLT-1 is an example of such a receptor and procoagulant proteins may, for example, bind, to TLT-1 (16-162), TLT-1 (20-125) or TLT-1 (126-162). The coagulation factor may be a serine protease in the zymogen form, e.g., FVII, FIX or FX or the corresponding activated form FVIIa, FIXa, and FXa, or a derivative of a serine protease; FV or a derivative thereof, FVIII or a derivative thereof or FXI or a derivative thereof. Coagulation factor and antibody or antibody fragment are optionally joined by means of a linker. Procoagulant proteins of the invention may be fusion proteins or chemical conjugates. Hence, the invention also relates to their manufacture. One process for preparing a composition that comprises at least a procoagulant protein of the invention involves chemically conjugating (i), a TLT-1 antibody or fragment thereof, with one reactive group (RS1) of a linker and reacting (ii), the coagulation factor, with another reactive group (RS2) of said linker.

In this case, said linker may be a polymer, such as polyethylene glycol (PEG).

The current invention also provides the following: an isolated nucleotide sequence that encodes any one of the procoagulant proteins according to the current invention; a vector that comprises an isolated nucleotide sequence that, in turn, encodes any one of the procoagulant proteins according to the current invention; an isolated cell that comprises a nucleotide sequence that encodes any one of the procoagulant proteins of the current invention. Said nucleotide sequence may, in turn, be expressed by an intracellular vector. Said isolated cell may be a eukaryotic cell, such as a mammalian cell, such as a BHK or a CHO or a HEK cell.

Similarly, the invention relates to a procoagulant protein for use as a medicament and for the treatment of a coagulopathy. In one embodiment, a therapeutically effective amount of said protein is parenterally administered, such as intravenously or subcutaneously administered, to an individual in need thereof. Such individual in need may have any congenital, acquired and/or iatrogenic coagulopathy.

DESCRIPTION OF THE DRAWINGS

FIG. 1: Human TLT-1 nucleotide and amino acid sequences. In FIG. 1, the nucleotide—(SEQ ID NO: 1) and amino acid (SEQ ID NO: 2) sequences representing hTLT-1 are shown. Here, nucleotide sequence position 1-45 encode the predicted signal peptide, the nucleotide sequence at position 46-486 encode the extracellular domain of hTLT-1, the nucleotide sequence position 487-555 encode the transmembrane region and the nucleotide sequence at position 556-933 encode the intracellular domain of hTLT-1.

FIG. 2: Nucleotide (SEQ ID NO: 3) and amino acid (SEQ ID NO: 4) sequences representing the extracellular domain of human TLT-1 containing a C-terminal His-6 tag. In FIG. 2, the nucleotide—and amino acid sequences representing the extracellular domain of hTLT-1 with a C-terminal His tag are shown. Here, the underlined sequence (7-15) indicates the positions of a kozak sequence, the nucleotide sequence at position 16-60 encodes the predicted signal peptide, the nucleotide sequence at position 61-501 encode the extracellular domain of hTLT-1 and the nucleotide sequence at position 502-519 encodes the 6×His tag (in bold). The restriction enzyme sites HindIII (nucleotide sequence at position 1-6) and EcoRI (nucleotide sequence at position 523-528) are also shown and the stop codon is marked with an asterisk (520-522).

FIG. 3A: the nucleotide sequence at position 1-57 encodes the LC signal peptide sequence; the nucleotide sequences at position 58-396 encodes the variable domain of 0012LC (SEQ ID NO: 9 and SEQ ID NO: 10).

FIG. 3B: the sequences in bold and grey represent positions of the 0012LC CDRs according to Kabat numbering (SEQ ID NO: 183).

FIG. 3C: the nucleotide sequence at position 1-54 encodes the 0012HC signal peptide, the nucleotide sequence at position 55-396 encodes the variable domain of 0012HC (SEQ ID NO: 11 and SEQ ID NO: 12).

FIG. 3D: the sequences in bold and grey represent positions of the 0012HC CDRs according to Kabat numbering (SEQ ID NO: 184).

FIG. 4: The variable domain of 0012LC together with constant region of human LC, kappa and a HPC4 tag (encoded by pTT-0012LC.HPC4) (SEQ ID NO: 186 and SEQ ID NO: 185). In FIG. 4, the nucleotide sequences at position 1-57 encodes the LC signal peptide, the nucleotide sequence 58-396 encodes the variable domain of 0012LC, the nucleotide sequence 397-714 encodes the constant region of human 0012LC, kappa and the nucleotide sequence 715-750 encodes a HPC4 tag.

FIG. 5: The variable domain of 0012HC together with the constant region of human IgG4 (pTT-0012HC) (SEQ ID NO: 13 and SEQ ID NO: 32). In FIG. 5, the nucleotide sequence 1-54 encodes the HC signal peptide, the nucleotide sequence 55-396 encodes the variable domain of 0012HC and the nucleotide sequence 397-1377 encodes the constant region of human IgG4 (in bold).

Citrated-stabilized human whole blood (HWB) is drawn from normal donors. Hemophilia-like conditions are obtained by incubation of HWB with 10 μg/ml anti-FVIII antibody (Sheep anti-Human Factor VIII; Hematologic Technologies Inc) for 30 min at room temp. Clot formation is measured by thrombelastography (5000 series TEG analyzer, Haemoscope Corporation, Niles, Ill., USA). Various concentrations (0; 0.25; 0.5; 1.0 nM) of FVIIa-Fab1029 or rFVIIa are added to hemophilia-like citrated HWB. Clotting is initiated when 340 μl of normal or hemophilia-like HWB is transferred to a thrombelastograph cup containing 20 μl 0.2 M $CaCl_2$ with 0.03 pM lipidated TF (Innovin®, Dade Behring GmbH (Marburg, Germany). The TEG trace is followed continuously for up to 120 min. The following TEG variables are recorded: R time (clotting time i.e. the time from initiation of coagulation until an amplitude of 2 mm was obtained), α-angle (clot development measured as the angle between the R value and the inflection point of the TEG trace), K (speed of clot kinetics to reach a certain level of clot strength, amplitude=20 mm), and MA (maximal amplitude of the TEG trace reflecting the maximal mechanical strength of the clot).

Figure 12:
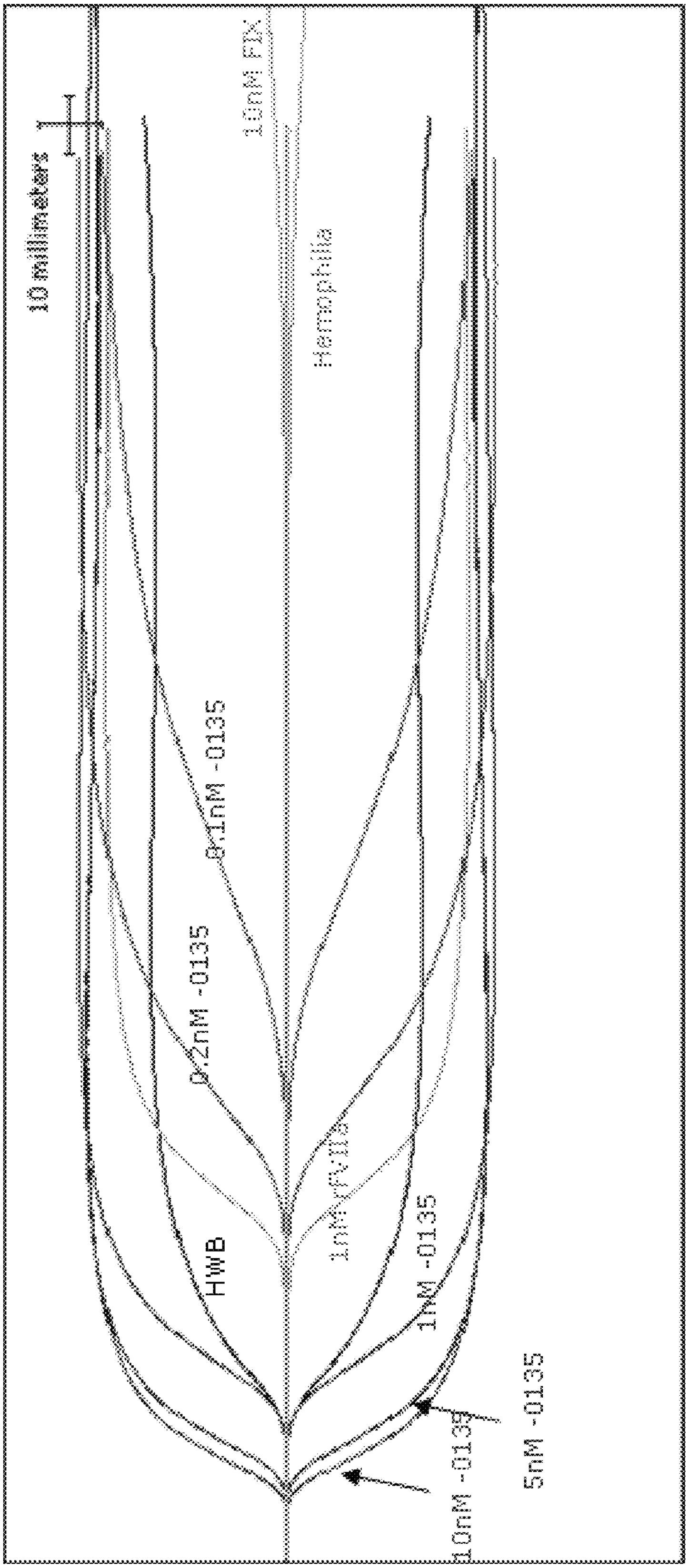

FIG. 12: Effect of FIX-Fab0135 on TF-induced fibrin clot formation in human whole blood (HWB) from a normal donor measured by thromb-elastography (TEG). Clot formation in re-calcified HWB (curve HWB) is induced by 0.03 pM TF (Innovin®). The curve "Hemophilia" shows the delayed and inadequate clot formation when HWB is supplemented with 10 μg/ml anti-FVIII antibody. Other curves show TEG traces obtained when the hemophilia A-like condition induced by the FVIII antibody is reverted by various concentrations (0.1; 0.2; 1.0; 5.0; 10 nM) of FIX-Fab0135. TEG curves obtained when FIX fusion protein is replaced by 1 nM rFVIIa or 10 nM rFIX are shown for comparison.

Figure 13:
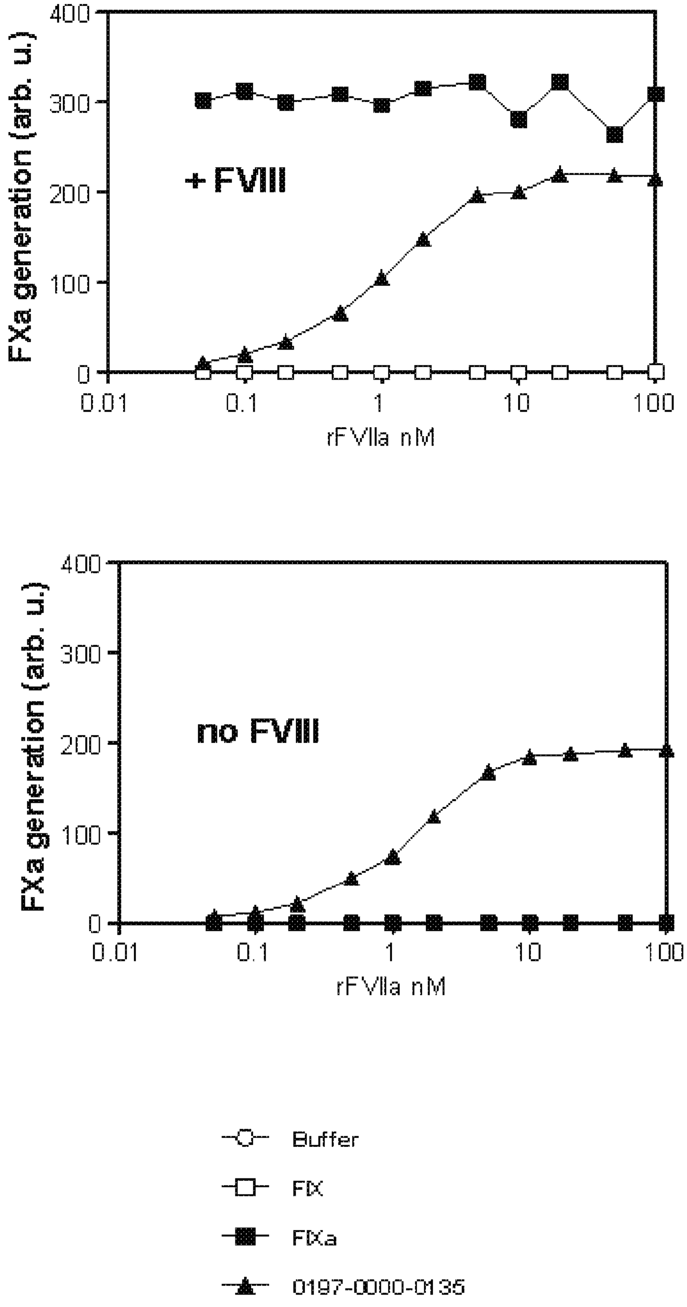

FIG. 13: FIX-Fab0135 targeted to TLT-1 enriched phospholipid vesiches markedly promotes FX activation induced by FVIIa in absence of FVIII. Various concentrations (0.05-100 nM) of rFVIIa are incubated for 15 min in Hepes buffer (○) or in Hepes buffer containing 10 nM FIX (□); 10 nM FIXa (■) or 10 nM FIX-Fab0135 (▲). This is then mixed and incubated for 3 min with 100 nM FX and TLT-1 enriched phospholipid vesicles at 1:4,000 dilution in absence or presence of 5 nM FVIII as indicated. The reaction is stopped with EDTA, and FXa generation is measured in a chromogenic assay.

Figure 14:
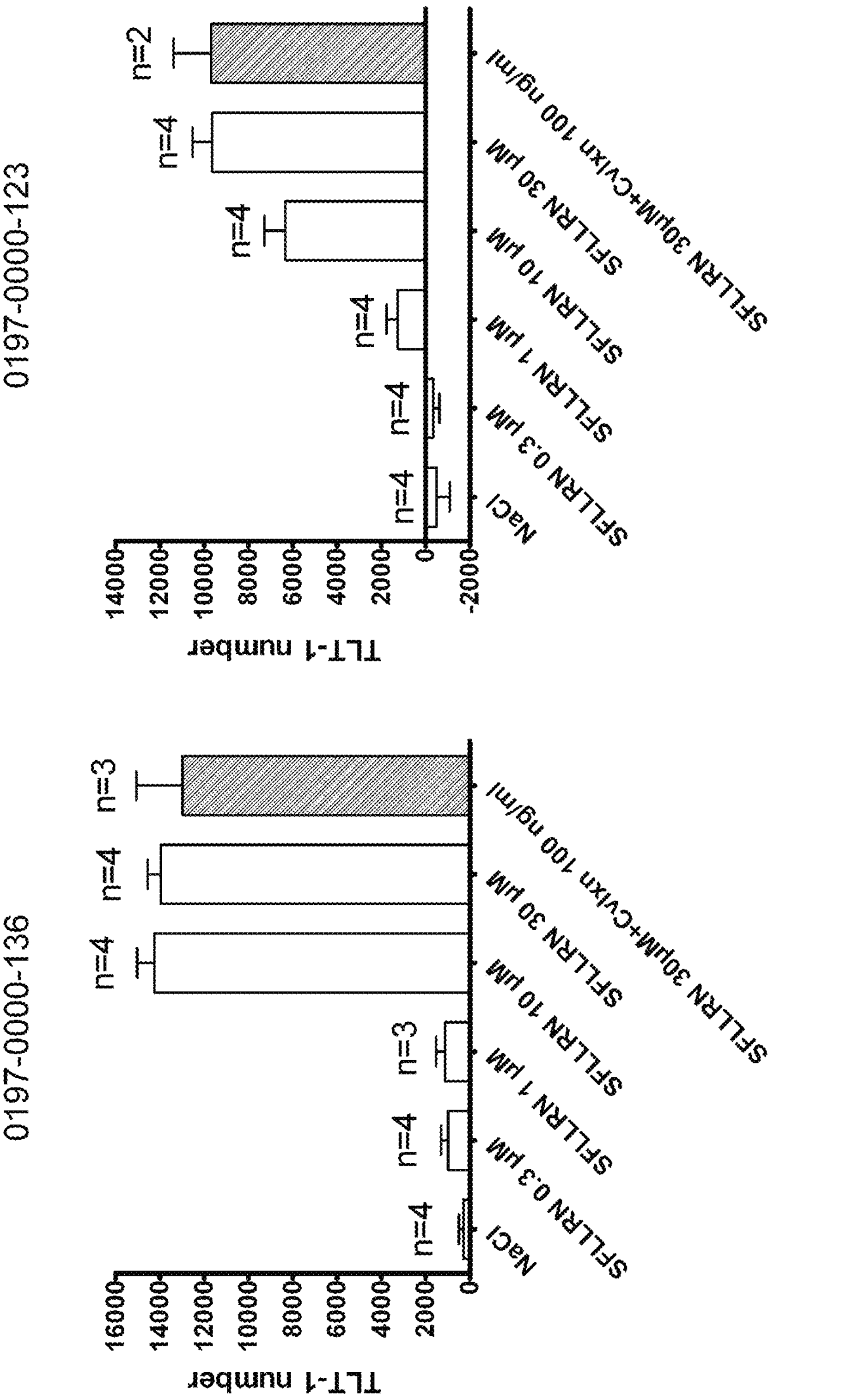

FIG. 14: TLT-1 expression on human platelets. The figure shows the TLT-1 number on platelets in whole blood gated on forward and side scatter in flow cytometry analysis. The mean fluorescence within the platelet gate was used to calculate the TLT-1 number using a standard curve obtained from beads with a definite number of binding sites for the detecting antibody. The platelets were activated with protease activated receptor-1 activating peptide SFLLRN (0.3-30 μM). To ensure maximum TLT-1 expression a combination of SFLLRN (30 μM) and Convulxin (Cvlxn) (100 ng/ml) was used as control. TLT-1 expression was measured by two different anti-TLT-1 antibodies mAb0136; left bar graph and mAb0123; right bar graph. Data are presented as mean±sem with the number of blood donors ranging from 2 to 4 in the different groups.

Figure 15:
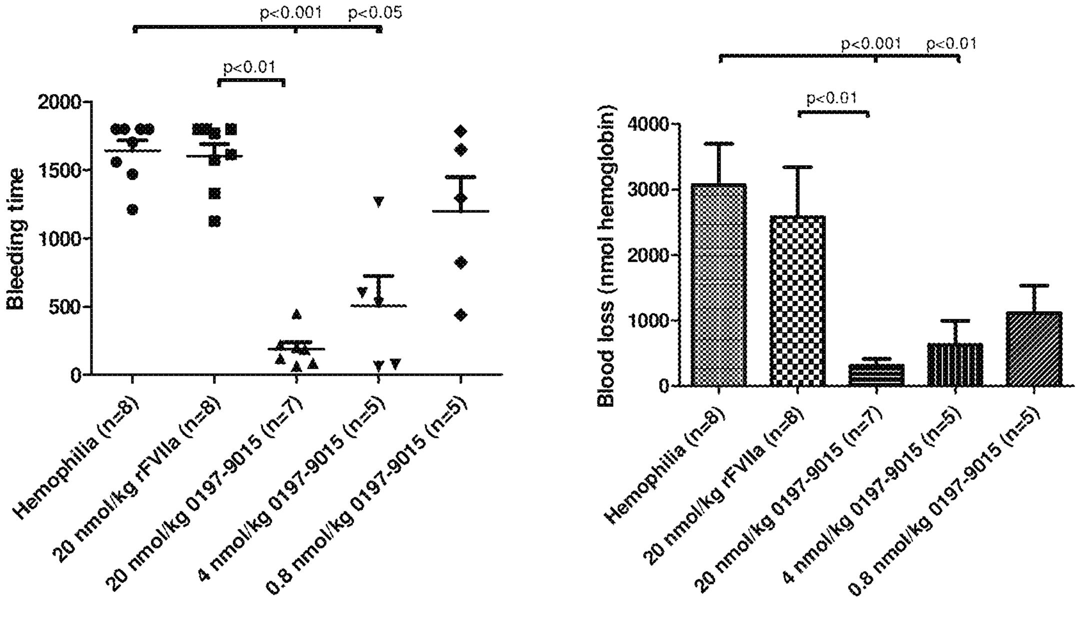

FIG. 15: FVIIa-Fab9015 dose-dependently reduced bleeding time (left) and blood loss (right) in TLT-1 KOKI mice with antibody induced haemopilia compared to haemopilic mice receiving vehicle. A dose of 20 nmol/kg FVIIa-Fab9015 was significantly more effective compared to 20 nmol/kg rFVIIa.

Figure 16:
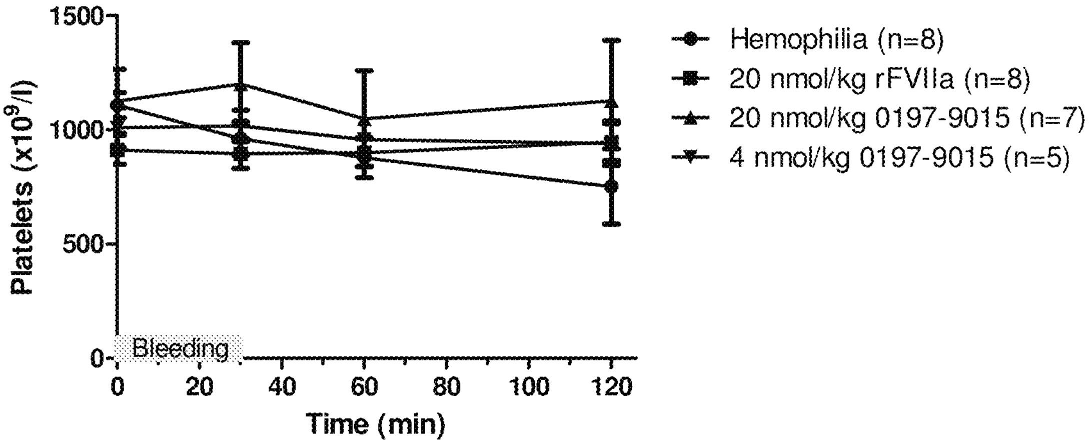

FIG. 16: Platelet counts in transient haemophilic TLT-1 KOKI mice dosed with FVIIa-Fab9015 (20 or 4 nmol/kg), rFVIIa (20 nmol/kg) or vehicle. The mice were dosed at −5 min, bleeding was observed from 0 to 30 min, and platelet counts were observed for 120 min after induction of bleeding.

Figure 17A:
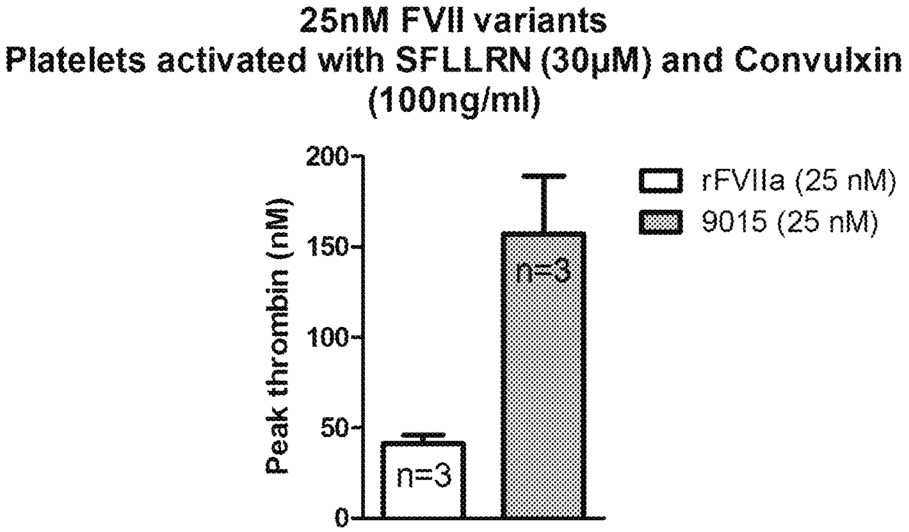

FIG. 17A: The bar-graph show peak amount thrombin generated by 25 nM of either rFVIIa (unfilled bar) or FVIIa-Fab9015 (filled bar). The thrombin generation was measured under induced haemophilia A conditions (sheep anti-human FVIII polyclonal antibodies) with a fixed platelet concentration of 150000 plts/μl. The reaction was started with platelet activation through the addition of PAR-1 activating peptide SFLLRN (30 μM) and the GPIV agonist Convulxin (100 ng/ml).

Figure 17B:
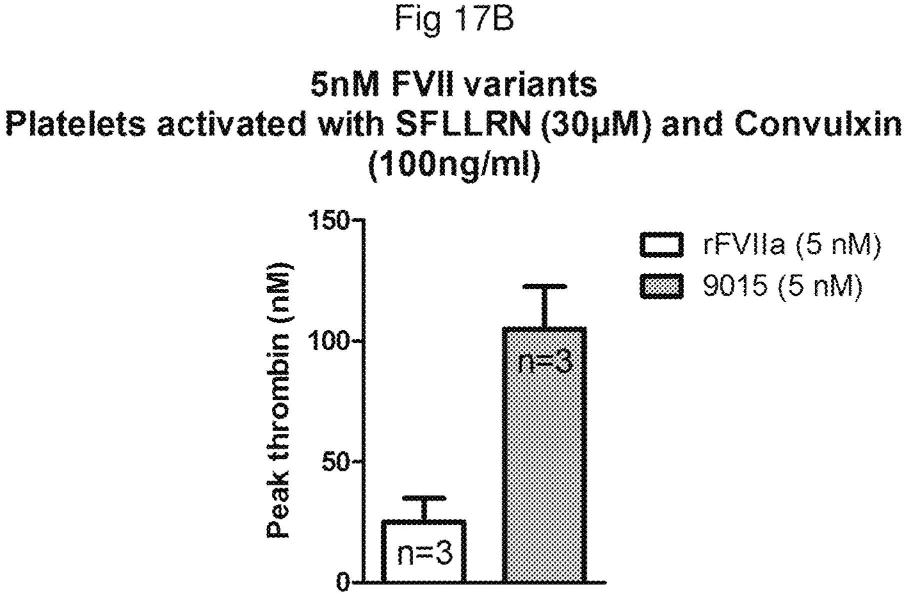

FIG. 17B: The bar-graph show peak amount thrombin generated by 5 nM of either rFVIIa (unfilled bar) or FVIIa-Fab9015 (filled bar). The thrombin generation was measured under haemophilia A conditions with a fixed platelet concentration of 150000 plts/μl. The reaction was started with platelet activation through the addition of PAR-1 activating peptide SFLLRN (30 μM) and the GPIV agonist Convulxin (100 ng/ml).

Figure 18:
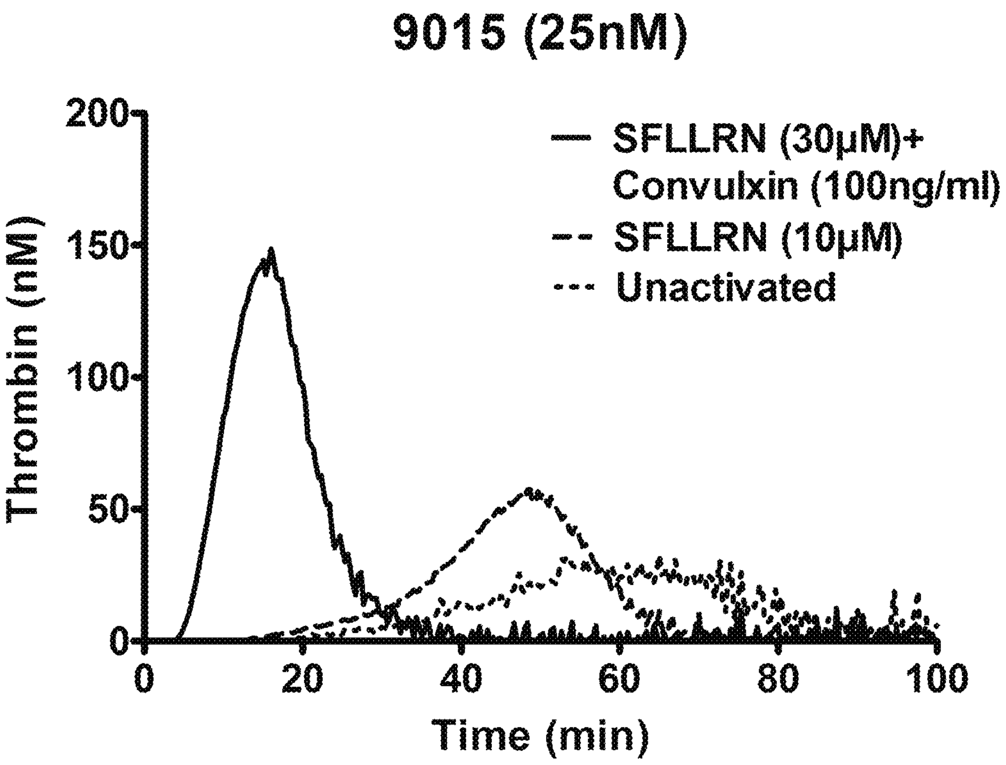

FIG. 18: The figure shows that the effect of FVIIa-Fab9015 was dependent on platelet activation. 25 nM FVIIa-Fab9015 was added to human platelet rich plasma (150000 plts/μl) made haemophilia A like though addition of sheep anti-human FVIII antibodies. Samples with unactivated platelets show poor thrombin generation (dotted line), PAR-1 activating peptide SFLLRN (10 μM) gives some increase in thrombin generation (broken line) and platelets activated with both SFLLRN (30 μM) and the GPVI agonist Convulxin (100 ng/ml) gives the largest thrombin generation (solid line).

Figure 19:
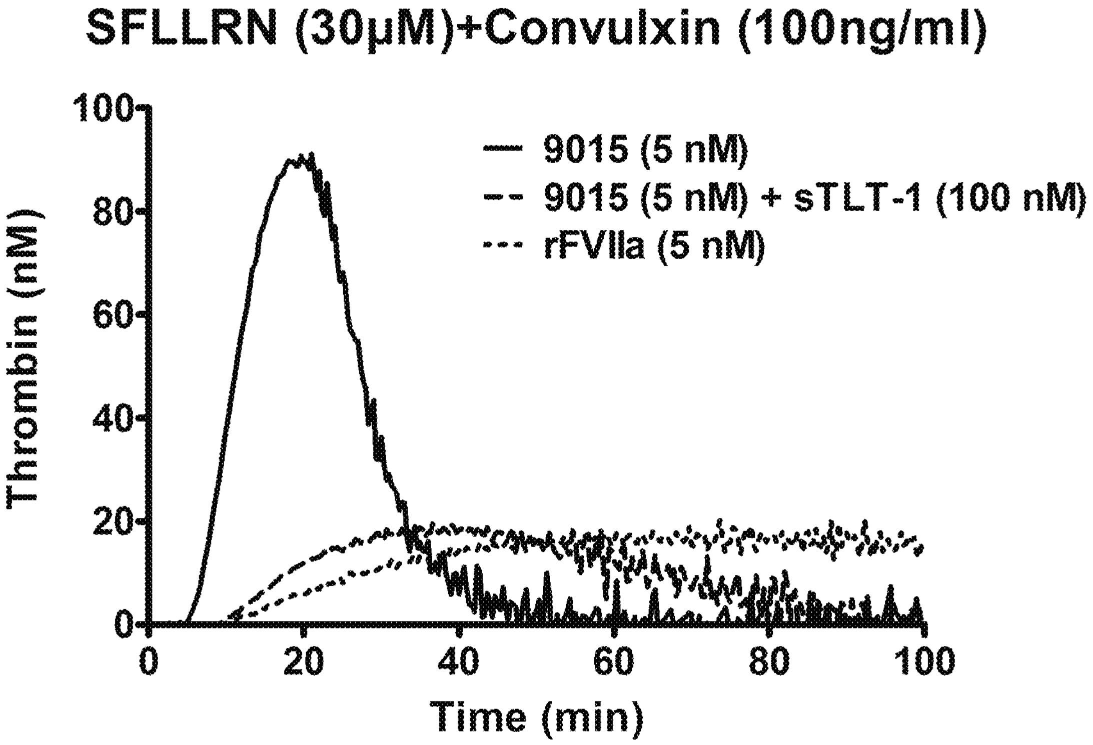

FIG. 19: The figure shows that the increase in thrombin generation with FVIIa-Fab9015 compared to rFVIIa was TLT-1 dependent. The original traces show thrombin generation in human platelet rich plasma (150000 plts/μl) made haemophilc A like through the addition of sheep anti-human FVIII polyclonal antibodies. Thrombin generation was started by the addition of PAR-1 activating peptide SFLLRN (30 μM) and GPVI agonist Convulxin (100 ng/ml). As shown by the traces, FVIIa-Fab9015 (5 nM) (solid line) gives a significant larger thrombin peak than rFVIIa (5 nM) (dotted line). By pre-incubating the samples with soluble TLT-1(100 nM) the FVIIa-Fab9015 thrombin generating capacity was significantly reduced (broken line). This confirms that the 9015 effect is dependent on TLT-1 binding on the activated platelet.

Figure 20:
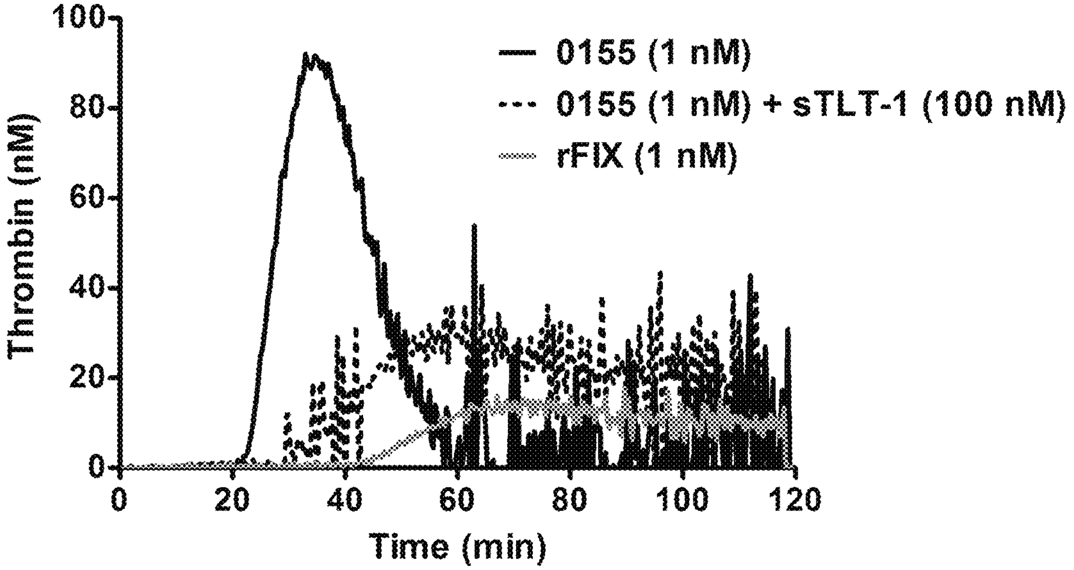

FIG. 20: The figure shows that the increase in thrombin generation with FIX-Fab0155 compared to rFIX was TLT-1 dependent. The original traces show thrombin generation in FIX deficient plasma containing human platelets (150000 plts/μl). Thrombin generation was started by the addition of PAR-1 activating peptide SFLLRN (30 μM) and GPVI agonist Convulxin (100 ng/ml). As shown by the traces, 1 nM FIX-Fab0155 (solid line) gives a significant larger thrombin peak than rFIX (grey line). Pre-incubation of soluble TLT-1 (100 nM) significantly reduced the thrombin generation capacity of FIX-Fab0155 (broken line) confirming TLT-1 dependency.

Figure 21:
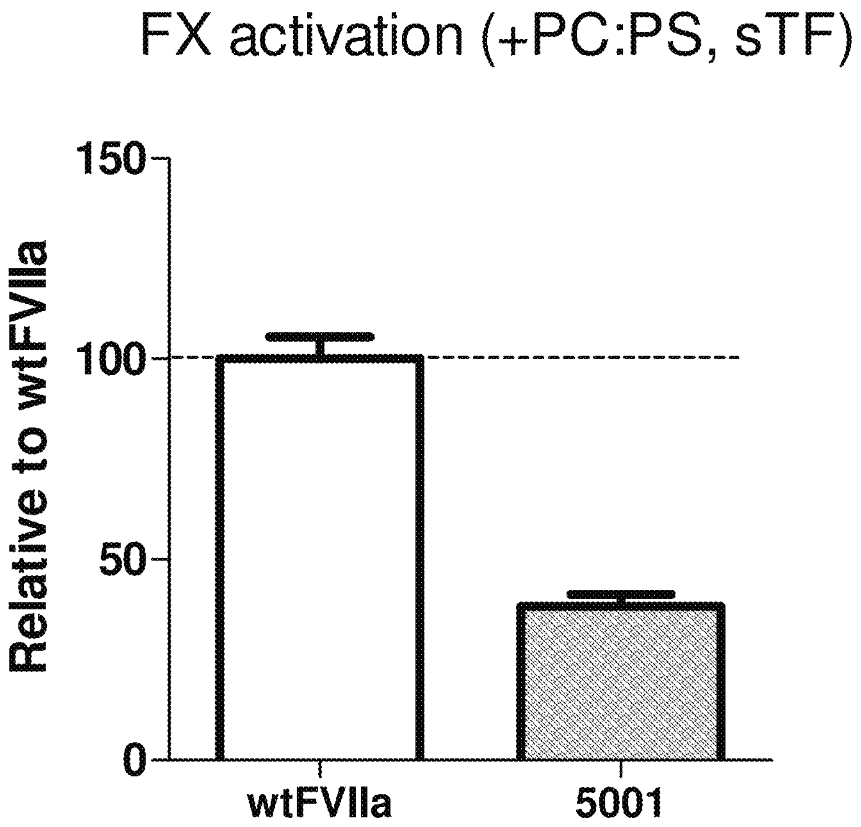

FIG. 21: Autoactivation of FVII-Fab5001 fusion protein in the presence of soluble Tissue Factor (sTF). Proteolytic activity was measured in the presence of phospholipids (PC:PS) and sTF. Results are averages of two independent measurements and given in relative $k_{cat}/K_m$ values compared to wtFVIIa.

Figure 22A:
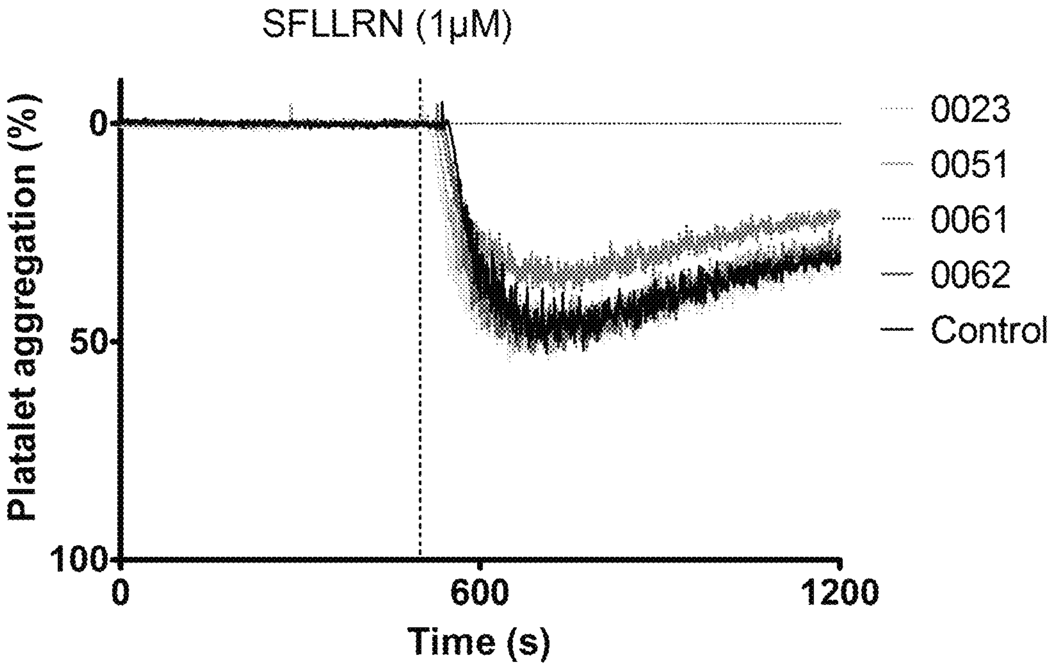

FIG. 22A: None of the TLT-1 antibodies (mAb0023, mAb0051, mAb0061, mAb0062) affect platelet aggregation. The figure shows original traces from light transmission measurements in platelet rich plasma where the platelets have been activated with SFLLRN (1 μM). The samples were pre-incubated with anti-TLT-1 antibody or irrelevant control antibody (10 nM) 3 min before platelet activation.

Figure 22B:
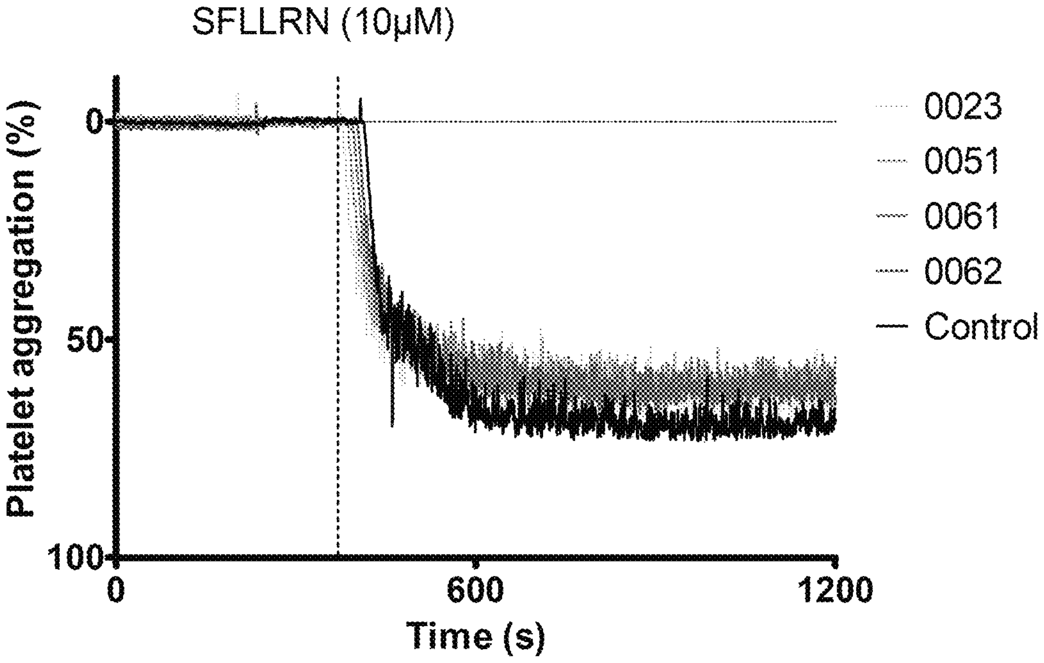

FIG. 22B: None of the TLT-1 antibodies (mAb0023, mAb0051, mAb0061, mAb0062) affects platelet aggregation. The figure shows original traces from light transmission measurements in platelet rich plasma in which the platelets have been activated with SFLLRN (10 μM). The samples have been pre-incubated with anti-TLT-1 antibody or irrelevant control antibody (10 nM) 3 min before platelet activation FIG. 23: Effect of FIX-mAb0145 on TF-induced fibrin clot formation in human whole blood (HWB) from a normal donor measured by thromb-elastography (TEG). The R time obtained from TEG traces with normal HWB and "hemophilia" blood supplemented with various concentrations of FIX-mAb0145 or rFIX are shown.

Figure 24:
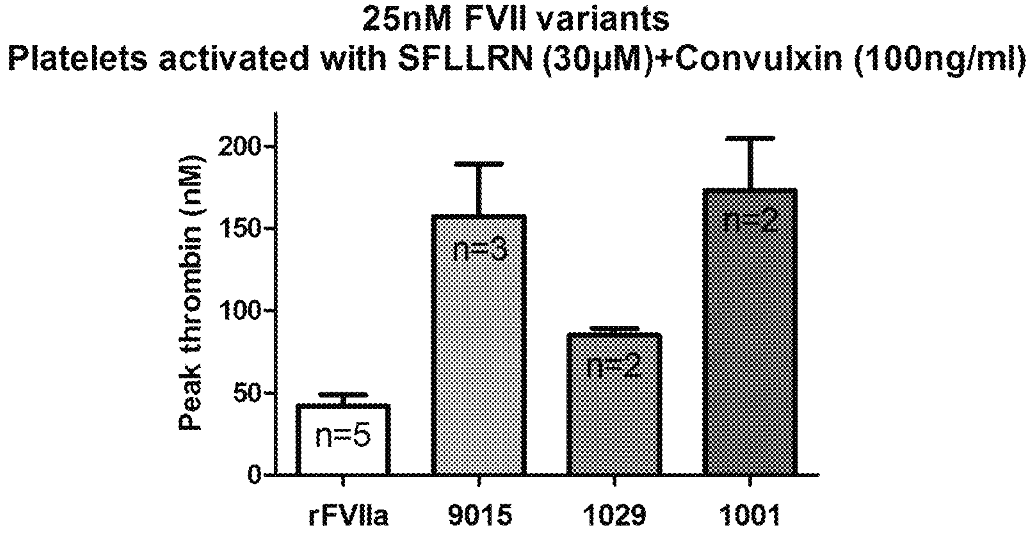

FIG. 24: The bar-graph show peak amount thrombin generated by 25 nM of the FVIIa-Fab9015, FVIIa-Fab1029 and FVIIa-Fab1001. All three constructs showed increased potency compared to rFVIIa (25 nM). The thrombin generation was measured under induced haemophilia A conditions (sheep anti-human FVIII polyclonal antibodies) with a fixed platelet concentration of 150000 plts/μl. The reaction was started with platelet activation through the addition of PAR-1 activating peptide SFLLRN (30 μM) and the GPIV agonist Convulxin (100 ng/ml). The bars show mean±SD of peak thrombin generation (n=2-5).

Figure 25:
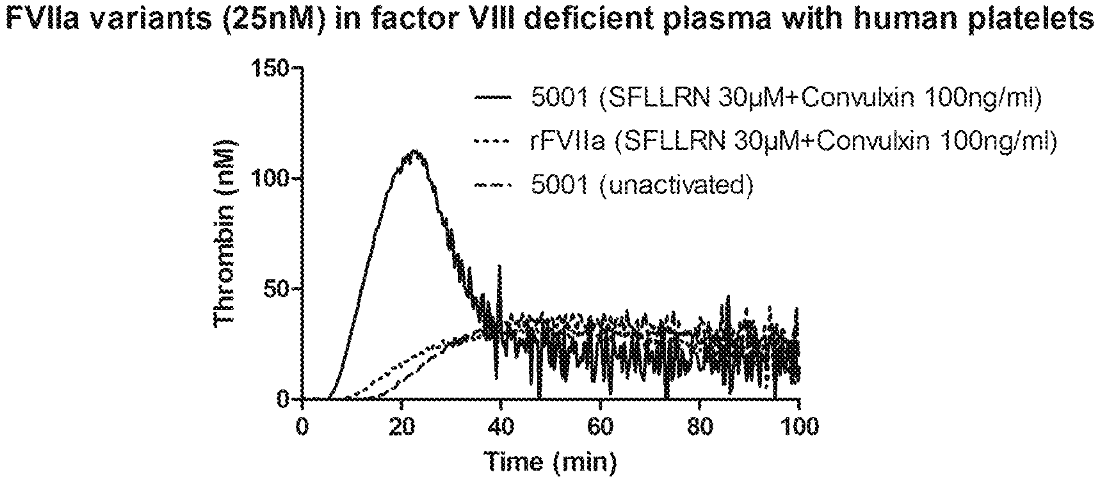

FIG. 25: The figure shows that increased potency of the FVIIa-Fab5001 compared to wild-type rFVIIa. The original traces show thrombin generation in factor VIII deficient plasma containing washed human platelets (150000 plts/μl). In the activated samples thrombin generation was started by the addition of the PAR-1 activating peptide SFLLRN (30 μM) and the GPVI agonist Convulxin (100 ng/ml). As shown by the traces FVIIa-Fab5001 (25 nM) (solid line) gives approximately a four fold larger thrombin peak than wild-type rFVIIa (25 nM) (dotted line). There was no enhancement of the potency with unactivated platelets (broken line).

SEQUENCES

The sequences are as follows:

SEQ ID NO: 1 provides the nucleotide sequence of human (h)TLT-1.

SEQ ID NO: 2 provides the amino acid sequence of hTLT-1.

SEQ ID NO: 3 provides the nucleotide sequence of the extracellular domain of hTLT-1-His6.

SEQ ID NO: 4 provides the amino acid sequence of the extracellular domain of hTLT-1-His6.

SEQ ID NOs: 5 to 8 provide the amino acid sequences of hTLT-1 fragments: hTLT-1.20-125, hTLT-1.16-162, hTLT-1.126-162 and hTLT-1.129-142.

SEQ ID NO: 9 provides the nucleotide sequence of the variable domain of mAb 0012 LC.

SEQ ID NO: 10 provides the amino acid sequence of the variable domain of mAb0012 LC.

SEQ ID NO: 11 provides the nucleotide sequence of the variable domain of 0012 HC.

SEQ ID NO: 12 provides the amino acid sequence of the variable domain of 0012 HC.

SEQ ID NO: 13 provides the nucleotide sequence of the heavy chain of mAb0012.

SEQ ID NO: 14 provides the nucleotide sequence of the light chain of mAb0012 and Fab0012.

SEQ ID NO: 15 provides the nucleotide sequence of the heavy chain of mAb0023.

SEQ ID NO: 16 provides the nucleotide sequence of the light chain of mAb0023 and Fab0023.

SEQ ID NO: 17 provides the nucleotide sequence of the heavy chain of mAb0051.

SEQ ID NO: 18 provides the nucleotide sequence of the light chain of mAb0051 and Fab0051.

SEQ ID NO: 19 provides the nucleotide sequence of the heavy chain of mAb0052.

SEQ ID NO: 20 provides the nucleotide sequence of the heavy chain of mAb0062.

SEQ ID NO: 21 provides the nucleotide sequence of the light chain of mAb0052, Fab0052 and mAb0062.

SEQ ID NO: 22 provides the nucleotide sequence of the heavy chain of mAb0061.

SEQ ID NO: 23 provides the nucleotide sequence of the heavy chain of mAb0082.

SEQ ID NO: 24 provides the nucleotide sequence of the light chain of mAb0061, Fab0061, mAb0082 and Fab0082.

SEQ ID NO: 25 provides the nucleotide sequence of Fab0012 VH-CH1.

SEQ ID NO: 26 provides the nucleotide sequence of Fab0023 VH-CH1.

SEQ ID NO: 27 provides the nucleotide sequence of Fab0051 VH-CH1.

SEQ ID NO: 28 provides the nucleotide sequence of Fab0052 VH-CH1.

SEQ ID NO: 29 provides the nucleotide sequence of Fab0061 VH-CH1.

SEQ ID NO: 30 provides the nucleotide sequence of Fab0082 VH-CH1.

SEQ ID NO: 31 provides the nucleotide sequence of hIgG4 hinge-CH2-CH3.

SEQ ID NO: 32 provides the amino acid sequence of mAb0012, HC (mouse VH-human IgG4 CH1-CH2-CH3).

SEQ ID NO: 33 provides the amino acid sequence of mAb0012, LC (mouse VL-human Kappa CL) and Fab0012, LC (mouse VL-human Kappa CL).

SEQ ID NO: 34 provides the amino acid sequence of mAb0023, HC (mouse VH-human IgG4 CH1-CH2-CH3).

SEQ ID NO: 35 provides the amino acid sequence of mAb0023, LC (mouse VL-human Kappa CL) and Fab0023, LC (mouse VL-human Kappa CL).

SEQ ID NO: 36 provides the amino acid sequence of mAb0051, HC (mouse VH-human IgG4 CH1-CH2-CH3).

SEQ ID NO: 37 provides the amino acid sequence of mAb0051, LC (mouse VL-human Kappa CL) and Fab0051, LC (mouse VL-human Kappa CL).

SEQ ID NO: 38 provides the amino acid sequence of mAb0052, HC (mouse VH-human IgG4 CH1-CH2-CH3).

SEQ ID NO2: 39 provides the amino acid sequence of mAb0052, LC (mouse VL-human Kappa CL); Fab0052, LC (mouse VL-human Kappa CL); mAb0062, LC (mouse VL-human Kappa CL).

SEQ ID NO: 40 provides the amino acid sequence of mAb0061, HC (mouse VH-human IgG4 CH1-CH2-CH3).

SEQ ID NO: 41 provides the amino acid sequence of mAb0061, LC (mouse VL-human Kappa CL); Fab0061, LC (mouse VL-human Kappa CL) and mAb0082, LC (mouse VL-human Kappa CL); Fab0082, LC (mouse VL-human Kappa CL).

SEQ ID NO: 42 provides the amino acid sequence of mAb0062, HC (mouse VH-human IgG4 CH1-CH2-CH3).

SEQ ID NO: 43 provides the amino acid sequence of mAb0082, HC (mouse VH-human IgG4 CH1-CH2-CH3).

SEQ ID NO: 44 provides the amino acid sequence of Fab0012, mouse VH-human IgG4 CH1.

SEQ ID NO: 45 provides the amino acid sequence of Fab0023, mouse VH-human IgG4 CH1.

SEQ ID NO: 46 provides the amino acid sequence of Fab0051, mouse VH-human IgG4 CH1.

SEQ ID NO: 47 provides the amino acid sequence of Fab0052, mouse VH-human IgG4 CH1.

SEQ ID NO: 48 provides the amino acid sequence of Fab0082, mouse VH-human IgG4 CH1.

SEQ ID NOs: 49-58 provide the amino acid sequences of optional linkers L2-L10. Optional linkers are numbered and listed in Table 3.

SEQ ID NO: 59 provides the amino acid sequence of purification tag HPC4.

SEQ ID NOs: 60-145 provide the nucleic acid sequences of the primers used during the development of the expression constructs described in examples 4, 5, 6, 7, 8, 9, 10, 11, 12, 13, 14, 15, 17, 18, 19, 20, 24, 25.

SEQ ID NO: 146 provides the amino acid sequence of Fab0061 VH-CH1.

SEQ ID NO: 147 provides the amino acid sequence of hIgG4-hinge-CH2-CH3.

SEQ ID NO: 148 provides the amino acid sequence of a His6 tag.

SEQ ID NO: 149 provides the amino acid sequence of hTLT-1.18-188.

SEQ ID NO: 150 provides the nucleic acid sequence of primer no. 1004.

SEQ ID NO: 151 provides the nucleic acid sequence of primer no. 1005.

SEQ ID NO: 152 provides the amino acid sequence of Fab0100 HC.

SEQ ID NO: 153 provides the amino acid sequence of Fab0100 LC.

SEQ ID NO: 154 provides the nucleic acid sequence of wild type human Factor FV.

SEQ ID NO: 155 provides the amino acid sequence of wild type human Factor FV.

SEQ ID NO: 156 provides the nucleic acid sequence of wild type human Factor FVII.

SEQ ID NO: 157 provides the amino acid sequence of wild type human Factor FVII.

SEQ ID NO: 158 provides the nucleic acid sequence of wild type human Factor FVIII.

SEQ ID NO: 159 provides the amino acid sequence of wild type human Factor FVIII.

SEQ ID NO: 160 provides the nucleic acid sequence of wild type human Factor FIX.

SEQ ID NO: 161 provides the amino acid sequence of wild type human Factor FIX.

SEQ ID NO: 162 provides the nucleic acid sequence of wild type human Factor FX.

SEQ ID NO: 163 provides the amino acid sequence of wild type human Factor FX.

SEQ ID NO: 164 provides the nucleic acid sequence of wild type human Factor FXI.

SEQ ID NO: 165 provides the amino acid sequence of wild type human Factor FXI.

SEQ ID NO: 166 provides the 0012LC.C36A-HPC4 DNA sequence.

SEQ ID NO: 167 provides the 0012LC.C36A-HPC4 amino acid sequence.

SEQ ID NO: 168 provides the 0012VH-CH1-HPC4 DNA sequence.

SEQ ID NO: 169 provides the 0012VH-CH1-HPC4 amino acid sequence.

SEQ ID NO: 170 provides the 0012VH.T60N-CH1-YGPPC DNA sequence.

SEQ ID NO: 171 provides the 0012VH.T60N-CH1-YGPPC.

SEQ ID NO: 172 provides the FIX-L4b-0012LC DNA sequence.

SEQ ID NO: 173 provides the FIX-L4b-0012LC amino acid sequence.

SEQ ID NO: 174 provides the amino acid sequence of 0003 Fab-LC: 0062Fab-LC-HPC4.

SEQ ID NO: 175 provides the amino acid sequence of 0003 Fab-HC: 0062Fab-VH-CH1-YGPPC.

SEQ ID NO: 176 provides the amino acid sequence of 0197-0000-0074 Fab-HC: 0197-0000-0051Fab-VH-CH1-YGPPC.

SEQ ID NO: 177 provides the amino acid sequence of 0074 Fab-LC: 0051Fab-LC-HPC4.

SEQ ID NO: 178 provides the amino acid sequence of 0004 Fab-HC: 0023Fab-VH-CH1-YGPPC.

SEQ ID NO: 179 provides the amino acid sequence of 0004Fab-LC: 0023Fab-LC-HPC4.

SEQ ID NO: 180 provides the amino acid sequence of human FVII-L4b-0062VH-CH1-HPC4.

SEQ ID NO: 181 provides the amino acid sequence of human FVII 407C.

SEQ ID NO: 182 provides the amino acid sequence of human FIX-L4b-0061LC.

DESCRIPTION OF THE INVENTION

Procoagulant proteins of the current invention comprise at least one coagulation factor, or functional variant thereof, and an antibody, or a fragment thereof, that is capable of binding to a receptor that is only present (in the ubiquitous sense of the word) on a platelet undergoing the morphological and functional changes associated with activation or an activated platelet. Such receptors might originate from the alpha- or dense granules of resting platelets, one particular exampleof such a receptor is TREM-like transcript 1 (TLT-1).

The procoagulant molecules may be fusion proteins. The term "fusion protein" herein refers to proteins that are created through the in-frame joining of two or more DNA sequences, which originally encode separate proteins or peptides, or fragments thereof. Translation of the fusion protein DNA sequence will result in a single protein sequence, which may have functional properties derived from each of the original proteins or peptides. DNA sequences encoding fusion proteins may be created artificially by standard molecular biology methods such as overlapping PCR or DNA ligation and the assembly is performed excluding the stop codon in the first 5'-end DNA sequence while retaining the stop codon in the 3'end DNA sequence. The resulting fusion protein DNA sequence may be inserted into an appropiate expression vector that supports the heterologous fusion protein expression in standard host organisms such as bacteria, yeast, fungus, insect cells or mammalian cells.

Fusion proteins may contain a linker or spacer peptide sequence that separates the protein or peptide parts which define the fusion protein. The linker or spacer peptide sequence may facilitate the correct folding of the individual protein or peptide parts and may make it more likely for the individual protein or peptide parts to retain their individual functional properties. Linker or spacer peptide sequences may be inserted into fusion protein DNA sequences during the in-frame assembly of the individual DNA fragments that make up the complete fusion protein DNA sequence, i.e., during overlapping PCR or DNA ligation.

Alternatively, the procoagulant proteins of the invention may be conjugates of their constituent coagulation factor and antibody counterparts, such that coagulation factor and antibody are manufactured independently of one another and, thereafter, joined synthetically.

As mentioned above, the procoagulant molecules of the invention may specifically bind TREM-like transcript 1 (TLT-1). Triggering receptors expressed on myeloid cells (TREMs) have a well-established role in the biology of various myeloid lineages, playing important roles in the regulation of innate and adaptive immunity. TLT-1 belongs to the same family of proteins, though the TLT-1 gene is expressed only in a single lineage, namely megakaryocytes and thrombocytes (platelets) and is exclusively found in the alpha-granules of megakaryocytes and platelets. TLT-1 is a transmembrane protein that is exposed on the surface of activated platelets upon alpha-granule release. To date, TLT-1 has not been found on the surface of resting platelets or on the surface of any other cell types.

The extracellular portion of TLT-1 is known to be composed of a single, immunoglobulin-like (Ig-like) domain connected to the platelet cell membrane by a linker region called the stalk (Gattis et al., Jour Biol Chem, 2006, Vol. 281, No. 19, pp. 13396-13403). The Ig-like domain of human TLT-1 (hTLT-1) is composed of 105 residues and is attached to the membrane by the 37-amino acid stalk. Thus, the Ig-like domain of TLT-1 is expected to have considerable freedom of movement.

The putative transmembrane segment of hTLT-1 is 20 amino acids long. TLT-1 also has a cytoplasmic Immune-receptor Tyrosine-based Inhibitory-Motif (ITIM), which may function as an intracellular signal transduction motif.

The role of TLT-1 in platelet biology has not yet been fully elucidated; it has been shown that TLT-1 binds fibrinogen and it is believed that TLT-1 plays a role in regulating coagulation and inflammation at the site of an injury. A soluble form of TLT-1 containing the Ig-like domain has been reported (Gattis et al., Jour Biol Chem, 2006, Vol. 281, No. 19, pp. 13396-13403). The specific functions of soluble versus platelet-bound TLT-1 remain to be established.

Giomerarelli at al. (Thrombosis and Haemostasis (2007) 97, 955-963) reported the generation of anti-TLT-1 scFv molecules using phage display techniques. Some of the anti-TLT-1 scFv molecules were found to inhibit thrombin-mediated human platelet aggregation. Thus, anti-TLT-1 scFc molecules with such features may have anti-thrombotic properties, similar to anti-GPIIb/IIIa scFv molecules described by Schwartz et al. (FASEB Journal, (2004), 18, 1704-1706).

The present invention relates to fusions proteins or conjugates comprising a coagulation factor attached to an anti-TLT-1 antibody, or antigen binding fragments thereof, including scFv. The anti-TLT-1 antibody or fragments thereof serve to target the linked clotting factor to the surface of activated platelets by binding to TLT-1 with the purpose of delivering a procoagulant activity at the activated platelet surface. In this context, inhibition of platelet aggregation is not a desireable property of the anti-TLT-1 antibody. Thus, anti-TLT-1 antibodies of the current invention are preferably not interfering with functions of TLT-1, and in particular do not inhibit platelet aggregation.

A receptor such as TLT-1 comprises epitopes that are useful targets for the procoagulant proteins of the current invention. Procoagulant proteins may bind any part of TLT-1 that would be available for binding in vivo, such as surface accessible residues of the Ig-like domain, or part of the stalk. Hence, fusion proteins may bind one or more residues within TLT-1 (20-125), TLT-1 (16-162), TLT-1 (126-162) and/or TLT-1 (129-142) (numbers in parenthesis refer to amino acid residues in SEQ ID NO: 2).

In a preferred embodiment, procoagulant proteins bind the stalk of TLT-1, such as one or more residues of TLT-1 (126-162) or TLT-1 (129-142). Procoagulant proteins that bind to the stalk of TLT-1 are unlikely to interfere with the function of the Ig-like domain. In another preferred embodiment, fusing the coagulation factor to the C-terminal of an antibody, or fragment thereof, will position the coagulation factor even more favourably on the cell surface of activated platelets, relative to that of FVII and FVIIa.

In another preferred embodiment, procoagulant proteins of the invention bind to TLT-1 without interfering platelet aggregation.

In another embodiment the procoagulant proteins of the invention bind to TLT-1 without competing with fibrinogen binding to TLT-1.

In terms of the current invention, TLT-1 may be from any vertebrate, such as any mammal, such as a rodent (such as a mouse, rat or guinea pig), a lagomorph (such as a rabbit), an artiodactyl (such as a pig, cow, sheep or camel) or a primate (such as a monkey or human being). TLT-1 is, preferably, human TLT-1. TLT-1 may be translated from any naturally occurring genotype or allele that gives rise to a functional TLT-1 protein. A non-limiting example of one human TLT-1 is the polypeptide sequence of SEQ ID NO: 2. SEQ ID NO: 2 includes the signal peptide (residues 1-15 (MGLTLLLLLLLGLEG) of SEQ ID NO: 2, and the mature TLT-1 polypeptide corresponds to residues 16-311 of SEQ ID NO: 2.

Procoagulant proteins of the invention comprise an antibody, or a fragment thereof, that has been raised against TLT-1. The antibody or fragment thereof may or may not result in a change in the conformational structure of TLT-1. Furthermore, the antibody or fragment thereof may or may not result in intracellular signalling, as a result of binding to TLT-1. In one embodiment, the antibody or fragment thereof is capable of binding to the stalk of TLT-1. Hence, the antibody or fragment thereof utilises a naturally occurring receptor, or portion thereof, in order to achieve the effect that is unique to and provided by the current invention.

The term "antibody" herein refers to a protein, derived from a germline immunoglobulin sequence, that is capable of specifically binding to an antigen which is TLT-1 or a portion thereof. The term includes full length antibodies of any isotype (that is, IgA, IgE, IgG, IgM and/or IgY) and any fragment or single chain thereof.

Full-length antibodies usually comprise at least four polypeptide chains: that is, two heavy (H) chains and two light (L) chains that are interconnected by disulfide bonds. One immunoglobulin sub-class of particular pharmaceutical interest is the IgG family, which may be sub-divided into isotypes IgG1, IgG2, IgG3 and IgG4. IgG molecules are composed of two heavy chains, interlinked by two or more disulfide bonds, and two light chains, each attached to a heavy chain by a disulfide bond. A heavy chain may comprise a heavy chain variable region (VH) and up to three heavy chain constant (CH) regions: CH1, CH2 and CH3. A light chain may comprise a light chain variable region (VL) and a light chain constant region (CL). VH and VL regions can be further subdivided into regions of hypervariability, termed complementarity determining regions (CDRs), interspersed with regions that are more conserved, termed framework regions (FR). VH and VL regions are typically composed of three CDRs and four FRs, arranged from amino-terminus to carboxy-terminus in the following order: FR1, CDR1, FR2, CDR2, FR3, CDR3, FR4. The hypervariable regions of the heavy and light chains form a domain that is capable of interacting with an antigen (TLT-1), whilst the constant region of an antibody may mediate binding of the immunoglobulin to host tissues or factors, including but not limited to various cells of the immune system (effector cells), Fc receptors and the first component (Clq) of the classical complement system.

The antibody component of the procoagulant proteins may be a monoclonal antibody. Such an antibody may be a chimeric antibody, a CDR-grafted antibody, a human antibody, a humanised antibody or an antigen binding portion of any thereof. For the production of antibodies, the experimental animal is a suitable mammal such as a goat, rabbit, rat or mouse.

In structural terms, a monoclonal antibody is represented by a single molecular species having a single binding specificity and affinity for a particular epitope. Monoclonal antibodies (mAbs) for the procoagulant proteins of the invention can be produced by a variety of well-known techniques, including conventional monoclonal antibody methodology e.g., the standard somatic cell hybridization technique of Kohler and Milstein (1975) *Nature* 256: 495, or viral or oncogenic transformation of B lymphocytes. The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

To generate hybridomas producing suitable monoclonal antibodies, splenocytes and/or lymph node cells from immunized mice can be isolated and fused to an appropriate immortalized cell line, such as a mouse myeloma cell line. The resulting hybridomas can be screened for the production of antigen-specific antibodies. The antibody secreting hybridomas can be replated, screened again, and if still positive for suitable IgG, the monoclonal antibodies can be subcloned at least twice by limiting dilution. The stable subclones can then be cultured in vitro to generate small amounts of antibody in tissue culture medium for characterization.

Antibodies for the invention may be prepared, expressed, created or isolated by recombinant means, such as (a) antibodies isolated from an animal (e.g., a mouse) that is transgenic or transchromosomal for the immunoglobulin genes of interest or a hybridoma prepared therefrom, (b) antibodies isolated from a host cell transformed to express the antibody of interest, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

Several suitable monoclonal antibodies, shown in Table 1, are herein identified by means of the prefix "mAb" together with a 4-digit number. Hence, the monoclonal antibody may be mAb0012 or a variant thereof. The monoclonal antibody may be mAb0023 or a variant thereof. The monoclonal antibody may be mAb0051 or a variant thereof. The monoclonal antibody may be mAb0061 or a variant thereof. The monoclonal antibody may be mAb0062 or a variant thereof. The monoclonal antibody may be mAb0082 or a variant thereof.

TABLE 1

Non-limiting examples of suitable monoclonal antibodies

| mAb ID | HC | LC |
|---|---|---|
| 0012 | SEQ ID NO: 32 | SEQ ID NO: 33 |
| 0023 | SEQ ID NO: 34 | SEQ ID NO: 35 |
| 0051 | SEQ ID NO: 36 | SEQ ID NO: 37 |
| 0052 | SEQ ID NO: 38 | SEQ ID NO: 39 |
| 0061 | SEQ ID NO: 40 | SEQ ID NO: 41 |
| 0062 | SEQ ID NO: 42 | SEQ ID NO: 39 |
| 0082 | SEQ ID NO: 43 | SEQ ID NO: 41 |

The term "antigen-binding portion" of an antibody refers to one or more fragments of an antibody that retain the ability to specifically bind to an antigen, such as TLT-1 or another target receptor, as described herein. It has been shown that the antigen-binding function of an antibody can be performed by fragments of a full-length antibody. The antibody component of the procoagulant proteins may therefore be a fragment of an antibody, such as a fragment of a monoclonal antibody. Examples of binding fragments encompassed within the term "antigen-binding portion" of an antibody include a Fab fragment, a $F(ab')_2$ fragment, a Fab' fragment, a Fd fragment, a Fv fragment, a ScFv fragment, a dAb fragment and an isolated complementarity determining region (CDR). Single chain antibodies such as scFv and heavy chain antibodies such as VHH and camel antibodies are also intended to be encompassed within the term "antigen-binding portion" of an antibody. These antibody fragments may be obtained using conventional techniques known to those of skill in the art, and the fragments may be screened for utility in the same manner as intact antibodies.

A "Fab" fragment includes a variable domain and a constant domain of the light chain and a variable domain and the first constant domain ($C_H1$) of the heavy chain. A Fab' fragment includes one or more carboxy terminal disulphide linkages to the heavy or light chains. $F(ab')_2$ antibody fragments comprise a pair of Fab fragments that are generally covalently linked near their carboxy termini by hinge cysteines. Other chemical couplings of antibody fragments are also known in the art.

An "Fv" fragment is an antibody fragment that contains a complete antigen recognition and binding site, and generally comprises a dimer of one heavy and one light chain variable domain in tight association that can be covalent in nature, for example in a single chain variable domain fragment (scFv). It is in this configuration that the three hypervariable regions of each variable domain interact to define an antigen-binding site on the surface of the $V_H$-$V_L$ dimer. Collectively, the six hypervariable regions or a subset thereof confer antigen binding specificity to the antibody. However, even a single variable domain comprising only three hypervariable regions specific for an antigen has the ability to recognize and bind antigen, although usually at a lower affinity than the entire binding site (Cai & Garen, *Proc. Natl. Acad. Sci. USA,* 93: 6280-6285, 1996). For example, naturally occurring camelid antibodies that only have a heavy chain variable domain (VHH) can bind antigen (Desmyter et al., *J. Biol. Chem.,* 277: 23645-23650, 2002; Bond et al., *J. Mol. Biol.* 2003; 332: 643-655).

"Single-chain Fv" or "scFv" antibody fragments comprise the $V_H$ and $V_L$ domains of an antibody, where these domains are present in a single polypeptide chain. Generally, the Fv polypeptide further comprises a polypeptide linker between the $V_H$ and $V_L$ domains that enables the scFv to form the desired structure for antigen binding. For a review of scFv, see Pluckthun, 1994, In: *The Pharmacology of Monoclonal Antibodies*, Vol. 113, Rosenburg and Moore eds. Springer-Verlag, New York, pp. 269-315.

The term "diabodies" refers to small antibody fragments with two antigen-binding sites, in which fragments comprise a heavy chain variable domain ($V_H$) connected to a light chain variable domain ($V_L$) in the same polypeptide chain ($V_H$ and $V_L$). By using a linker that is too short to allow pairing between the two variable domains on the same chain, the variable domains are forced to pair with complementary domains of another chain, creating two antigen-binding sites. Diabodies are described more fully, for example, in EP 404,097; WO 93/11161; and Hollinger et al., 1993, *Proc. Natl. Acad. Sci. USA,* 90:6444-6448.

The expression "linear antibodies" refers to antibodies as described in Zapata et al., 1995, *Protein Eng.,* 8(10):1057-1062. Briefly, these antibodies contain a pair of tandem Fd segments ($V_H$-$C_H1$-$V_H$-$C_H1$) that, together with complementary light chain polypeptides, form a pair of antigen binding regions. Linear antibodies can be bispecific or monospecific.

The term "monobody" as used herein, refers to an antigen binding molecule with a heavy chain variable domain and no light chain variable domain. A monobody can bind to an antigen in the absence of light chains and typically has three hypervariable regions, for example CDRs designated CDRH1, CDRH2, and CDRH3. A heavy chain IgG monobody has two heavy chain antigen binding molecules connected by a disulfide bond. The heavy chain variable domain comprises one or more hypervariable regions, preferably a CDRH3 or HVL-H3 region.

The term "hypervariable region", when used herein, refers to the amino acid residues of an antibody that are responsible for antigen-binding. The hypervariable region comprises amino acid residues from a "complementarity-determining region" or "CDR" (defined by sequence as residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (defined by structure and differing for each antibody; see, for example: Chothia and Lesk, 1987, *J. Mol. Biol.* 196:901-917). In one example, HVL residues can include, 26-32 (L1), 50-52 (L2) and 91-96 (L3) in the light chain variable domain and 26-32 (H1), 53-55 (H2) and 96-101 (H3) in the heavy chain variable domain.

In one embodiment of the invention, the TLT-1 binding portion of the procoagulant protein is a Fab fragment. Several suitable Fab fragments, shown in Table 2, are herein identified by means of the prefix "Fab" together with a 4-digit number. The Fab fragment may be Fab0003 or a variant thereof. The Fab fragment may be Fab0004 or a variant thereof. The Fab fragment may be Fab0012 or a variant thereof. The Fab fragment may be Fab0023 or a variant thereof. The Fab fragment may be Fab0051 or a variant thereof. The Fab fragment may be Fab0052 or a variant thereof. The Fab fragment may be Fab0061 or a variant thereof. The Fab fragment may be Fab0062 or a variant thereof. The Fab fragment may be Fab0074 or a variant thereof. The Fab fragment may be Fab0082 or a variant thereof. The Fab fragment may be Fab0084 or a variant thereof.

TABLE 2

Non-limiting examples of suitable Fab fragments

| Fab ID | VH-CH1 | LC |
|---|---|---|
| Fab0003 | SEQ ID NO: 175 | SEQ ID NO: 174 |
| Fab0004 | SEQ ID NO: 178 | SEQ ID NO: 179 |
| Fab0012 | SEQ ID NO: 44 | SEQ ID NO: 33 |
| Fab0023 | SEQ ID NO: 45 | SEQ ID NO: 35 |
| Fab0051 | SEQ ID NO: 46 | SEQ ID NO: 37 |
| Fab0052 | SEQ ID NO: 47 | SEQ ID NO: 39 |
| Fab0061 | SEQ ID NO: 146 | SEQ ID NO: 41 |
| Fab0074 | SEQ ID NO: 176 | SEQ ID NO: 177 |
| Fab0082 | SEQ ID NO: 48 | SEQ ID NO: 41 |
| Fab0084 | SEQ ID NO: 171 | SEQ ID NO: 167 |

As mentioned above, an antibody for the invention may be a human antibody or a humanised antibody. The term "human antibody", as used herein, is intended to include antibodies that have variable regions in which both the framework and CDR regions are derived from human germline immunoglobulin sequences. Furthermore, if the antibody contains a constant region, the constant region is also derived from human germline immunoglobulin sequences.

The human antibodies of the invention may include amino acid residues not encoded by human germline immunoglobulin sequences (e.g., mutations introduced by random or site-specific mutagenesis in vitro or by somatic mutation in vivo). However, the term “human antibody”, as used herein, is not intended to include antibodies in which CDR sequences derived from the germline of another mammalian species, such as a mouse, have been grafted onto human framework sequences.

Such a human antibody may be a human monoclonal antibody. Such a human monoclonal antibody may be produced by a hybridoma which includes a B cell obtained from a transgenic nonhuman animal, e.g., a transgenic mouse whose genome comprises a human heavy chain transgene and a light chain transgene fused to an immortalized cell.

Human antibodies may be prepared by in vitro immunisation of human lymphocytes followed by transformation of the lymphocytes with Epstein-Barr virus.

The term “human antibody derivatives” refers to any modified form of the human antibody, e.g., a conjugate of the antibody and another agent or antibody.

The term “humanized antibody” herein refers to antibodies in which CDR sequences derived from the germline of another mammalian species, such as a mouse, have been grafted onto human framework sequences. Additional framework region modifications may be made within the human framework sequences.

Antibodies of the invention can be tested for binding to the target protein by, for example, standard ELISA or Western blotting. An ELISA assay can also be used to screen for hybridomas that show positive reactivity with the target protein. The binding specificity of an antibody may also be determined by monitoring binding of the antibody to cells expressing the target protein, for example, by flow cytometry.

The specificity of an antibody of the invention for the target protein may be further studied by determining whether or not the antibody binds to other proteins. For example, where it is desired to produce an antibody that specifically binds TLT-1 or a particular part, e.g. epitope, of TLT-1, the specificity of the antibody may be assessed by determining whether or not the antibody also binds to other molecules or modified forms of TLT-1 that lack the part of interest.

Polypeptide or antibody “fragments” according to the invention may be made by truncation of the corresponding monoclonal antibodies, e.g. by removal of one or more amino acids from the N and/or C-terminal ends of a polypeptide. Up to 10, up to 20, up to 30, up to 40 or more amino acids may be removed from the N and/or C terminal in this way. Fragments may also be generated by one or more internal deletions.

In terms of the current invention, “epitope” refers to the area or region on an antigen (Ag), which is a molecular structure on the surface of an activated platelet, to which the antibody (Ab) portion of the procoagulant protein is capable of specifically binding, i.e. the area or region that is in physical contact with the Ab. An antigen’s epitope may comprise amino acid residues in the Ag that are directly involved in binding to a Ab (the immunodominant component of the epitope) and other amino acid residues, which are not directly involved in the binding, such as amino acid residues of the Ag which are effectively blocked by the Ab (in other words, the amino acid residue is within the “solvent-excluded surface” and/or the “footprint” of the Ab). The term epitope herein includes both types of binding sites within any particular region of a receptor, such as TLT-1, that specifically binds to an anti-TLT-1 antibody, or fragment thereof, unless otherwise stated (e.g., in some contexts the invention relates to antibodies that bind directly to particular amino acid residues). Receptors such as TLT-1 may comprise a number of different epitopes, which may include, without limitation, (1) linear peptide epitopes, (2) conformational epitopes which include of one or more non-contiguous amino acids located near each other in the mature receptor conformation; and (3) post-translational epitopes, which include, either in whole or part, of molecular structures covalently attached to TLT-1, such as carbohydrate groups.

The epitope for a given antibody (Ab)/antigen (Ag) pair can be defined and characterized at different levels of detail using a variety of experimental and computational epitope mapping methods. The experimental methods include mutagenesis, X-ray crystallography, Nuclear Magnetic Resonance (NMR) spectroscopy, Hydrogen deuterium eXchange Mass Spectrometry (HX-MS) and various competition binding methods. As each method relies on a unique principle, the description of an epitope is intimately linked to the method by which it has been determined. Thus, the epitope for a given Ab/Ag pair will be defined differently depending on the epitope mapping method employed.

At its most detailed level, the epitope for the interaction between the Ag and the Ab can be defined by the spatial coordinates defining the atomic contacts present in the Ag-Ab interaction, as well as information about their relative contributions to the binding thermodynamics. At a less detailed level the epitope can be characterized by the spatial coordinates defining the atomic contacts between the Ag and Ab. At a further less detailed level the epitope can be characterized by the amino acid residues that it comprises as defined by a specific criterium, e.g. distance between atoms in the Ab and the Ag. At a further less detailed level the epitope can be characterized through function, e.g. by competition binding with other Abs. The epitope can also be defined more generically as comprising amino acid residues for which substitution by another amino acid will alter the characteristics of the interaction between the Ab and Ag.

In the context of an X-ray derived crystal structure defined by spatial coordinates of a complex between an Ab, e.g. a Fab fragment, and its Ag, the term epitope is herein, unless otherwise specified or contradicted by context, specifically defined as platelet receptor residues characterized by having a heavy atom (i.e. a non-hydrogen atom) within a distance of 4 Å from a heavy atom in the Ab.

From the fact that descriptions and definitions of epitopes, dependent on the epitope mapping method used, are obtained at different levels of detail, it follows that comparison of epitopes for different Abs on the same Ag can similarly be conducted at different levels of detail.

Epitopes described on the amino acid level, e.g. determined from an X-ray structure, are said to be identical if they contain the same set of amino acid residues. Epitopes are said to overlap if at least one amino acid is shared by the epitopes. Epitopes are said to be separate (unique) if no amino acid residue is shared by the epitopes.

Epitopes characterized by competition binding are said to be overlapping if the binding of the corresponding Ab’s are mutually exclusive, i.e. if binding of one Ab excludes simultaneous binding of the other Ab. The epitopes are said to be separate (unique) if the Ag is able to accommodate binding of both corresponding Ab’s simultaneously. Furthermore, there are instances when one or more antibodies do not have overlapping epitopes but can not bind simultaneously. Due to tertiary and quaternary structure of an antigen, one antibody may not be able to access its epitope due to previous binding of another antibody.

Procoagulant proteins of the invention may be capable of binding to the same epitope as mAb0012. Procoagulant proteins may be capable of binding to the same epitope as mAb0023. Procoagulant proteins may be capable of binding to the same epitope as mAb0051. Procoagulant proteins may be capable of binding to the same epitope as mAb0061. Procoagulant proteins may be capable of binding to the same epitope as mAb0062. Procoagulant proteins may be capable of binding to the same epitope as mAb0082.

The epitope may comprise one or more residues selected from the group consisting of K133, I134, G135, S136, L137, A138, N140, A141, F142, S143, D144, P145 and A146 of SEQ ID NO: 4 (corresponding to K133, I134, G135, S136, L137, A138, N140, A141, F142, S143, D144, P145 and A146 of SEQ ID NO: 2).

The epitope may comprise one or more residues selected from the group consisting of V17, Q18, C19, H20, Y21, R22, L23, Q24, D25, V26, K27, A28, L63, G64, G65, G66, L67, L68, G89, A90, R91, G92, P93, Q94, I95 and L96 of SEQ ID NO: 5 (corresponding to V36, Q37, C38, H39, Y40, R41, L42, Q43, D44, V45, K46, A47, L82, G83, G84, G85, L86, L87, G108, A109, R110, G111, P112, Q113, I114 and L115 of SEQ ID NO: 2).

The epitope may comprise one or more residues selected from the group consisting of L36, P37, E38, G39, C40, Q41, P42, L43, V44, S45, S46, A47, V73, T74, L75, Q76, E77, E78, D79, A80, G81, E82, Y83, G84, C85, M86, R91, G92, P93, Q94, I95, L96, H97, R98, V99, S100 and L101 of SEQ ID NO: 5 (corresponding to L55, P56, E57, G58, C59, Q60, P61, L62, V63, S64, S65, A66, V92, T93, L94, Q95, E96, E97, D98, A99, G100, E101, Y102, G103, C104, M105, R110, G111, P112, Q113, I114, L115, H116, R117, V118, S119 and L120 of SEQ ID NO: 2).

The epitope may comprise one or more residues selected from the group consisting of V17, Q18, C19, H20, Y21, R22, L23, Q24, D25, V26, K27, A28, R91, G92, P93, Q94, I95, L96, H97, R98, V99, S100 and L101 of SEQ ID NO: 5 (corresponding to V36, Q37, C38, H39, Y40, R41, L42, Q43, D44, V45, K46, A47, R110, G111, P112, Q113, I114, L115, H116, R117, V118, S119 and L120 of SEQ ID NO: 2).

The epitope may comprise one or more residues selected from the group consisting of E5, T6, H7, K8, I9, G10, S11, L12, A13, E14, N15, A16, F17, S18, D19 and P20 of SEQ ID NO: 7 (corresponding to E130, T131, H132, K133, I134, G135, S136, L137, A138, E139, N140, A141, F142, S143, D144 and P145 of SEQ ID NO: 2).

The epitope may comprise one or more residues selected from the group consisting of K8, I9, G10, S11, L12, A13, N15, A16, F17, S18, D19, P20 and A21 of SEQ ID NO: 7 (corresponding to K133, I134, G135, S136, L137, A138, N140, A141, F142, S143, D144, P145 and A146 of SEQ ID NO: 2).

The definition of the term "paratope" is derived from the above definition of "epitope" by reversing the perspective. Thus, the term "paratope" refers to the area or region on the Ab to which an Ag specifically binds, i.e. to which it makes physical contact to the Ag.

The paratope may comprise one or more residues selected from the group consisting of H50, N52, Y56, H58, Y73, F79, S115, T116, V118 and Y120 of the anti-TLT-1 light (L) chain (SEQ ID NO: 33), and residues V20, F45, R49, Y50, W51, E68, T75, N77, S116, G117, V118 and T120 of the anti-TLT-1 heavy (H) chain (SEQ ID NO: 32).

In the context of an X-ray derived crystal structure defined by spatial coordinates of a complex between an Ab, e.g. a Fab fragment, and its Ag, the term paratope is herein, unless otherwise specified or contradicted by context, specifically defined as Ag residues characterized by having a heavy atom (i.e. a non-hydrogen atom) within a distance of 4 Å from a heavy atom in the platelet receptor.

The epitope and paratope for a given antibody (Ab)/antigen (Ag) pair may be identified by routine methods. For example, the general location of an epitope may be determined by assessing the ability of an antibody to bind to different fragments or variants of TLT-1. The specific amino acids within TLT-1 that make contact with an antibody (epitope) and the specific amino acids in an antibody that make contact with TLT-1 (paratope) may also be determined using routine methods, such as those described in the examples. For example, the antibody and target molecule may be combined and the Ab/Ag complex may be crystallised. The crystal structure of the complex may be determined and used to identify specific sites of interaction between the antibody and its target.

Fusion proteins comprising an antibody or fragment thereof may also be defined in terms of their complementarity-determining regions (CDRs). The term "complementarity-determining region" or "hypervariable region" herein refers to the amino acid residues of an antibody that are responsible for antigen binding. The complementarity-determining regions or "CDRs" are generally comprised of amino acid residues 24-34 (L1), 50-56 (L2) and 89-97 (L3) in the light-chain variable domain and 31-35 (H1), 50-65 (H2) and 95-102 (H3) in the heavy-chain variable domain; (Kabat et al. (1991) Sequences of Proteins of Immunological Interest, Fifth Edition, U.S. Department of Health and Human Services, NIH Publication No. 91-3242) and/or those residues from a "hypervariable loop" (residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196:901-917). Typically, the numbering of amino acid residues in this region is performed by the method described in Kabat et al., supra. Phrases such as "Kabat position", "Kabat residue", and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a FR or CDR of the variable domain. For example, a heavy chain variable domain may include amino acid insertions (residue 52a, 52b and 52c according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "framework region" or "FR" residues refer to those VH or VL amino acid residues that are not within the CDRs, as defined herein.

In one embodiment, the heavy chain of an antibody, or fragment thereof, for the procoagulant proteins of the invention comprises:

- a CDR1 sequence of amino acids 50 to 54 (DYFMY) of SEQ ID NO: 34, wherein one of these amino acids may be substituted by a different amino acid; and/or
- a CDR2 sequence of amino acids 69 to 85 (YISNGGDSSSYPDTVKG) of SEQ ID NO: 34, wherein one, two, three or four of these amino acids may be substituted by a different amino acid; and/or a CDR3 sequence of amino acids 118 to 129 (NKNWDDYYDMDY) of SEQ ID NO: 34, wherein one, two or three of these amino acids may be substituted by a different amino acid.

In another embodiment, the light chain of an antibody, or fragment thereof, for the procoagulant proteins of the invention comprises:

a CDR1 sequence of amino acids 44 to 60 (KSSQSLLNSRTRKNYLA) of SEQ ID NO: 35, wherein one, two, three or four of these amino acids may be substituted with a different amino acid; and/or a CDR2 sequence of amino acids 76 to 82 (WASTRES) of SEQ ID NO: 35, wherein one or two of these amino acids may be substituted with a different amino acid; and/or a CDR3 sequence of amino acids 115 to 122 (KQSYNLLT) of SEQ ID NO: 35, wherein one or two of these amino acids may be substituted with a different amino acid.

In another embodiment, the heavy chain of an antibody, or fragment thereof, for the procoagulant proteins of the invention comprises:

a CDR1 sequence of amino acids 50 to 54 (DYSMH) of SEQ ID NO: 36, wherein one of these amino acids may be substituted by a different amino acid; and/or a CDR2 sequence of amino acids 69 to 85 (VISTYYGDVRYNQKFKG) of SEQ ID NO: 36, wherein one, two, three or four of these amino acids may be substituted by a different amino acid; and/or a CDR3 sequence of amino acids 118 to 129 (APMITTGAWFAY) of SEQ ID NO: 36, wherein one, two or three of these amino acids may be substituted by a different amino acid.

In another embodiment, the light chain of an antibody, or fragment thereof, for the procoagulant proteins of the invention comprises:

a CDR1 sequence of amino acids 44 to 54 (KASQSVSNDVA) of SEQ ID NO: 37, wherein one, two or three of these amino acids may be substituted with a different amino acid; and/or a CDR2 sequence of amino acids 70 to 76 (YASSRYT) of SEQ ID NO: 37, wherein one or two of these amino acids may be substituted with a different amino acid; and/or a CDR3 sequence of amino acids 109 to 117 (QQDYSSPYT) of SEQ ID NO: 37, wherein one or two of these amino acids may be substituted with a different amino acid.

In another embodiment, the heavy chain of an antibody, or fragment thereof, for the procoagulant proteins of the invention comprises:

a CDR1 sequence of amino acids 50 to 54 (SHWIE) of SEQ ID NO: 42, wherein one of these amino acids may be substituted by a different amino acid; and/or a CDR2 sequence of amino acids 69 to 85 (EILPGSGNTNYNEKFKG) of SEQ ID NO: 42, wherein one, two, three or four of these amino acids may be substituted by a different amino acid; and/or a CDR3 sequence of amino acids 118 to 130 (GYYGLNYDWYFDV) of SEQ ID NO: 42, wherein one, two or three of these amino acids may be substituted by a different amino acid.

In another embodiment, the light chain of an antibody, or fragment thereof, for the procoagulant proteins of the invention comprises:

a CDR1 sequence of amino acids 44 to 54 (RASQDISNYLN) of SEQ ID NO: 39, wherein one, two or three of these amino acids may be substituted with a different amino acid; and/or a CDR2 sequence of amino acids 70 to 76 (YTSRLHS) of SEQ ID NO: 39, wherein one or two of these amino acids may be substituted with a different amino acid; and/or a CDR3 sequence of amino acids 109 to 117 (QQDTKLPYT) of SEQ ID NO: 39, wherein one or two of these amino acids may be substituted with a different amino acid.

In another embodiment, the heavy chain of an antibody, or fragment thereof, for the procoagulant proteins of the invention comprises:

a CDR1 sequence of amino acids 49 to 53 (RYWMT) of SEQ ID NO: 40, wherein one of these amino acids may be substituted by a different amino acid; and/or a CDR2 sequence of amino acids 68 to 84 (EINPDSSTINYNPSLKD) of SEQ ID NO: 40, wherein one, two, three or four of these amino acids may be substituted by a different amino acid; and/or a CDR3 sequence of amino acids 117 to 121 (GVFTS) of SEQ ID NO: 40, wherein one, two or three of these amino acids may be substituted by a different amino acid.

In another embodiment, the light chain of an antibody, or fragment thereof, for the procoagulant proteins of the invention comprises:

a CDR1 sequence of amino acids 43 to 58 (RSSQSLVHRNGNTYFH) of SEQ ID NO: 41, wherein one, two, three or four of these amino acids may be substituted with a different amino acid; and/or a CDR2 sequence of amino acids 74 to 80 (KVSNRFS) of SEQ ID NO: 41, wherein one or two of these amino acids may be substituted with a different amino acid; and/or a CDR3 sequence of amino acids 113 to 121 (SQSTHVPYT) of SEQ ID NO: 41, wherein one or two of these amino acids may be substituted with a different amino acid.

In another embodiment, the heavy chain of an antibody, or fragment thereof, for the procoagulant proteins of the invention comprises:

a CDR1 sequence of amino acids 49 to 53 (RYWMT) of SEQ ID NO: 32, wherein one of these amino acids may be substituted by a different amino acid; and/or a CDR2 sequence of amino acids 68 to 84 (EINPDSSTINYTPSLKD) of SEQ ID NO: 32, wherein one, two, three or four of these amino acids may be substituted by a different amino acid; and/or a CDR3 sequence of amino acids 117 to 121 (GVFTS) of SEQ ID NO: 32, wherein one, two or three of these amino acids may be substituted by a different amino acid.

In another embodiment, the light chain of an antibody, or fragment thereof, for the procoagulant proteins of the invention comprises:

a CDR1 sequence of amino acids 43 to 58 (RSSQSLVHRNGNTYFH) of SEQ ID NO: 33, wherein one, two, three or four of these amino acids may be substituted with a different amino acid; and/or a CDR2 sequence of amino acids 74 to 80 (KVSNRFS) of SEQ ID NO: 33, wherein one or two of these amino acids may be substituted with a different amino acid; and/or a CDR3 sequence of amino acids 113 to 121 (SQSTHVPYT) of SEQ ID NO: 33, wherein one or two of these amino acids may be substituted with a different amino acid.

Monoclonal antibodies, or fragments thereof, for the procoagulant proteins of the current invention may be glycosylation variants. Glycosylation variants of antibodies are variants in which the glycosylation pattern of an antibody is altered. By altering is meant deleting one or more carbohydrate moieties found in the antibody, adding one or more carbohydrate moieties to the antibody, changing the composition of glycosylation (glycosylation pattern), the extent of glycosylation.

Antibodies are glycosylated at conserved positions in their constant regions (Jefferis and Lund, *Chem. Immunol.* 1997; 65:111-128; Wright and Morrison, *Trends Biotechnol.* 1997; 15:26-32). The oligosaccharide side chains of the inmunoglobulins can affect a protein's function (Boyd et al., *Mol. Immunol.* 1996; 32:1311-1318), and the intramolecular interaction between portions of the glycoprotein can affect the conformation and presented three-dimensional surface of the glycoprotein. Oligosaccharides may also serve to target a given glycoprotein to certain molecules based upon specific recognition structures. For example, it has been reported that in agalactosylated IgG, the oligosaccharide moiety "flips" out of the inter-CH2 space and terminal N-acetylglucosamine residues become available to bind mannose binding protein (Malhotra et al., Nature Med. 1995; 1:237-243). Removal by glycopeptidase of the oligosaccharides from CAMPATH-1H (a recombinant humanized murine monoclonal IgG1 antibody which recognizes the CDw52 antigen of human lymphocytes) produced in Chinese Hamster Ovary (CHO) cells resulted in a complete reduction in complement mediated lysis (CMCL) (Boyd et al., *Mol. Immunol.* 1996; 32:1311-1318), while selective removal of sialic acid residues using neuraminidase resulted in no loss of DMCL. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al. *Nature Biotech.* 1999; 17:176-180).

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Similarly, removal of glycosylation sites can be accomplished by amino acid alteration within the native glycosylation sites of the antibody.

The amino acid sequence is usually altered by altering the underlying nucleic acid sequence. Nucleic acid molecules encoding amino acid sequence variants of a TLT-1 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the TLT-1 antibody.

The glycosylation (including glycosylation pattern) of antibodies may also be altered without altering the amino acid sequence or the underlying nucleotide sequence. Glycosylation largely depends on the host cell used to express the antibody. Since the cell type used for expression of recombinant glycoproteins, e.g. antibodies, as potential therapeutics is rarely the native cell, significant variations in the glycosylation pattern of the antibodies can be expected (see, e.g. Hse et al., *J. Biol. Chem.* 1997; 272:9062-9070). In addition to the choice of host cells, factors which affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example using endoglycosidase H (Endo H). In addition, the recombinant host cell can be genetically engineered, e.g. make defective in processing certain types of polysaccharides. These and similar techniques are well known in the art.

The glycosylation structure of antibodies can be readily analyzed by conventional techniques of carbohydrate analysis, including lectin chromatography, NMR, Mass spectrometry, HPLC, GPC, monosaccharide compositional analysis, sequential enzymatic digestion, and HPAEC-PAD, which uses high pH anion exchange chromatography to separate oligosaccharides based on charge. Methods for releasing oligosaccharides for analytical purposes are also known, and include, without limitation, enzymatic treatment, elimination using harsh alkaline environment to release mainly O-linked structures, and chemical methods using anhydrous hydrazine to release both N- and O-linked oligosaccharides.

In addition to their TLT-1-binding portion, which involves a monoclonal antibody or fragment thereof, procoagulant proteins of the invention also comprise a coagulation factor component, whose function is to upregulate blood coagulation in the vicinity of the activated platelet.

Coagulation factors of procoagulant fusion proteins or conjugates of the present invention may be in their inactive form or in their activated form. The coagulation factor may be a serine protease, in which case the inactive form of the coagulation factor corresponds to the zymogen form and the activated form corresponds to the catalytically active form. The coagulation factor may be a FVII polypeptide (FVII or FVIIa), a FVIII polypeptide (i.e. FVIII or FVIIIa), a FIX polypeptide (FIX or FIXa), a FX polypeptide (FX or FXa) or a FXI polypeptide (FXI or FXIa). FVII, FVIII, FIX, FX and FXI polypeptides of the present invention also includes variants, such as truncated variants, and derivatives of said coagulation factors. FVII, FIX, FX and FXI variants will include truncated des-Gla variants, i.e. variants of said coagulation factors lacking the Gla-domain responsible for interaction with phospholipid membranes of said coagulation factors.

If the coagulation factor is a FVII polypeptide, the FVII component may be able to bind to tissue factor and it is, preferably, able to cleave FIX or FX. If the coagulation factor is a FVIII polypeptide, the FVIII component is, preferably, able to bind to FIXa and support cleavage of FX. If the coagulation factor is a FIXa polypeptide, it is preferably able to cleave FX. If the coagulation factor is FXa, then it is preferably able to cleave prothrombin (FII). If the coagulation factor is a FXIa polypeptide then it is preferably able to cleave FIX.

In one particular embodiment, the coagulation factor is a FV polypeptide. Factor V is synthesized by the liver and secreted Factor V circulates in plasma as a 330-kDa single-chain polypeptide that is the inactive procoagulant (Huang et al. (2008) Haemophilia 14: 1164-9). FV is composed of 2196 amino acids, including a 28 amino acids signal peptide. It is composed of six domains A1 (Aa 30-329), A2 (Aa 348-684), B (Aa 692-1573), A3 (Aa 1578-1907), C1 (Aa 1907-2061), and C2 (Aa 2066-2221). The A and C domains of the two proteins are approximately 40% homologous with the equivalent domains of FVIII, but the B domains are not conserved. As is the case with FVIII, FV activity is tightly regulated via site-specific proteolysis. Thrombin, and to a lesser extent Factor Xa (FXa), are primarily responsible for FV activation via proteolytic cleavages at positions $Arg^{709}$-$Ser^{710}$, $Arg^{1018}$-$Thr^{1019}$ and $Arg^{1545}$-$Ser^{1546}$. These cleavages release the B domain and create a dimeric molecule composed of a 105-kDa heavy chain that contains the A1 and A2 domains and a 71- to 74-kDa light chain that contains the A3, C1, and C2 domains. These two chains are held together by calcium at residues $Asp^{139}$ and $Asp^{140}$ and hydrophobic interactions. The heavy chain provides the contacts for both FXa and prothrombin, whereas the two C domains in the light chain are needed for the interaction of FVa with the phospholipid surface. Thus, Factor V is active as a cofactor for FXa of the thrombinase complex and the activated FXa enzyme requires calcium and FVa to convert prothrombin to thrombin on the cell surface membrane. The A3 domain in the light chain is involved in both FXa and phospholipid interactions. Taken together, the two FVa chains link FXa to the phospholipid surface formed by the platelet plug at the site of injury and enable FXa to efficiently bind and cleave prothrombin to generate thrombin. Factor V is able to bind to activated platelets. Although FV is predominately found as a soluble component in blood plasma, a fraction of FV is also present in the α-granula of platelets, which is important for normal hemostasis as evidenced by platelet specific Factor V deficiency (Janeway et al. (1996) Blood 87: 3571-8).

One wild type human Factor V sequence is provided in SEQ ID NO: 155. The term "Factor V polypeptide" herein refers to wild type Factor V molecules as well as FV variants, FV derivatives and FV conjugates. Such variants, derivatives and conjugates may exhibit substantially the same, or improved, biological activity relative to wild-type human Factor V.

For the purpose of the current invention, Factor V may be plasma-derived or recombinantly produced, using well known methods of production and purification. The degree and location of glycosylation, gamma-carboxylation and other post-translational modifications may vary depending on the chosen host cell and its growth conditions.

Factor V polypeptides may be tested using commercially available clotting assays, such as the in vitro Hemoclot Factor V Reagent assay (Aniara, Ohio, USA: Cat. No. ACK071K).

In one particular embodiment, the coagulation factor is a FVIIa polypeptide. Factor VII (FVII) is a glycoprotein primarily produced in the liver. The mature protein is composed of 406 amino acid residues and is composed of four domains as defined by homology. There is an N-terminal Gla domain followed by two epidermal growth factor (EGF)-like domains and a C-terminal serine protease domain. FVII circulates in plasma as a single-chain molecule. Upon activation to activated FVII (FVIIa), the molecule is cloven between residues Arg152 and Ile153, resulting in a two-chain protein held together by a disulphide bond. The light chain contains the Gla and EGF-like domains, whereas the heavy chain is the protease domain. FVIIa requires binding to its cell-surface cofactor tissue factor to become fully biologically active.

The term "Factor VII(a)" herein encompasses the uncloven zymogen, Factor VII, as well as the cloven and thus activated protease, Factor VIIa. "Factor VII(a)" includes natural allelic variants of FVII(a) that may exist and occur from one individual to another. One wild type human Factor VIIa sequence is provided in SEQ ID NO: 157, as well as in Proc Natl Acad Sci USA 1986; 83:2412-2416.

The term "Factor VII(a) polypeptide" herein refers to wild type Factor VIIa molecules as well as FVII(a) variants, FVII(a) derivatives and FVII(a) conjugates. Such variants, derivatives and conjugates may exhibit substantially the same, or improved, biological activity relative to wild-type human Factor VIIa.

The term "FVII(a) variant", as used herein, is intended to designate Factor FVII having the sequence of SEQ ID NO: 157, wherein one or more amino acids of the parent protein have been substituted by another amino acid and/or wherein one or more amino acids of the parent protein have been deleted and/or wherein one or more amino acids have been inserted in protein and/or wherein one or more amino acids have been added to the parent protein. Such addition can take place either at the N-terminal end or at the C-terminal end of the parent protein or both. The "analogue" or "analogues" within this definition still have FVII activity in its activated form. In one embodiment a variant is at least 90% identical with the sequence of of SEQ ID NO: 157. In another embodiment a variant is at least 95%, such as at least 96%, such as at least 97%, such as at least 98%, such as at least 99% identical with the sequence of of SEQ ID NO: 157. As used herein, any reference to a specific position refers to the corresponding position in SEQ ID NO: 157.

Non-limiting examples of FVII(a) variants that have substantially the same or increased proteolytic activity compared to recombinant wild type human Factor VII(a) include those disclosed in WO 01/83725, WO 02/22776, WO 02/077218, WO 03/027147, WO 03/037932, WO 04/029090, WO 05/024006, WO 07/031559 and EP 05108713.8, U.S. Pat. No. 7,173,000 B2; and JP4451514 B2.

The term "improved biological activity" refers to FVII(a) polypeptides that exhibit i) substantially the same or increased proteolytic activity compared to recombinant wild type human Factor VIIa in the presence and/or absence of tissue factor or ii) to FVII(a) polypeptides with substantially the same or increased TF affinity compared to recombinant wild type human Factor VIIa or iii) to FVII(a) polypeptides with substantially the same or increased half life in plasma compared to recombinant wild type human Factor VIIa, or iv) to FVII(a) polypeptides with substantially the same or increased affinity for the activated platelet. The biological activity of a FVIIa polypeptide may be measured using a variety of assays known to the person skilled in the art, such as the in vitro hydrolysis and in vitro proteolysis assays described in examples 26 and 27.

For the purpose of the current invention, Factor VII(a) may be plasma-derived or recombinantly produced, using well known methods of production and purification. The degree and location of glycosylation, gamma-carboxylation and other post-translational modifications may vary depending on the chosen host cell and its growth conditions.

```
SEQ ID NO: 157 modified with γ at Gamma-
Carboxylated residues:
Wild type human coagulation Factor VII
ANAFLγγLRPGSLγRγCKγγQCSFγγARγIFKDAγRTKLFWISYSDGDQ

CASSPCQNGGSCDQLQSYICFCLPAFEGRNCETHKDDQLICVNENGGCE

QYCSDHTGTKRSCRCHEGYSLLADGVSCTPTVEYPCKIPILEKNASKPQ

GRIVGGKVCPKGECPWQVLLLVNGAQLCGGTLINTIWVVSAAHCFKIKN

WRNLIAVLGEHDLSEHDGDEQSRRVAQVIIPSTYVPGTTNHDIALLRLH

QPVVLTDHVVPLCLPERTFSERTLAFVRFSLVSGWGQLLDRGATALELM

VLNVPRLMTQDCLQQSRKVGDSPNITEYMFCAGYSDGSKDSCKGDSGGP

HATHYRGTWYLTGIVSWGQGCAVGHFGVYTRVSQYIEWLQKLMRSEPRP

GVLLRAPFP
```

In another particular embodiment, the coagulation factor is a FVIII polypeptide. Factor VIII (FVIII) is a large, complex glycoprotein that is primarily produced by hepatocytes. FVIII is composed of 2351 amino acids, including a signal peptide, and contains several distinct domains as defined by homology. There are three A-domains, a unique B-domain, and two C-domains. The domain order can be listed as NH2-A1-A2-B-A3-C1-C2-COOH. FVIII circulates in plasma as two chains, separated at the B-A3 border. The chains are connected by bivalent metal ion-bindings. The A1-A2-B chain is termed the heavy chain (HC) while the A3-C1-C2 is termed the light chain (LC). Small acidic regions C-terminal of the A1 (the $a_1$ region) and A2 (the $a_2$ region) and N-terminal of the A3 domain (the $a_3$ region) play important roles in its interaction with other coagulation proteins, including thrombin and von Willebrand factor (vWF or VWF), the carrier protein for FVIII, in vivo.

Endogenous FVIII molecules circulate in vivo as a pool of molecules with B domains of various sizes, the shortest having C-terminal at position 740, i.e. at the C-terminal of A2-$a_2$. These FVIII molecules with B-domains of different length all have full procoagulant activity. Upon activation with thrombin, FVIII is cloven C-terminal of A1-$a_1$ at position 372, C-terminal of A2-$a_2$ at position 740, and between $a_3$ and A3 at position 1689, the latter cleavage releases the $a_3$ region, with concomitant loss of affinity for vWF. The activated FVIII molecule is termed FVIIIa. Activation allows interaction of FVIIIa with phospholipid surfaces like activated platelets and activated factor IX (FIXa): the tenase complex is formed, allowing efficient activation of factor X (FX).

The terms "Factor VIII(a)" and "FVIII(a)" include both FVIII and FVIIIa. "Factor VIII" or "FVIII" herein refers to a human plasma glycoprotein that is a member of the intrinsic coagulation pathway and is essential to blood coagulation. "Native FVIII" is the human FVIII molecule derived from the full length sequence as shown in SEQ ID NO: 159 (amino acid 1-2332). "FVIII(a)" includes natural allelic variants of FVIII(a) that may exist and occur from one individual to another.

FVIII molecules/variants may be B domain-truncated FVIII molecules wherein the remaining domains correspond closely to the sequences as set forth in amino acid numbers 1-740 and 1649-2332 of SEQ ID NO: 159. In such variants, as well as in FVIII derived from the full-length sequence, mutations may be introduced in order to, for example, reduce vWF binding capacity. Amino acid modifications, such as substitutions and deletions, may be introduced into the molecule in order to modify the binding capacity of FVIII with various other components such as LRP, various receptors, other coagulation factors, cell surfaces, introduction and/or abolishment of glycosylation sites. Other mutations that do not abolish FVIII activity may also be accommodated in a FVIII molecule/variant that may be used for the purposes of the present invention.

The B domain of FVIII spans amino acids 741-1648 of SEQ ID NO: 159. The B domain is cloven at several different sites, generating large heterogeneity in circulating plasma FVIII molecules. The exact function of the heavily glycosylated B domain is unknown. What is known is that the B domain is indispensable for FVIII activity in the coagulation cascade. Recombinant FVIII is thus frequently produced in the form of B domain-deleted/truncated variants.

Endogenous full length FVIII is synthesized as a single-chain precursor molecule. Prior to secretion, the precursor is cloven into the heavy chain and the light chain. Recombinant B domain-deleted FVIII can be produced by means of two different strategies. Either the heavy chain without the B-domain and the light chain are synthesized individually as two different polypeptide chains (two-chain strategy) or the B domain-deleted FVIII is synthesized as a single precursor polypeptide chain (single-chain strategy) that is cloven into the heavy and light chains in the same way as the full-length FVIII precursor.

In a B domain-deleted FVIII precursor polypeptide, produced by the single-chain strategy, the heavy and light chain moieties are often separated by a linker. To minimize the risk of introducing immunogenic epitopes in the B domain-deleted FVIII, the sequence of the linker is preferably derived from the FVIII B-domain. As a minimum, the linker must comprise a recognition site for the protease that cleaves the B domain-deleted FVIII precursor polypeptide into the heavy and light chain. In the B domain of full length FVIII, amino acid 1644-1648 constitutes this recognition site. The thrombin cleavage site leading to removal of the linker on activation of B domain-deleted FVIII is located in the heavy chain. Thus, the size and amino acid sequence of the linker is unlikely to influence its removal from the remaining FVIII molecule by thrombin activation. Deletion/truncation of the B domain is an advantage for production of FVIII. Nevertheless, parts of the B domain can be included in the linker without reducing the productivity. The negative effect of the B domain on productivity has not been attributed to any specific size or sequence of the B domain.

FVIII molecules for the present invention are capable of functioning in the coagulation cascade in a manner that is functionally similar, or equivalent, to FVIII, inducing the formation of FXa via interaction with FIXa on an activated platelet and supporting the formation of a blood clot. FVIII activity can be assessed in vitro using techniques well known in the art. Clot analyses, FX activation assays (often termed chromogenic assays), thrombin generation assays and whole blood thromboelastography are examples of such in vitro techniques, two of which are described in examples 28 and 29. FVIII molecules according to the present invention have FVIII activity that is at least that of native human FVIII.

The term "FVIII variant", as used herein, is intended to designate Factor FVIII having the sequence of SEQ ID NO: 159, wherein one or more amino acids of the parent protein have been substituted by another amino acid and/or wherein one or more amino acids of the parent protein have been deleted and/or wherein one or more amino acids have been inserted in protein and/or wherein one or more amino acids have been added to the parent protein. Such addition can take place either at the N-terminal end or at the C-terminal end of the parent protein or both. The "analogue" or "analogues" within this definition still have FVIII activity in its activated form. In one embodiment a variant is at least 90% identical with the sequence of of SEQ ID NO: 159. In another embodiment a variant is at least 95%, such as at least 96%, such as at least 97%, such as at least 98%, such as at least 99% identical with the sequence of of SEQ ID NO: 159. As used herein, any reference to a specific position refers to the corresponding position in SEQ ID NO: 159.

For the purpose of the current invention, FVIII may be plasma-derived or recombinantly produced, using well known methods of production and purification. The degree and location of glycosylation, gamma-carboxylation and other post-translational modifications may vary depending on the chosen host cell and its growth conditions.

In another particular embodiment, the coagulation factor is a Factor IX polypeptide. Factor IX (FIX) is, in its active form FIXa, a trypsin-like serine protease that serves a key role in haemostasis by generating, as part of the tenase complex, most of the factor Xa required to support proper thrombin formation during coagulation (reviewed in (Hoffman and Monroe, III 2001)).

Factor IX (FIX) is a vitamin K-dependent coagulation factor with structural similarities to factor VII, prothrombin, factor X, and protein C. The circulating zymogen form is composed of of 415 amino acids divided into four distinct domains comprising an N-terminal γ-carboxyglutamic acid-rich (Gla) domain, two EGF domains and a C-terminal trypsin-like serine protease domain. Activation of FIX occurs by limited proteolysis at $Arg^{145}$-$Ala^{146}$ and $Arg^{180}$-$Val^{181}$ releasing a 35-aa fragment, the so-called activation peptide (Schmidt and Bajaj 2003). The activation peptide is heavily glycosylated, containing two N-linked and up to four O-linked glycans.

"Factor IX" or "FIX", as used herein, refers to a human plasma Factor IX glycoprotein that is a member of the intrinsic coagulation pathway and is essential to blood coagulation. "Factor IX(a)" includes natural allelic variants of FIX(a) that may exist and occur from one individual to another. Factor IX(a) may be plasma-derived or recombinantly produced using well known methods of production and purification. The degree and location of glycosylation, gamma-carboxylation and other post-translation modifications may vary depending on the chosen host cell and its growth conditions. Unless otherwise specified or indicated, Factor IX means any functional human Factor IX protein molecule in its normal role in coagulation, including any fragment, analogue and derivative thereof.

One example of a "wild type FIX" is the full length human FIX molecule, as shown in SEQ ID NO: 161.

The terms "FIX analogue", as used herein, is intended to designate Factor FIX having the sequence of SEQ ID NO: 161, wherein one or more amino acids of the parent protein have been substituted by another amino acid and/or wherein one or more amino acids of the parent protein have been deleted and/or wherein one or more amino acids have been inserted in protein and/or wherein one or more amino acids have been added to the parent protein. Such addition can take place either at the N-terminal end or at the C-terminal end of the parent protein or both. The "analogue" or "analogues" within this definition still have FIX activity in its activated form. In one embodiment a variant is at least 90% identical with the sequence of SEQ ID NO: 161. In a further embodiment a variant is at least 95% identical with the sequence of of SEQ ID NO: 161. As used herein any reference to specific positions refers to the corresponding position in SEQ ID NO: 161. Non-limiting examples of FIX(a) variants that have substantially the same activity, FVIII bypassing activity or increased proteolytic activity compared to recombinant wild type human Factor IX(a) include those disclosed in Milanov P, Ivanciu L, Abriss D, Quade-Lyssy P, Miesbach W, Alesci S, Tonn T, Grez M, Seifried E, Schüttrumpf (2012) J. Blood 119: 602-11 and US 2011/0217284 A1. Unless otherwise specified, Factor IX domains include the following amino acid residues: Gla domain being the region from reside Tyr1 to residue Lys43; EGF1 being the region from residue Gln44 to residue Leu84; EGF2 being the region from residue Asp85 to residue Arg145; the Activation Peptide being the region from residue Ala146 to residue Arg180; and the Protease Domain being the region from residue Val181 to Thr414. The light chain refers to the region encompassing the Gla domain, EGF1 and EGF2, while the heavy chain refers to the Protease Domain.

Factor IX may be plasma-derived or recombinantly produced, using well known methods of production and purification. The degree and location of glycosylation, gamma-carboxylation and other post-translational modifications may vary depending on the chosen host cell and its growth conditions.

A commercially available assay kit known as 'Hyphen BioMed Chromogenic Factor IX kit (Aniara)' may be used to assess the activity level of the FIX polypeptide. In this assay, Factor XIa activates Factor IX into Factor IXa, which together with activated Factor VIII:C, phospholipids and $Ca^{2+}$, activates Factor X into Factor Xa. The amount of generated Factor Xa was measured at 405 nm by the amount of pNA released from the Factor Xa specific chromogenic substrate SXa-11.

Gamma-Carboxylated residues in the FVII sequence below are represented by "γ".

```
SEQ ID NO: 161:
Wild type human coagulation Factor IX
YNSGKLγγFVQGNLγRγCMγγKCSFγγARγVFγNTγRTTγFWKQYVDGDQ

CESNPCLNGGSCKDDINSYECWCPFGFEGKNCELDVTCNIKNGRCEQFCK

NSADNKVVCSCTEGYRLAENQKSCEPAVPFPCGRVSVSQTSKLTRAEAVF

PDVDYVNSTEAETILDNITQSTQSFNDFTRVVGGEDAKPGQFPWQVVLNG

KVDAFCGGSIVNEKWIVTAAHCVETGVKITVVAGEHNIEETEHTEQKRNV

IRIIPHHNYNAAINKYNHDIALLELDEPLVLNSYVTPICIADKEYNIFLK

FGSGYVSGWGRVFHKGRSALVLQYLRVPLVDRATCLRSTKFTYNNMFCAG

FHEGGRDSCQGDSGGPHVTEVEGTSFLTGIISWGEECAMKGKYGIYTKVS

RYVNWIKEKTKLT
```

In another particular embodiment, the coagulation factor is a FX polypeptide. Coagulation factor X (FX) is a vitamin K-dependent coagulation factor with structural similarities to factor VII, prothrombin, factor IX (FIX), and protein C. It is synthesised with a 40-residue pre-pro-sequence containing a hydrophobic signal sequence (Aa 1-31) that targets the protein for secretion. The pro-peptide is important for directing γ-carboxylation to the light chain of Factor X. The circulating human FX zymogen is composed of 445 amino acids divided into four distinct domains comprising an N-terminal gamma-carboxyglutamic acid rich (Gla) domain, two EGF domains, and a C-terminal trypsin-like serine protease domain. The mature two-chain form of FX is composed of a light chain (Aa41-179) and a heavy chain (Aa183-488) held together by a disulfide bridge ($Cys^{172}$-$Cys^{342}$). The light chain contains 11 Gla residues, which are important for $Ca^{2+}$-dependent binding of FX to negatively charged phospholipid membranes. Wild-type human coagulation factor X has two N-glycosylation sites ($Asn^{221}$ and $Asn^{231}$) and two O-glycosylation sites ($Thr^{199}$ and $Thr^{211}$) in the activation peptide. β-hydroxylation occurs at $Asp^{103}$ in the first EGF domain, resulting in β-hydroxyaspartic acid (Hya). Activation of FX occurs by limited proteolysis at $Arg^{234}$-$Ile^{235}$ releasing a 52 amino acid activation peptide (Aa 183-234). In the extrinsic pathway, this occurs upon exposure of Tissue factor (TF) on the membrane of subendothelial cells to plasma and subsequent activation of FVIIa. Activation via the intrinsic pathway occurs with the interaction of factor IXa, factor VIIIa, calcium and acidic phospholipid surfaces. Prothrombin is the most important substrate of Factor Xa, but the activation requires FXa's co-factor factor Va, calcium and acidic phospholipid surface. FX deficiency is a rare autosomal recessive bleeding disorder with an incidence of 1:1,000,000 in the general population (Dewerchin et al. (2000) Thromb Haemost 83: 185-190). Although it produces a variable bleeding tendency, patients with a severe FX deficiency tend to be the most seriously affected among patients with rare coagulation defects. The prevalence of heterozygous FX deficiency is about 1:500, but is usually clinically asymptomatic.

One example of a "wild type FX" is the full length human FX molecule, as shown in SEQ ID NO: 163.

"Factor X polypeptide" herein refers to any functional Factor X protein molecule capable of activating thrombin, including fragments, analogues and derivatives of SEQ ID NO: 163.

The term "FX analogue", as used herein, is intended to designate Factor FX having the sequence of SEQ ID NO: 163, wherein one or more amino acids of the parent protein have been substituted by another amino acid and/or wherein one or more amino acids of the parent protein have been deleted and/or wherein one or more amino acids have been inserted in protein and/or wherein one or more amino acids have been added to the parent protein. Such addition can take place either at the N-terminal end or at the C-terminal end of the parent protein or both. The "analogue" or "analogues" within this definition still have FX activity in its activated form. In one embodiment a variant is at least 90% identical with the sequence of SEQ ID NO: 163. In a further embodiment a variant is at least 95% identical with the sequence of SEQ ID NO: 163. As used herein any reference to specific positions refers to the corresponding position in SEQ ID NO: 163.

FX may be plasma-derived or recombinantly produced, using well known methods of production and purification. The degree and location of glycosylation, gamma-carboxylation and other post-translational modifications may vary depending on the chosen host cell and its growth conditions.

In another particular embodiment, the coagulation factor is a Factor XI polypeptide. Factor XI (FXI) is the zymogen of a blood coagulation protease, factor XIa (FXIa), which contributes to hemostasis through activation of factor IX. The factor is produced by the liver (Emsley et al. (2010) Blood 115:2569-77). The protein is a 160-kDa disulfide-linked dimer of identical 607 amino acid subunits, each containing 4 90- or 91-amino acid repeats called apple domains (from the N-terminus: A1: Aa 20-103, A2: Aa 110-193, A3: Aa 200-283, A4: Aa 291-374) and a C-terminal trypsin-like catalytic domain. The protein is expressed with a signal peptide Aa1-18. The structure is different from those of the well-characterized vitamin K-dependent coagulation proteases. FXI circulates in blood as a complex with high molecular weight kininogen (HK). Prekallikrein (PK), the zymogen of the protease-kallikrein, is a monomeric homolog of FXI with the same domain structure that also circulates in complex with HK. The zymogen factor is activated into factor XIa by Factor XIIa (FXIIa), thrombin, and is also autocatalytic. Cleavage activation occurs at the activation loop containing the Arg369-Ile370 cleavage site. Since FXI deficiency causes relatively mild bleeding, FXI has a speculative role in early fibrin generation. FXIa is postulated to be part of a feedback loop that sustains thrombin generation through FIX activation to consolidate coagulation. Certain tissues with robust fibrinolytic activity seem important for FXIa activity, including oropharynx and urinary tract, as these are common sites of bleeding in FXI-deficient patients. Congenital FXI deficiency is associated with a mild to moderate bleeding disorder. More than 180 other FXI gene mutations associated with FXI deficiency have been reported (www.factorxi.org, www.ist-h.org), including more than 100 single amino acid (missense) substitutions. Severe deficiency is prevalent in people of Jewish ancestry (Seligsohn et al. (2007) Thromb Haemost. 98:84-89). The carrier rate is approximately 5% in Ashkenazi Jews, with severe (homozygous) deficiency found in 1 in 450 persons. As an example, a severe mutation at Glu117Stop results in a truncated protein and homozygotes lacks completely plasma FXI antigen.

Factor XIa activates factor IX by selectively cleaving $Arg^{145}$-$Ala^{146}$ and $Arg^{180}$-$Val^{181}$.

The term "FXI analogue", as used herein, is intended to designate Factor XI having the sequence of SEQ ID NO: 165, wherein one or more amino acids of the parent protein have been substituted by another amino acid and/or wherein one or more amino acids of the parent protein have been deleted and/or wherein one or more amino acids have been inserted in protein and/or wherein one or more amino acids have been added to the parent protein. Such addition can take place either at the N-terminal end or at the C-terminal end of the parent protein or both. The "analogue" or "analogues" within this definition still have FX activity in its activated form. In one embodiment a variant is at least 90% identical with the sequence of SEQ ID NO: 165. In a further embodiment a variant is at least 95% identical with the sequence of SEQ ID NO: 165. As used herein any reference to a specific positions refers to the corresponding position in SEQ ID NO: 165.

FXI may be plasma-derived or recombinantly produced, using well known methods of production and purification. The degree and location of glycosylation, and other post-translational modifications may vary depending on the chosen host cell and its growth conditions.

The term "identity", as known in the art, refers to a relationship between the sequences of two or more polypeptides, as determined by comparing the sequences. In the art, "identity" also means the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3 times the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al., Atlas of Protein Sequence and Structure, vol. 5, supp.3 (1978) for the PAM 250 comparison matrix; Henikoff et al., Proc. Natl. Acad. Sci USA 89, 10915-10919 (1992) for the BLOSUM 62 comparison matrix) is also used by the algorithm.

Preferred parameters for a peptide sequence comparison include the following: Algorithm: Needleman et al., J. Mol. Biol. 48, 443-453 (1970); Comparison matrix: BLOSUM 62 from Henikoff et al., PNAS USA 89, 10915-10919 (1992); Gap Penalty: 12, Gap Length Penalty: 4, Threshold of Similarity: 0.

The GAP program is useful with the above parameters. The aforementioned parameters are the default parameters for peptide comparisons (along with no penalty for end gaps) using the GAP algorithm.

Hence, the procoagulant proteins of the current invention comprise (i) at least one coagulation factor component and (ii) an antibody or fragment thereof that is capable of binding a receptor, and/or a fragment thereof, wherein the receptor is present only (in the non-ubiquitous sense of the word) on the surface of activated platelets. In one preferred embodiment, said receptor is TLT-1. The procoagulant proteins of the current invention are preferably engineered such that their constituent parts may function independently of one another. For example, said coagulation factor component of the current invention is capable of upregulating blood coagulation. Likewise, said "antibody" component of the invention is preferably able to bind a receptor such as TLT-1, unhindered by the presence of said coagulation factor component. The carboxy terminus of the coagulation factor component may be covalently attached to the amino terminus of the antibody component of the construct, or vice versa. Said antibody component of the construct will preferably not bind to or demonstrate little affinity for any other triggering receptor expressed on myeloid cells (TREM). The construct of the current invention may or may not comprise a linker between said coagulation factor and said antibody constituents. Said optional linker may be any one of the linkers described in Table 3, or may be any other linker that binds both coagulation factor and antibody constituent parts of the construct, such that both are functional. In one embodiment, the coagulation factor and anti-TLT-1 components are expressed as fusion proteins. In one embodiment, the coagulation factor and anti-TLT-1 components are chemically conjugated.

Procoagulant proteins wherein part (ii) is a mAb may comprise two coagulation factor polypeptides (part (i)). The coagulation factor may be fused to a HC of the mAb; The coagulation factor may be fused to a LC of the mAb. The coagulation factor may be fused to a antibody, or fragment thereof, which, in turn, is fused to a HC of the mAb or a LC of the mAb.

Thus, a procoagulant protein of the present invention may comprise (i) at least one FV polypeptide and (ii) an antibody, or fragment thereof, that is capable of binding TLT-1.

A procoagulant protein of the present invention may comprise (i) at least one FVII polypeptide and (ii) an antibody, or fragment thereof, that is capable of binding TLT-1.

A procoagulant protein of the present invention may comprise (i) at least one FVIII polypeptide and (ii) an antibody, or fragment thereof, that is capable of binding TLT-1.

A procoagulant protein of the present invention may comprise (i) at least one FIX polypeptide and (ii) an antibody, or fragment thereof, that is capable of binding TLT-1.

A procoagulant protein of the present invention may comprise (i) at least one FX polypeptide and (ii) an antibody, or fragment thereof, that is capable of binding TLT-1.

A procoagulant protein of the present invention may comprise (i) at least one FXI polypeptide and (ii) an antibody, or fragment thereof, that is capable of binding TLT-1.

Procoagulant proteins may further comprise a linker. Non-limiting examples of linker amino acid sequences, which may be utilised when the procoagulant proteins are manufactured as fusion proteins, are shown in Table 3. Hence, said linker may be L1. The linker may be L2. The linker may be L3. The linker may be L4. The linker may be L5. The linker may be L6. The linker may be L7. The linker may be L8. The linker may be L9. The linker may be L10.

TABLE 3

| Non-limiting examples of optional linkers | | |
|---|---|---|
| Linker ID | Length (AA) | Linker sequence |
| L0 | 0 | no linker |
| L1 | 2 | GS |
| L2 | 7 | GSGGGGS (SEQ ID NO: 189) |
| L3 | 12 | GSGGGGSGGGGS (SEQ ID NO: 190) |
| L4a | 17 | GSGGGGSGGGGSGGGGS (SEQ ID NO: 191) |
| L4b | 17 | GGGGSGGGGSGGGGSGS (SEQ ID NO: 192) |
| L5 | 22 | GGGGSGSGGGGSGGGGSGGGGS (SEQ ID NO: 193) |
| L6 | 27 | GGGGSGGGGSGSGGGGSGGGGSGGGGS (SEQ ID NO: 194) |
| L7 | 32 | GGGGSGGGGSGGGGSGSGGGGSGGGGSGGGGS (SEQ ID NO: 195) |
| L8 | 37 | GGGGSGGGGSGGGGSGGGGSGSGGGGSGGGGSGGGGS (SEQ ID NO: 196) |
| L9 | 42 | GGGGSGGGGSGGGGSGGGGSGGGGSGSGGGGSGGGGSGGGGS (SEQ ID NO: 197) |
| L10 | 16 | YGPPSPSSPAPEFLGG (SEQ ID NO: 198) |

As mentioned above, the extracellular part of TLT-1 is composed of an immunoglobulin-like domain and a stalk. Procoagulant proteins of the invention may be capable of binding to either of these. When part (ii) of the procoagulant protein is capable of binding the immunoglobulin-like domain, a longer linker may allow part (i) of said fusion protein to adapt a functionally relevant position and orientation on the surface of the activated platelet, thereby facilitating its function.

A procoagulant protein that is capable of binding the stalk of TLT-1 is adjacent to the platelet membrane. A procoagulant protein that is capable of binding the stalk may comprise a linker but the inclusion of a linker does not necessarily affect the function of the coagulation factor part of the fusion protein.

As described above, procoagulant proteins of the invention are capable of binding a receptor that is present on platelets that are undergoing activation or that are fully activated, such as TLT-1. The term "binding affinity" is intended to refer to the property of procoagulant proteins, or the antibody component of procoagulant proteins, to bind or not to bind to their target. Binding affinity may be quantified by determining the binding constant ($K_D$) for an antibody component and its target. Similarly, the specificity of binding of an antibody component to its target may be defined in terms of the comparative binding constants ($K_D$) of the antibody for its target as compared to the binding constant with respect to the antibody and another, non-target molecule.

Typically, the $K_D$ for the antibody with respect to the target will be 2-fold, preferably 5-fold, more preferably 10-fold less than $K_D$ with respect to the other, non-target molecule such as unrelated material or accompanying material in the environment. More preferably, the $K_D$ will be 50-fold less, even more preferably 100-fold less, and yet more preferably 200-fold less.

The value of this binding constant can be determined directly by well-known methods, and can be computed even for complex mixtures by methods such as those, for example, set forth in Caceci et al. (Byte 9:340-362, 1984). For example, the $K_D$ may be established using a double-filter nitrocellulose filter binding assay such as that disclosed by Wong & Lohman (Proc. Natl. Acad. Sci. USA 90, 5428-5432, 1993). Other standard assays to evaluate the binding ability of antibodies towards targets are known in the art, including for example, ELISAs, Western blots, RIAs, and flow cytometry analysis. The binding kinetics (e.g., association rate and dissociation rate constants) and binding affinity of the antibody can also be assessed by standard assays known in the art, such as by surface plasmon resonce (SPR) analysis.

A competitive binding assay can be conducted in which the binding of the antibody to the target is compared to the binding of the target by another, known ligand of that target, or another antibody.

$K_D$ values for the antibody, or fragment thereof, of the invention may also be at least $1\times10^{-15}$M, such as at least $1\times10^{-14}$M, such as at least $1\times10^{-13}$M, such as at least $1\times10^{-12}$M, such as at least $1\times10^{-11}$M, such as at least $1\times10^{-10}$M, such as approximately $3\times10^{-9}$M, such as at least $1\times10^{-9}$M, or at least $1\times10^{-8}$M. An antibody of the invention may have a Kd (or Ki) for its target of $1\times10^{-7}$M or less, $1\times10^{-8}$M or less or $1\times10^{-9}$M or less.

Preferred $K_D$ values for the antibody, or fragment thereof, may be $1\times10^{-15}$M to $1\times10^{-14}$M, such as $1\times10^{-14}$M to $1\times10^{-13}$M $1\times10^{-13}$M to $1\times10^{-12}$M, such as $1\times10^{-12}$M to $1\times10^{-11}$M, such as $1\times10^{-11}$M to $1\times10^{-10}$M, such as $1\times10^{-10}$M to $1\times10^{-9}$M such as approximately $3\times10^{-9}$M, such as $1\times10^{-9}$M to $2\times10^{-8}$M.

An antibody or fragment thereof that specifically binds its target may bind its target with a high affinity, such as a $K_D$ as discussed above, and may bind to other, non-target molecules with a lower affinity. For example, the antibody may bind to a non-target molecules with a $K_D$ of $1\times10^{-6}$M or more, more preferably $1\times10^{-5}$ M or more, more preferably $1\times10^{-4}$ M or more, more preferably $1\times10^{-3}$ M or more, even more preferably $1\times10^{-2}$ M or more. A procoagulant protein of the invention is preferably capable of binding to its target with an affinity that is at least two-fold, 10-fold, 50-fold, 100-fold, 200-fold, 500-fold, 1,000-fold or 10,000-fold or greater than its affinity for binding to another non-target molecule, such as other TREMs than TLT-1.

The functional effects of the invented procoagulant proteins may be assessed by means of various in vitro and in vivo experiments. In vitro experiments may be designed to assess the function of the fusion proteins as a whole, as well as their component (i) coagulation factor and (ii) antibody parts. In vivo, fusion proteins may be tested in a tail-bleeding model in haemophilic mice that are transfused with human platelets. Furthermore in vivo, fusion proteins may be tested in a tail-bleeding model in haemophilic mice with the human TLT-1 gene inserted ("humanized" with respect to TLT-1).

As mentioned above, the procoagulant proteins may be provided in the form of fusion proteins or chemical conjugates. In the former case, the invention also relates to polynucleotides that encode the procoagulant proteins of the invention. Thus, a polynucleotide of the invention may encode any procoagulant protein as described herein. The terms “nucleic acid molecule” and “polynucleotide” are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or purified form.

A nucleic acid sequence which “encodes” a selected polypeptide is a nucleic acid molecule which is transcribed (in the case of DNA) and translated (in the case of mRNA) into a polypeptide in vivo, when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

Polynucleotides of the invention can be synthesised according to methods well known in the art, as described by way of example in Sambrook et al. (1989, Molecular Cloning—a laboratory manual; Cold Spring Harbor Press).

The nucleic acid molecules of the present invention may be provided in the form of an expression cassette which includes control sequences operably linked to the inserted sequence, thus allowing for expression of the antibody of the invention in vivo. These expression cassettes, in turn, are typically provided within vectors (e.g., plasmids or recombinant viral vectors). Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a polypeptide of the invention.

The present invention thus includes expression vectors that comprise such polynucleotide sequences. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al.

The invention also includes isolated cells that have been modified to express fusion proteins according to the invention. Such cells include transient, or—preferably—stable higher eukaryotic cell lines, such as mammalian cells or insect cells; lower eukaryotic cells, such as yeast; or prokaryotic cells such as bacterial cells. Particular examples of cells which may be modified by insertion of vectors or expression cassettes encoding for a construct of the invention include mammalian HEK293T, CHO, HeLa and COS cells. Preferably the cell line selected will be one which is not only stable, but also allows for mature glycosylation and cell surface expression of a polypeptide.

Such cell lines of the invention may be cultured using routine methods to produce a fusion protein or construct according to the invention. Alternatively, polynucleotides, expression cassettes or vectors of the invention may be administered to a cell from a subject ex vivo and the cell then returned to the body of the subject.

Alternatively, procoagulant proteins may be obtained by chemical conjugation of the antibody (such as a mAb), or fragment thereof, and the coagulation factor. In this case, a linker between the two proteins may contain one or more chemical moieties which are not present in those amino acids that are encoded by DNA.

In one embodiment, a chemical moiety used in the linker comprises the biradical with the structure

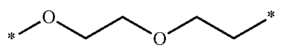

wherein * shows the positions of connection of this biradical.

The term “biradical” refers to an even-electron chemical compound with two free radical centres which act independently of one another.

In another embodiment, a chemical moiety used in the linker comprises a polymer: a macromolecule composed of repeating structural units that are typically connected by covalent chemical bonds. Such a polymer may be hydrophilic.

The term hydrophilic or “water-soluble” refers to moieties that have some detectable degree of solubility in water. Methods to detect and/or quantify water solubility are well known in the art.

Exemplary water-soluble polymers according to the invention include peptides, saccharides, (poly)ethers, (poly) amines, (poly)carboxylic acids and the like. Peptides can have mixed sequences and be composed of a single amino acid, e.g., (poly)lysine. An exemplary polysaccharide is (poly)sialic acid. An exemplary (poly)ether is (poly)ethylene glycol. (Poly)ethylene imine is an exemplary polyamine, and (poly)acrylic acid is a representative (poly)carboxylic acid.

The hydrophilic polymer according to the present invention is, preferably, non-naturally occurring. In one example, the non-naturally occurring modifying group is a polymeric modifying group, in which at least one polymeric moiety is non-naturally occurring. In another example, the non-naturally occurring modifying group is a modified carbohydrate. The locus of functionalization with the modifying group is selected such that it does not prevent the “modified sugar” from being added enzymatically to a polypeptide. “Modified sugar” also refers to any glycosyl mimetic moiety that is functionalized with a modifying group and which is a substrate for a natural or modified enzyme, such as a glycosyltransferase.

Many other polymers are also suitable for the invention. Polymer backbones that are non-peptidic and water-soluble, are particularly useful in the invention. Examples of suitable polymers include, but are not limited to, other poly(alkylene glycols), such as poly(propylene glycol) (“PPG”), copolymers of ethylene glycol and propylene glycol and the like, poly(oxyethylated polyol), poly(olefmic alcohol), poly(vinylpyrrolidone), poly(hydroxypropylmethacrylamide), poly([alpha]-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, as well as copolymers, terpolymers, and mixtures thereof.

The polymeric linker may alter a property of the procoagulant protein, such as its bioavailability, biological activity or its half-life in the body.

The polymeric linker is, preferably, linear.

Although the molecular weight of each individual polymer chain may vary, it is typically in the range of from about 1,000 Da (1 kDa) to about 40,000 Da (40 kDa), such as about 1,000 Da to about 12,000 Da such as about 2,000 Da to about 11,000 Da, such as about 2,000 Da to about 3,000 Da; about 3,000 Da to about 4,000 Da; about 4,000 to about 5,000 Da; about 5,000 to about 6,000 Da; about 6,000 to about 7,000 Da; about 7,000 to about 8,000 Da; about 8,000 to about 9,000 Da; about 9,000 to about 10,000 Da; or about 10,000 to about 11,000 Da. It should be understood that these sizes represent estimates rather than exact measures. According to a preferred embodiment, the molecules according to the invention are conjugated with a heterogenous population of hydrophilic polymers.

In a particular embodiment, a chemical moiety used in the linker comprises polyethylene glycol (PEG).

The term "PEG" herein refers to a biradical comprising the structure

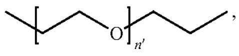

wherein n' is an integer larger than 1.

PEG is prepared by polymerization of ethylene oxide and is commercially available over a wide range of molecular weights. The PEG for use according to the present invention is, preferably, linear.

Furthermore, "PEG" may refer to a polyethylene glycol compound, or derivative thereof, with or without coupling agents, coupling or activating moieties (e.g., with carboxylic acid/active ester, keto, alkoxyamine, thiol, triflate, tresylate, aziridine, oxirane, alkyne, azide or a maleimide moiety).

In one particular embodiment the PEG for use according to the invention is monodisperse. In another particular embodiment, the PEG for use according to the invention is polydisperse.

Polydisperse PEG is composed of PEG molecules that have various molecular weights. The size distribution can be characterized statistically by its weight average molecular weight (Mw) and its number average molecular weight (Mn), the ratio of which is called the polydispersity index (Mw/Mn) (see e.g. "Polymer Synthesis and Characterization", 3. A. Nairn, University of Utah, 2003). Mw and Mn can be measured by mass spectroscopy.

The polydispersity index may be a number that is greater than or equal to one and it may be estimated from Gel Permeation Chromatographic data. When the polydispersity index is 1, the product is monodisperse and is thus made up of compounds with a single molecular weight. When the polydispersity index is greater than 1 the polymer is polydisperse, and the polydispersity index tells how broad the distribution of polymers with different molecular weights is. The polydispersity index typically increases with the molecular weight of the PEG. In particular embodiments, the polydispersity index of the PEG for use according to the invention is i) below 1.06, ii) below 1.05, iii) below 1.04, iv) below 1.03 or v) between 1.02 and 1.03.

Different forms of PEG are available, depending on the initiator used for the polymerization process.

Numerous methods for conjugation of PEG substituents are described in *Advanced Drug Delivery Reviews,* 2002, 54, 459-476, *Nature Reviews Drug Discovery,* 2003, 2, 214-221 DOI:10.1038/nrd1033, *Adv Polym Sci,* 2006, 192, 95-134, DOI 10.1007/12_022, Springer-Verlag, Berlin Heidelberg, 2005, and references therein. Alternatively, conjugation of the hydrophilic polymer substituent could take place by use of enzymatic methods. Such methods are for instance use of glycosyltransferases as described in WO2003/031464 or use of transglutaminases as described in WO2006134148.

To effect covalent attachment of the polymer molecule(s) to the polypeptide, the hydroxyl end groups of the polymer molecule are provided in activated form, i.e. with reactive functional groups. Suitable activated polymer molecules are commercially available, e.g. from Sigma-Aldrich Corporation, St. Louis, Mo., USA, Rapp Polymere GmbH, Tubingen, Germany, or from PolyMASC Pharmaceuticals plc, UK. Alternatively, the polymer molecules can be activated by conventional methods known in the art, e.g. as disclosed in WO 90/13540. Specific examples of activated PEG polymers are disclosed in U.S. Pat. Nos. 5,932,462 and 5,643,575. Furthermore, the following publications disclose useful polymer molecules and/or PEGylation chemistries: WO2003/031464, WO2004/099231.

The conjugation of the monoclonal antibody, fragment thereof or coagulation factor with the activated polymer molecules may be conducted by use of any conventional method, e.g. as described in the following references (which also describe suitable methods for activation of polymer molecules): R. F. Taylor, (1991), "Protein immobilisation. Fundamental and applications", Marcel Dekker, N.Y.; S. S. Wong, (1992), "Chemistry of Protein Conjugation and Crosslinking", CRC Press, Boca Raton; G. T. Hermanson et al., (1993), "Immobilized Affinity Ligand Techniques", Academic Press, N.Y., 'Bioconjugate Techniques, Second Edition, Greg T. Hermanson, 2008, Amsterdam, Elsevier). The skilled person will be aware that the activation method and/or conjugation chemistry to be used depends on the attachment group(s) of the polypeptide (examples of which are given further above), as well as the functional groups of the polymer (e.g. being amine, hydroxyl, carboxyl, aldehyde, sulfhydryl, succinimidyl, maleimide, vinylsulfone or haloacetate). The PEGylation may be directed towards conjugation to all available attachment groups on the polypeptide (i.e. such attachment groups that are exposed at the surface of the polypeptide) or may be directed towards one or more specific attachment groups, e.g. the N-terminal amino group. Furthermore, the conjugation may be achieved in one step or in a stepwise manner.

In another embodiment, a chemical moiety used as the linker is hydroxyethyl starch. The term "hydroxyethyl starch" (HES/HAES), as used herein, refers to a nonionic starch derivative. Different types of hydroxyethyl starches are typically described by their average molecular weight, typically around 130 to 200 kDa.

In another embodiment, a chemical moiety used in the linker comprises polysialic acid.

In another embodiment, a chemical moiety used in the linker is attached to at least one of the proteins to a glycan: a polysaccharide or an oligosaccharide that is attached to a protein.

In another embodiment, a chemical moiety used in the linker is attached to at least one of the proteins to an O-linked glycan.

In another embodiment, a chemical moiety used in the linker is attached to at least one of the proteins to an N-linked glycan.

Both N-glycans and O-glycans are attached to proteins such as mAbs and coagulation factors by the cells producing these proteins. The cellular N-glycosylation machinery recognizes and glycosylates N-glycosylation signals (N—X—S/T motifs) in the amino acid chain, as the nascent protein is translocated from the ribosome to the endoplasmic reticulum (Kiely et al. 1976; Glabe et al. 1980). Likewise, O-glycans are attached to specific O-glycosylation sites in the amino acid chain, but the motifs triggering O-glycosylation are much more heterogenous than the N-glycosylation signals, and our ability to predict O-glycosylation sites in amino acid sequences is still inadequate (Julenius et al. 2004). Methods of conjugating polypeptides with various polymeric side groups are described e.g. in WO0331464.

In another embodiment, a chemical moiety used in the linker comprises a chemical moiety, which is used to attach said linker to at least one of the proteins with a structure selected of the biradicals:

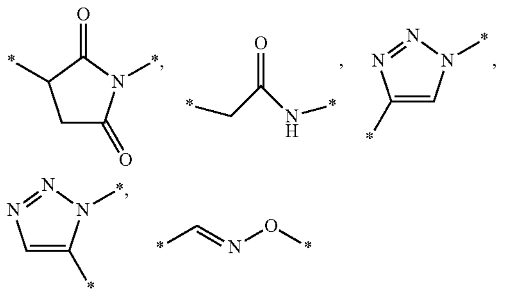

In one embodiment, the linker comprises the biradical structure of

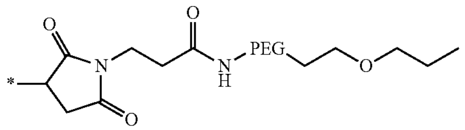

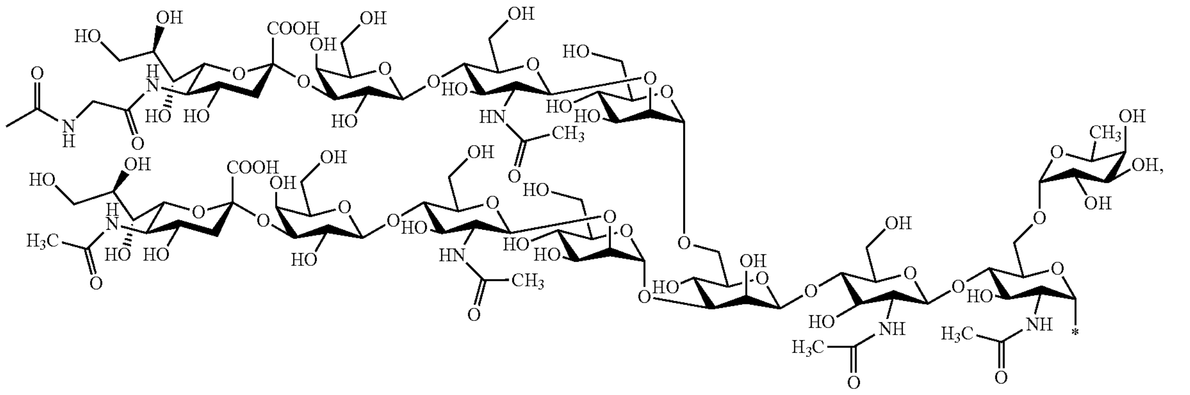

wherein * shows the positions of connection of this biradical.

In another embodiment, the linker comprises the structure

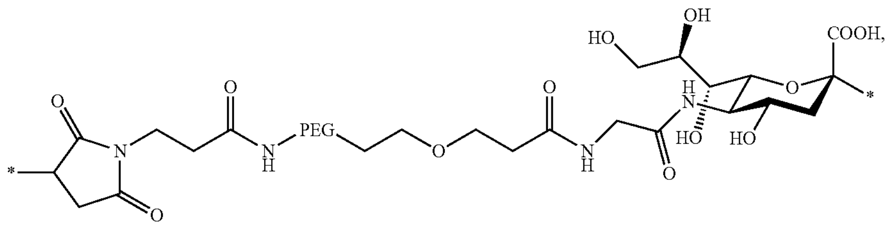

wherein * shows the positions of connection of this biradical.

A compound of the general formula

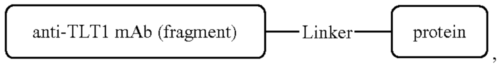

wherein "anti-TLT-1 mAb (fragment)" may be a full size mAb against TLT-1 or a fragment or an analogue intellectually derived thereof such as but not limited to, a FAB-fragment or a sc-FAB with none, one or more point mutations, the linker may be a water soluble polymer such as but not limited to e.g. PEG, polysialic acid, or hydroxyethyl starch, and protein is any protein which is thought to has one or more improved properties when attached to anti-TLT-1 mAb (fragment) may be for example prepared in a two step procedure.

During the first step, a linker, with two different reactive groups RS1 and RS2 may be attached to the anti-TLT-1 mAb (fragment). The reaction may be run with low site selectivity or in a selective way, such that RS1 only reacts at one or few position of the anti TLT-1 mAb (fragment). As a non-exclusive example, RS1 could be an aldehyde and react by reductive amination only with N-termini of the anti TLT-1 mAb (fragment) by reductive amination, known to a person trained in the art. Another non-exclusive example RS1 could be a maleimide group, which may react with a free thiol on the anti TLT-1 mAb (fragment).

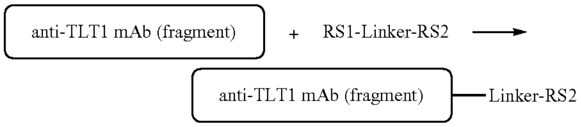

During the second step, the reactive group RS2 may be reacted with low site selectivity or site selectivity with a FVIIa molecule. As a non-exclusive example, a site selective reaction at FVIIa may be obtained when RS2 is a sialic acid derivative, which can react in the presence of a suitable enzyme such as but not limited to ST3Gal-III with N-linked glycans, which do not end exclusively with sialic acids.

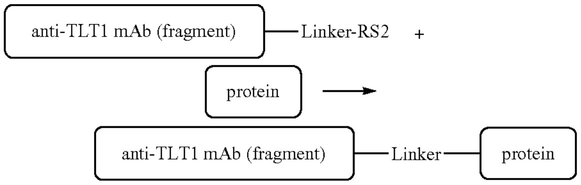

The order of attachment of the linker to the two proteins, namely the anti-TLT-1 mAb (fragment) and the protein may be switched, thereby attaching the RS1-Linker-RS2 molecule first to the protein molecule and then to the anti TLT-1 mAb (fragment).

In another aspect, the present invention provides compositions and formulations comprising molecules of the invention, such as the fusion proteins, polynucleotides, vectors and cells described herein. For example, the invention provides a pharmaceutical composition that comprises one or more fusion proteins of the invention, formulated together with a pharmaceutically acceptable carrier.

Accordingly, one object of the invention is to provide a pharmaceutical formulation comprising such an antibody which is present in a concentration from 0.25 mg/ml to 250 mg/ml, and wherein said formulation has a pH from 2.0 to 10.0. The formulation may further comprise a buffer system, preservative(s), tonicity agent(s), chelating agent(s), stabilizers and surfactants. The use of preservatives, isotonic agents, chelating agents, stabilizers and surfactants in pharmaceutical compositions is well-known to the skilled person. Reference may be made to Remington: *The Science and Practice of Pharmacy*, $19^{th}$ edition, 1995.

In one embodiment, the pharmaceutical formulation is an aqueous formulation. Such a formulation is typically a solution or a suspension. The terms "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, to which the physician or the patient adds solvents and/or diluents prior to use.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

The term "treatment", as used herein, refers to the medical therapy of any human or other animal subject in need thereof. Said subject is expected to have undergone physical examination by a medical practitioner, who has given a tentative or definitive diagnosis which would indicate that the use of said specific treatment is beneficial to the health of said human or other animal subject. The timing and purpose of said treatment may vary from one individual to another, according to the status quo of the subject's health. Preventative or prophylactic administration of antibodies of the invention is also contemplated, with prevention being defined as delaying or averting manifestation aggravation of one or more symptoms of a disease or disorder. Thus, said treatment may be prophylactic, palliative, symptomatic and/or curative.

In terms of the present invention, prophylactic, palliative, symptomatic and/or curative treatments may represent separate aspects of the invention.

A coagulopathy that results in an increased haemorrhagic tendency may be caused by any qualitative or quantitative deficiency of any pro-coagulative component of the normal coagulation cascade or any upregulation of fibrinolysis. Such coagulopathies may be congenital and/or acquired and/or iatrogenic and are identified by a person skilled in the art.

Non-limiting examples of congenital hypocoagulopathies are haemophilia A, haemophilia B, Factor VII deficiency, Factor X deficiency, Factor XI deficiency, von Willebrand's disease and thrombocytopenias such as Glanzmann's thombasthenia and Bernard-Soulier syndrome.

A non-limiting example of an acquired coagulopathy is serine protease deficiency caused by vitamin K deficiency; such vitamin K-deficiency may be caused by administration of a vitamin K antagonist, such as warfarin. Acquired coagulopathy may also occur following extensive trauma. In this case otherwise known as the "bloody vicious cycle", it is characterised by haemodilution (dilutional thrombocytopaenia and dilution of clotting factors), hypothermia, consumption of clotting factors and metabolic derangements (acidosis). Fluid therapy and increased fibrinolysis may exaserbate this situation. Said haemorrhage may be from any part of the body.

Haemophilia A with “inhibitors” (that is, allo-antibodies against factor VIII) and haemophilia B with “inhibitors” (that is, allo-antibodies against factor IX) are non-limiting examples of coagulopathies that are partly congenital and partly acquired.

A non-limiting example of an iatrogenic coagulopathy is an overdosage of anticoagulant medication—such as heparin, aspirin, warfarin and other platelet aggregation inhibitors—that may be prescribed to treat thromboembolic disease. A second, non-limiting example of iatrogenic coagulopathy is that which is induced by excessive and/or inappropriate fluid therapy, such as that which may be induced by a blood transfusion.

In one embodiment of the current invention, haemorrhage is associated with haemophilia A or B. In another embodiment, haemorrhage is associated with haemophilia A or B with acquired inhibitors. In another embodiment, haemorrhage is associated with von Willebrand’s disease. In another embodiment, haemorrhage is associated with severe tissue damage. In another embodiment, haemorrhage is associated with severe trauma. In another embodiment, haemorrhage is associated with surgery. In another embodiment, haemorrhage is associated with haemorrhagic gastritis and/or enteritis. In another embodiment, the haemorrhage is profuse uterine bleeding, such as in placental abruption. In another embodiment, haemorrhage occurs in organs with a limited possibility for mechanical haemostasis, such as intracranially, intraaurally or intraocularly. In another embodiment, haemorrhage is associated with anticoagulant therapy.

In a further embodiment, haemorrhage may be associated with thrombocytopaenia. In individuals with thrombocytopaenia, constructs of the current invention may be co-administered with platelets.

The following is a non-limiting list of embodiments of the present invention:

Embodiment 1: A procoagulant protein comprising (i) at least one coagulation factor, covalently attached to (ii) an antibody, or fragment thereof, that is capable of binding (iii) TLT-1, and/or a fragment or variant thereof.

Embodiment 2: The procoagulant protein according to embodiment 1, wherein (iii) is TLT-1, or a fragment or variant thereof. Embodiment 3: The procoagulant protein according to embodiment 2, wherein (iii) is TLT-1 (16-162).

Embodiment 4: The procoagulant protein according to embodiment 2, wherein (iii) is TLT-1 (20-125).

Embodiment 5: The procoagulant protein according to embodiment 2, wherein (iii) is TLT-1 (126-162).

Embodiment 6: The procoagulant protein according to any one of embodiments 1-2, wherein (i) is a serine protease or a derivative thereof.

Embodiment 7: The procoagulant protein according to embodiment 3, wherein (i) is a Factor VII polypeptide.

Embodiment 8: The procoagulant protein according to embodiment 3, wherein (i) is a Factor IX polypeptide.

Embodiment 9: The procoagulant protein according to embodiment 3, wherein (i) is a Factor X polypeptide.

Embodiment 10: The procoagulant protein according to any one of embodiments 1-2, wherein (i) is a Factor V polypeptide.

Embodiment 11: The procoagulant protein according to any one of embodiments 1-2, wherein (i) is a Factor VIII polypeptide.

Embodiment 12: The procoagulant protein according to any one of embodiments 1-2, wherein (i) is a Factor XI polypeptide.

Embodiment 13: The procoagulant protein according to any one of embodiments 1-6, wherein (ii) is a monoclonal antibody or a fragment thereof.

Embodiment 14: The procoagulant protein according to embodiment 10, wherein (ii) is a Fab fragment, a $F(ab')_2$ fragment, a Fab' fragment, a Fd fragment, a Fv fragment, a ScFv fragment, a dAb fragment or an isolated complementarity determining region (CDR).

Embodiment 15: The procoagulant protein according embodiment 11, wherein (ii) is a Fab fragment.

Embodiment 16: The procoagulant protein according to any one of embodiments 13-15, wherein the epitope of (ii) comprises one or more residues selected from the group consisting of V17, Q18, C19, H20, Y21, R22, L23, Q24, D25, V26, K27, A28, L63, G64, G65, G66, L67, L68, G89, A90, R91, G92, P93, Q94, I95 and L96 of SEQ ID NO: 5.

Embodiment 17: The procoagulant protein according to any one of embodiments 13-15, wherein (ii) is an antibody, or a fragment thereof, which is capable of binding to the same epitope as mAb0023.

Embodiment 18: A procoagulant protein according to any of embodiments 16-17, wherein the heavy chain of (ii) comprises:

a CDR1 sequence of amino acids 50 to 54 (DYFMY) of SEQ ID NO: 34, wherein one of these amino acids may be substituted by a different amino acid; and/or a CDR2 sequence of amino acids 69 to 85 (YISNGGDSSSYPDTVKG) of SEQ ID NO: 34, wherein one, two, three or four of these amino acids may be substituted by a different amino acid; and/or a CDR3 sequence of amino acids 118 to 129 (NKNWDDYYDMDY) of SEQ ID NO: 34, wherein one, two or three of these amino acids may be substituted by a different amino acid.

Embodiment 19: A procoagulant protein according to any of embodiments 16-18, wherein the light chain of (ii) comprises:

a CDR1 sequence of amino acids 44 to 60 (KSSQSLLNSRTRKNYLA) of SEQ ID NO: 35, wherein one, two, three or four of these amino acids may be substituted with a different amino acid; and/or a CDR2 sequence of amino acids 76 to 82 (WASTRES) of SEQ ID NO: 35, wherein one or two of these amino acids may be substituted with a different amino acid; and/or a CDR3 sequence of amino acids 115 to 122 (KQSYNLLT) of SEQ ID NO: 35, wherein one or two of these amino acids may be substituted with a different amino acid.

Embodiment 20: A procoagulant protein according to any of embodiments 16-17, wherein the heavy chain of (ii) comprises:

a CDR1 sequence of amino acids 50 to 54 (DYFMY) of SEQ ID NO: 34, wherein one of these amino acids may be substituted by a different amino acid; and/or a CDR2 sequence of amino acids 69 to 85 (YISNGGDSSSYPDTVKG) of SEQ ID NO: 34, wherein one, two, three or four of these amino acids may be substituted by a different amino acid; and/or a CDR3 sequence of amino acids 118 to 129 (NKNWDDYYDMDY) of SEQ ID NO: 34, wherein one, two or three of these amino acids may be substituted by a different amino acid.

and wherein the light chain of (ii) comprises:

a CDR1 sequence of amino acids 44 to 60 (KSSQSLLNSRTRKNYLA) of SEQ ID NO: 35, wherein one, two, three or four of these amino acids may be substituted with a different amino acid; and/or a CDR2 sequence of amino acids 76 to 82 (WASTRES) of SEQ ID NO: 35, wherein one or two of these amino acids may be substituted with a different amino acid; and/or a CDR3 sequence of amino acids 115 to 122 (KQSYNLLT) of SEQ ID NO: 35, wherein one or two of these amino acids may be substituted with a different amino acid.

Embodiment 21: A procoagulant protein according to embodiment 20, wherein the heavy chain of (ii) comprises:

a CDR1 sequence of amino acids 50 to 54 (DYFMY) of SEQ ID NO: 34; and a CDR2 sequence of amino acids 69 to 85 (YISNGGDSSSYPDTVKG) of SEQ ID NO: 34; and a CDR3 sequence of amino acids 118 to 129 (NKNWDDYYDMDY) of SEQ ID NO: 34, and wherein the light chain of (ii) comprises:

a CDR1 sequence of amino acids 44 to 60 (KSSQSLLNSRTRKNYLA) of SEQ ID NO: 35; and a CDR2 sequence of amino acids 76 to 82 (WASTRES) of SEQ ID NO: 35; and a CDR3 sequence of amino acids 115 to 122 (KQSYNLLT) of SEQ ID NO: 35.

Embodiment 22: The procoagulant protein according to any one of embodiments 13-15, wherein the epitope of (ii) comprises one or more residues selected from the group consisting of L36, P37, E38, G39, C40, Q41, P42, L43, V44, S45, S46, A47, V73, T74, L75, Q76, E77, E78, D79, A80, G81, E82, Y83, G84, C85, M86, R91, G92, P93, Q94, I95, L96, H97, R98, V99, S100 and L101 of SEQ ID NO: 5.

Embodiment 23: The procoagulant protein according to any one of embodiments 13-15, wherein (ii) is an antibody, or a fragment thereof, which is capable of binding to the same epitope as mAb0051.

Embodiment 24: A procoagulant protein according to any one of embodiments 22-23, wherein the heavy chain of (ii) comprises:

a CDR1 sequence of amino acids 50 to 54 (DYSMH) of SEQ ID NO: 36, wherein one of these amino acids may be substituted by a different amino acid; and/or a CDR2 sequence of amino acids 69 to 85 (VISTYYGDVRYNQKFKG) of SEQ ID NO: 36, wherein one, two, three or four of these amino acids may be substituted by a different amino acid; and/or a CDR3 sequence of amino acids 118 to 129 (APMITTGAWFAY) of SEQ ID NO: 36, wherein one, two or three of these amino acids may be substituted by a different amino acid.

Embodiment 25: A procoagulant protein according to any of embodiments 22-24, wherein the light chain of (ii) comprises:

a CDR1 sequence of amino acids 44 to 54 (KASQSVSNDVA) of SEQ ID NO: 37, wherein one, two or three of these amino acids may be substituted with a different amino acid; and/or a CDR2 sequence of amino acids 70 to 76 (YASSRYT) of SEQ ID NO: 37, wherein one or two of these amino acids may be substituted with a different amino acid; and/or a CDR3 sequence of amino acids 109 to 117 (QQDYSSPYT) of SEQ ID NO: 37, wherein one or two of these amino acids may be substituted with a different amino acid.

Embodiment 26: A procoagulant protein according to any one of embodiments 22-23, wherein the heavy chain of (ii) comprises:

a CDR1 sequence of amino acids 50 to 54 (DYSMH) of SEQ ID NO: 36, wherein one of these amino acids may be substituted by a different amino acid; and/or a CDR2 sequence of amino acids 69 to 85 (VISTYYGDVRYNQKFKG) of SEQ ID NO: 36, wherein one, two, three or four of these amino acids may be substituted by a different amino acid; and/or a CDR3 sequence of amino acids 118 to 129 (APMITTGAWFAY) of SEQ ID NO: 36, wherein one, two or three of these amino acids may be substituted by a different amino acid.

and wherein the light chain of (ii) comprises:

a CDR1 sequence of amino acids 44 to 54 (KASQSVSNDVA) of SEQ ID NO: 37, wherein one, two or three of these amino acids may be substituted with a different amino acid; and/or a CDR2 sequence of amino acids 70 to 76 (YASSRYT) of SEQ ID NO: 37, wherein one or two of these amino acids may be substituted with a different amino acid; and/or a CDR3 sequence of amino acids 109 to 117 (QQDYSSPYT) of SEQ ID NO: 37, wherein one or two of these amino acids may be substituted with a different amino acid.

Embodiment 27: A procoagulant protein according to embodiment 26, wherein the heavy chain of (ii) comprises:

a CDR1 sequence of amino acids 50 to 54 (DYSMH) of SEQ ID NO: 36; and a CDR2 sequence of amino acids 69 to 85 (VISTYYGDVRYNQKFKG) of SEQ ID NO: 36; and a CDR3 sequence of amino acids 118 to 129 (APMITTGAWFAY) of SEQ ID NO: 36;

and wherein the light chain of (ii) comprises:

a CDR1 sequence of amino acids 44 to 54 (KASQSVSNDVA) of SEQ ID NO: 37; and a CDR2 sequence of amino acids 70 to 76 (YASSRYT) of SEQ ID NO: 37; and a CDR3 sequence of amino acids 109 to 117 (QQDYSSPYT) of SEQ ID NO: 37.

Embodiment 28: The procoagulant protein according to any one of embodiments 13-15, wherein the epitope of (ii) comprises one or more residues selected from the group consisting of V17, Q18, C19, H20, Y21, R22, L23, Q24, D25, V26, K27, A28, R91, G92, P93, Q94, I95, L96, H97, R98, V99, S100 and L101 of SEQ ID NO: 5.

Embodiment 29: The procoagulant protein according to any one of embodiments 13-15, wherein (ii) is an antibody, or a fragment thereof, which is capable of binding to the same epitope as mAb0062.

Embodiment 30: A procoagulant protein according to any one of embodiments 28-29, wherein the heavy chain of (ii) comprises:

a CDR1 sequence of amino acids 50 to 54 (SHWIE) of SEQ ID NO: 42, wherein one of these amino acids may be substituted by a different amino acid; and/or a CDR2 sequence of amino acids 69 to 85 (EILPGSGNTNYNEKFKG) of SEQ ID NO: 42, wherein one, two, three or four of these amino acids may be substituted by a different amino acid; and/or a CDR3 sequence of amino acids 118 to 130 (GYYGLNYDWYFDV) of SEQ ID NO: 42, wherein one, two or three of these amino acids may be substituted by a different amino acid.

Embodiment 31: A procoagulant protein according to any of embodiments 28-30, wherein the light chain of (ii) comprises:

a CDR1 sequence of amino acids 44 to 54 (RASQDISNYLN) of SEQ ID NO: 39, wherein one, two or three of these amino acids may be substituted with a different amino acid; and/or a CDR2 sequence of amino acids 70 to 76 (YTSRLHS) of SEQ ID NO: 39, wherein one or two of these amino acids may be substituted with a different amino acid; and/or a CDR3 sequence of amino acids 109 to 117 (QQDTKLPYT) of SEQ ID NO: 39, wherein one or two of these amino acids may be substituted with a different amino acid.

Embodiment 32: A procoagulant protein according to any of embodiments 28-31, wherein the heavy chain of (ii) comprises:

a CDR1 sequence of amino acids 50 to 54 (SHWIE) of SEQ ID NO: 42, wherein one of these amino acids may be substituted by a different amino acid; and/or a CDR2 sequence of amino acids 69 to 85 (EILPGSGNTNYNEKFKG) of SEQ ID NO: 42, wherein one, two, three or four of these amino acids may be substituted by a different amino acid; and/or a CDR3 sequence of amino acids 118 to 130 (GYYGLNYDWYFDV) of SEQ ID NO: 42, wherein one, two or three of these amino acids may be substituted by a different amino acid.

and wherein the light chain of (ii) comprises:

a CDR1 sequence of amino acids 44 to 54 (RASQDISNYLN) of SEQ ID NO: 39, wherein one, two or three of these amino acids may be substituted with a different amino acid; and/or a CDR2 sequence of amino acids 70 to 76 (YTSRLHS) of SEQ ID NO: 39, wherein one or two of these amino acids may be substituted with a different amino acid; and/or a CDR3 sequence of amino acids 109 to 117 (QQDTKLPYT) of SEQ ID NO: 39, wherein one or two of these amino acids may be substituted with a different amino acid.

Embodiment 33: A procoagulant protein according to embodiment 32, wherein the heavy chain of (ii) comprises:

a CDR1 sequence of amino acids 50 to 54 (SHWIE) of SEQ ID NO: 42; and a CDR2 sequence of amino acids 69 to 85 (EILPGSGNTNYNEKFKG) of SEQ ID NO: 42; and a CDR3 sequence of amino acids 118 to 130 (GYYGLNYDWYFDV) of SEQ ID NO: 42;

and wherein the light chain of (ii) comprises:

a CDR1 sequence of amino acids 44 to 54 (RASQDISNYLN) of SEQ ID NO: 39; and a CDR2 sequence of amino acids 70 to 76 (YTSRLHS) of SEQ ID NO: 39; and a CDR3 sequence of amino acids 109 to 117 (QQDTKLPYT) of SEQ ID NO: 39.

Embodiment 34: The procoagulant protein according to any one of embodiments 13-15, wherein the epitope of (ii) comprises one or more residues selected from the group consisting of E5, T6, H7, K8, I9, G10, S11, L12, A13, E14, N15, A16, F17, S18, D19, P20 and A21 of SEQ ID NO: 7.

Embodiment 35: The procoagulant protein according to embodiment 34, wherein said residues are K8, I9, G10, S11, L12, A13, N15, A16, F17, S18, D19, P20 and A21.

Embodiment 36: The procoagulant protein according to any one of embodiments 13-15, wherein the epitope of (ii) comprises one or more residues selected from the group consisting of K118, I119, G120, S121, L122, A123, E124, N125, A126, F127 of SEQ ID NO: 6.

Embodiment 37: The procoagulant protein according to any one of embodiments 13-15, wherein (ii) is an antibody, or a fragment thereof, which is capable of binding to the same epitope as mAb0061 or mAb0082.

Embodiment 38: A procoagulant protein according to any one of embodiments 34-37, wherein the heavy chain of (ii) comprises:

a CDR1 sequence of amino acids 49 to 53 (RYWMT) of SEQ ID NO: 40, wherein one of these amino acids may be substituted by a different amino acid; and/or a CDR2 sequence of amino acids 68 to 84 (EINPDSSTINYNPSLKD) of SEQ ID NO: 40, wherein one, two, three or four of these amino acids may be substituted by a different amino acid; and/or a CDR3 sequence of amino acids 117 to 121 (GVFTS) of SEQ ID NO: 40, wherein one, two or three of these amino acids may be substituted by a different amino acid.

Embodiment 39: A procoagulant protein according to any of embodiments 34-38, wherein the light chain of (ii) comprises:

a CDR1 sequence of amino acids 43 to 58 (RSSQSLVHRNGNTYFH) of SEQ ID NO: 41, wherein one, two, three or four of these amino acids may be substituted with a different amino acid; and/or a CDR2 sequence of amino acids 74 to 80 (KVSNRFS) of SEQ ID NO: 41, wherein one or two of these amino acids may be substituted with a different amino acid; and/or a CDR3 sequence of amino acids 113 to 121 (SQSTHVPYT) of SEQ ID NO: 41, wherein one or two of these amino acids may be substituted with a different amino acid.

Embodiment 40: A procoagulant protein according to any of embodiments 34-39, wherein the heavy chain of (ii) comprises:

a CDR1 sequence of amino acids 49 to 53 (RYWMT) of SEQ ID NO: 40, wherein one of these amino acids may be substituted by a different amino acid; and/or a CDR2 sequence of amino acids 68 to 84 (EINPDSSTINYNPSLKD) of SEQ ID NO: 40, wherein one, two, three or four of these amino acids may be substituted by a different amino acid; and/or a CDR3 sequence of amino acids 117 to 121 (GVFTS) of SEQ ID NO: 40, wherein one, two or three of these amino acids may be substituted by a different amino acid.

and wherein the light chain of (ii) comprises:

a CDR1 sequence of amino acids 43 to 58 (RSSQSLVHRNGNTYFH) of SEQ ID NO: 41, wherein one, two, three or four of these amino acids may be substituted with a different amino acid; and/or a CDR2 sequence of amino acids 74 to 80 (KVSNRFS) of SEQ ID NO: 41, wherein one or two of these amino acids may be substituted with a different amino acid; and/or a CDR3 sequence of amino acids 113 to 121 (SQSTHVPYT) of SEQ ID NO: 41, wherein one or two of these amino acids may be substituted with a different amino acid.

Embodiment 41: A procoagulant protein according to embodiment 40, wherein the heavy chain of (ii) comprises:
- a CDR1 sequence of amino acids 49 to 53 (RYWMT) of SEQ ID NO: 40; and
- a CDR2 sequence of amino acids 68 to 84 (EINPDSSTINYNPSLKD) of SEQ ID NO: 40; and
- a CDR3 sequence of amino acids 117 to 121 (GVFTS) of SEQ ID NO: 40;

and wherein the light chain of (ii) comprises:
- a CDR1 sequence of amino acids 43 to 58 (RSSQSLVHRNGNTYFH) of SEQ ID NO: 41; and
- a CDR2 sequence of amino acids 74 to 80 (KVSNRFS) of SEQ ID NO: 41; and
- a CDR3 sequence of amino acids 113 to 121 (SQSTHVPYT) of SEQ ID NO: 41.

Embodiment 42: A procoagulant protein according to any of embodiments 34-37, wherein the heavy chain of (ii) comprises:
- a CDR1 sequence of amino acids 49 to 53 (RYWMT) of SEQ ID NO: 50, wherein one of these amino acids may be substituted by a different amino acid; and/or
- a CDR2 sequence of amino acids 68 to 84 (EINPDSSTINYAPSLKD) of SEQ ID NO: 50, wherein one, two, three or four of these amino acids may be substituted by a different amino acid; and/or
- a CDR3 sequence of amino acids 117 to 121 (GVFTS) of SEQ ID NO: 50, wherein one of these amino acids may be substituted by a different amino acid;

and wherein the light chain of (ii) comprises:
- a CDR1 sequence of amino acids 43 to 58 (RSSQSLVHRNGNTYFH) of SEQ ID NO: 41, wherein one, two, three or four of these amino acids may be substituted with a different amino acid; and/or
- a CDR2 sequence of amino acids 74 to 80 (KVSNRFS) of SEQ ID NO: 41, wherein one or two of these amino acids may be substituted with a different amino acid; and/or
- a CDR3 sequence of amino acids 113 to 121 (SQSTHVPYT) of SEQ ID NO: 41, wherein one or two of these amino acids may be substituted with a different amino acid.

Embodiment 43: A procoagulant protein according to embodiment 42, wherein the heavy chain of (ii) comprises:
- a CDR1 sequence of amino acids 49 to 53 (RYWMT) of SEQ ID NO: 50; and
- a CDR2 sequence of amino acids 68 to 84 (EINPDSSTINYAPSLKD) of SEQ ID NO: 50; and
- a CDR3 sequence of amino acids 117 to 121 (GVFTS) of SEQ ID NO: 50;

and wherein the light chain of (ii) comprises:
- a CDR1 sequence of amino acids 43 to 58 (RSSQSLVHRNGNTYFH) of SEQ ID NO: 41; and
- a CDR2 sequence of amino acids 74 to 80 (KVSNRFS) of SEQ ID NO: 41; and
- a CDR3 sequence of amino acids 113 to 121 (SQSTHVPYT) of SEQ ID NO: 41.

Embodiment 44: The procoagulant protein according to any one of embodiments 13-15, wherein the paratope of (ii) comprises one or more residues selected from the group consisting of H50, N52, Y56, H58, Y73, F79, S115, T116, V118 and Y120 of the anti-TLT-1 light (L) chain (SEQ ID NO: 33), and residues V20, F45, R49, Y50, W51, E68, T75, N77, S116, G117, V118 and T120 of the anti-TLT-1 heavy (H) chain (SEQ ID NO: 32)

Embodiment 45: The procoagulant protein according to any one of embodiments 13-15 and 44, wherein the epitope of (ii) comprises one or more residues selected from the group consisting of K133, I134, G135, S136, L137, A138, N140, A141, F142, S143, D144, P145 and A146 of SEQ ID NO: 4.

Embodiment 46: The procoagulant protein according to any one of embodiments 13-15, wherein (ii) is an antibody, or a fragment thereof, which is capable of binding to the same epitope as mAb0012.

Embodiment 47: A procoagulant protein according to any of embodiments 44-46, wherein the heavy chain of (ii) comprises:
- a CDR1 sequence of amino acids 49 to 53 (RYWMT) of SEQ ID NO: 32, wherein one of these amino acids may be substituted by a different amino acid; and/or
- a CDR2 sequence of amino acids 68 to 84 (EINPDSSTINYTPSLKD) of SEQ ID NO: 32, wherein one, two, three or four of these amino acids may be substituted by a different amino acid; and/or
- a CDR3 sequence of amino acids 117 to 121 (GVFTS) of SEQ ID NO: 32, wherein one, two or three of these amino acids may be substituted by a different amino acid.

Embodiment 48: A procoagulant protein according to any of embodiments 44-47, wherein the light chain of (ii) comprises:
- a CDR1 sequence of amino acids 43 to 58 (RSSQSLVHRNGNTYFTH) of SEQ ID NO: 33, wherein one, two, three or four of these amino acids may be substituted with a different amino acid; and/or
- a CDR2 sequence of amino acids 74 to 80 (KVSNRFS) of SEQ ID NO: 33, wherein one or two of these amino acids may be substituted with a different amino acid; and/or
- a CDR3 sequence of amino acids 113 to 121 (SQSTHVPYT) of SEQ ID NO: 33, wherein one or two of these amino acids may be substituted with a different amino acid.

Embodiment 49: A procoagulant protein according to any of embodiments 44-48, wherein the heavy chain of (ii) comprises:
- a CDR1 sequence of amino acids 49 to 53 (RYWMT) of SEQ ID NO: 32, wherein one of these amino acids may be substituted by a different amino acid; and/or
- a CDR2 sequence of amino acids 68 to 84 (EINPDSSTINYTPSLKD) of SEQ ID NO: 32, wherein one, two, three or four of these amino acids may be substituted by a different amino acid; and/or
- a CDR3 sequence of amino acids 117 to 121 (GVFTS) of SEQ ID NO: 32, wherein one, two or three of these amino acids may be substituted by a different amino acid and wherein the light chain of (ii) comprises:
- a CDR1 sequence of amino acids 43 to 58 (RSSQSLVHRNGNTYFTH) of SEQ ID NO: 33, wherein one, two, three or four of these amino acids may be substituted with a different amino acid; and/or
- a CDR2 sequence of amino acids 74 to 80 (KVSNRFS) of SEQ ID NO: 33, wherein one or two of these amino acids may be substituted with a different amino acid; and/or
- a CDR3 sequence of amino acids 113 to 121 (SQSTHVPYT) of SEQ ID NO: 33, wherein one or two of these amino acids may be substituted with a different amino acid.

Embodiment 50: A procoagulant protein according to embodiment 49, wherein the heavy chain of (ii) comprises:
- a CDR1 sequence of amino acids 49 to 53 (RYWMT) of SEQ ID NO: 32; and a CDR2 sequence of amino acids 68 to 84 (EINPDSSTI-NYTPSLKD) of SEQ ID NO: 32; and a CDR3 sequence of amino acids 117 to 121 (GVFTS) of SEQ ID NO: 32;

and wherein the light chain of (ii) comprises:

a CDR1 sequence of amino acids 43 to 58 (RSSQSLVHRNGNTYFTH) of SEQ ID NO: 33; and a CDR2 sequence of amino acids 74 to 80 (KVSNRFS) of SEQ ID NO: 33; and a CDR3 sequence of amino acids 113 to 121 (SQSTHVPYT) of SEQ ID NO: 33.

Embodiment 51: The procoagulant protein according to any one of embodiments 1-50, wherein (ii) is a human monoclonal antibody or a fragment thereof.

Embodiment 52: The procoagulant protein according to any one of embodiments 1-50, wherein (ii) is a chimeric antibody or a fragment thereof.

Embodiment 53: The procoagulant protein according to any one of embodiments 1-50, wherein (ii) is a humanised antibody or a fragment thereof.

Embodiment 54: The procoagulant protein according to any one of embodiments 51-53, wherein the isotype of (ii) is IgG.

Embodiment 55: The procoagulant protein according to embodiment 54, wherein the isotype is IgG1, IgG2 or IgG4.

Embodiment 56: The procoagulant protein according to embodiment 55, wherein the isotype is IgG4.

Embodiment 57: The procoagulant protein according to any one of embodiments 1-56, further comprising a linker between (i) and (ii).

Embodiment 58: The procoagulant protein according to any one of embodiments 1-57, which is a fusion protein.

Embodiment 59: The procoagulant protein according to any one of embodiments 1-57, which is a conjugate of (i) and (ii).

Embodiment 60: The conjugate according to embodiment 59, wherein (i) and (ii) are covalently connected by a linker comprising polyethyleneglycol (PEG).

Embodiment 61: The conjugate according to any one of embodiments 59-60, wherein (i) and (ii) are covalently conjugated via a glycan of at least one of said proteins.

Embodiment 62: A process for preparing a composition comprising at least one conjugate according to any one of embodiments 59-61, comprising chemically conjugating (i) the -TLT-1 antibody or fragment thereof with one reactive group (RS1) of a linker and reacting (ii) the coagulation factor with another reactive group (RS2) of said linker.

Embodiment 63: The process as defined in embodiment 62, wherein (i) is a monoclonal antibody.

Embodiment 64: The process as defined in embodiment 62, wherein (i) is a fragment of a monoclonal antibody.

Embodiment 65: The process as defined in embodiment 64, wherein (i) is a Fab fragment.

Embodiment 66: The process as defined in embodiment 65, wherein said Fab fragment contains one Cys mutation in the constant region.

Embodiment 67: The process as defined in embodiment 62, wherein (i) is a sc-Fab fragment.

Embodiment 68: The process as defined in any one of embodiments 62-67, wherein (ii) is a FV polypeptide.

Embodiment 69: The process as defined in any one of embodiments 62-67, wherein (ii) is a FVIIa polypeptide.

Embodiment 70: The process as defined in any one of embodiments 62-67, wherein (ii) is a FVIII polypeptide.

Embodiment 71: The process as defined in any one of embodiments 62-67, wherein (ii) is a FIX polypeptide.

Embodiment 72: The process as defined in any one of embodiments 62-67, wherein (ii) is a FX polypeptide.

Embodiment 73: The process as defined in any one of embodiments 62-67, wherein (ii) is a FXI polypeptide.

Embodiment 74: The process as defined in any one of embodiments 62-73, wherein said linker is a water soluble.

Embodiment 75: The process as defined in any one of embodiments 62-74, wherein said linker is polymer.

Embodiment 76: The process as defined in any one of embodiments 74-75, wherein (ii) is polyethylene glycol (PEG).

Embodiment 77: The process as defined in any one of embodiments 74-75, wherein (ii) is polysialic acid.

Embodiment 78: The process as defined in any one of embodiments 74-75, wherein (ii) is hydroxyethyl starch.

Embodiment 79: The process as defined in any one of embodiments 62-78, wherein RS1 is an aldehyde.

Embodiment 80: The process as defined in any one of embodiments 62-78, wherein RS1 is a maleimide group.

Embodiment 81: The process as defined in any one of embodiments 62-78, wherein RS1 is activated carbohydrate derivative capable of reacting in an enzyme-catalysed reaction.

Embodiment 82: The process as defined in any one of embodiments 81, wherein RS1 is an activated sialic acid derivative capable of reacting in an enzyme-catalysed reaction.

Embodiment 83: The process as defined in embodiment 82, wherein RS1 is $O^2$-[5]cytidylyl-ξ-neuraminic acid.

Embodiment 84: The process as defined in any one of embodiments 62-83, wherein RS2 is an aldehyde.

Embodiment 85: The process as defined in any one of embodiments 62-83, wherein RS2 is a maleimide group.

Embodiment 86: The process as defined in any one of embodiments 62-83, wherein RS2 is activated carbohydrate derivative capable of reacting in an enzyme-catalysed reaction.

Embodiment 87: The process as defined in any one of embodiments 62-83, wherein RS2 is a sialic acid derivative.

Embodiment 88: The procoagulant protein according to any one of embodiments 1-61, in which (ii) has a $K_D$ of less than 100 nM, such as less than 10 nM.

Embodiment 89: A method of targeting a coagulation factor, or a functional fragment thereof, to the surface of activated platelets, said method comprising the contacting of activated platelets with a procoagulant protein according to any one of embodiments 1-61.

Embodiment 90: A procoagulant protein according to any one of embodiments 1-61 for use as a medicament.

Embodiment 91: The procoagulant protein of embodiment 87 for use as a procoagulant.

Embodiment 92: A pharmaceutical formulation comprising the procoagulant protein according to any one of embodiments 1-61.

Embodiment 93: The procoagulant protein according to any one of embodiments 1-61 or the pharmaceutical formulation according to embodiment 92 for use in the treatment of a coagulopathy.

Embodiment 94: Use of the procoagulant protein according to any one of embodiments 1-61 for the manufacture of a medicament for the treatment of a coagulopathy.

Embodiment 95: Use according to any one of embodiments 93 or 94, wherein said coagulopathy is haemophilia A, with or without inhibitors, or haemophilia B, with or without inhibitors.

Embodiment 96: A method of treating coagulopathy, comprising administering an effective amount of the procoagulant protein according to any one of embodiments 1-61 or the formulation of embodiment 93 to an individual in need thereof.

Embodiment 97: The method according to embodiment 95, wherein said coagulopathy is haemophilia A, with or without inhibitors, and haemophilia B, with or without inhibitors.

Embodiment 98: A polynucleotide that encodes the procoagulant protein according to any one of embodiments 1-61.

Embodiment 99: An isolated cell that comprises the fusion protein according to any one of embodiments 1-61 and/or the polynucleotide according to embodiment 97.

Embodiment 100: A procoagulant protein to any one of embodiments 1-61, wherin (ii) bind to TLT-1 without competing with fibrinogen binding to TLT-1.

Embodiment 101: A procoagulant protein to any one of embodiments 1-61, wherin (ii) does not inhibit platelet aggregation.

The present invention is further illustrated by the following examples which should not be construed as further limiting. The contents of all figures and all references cited throughout this application are expressly incorporated herein by reference.

EXAMPLES

In the examples, anti-TLT-1 antibodies and fragments thereof, e.g. Fab fragments, were used to target coagulation factors to activated platelets. To ease interpretation of the data presented in the examples, Table 3a summarizes information regarding some of the anti-TLT-1 antibodies and fragments thereof further described below. In Table 3A, parent antibodies, variants, fragments, fusions and conjugates thereof are listed with reference to the parent mAb and type of protein. Name refers to the name of the protein, Parent refers to the antibody from which the anti-TLT-1 mAb, Fab or fusion/conjugate is derived and Type defines if the protein is a mAb, a Fab, a DNA fusion (fusion) with a coagulation factor or a chemical conjugate with a coagulation factor (conjugate).

TABLE 3A

Overview of antibodies (mAbs), antibody fragments (Fabs) and Fusion-proteins

| Name | Parent | Type |
|---|---|---|
| mAb0012 | mAb0012 | mAb |
| mAb0023 | mAb0023 | mAb |
| mAb0051 | mAb0051 | mAb |
| mAb0052 | mAb0052 | mAb |
| mAb0061 | mAb0012 | mAb |
| mAb0062 | mAb0052 | mAb |
| mAb0082 | mAb0012 | mAb |
| Fab0003 | mAb0052 | Fab |
| Fab0004 | mAb0023 | Fab |
| Fab0012 | mAb0012 | Fab |
| Fab0023 | mAb0023 | Fab |
| Fab0051 | mAb0051 | Fab |
| Fab0052 | mAb0052 | Fab |
| Fab0061 | mAb0012 | Fab |
| Fab0074 | mAb0051 | Fab |
| Fab0082 | mAb0012 | Fab |
| Fab0084 | mAb0012 | Fab |
| FVIIa-Fab1001 | mAb0012 | Conjugate (FVIIa) |
| FVIIa-Fab1029 | mAb0012 | Conjugate (FVIIa) |
| FVII-Fab5001 | mAb0052 | Fusion (FVII) |
| FVIIa-Fab9015 | mAb0012 | Conjugate (FVIIa) |
| FIX-Fab0135 | mAb0012 | Fusion (FIX) |
| FIX-mAb0145 | mAb0012 | Conjugate (FIX) |
| FIX-Fab0155 | mAb0012 | Conjugate (FIX) |

Example 1

Cloning and Expression of hTLT-1 ECD-His Antigen

Nucleotide sequences encoding the extracellular domain of human TLT-1 (hTLT-1) (FIG. 1) together with a C-terminal His-6 tag were PCR amplified with a forward primer containing a HindIII recognition site together with a kozak sequence, and a reverse primer containing a stop codon and an EcoRI recognition site (FIG. 2). The HindIII- and EcoRI digested PCR fragment was inserted into the HindIII- and EcoRI sites of a pTT-based expression vector. The pTT vector is essentially described in Durocher, Y. et al., (2002) Nucleic Acid Res, 30: E9. The resulting expression plasmid was designated pTT-hTLT-1 ECD-His. The nucleotide and amino acid sequences for hTLT-1 ECD-His is shown in SEQ ID NO: 3 and 4. pTT-hTLT-1 ECD-His was transfected into HEK293-6E suspension cells in order to transiently express hTLT-1 ECD-His. HEK293-6E cells were grown in Freestyle HEK293 medium (GIBCO, cat. no. 12338-018) supplemented with 1% P/S (GIBCO cat. no. 15140-122), 0.1% pluronic (GIBCO, cat. no. 24040-032) and 25 ug/mL Geneticin (GIBCO, cat. no. 10131-019) and cells were transfected at a cell density of 1 mill/mL using 293fectin (Invitrogen, cat. no. 12347-019). For each liter of HEK293-6E cells, the transfection was performed by diluting 1 mg of pTT-hTLT-1 ECD-His DNA into 30 mL Optimem (dilution A) and by diluting 1 mL 293fectin into 30 mL Optimem (GIBCO, cat. no. 51985-026, dilution B). Dilution A and B were mixed and incubated at room temperature for 30 minutes. The transfection mix was hereafter added to the HEK293-6E cells and cells were incubated at 37° C. in a humified incubator with orbital rotation (125 rpm). Five to seven days post-tranfection, cells were removed by centrifugation and the resulting hTLT-1 ECD-His containing supernatants were sterile-filtrated prior to purification.

Example 2

Purification and Characterisation of hTLT-1 ECD-His Protein

Purification of the hTLT-1 ECD-His protein was conducted as a 2-step process composed of 1) His-affinity chromatography using the Cobalt-loaded resin TALON (Clontech, cat. no. 635506) and 2) anion-exchange chromatography using the fine-particle resin Source 15Q (GE Healthcare, cat. no. 17-0947). The purifications were conducted using an ÄktaExplorer chromatography system (GE Healthcare, cat. no. 18-1112-41). The buffer systems used for the first purification step was an equilibration buffer composed of 20 mM Hepes, pH 7.0, 150 mM NaCl, a wash buffer composed of 20 mM Hepes, pH 7.0, 0.5 M NaCl and an elution buffer composed of 20 mM Hepes, pH 7.0, 150 mM Imidazole. The cell supernatant was applied directly without any adjustments onto a pre-equilibrated TALON column. The column was washed with 20 column volumes of equilibration buffer, 20 column volumes of wash buffer and last with 20 column volumes of equilibration buffer. The protein was eluted isocratically in approximately 5 column volumes of elution buffer. The molecular mass of the eluted protein was analysed using SDS-PAGE/Coomassie NuPage 4-12% Bis-Tris gels (Invitrogen, cat. no. NP0321BOX) and Matrix Assisted Laser Desorption Ionisation Time-of-Flight Mass Spectrometry (MALDI-TOF MS) setup on a Microflex system (Bruker Daltonics). Here, two distinct protein masses were observed of approximately 16.7 and 33.4 kDa of almost equal amounts. The observed masses corresponded to monomer and dimer forms of hTLT-1 ECD-His. Reducing the protein resulted in complete abolishment of the 33.4 kDa protein, while intensifying the 16.7 kDa protein as judged from a SDS-PAGE/Coomassie analysis. Thus, the hTLT-1 ECD-His protein contained an interlinked C-C dimer. To segregate monomer from dimer, a second purification step was employed. The buffer systems used for this purification step was an equilibration buffer composed of 50 mM Hepes, pH 8.0 and an elution buffer composed of 50 mM Hepes, pH 8.0, 1 M NaCl. The sample was adjusted to a pH of 8.0 using 1 M NaOH and then diluted to a conductivity of approximately 10 mS/cm. The protein was applied to a pre-equilibrated Source 15Q column, washed with 5 column volumes of equilibration and eluted using 0-100% elution buffer over 20 column volumes. Based on UV280 monitoring, two peaks were apparent with almost base-line separation. Analyzing fractions over the two peaks using SDS-PAGE/Coomassie, MALDI-TOF MS and Dynamic Light-Scattering (DLS) using a Dynapro instrument (Wyatt Technology) analyses showed the presence of monomer hTLT-1 ECD-His protein in the peak eluting first and Cys-Cys dimer in the peak eluting second. A pool was prepared containing the monomer hTLT-1 ECD-His protein only. The final protein integrity was analyzed based on a Size-Exclusion High-Performance Liquid Chromatographic (SEC-HPLC) method setup on an Agilent LC 1100/1200 system and using a BIOSep-SEC-53000 300×7.8 mm column (Phenomenex, cat. no. 00H-2146-K0) and a running buffer composed of 200 mM NaPhosphate pH 6.9, 300 mM NaCl and 10% isopropanol. The protein eluted as a single symmetric peak at a retention time of approximately 9.9 min at a flow rate of 1 ml/min.

A batch of hTLT-1 ECD-His was prepared for an immunization study for production of monoclonal anti-TLT-1 antibodies. Thus, the protein was dialyzed into an isotonic PBS buffer using a Slide-A-Lyzer Dialysis Cassette 10 kDa MWCO (Pierce, cat. no. 66453). To measure the final protein concentration, a NanoDrop spectropho-tometer (Thermo Scientific) was used together with an extinction coefficient of 0.55.

Example 3

Preparation of Monoclonal TLT-1 Antibodies

RBF mice were immunized by injecting 50 μg of hTLT-1 ECD-His. FCA subcutaneously followed by two injections with 20 μg of hTLT-1 ECD-His in FIA. High responder mice were boosted intravenously with 25 μg of hTLT-1 ECD-His and the spleens were harvested after 3 days. Spleen cells were fused with the myeloma Fox cell line. Supernatants were screened for hTLT-1 specific antibody production in a specific ELISA and in a FACS assay utilizing hTLT-1- or Mock-transfected CHO cells as positive and negative target cells, respectively. A secondary screen was done on resting versus dual agonistic activated platelets of human, cynomolgous monkey, dog, rabbit or mouse origin.

Example 4

Cloning and Sequencing of Anti-TLT-1 mAb LC and HC cDNAs from Hybridoma

Total RNA was extracted from four different anti-TLT-1 mAb expressing hybridoma designated: 0012Hyb, 0023Hyb, 0051Hyb and 0052Hyb. The RNA was extracted from hybridoma cells using RNeasy mini kit (Qiagen, cat. no. 74106) and an aliquot of the resulting RNA was used as template for first-stranded cDNA synthesis using SMART RACE cDNA Amplification kit (Clontech, cat. no. 634914) following the instruction of the manufacturer for 5' RACE and using 5' RACE CDS primer A together with SMART II A RNA oligonucleotide. The light chain (LC) and heavy chain (HC) coding region cDNAs from each of the four anti-TLT-1 hybridomas were hereafter PCR amplified using UPM forward primer mix together with either a mouse LC,kappa specific reverse primer (reverse primer number 339, 348, or 610) or together with a reverse primer recognizing mouse IgG1, IgG2a, IgG2b or IgG3 sequences (reverse primer number 341, 347, 613, 614, 615, or 616, primer sequences are shown in Table 4 and SEQ ID NOs 60-145). The PCR reactions were performed using phusion PCR mix (FinnZymes, cat no.: F-531L). The resulting PCR fragments were cloned using Zero blunt Topo PCR cloning kit for sequencing (Invitrogen, cat. no. K287540) and sequenced. The variable domain sequences for 0012LC and HC are shown in FIG. 3.

Example 5

Development of pTT-0012HC, pTT-0023HC, pTT-0051HC and pTT-0052HC Expression Constructs The HC variable domain ($V_H$) encoding DNA sequences isolated from each of the four different anti-TLT-1 hybridomas were PCR amplified with forward primers containing a HinDIII restriction enzyme site and reverse primers containing a NheI restriction enzyme site for cloning purposes. The 0012$V_H$, 0023$V_H$, 0051$V_H$ and 0052$V_H$ DNA sequences were PCR amplified using phusion PCR mix (FinnZymes, cat No. F-531L) with the following primer number pairs: 490 (forward)+491 (reverse), 546 (forward)+547 (reverse), 627 (forward)+628 (reverse), and 617 (forward)+618 (reverse, primer sequences are shown in Table 4 and SEQ ID NOs 60-145), respectively, and inserted into the HinDIII and NheI restriction enzyme sites of a pTT based vector designated pTT-hIgG4, containing the constant region encoding sequences for human IgG4 HC (ie CH1-hinge-CH2-CH3). The pTT vector is essentially described in Durocher, Y. et al., (2002) Nucleic Acid Res, 30: E9 (FIG. 22). The resulting vectors were designated pTT-0012HC (FIG. 5), pTT-0023HC, pTT-0051HC, and pTT-0052HC. The anti-TLT-1 HC amino acid sequences encoded by the expression vectors are shown (SEQ. ID NO: 0012HC: 32, 0023HC: 34, 0051HC: 36, 0052HC: 38).

Example 6

Development of pTT-0012LC, pTT-0023LC, pTT-0051LC and pTT-0052LC Expression Constructs The LC variable domain ($V_L$) encoding DNA sequences isolated from each of the four different anti-TLT-1 hybridomas were PCR amplified with forward primers containing a HinDIII restriction enzyme site and reverse primers containing a BsiWI restriction enzyme site for cloning purposes. The 0012$V_L$, 0023$V_L$, 0051$V_L$ and 0052$V_L$ DNA sequences were PCR amplified with the following primers number pairs: 493 (forward)+495 (reverse), 548 (forward)+549 (reverse), 492 (forward)+494 (reverse), and 619 (forward)+620 (reverse primer sequences are shown in Table 4 and SEQ ID NOs 60-145), respectively, and inserted into the HinDIII and BsiWI restriction enzyme sites of a pTT-based vector designated, pTT-hLC,Kappa, containing the constant region encoding sequences for human LC, kappa. The resulting vectors were designated pTT-0012LC, pTT-0023LC, pTT-0051LC, and pTT-0052LC. The anti-TLT-1 LC amino acid sequence encoded by the expression vectors are shown in (SEQ ID NO: 0012LC: 33, 0023LC: 35, 0051LC: 37, 0052LC: 39).

Example 7

Development of pTT-0012HC.T60N, pTT-0012HC.T60A, pTT-0012LC.C36A and pTT-0052HC.C91Y The 0012$V_H$ amino acid sequence contains a potential N-linked glycosylation site (T60, kabat numbering) and the 0012$V_L$ and the 0052$V_H$ amino acid sequences each contain an unpaired Cys (C36 and C91, respectively, kabat numbering). Expression vectors encoding 0012HC.T60N or 0012HC.T60A or 0012LC.C36A or 0052HC.C91Y were developed using site directed mutagenesis (Quickchange II, Stratagene, Catalog number 20523-5) following the instructions of the manufacturer. The site-directed mutagenesis reactions were performed using a) pTT-0012HC DNA as template and primer numbers 682 (forward)+683 (reverse) for pTT-0012HC.T60N, b) pTT-0012HC DNA as template and primer numbers 688 (forward)+689 (reverse) for pTT-0012HC.T60A, c) pTT-0012LC DNA as template and primer numbers 598 (forward)+599 (reverse) for pTT-0012LC.C36A, d) pTT-0052HC DNA as template and the following primer numbers 684 (forward)+685 (reverse, primer sequences are shown in Table 4 and SEQ ID NOs 60-145) for pTT-0052HC.C91Y. The resulting expression vectors were sequenced in order to verify DNA sequences. The anti-TLT-1 HC and LC amino acid sequence encoded by the pTT-0012HC.T60N, pTT-0012HC.T60A and pTT-0012LC.C36A expression vectors are shown in (SEQ ID NO: 0012HC.T60N (also called 0061HC): 40, 0012HC.T60A (also called 0082HC): 43, 0012LC.C36A (also called 0061LC): 41). The 0012LC.C36A amino acid sequence is also shown without the N-terminal signal peptide sequence in SEQ ID NO: 153.

Example 8

Development of pTT-0012LC-HPC4, pTT-0012LC.C36A-HPC4, pTT-0023LC-HPC4, pTT-0051LC-HPC4 and pTT-0052LC-HPC4 Expression Constructs $V_L$ encoding DNA sequences isolated from each of the four different anti-TLT-1 hybridomas were PCR amplified with forward primers containing a HinDIII restriction enzyme site and reverse primers containing a BsiWI restriction enzyme site for cloning purposes. 0012$V_L$, 0012$V_L$.C36A, 0023$V_L$, 0051$V_L$ and 0052$V_L$ DNA sequences were PCR amplified with the following primer numberss: 493 (forward)+495 (reverse), 493 (forward)+495 (reverse), 548 (forward)+549 (reverse), 492 (forward)+494 (reverse), and 619 (forward)+620 (reverse, primer sequences are shown in Table 4 and SEQ ID NOs: 60-145) respectively, using phusion PCR mix (FinnZymes, cat No. F-531L). The human $C_L$,kappa encoding sequence was PCR amplified with forward primer number 486 and reverse primer number 485. Forward primer number 486 contains a BsiWI restriction enzyme site and reverse primer 485 encodes a HPC4 tag followed by a stop codon and contains a 3' flanking EcoRI site for cloning purposes. The PCR reaction was performed using phusion PCR mix (FinnZymes, cat No. F-531L). HindIII+BsiWI digested 0012$V_L$ PCR fragment was mixed with BsiWI+EcoRI digested human $C_L$,kappa-HPC4 PCR fragment and inserted into the HinDIII+EcoRI sites of a pTT-based expression vector resulting in pTT-0012LC-HPC4 (FIG. 4). In order to develop corresponding expression vectors encoding the LC-HPC4 version of the remaining four anti-TLT-1 LC sequences, the 0012$V_L$ sequence in pTT-0012LC-HPC4 was excised with HinDIII+BsiWI and replaced with HinDIII+BsiWI digested 0023$V_L$, 0051$V_L$, 0052$V_L$ and 0012$V_L$.C36A PCR fragments. The resulting four expression vectors were designated: pTT-0023LC-HPC4, pTT-0051LC-HPC4, pTT-0052LC-HPC4 and pTT-0012LC.C36A.HPC4 (FIG. 4B). The amino acid sequences encoded by pTT-0012LC.C36A-HPC4, pTT-0023LC-HPC4, pTT-0051LC-HPC4 and pTT-0052LC-HPC4 are shown in SEQ ID NO: 0012LC.C36A-HPC4 (also called 0061LC-HPC4): 167, 0023LC-HPC4: 179, 0051LC-HPC4: 177, 0052LC-HPC4 (also called 0062LC-HPC4): 174.

Example 9

Development of pTT-0012$V_H$.T60N-CH1-YGPPC, pTT-0023$V_H$-CH1-YGPPC, pTT-0051$V_H$-CH1-YGPPC, and pTT-0052$V_H$.C91Y-CH1-YGPPC Expression Constructs The 0012$V_H$.T60N-CH1-YGPPC, 0023$V_H$-CH1-YGPPC, 0051$V_H$-CH1-YGPPC and 0052$V_H$.C91Y-CH1-YGPPC sequence (YGPPC is a partial human IgG4 hinge amino acid sequence) was PCR amplified from pTT-0012HC.T60N, pTT-0023HC, pTT-0051HC and pTT-0052HC.C91Y respectively using forward and reverse primer pairs: 572 (forward)+698 (reverse), 576 (forward)+698 (reverse), 627 (forward)+698 (reverse) and 617 (forward)+698 (reverse), respectively. The forward primers contain a HinDIII restriction enzyme site and the reverse primer 698 contains a stop codon and an EcoRI site for cloning purposes. The resulting PCR fragment was digested with HinDIII+EcoRI and inserted into the HinDIII+EcoRI sites of a pTT based vector. The resulting expression vectors were designated pTT-0012$V_H$.T60N-CH1-YGPPC (FIG. 4A), pTT-0023$V_H$-CH1-YGPPC, pTT-0051$V_H$-CH1-YGPPC and pTT-0052$V_H$.C91Y-CH1-YGPPC. The amino acid sequences encoded by pTT-0012$V_H$.T60N-CH1-YGPPC (FIG. 4A), pTT-0023$V_H$-CH1-YGPPC, pTT-0051$V_H$-CH1-YGPPC and pTT-0052$V_H$.C91Y-CH1-YGPPC is shown in SEQ ID NO: 0012$V_H$.T60N-CH1-YGPPC (also called 0061VH-CH1-YGPPC): 171, 0023$V_H$-CH1-YGPPC: 178, 0051$V_H$-CH1-YGPPC 176, 0052$V_H$.C91Y-CH1-YGPPC (also called 0062VH-CH1-YGPPC): 175.

Example 10

Development of pTT-0012$V_H$-CH1, pTT-0012$V_H$-CH1-HPC4, pTT-0023$V_H$-CH1, pTT-0023$V_H$-CH1-HPC4, pTT-0051$V_H$-CH1, pTT-0051$V_H$-CH1-HPC4, pTT-0052$V_H$-CH1 and pTT-0052$V_H$-CH1-HPC4 Expression Constructs The 0012$V_H$, 0023$V_H$, 0051$V_H$, and 0052$V_H$ sequences isolated from 0012Hyb, 0023Hyb, 0051Hyb, 0052Hyb were PCR amplified with primer numbers: 490 (forward)+491 (reverse), 546 (forward)+547 (reverse), 627 (forward)+628 (reverse), 617 (forward)+618 (reverse, primer sequences are shown in Table 4 and SEQ ID NOs 60-145), respectively, using phusion PCR mix (FinnZymes, cat No. F-531L). All forward primers (490, 546, 627, and 617) contained a HinDIII site and all reverse primers (491, 547, 628, and 618) contained a NheI site for cloning purposes. The human $IgG_4$ CH1 region was PCR amplified either with primer numbers: 489 (forward)+488 (reverse), or primer numbers 489 (forward)+487 (reverse). Forward primer number 489 contained a NheI site, the 488 reverse primer number contained a stop codon and an EcoRI site, and the 487 reverse primer number contained an HPC4 tag encoding sequence, a stop codon followed by an EcoRI site for cloning purposes. HinDIII+NheI digested 0012$V_H$ PCR fragment was combined with either NheI+EcoRI digested human $IgG_4$ CH1 PCR fragment or with NheI+EcoRI digested human $IgG_4$ CH1-HPC4 PCR fragment and cloned into the HindIII+EcoRI sites for a pTT based vector. The resulting vectors were designated pTT-0012$V_H$-CH1 and pTT-0012$V_H$-CH1-HPC4, respectively. The pTT-0012$V_H$-CH1-HPC4 vector is shown in FIG. 5B. The 0012$V_H$-CH1-HPC4 amino acid and DNA sequences are shown in SEQ ID NOs 168-169. The $V_H$ domains of pTT-0012$V_H$-CH1 and of pTT-0012$V_H$-CH1-HPC4 were excised by HindIII+NheI digestion and HinDIII+NheI digested 0197-0000-0023$V_H$, 0197-0000-0051$V_H$ and 0197-0000-0052$V_H$ PCR fragments were inserted. The resulting expression vectors were designated: pTT-0023$V_H$-CH1, pTT-0023$V_H$-CH1-HPC4, pTT-0051$V_H$-CH1, pTT-0051$V_H$-CH1-HPC4, pTT-0052$V_H$-CH1, and pTT-0052$V_H$-CH1-HPC4.

Example 11

Development of pTT-0012$V_H$.T60N-CH1, pTT-0012$V_H$.T60N-CH1-HPC4, pTT-0052$V_H$.C91Y-CH1 and pTT-0052$V_H$.C91Y-CH1-HPC4 Expression Constructs The 0012$V_H$.T60N-CH1 and 0052$V_H$.C91Y-CH1 sequence (including the signal peptide encoding sequence) was PCR amplified from pTT-0012HC.T60N and pTT-0052HC.C91Y, respectively using phusion PCR mix (FinnZymes, cat No. F-531L). For the 0012$V_H$.T60N-CH1 PCR fragment the forward primer number 572 containing a HinDIII restriction enzyme site and reverse primer number 488 containing a EcoRI site for cloning purposes or reverse primer 487 containing a HPC4 tag encoding sequence together with a EcoRI site for cloning purposes were employed. For the 0052$V_H$.C91Y-CH1 PCR fragment the forward primer number 617 together with either reverse primer number 488 or 487 were employed (primer sequences are shown in Table 4 and SEQ ID NOs 60-145). The resulting PCR fragments were digested with HinDIII+EcoRI and inserted into the HinDIII+EcoRI sites of a pTT based vector. The resulting expression vectors were designated pTT-0012$V_H$.T60N-CH1, pTT-0012$V_H$.T60N-CH1-HPC4, pTT-0052$V_H$.C91Y-CH1 and pTT-0052$V_H$.C91Y-CH1-HPC4. The amino acid sequence encoded by pTT-0012$V_H$.T60N-CH1 is shown in SEQ ID NO: 0012$V_H$.T60N-CH1 (also called 0061VH-CH1): 146 while the corresponding amino acid sequence without the N-terminal signal peptide sequence is shown in SEQ ID NO: 152.

Example 12

Development of pTT-FIX-L4b-0012LC and pTT-FIX-L4b-0012LC.C36A Expression Construct The FIX DNA sequence (including the signalpeptide encoding sequence) was PCR amplified from human FIX DNA sequences using forward primer 753 and reverse primer 754. Forward primer 753 inserts a 5'end HinDIII restriction enzyme site and reverse primer 754 inserts a 17 amino acid long glycine-serine linker (L4b: GGGGSGGGGSGGGGSGS SEQ ID NO:192) containing a 3'end BamHI restriction enzyme site for cloning purposes. The FIX-L4b PCR fragment was inserted into the HinDIII+BamHI sites of pTT-hTF.1-219-L4b-0012LC i.e. replacing hTF.1-219 DNA sequences and resulting in the FIX-L4b-0012LC expresssion construct designated pTT-FIX-L4b-0012LC (FIG. 5A). The FIX-L4b-0012LC amino acid and DNA sequences are shown in SEQ ID NO: 172-173.

In order to develop an expression plasmid encoding pTT-FIX-L4b-0012LC.C36A the 0012LC.C36A coding region excluding the signal peptide sequence was PCR amplified using pTT-0012LC.C36A as template and using forward primer 1055 containing a 5'end BamHI site and reverse primer 1056 containing a stop codon and an EcoRI site for cloning purposes (Table 4). The resulting PCR fragment was inserted into the BamHI and EcoRI sites of pTT-FIX-L4b-0012LC i.e. replacing the 0012LC DNA sequence with 0012LC.C36A DNA sequence. The resulting expression vector was called pTT-FIX-L4b-0012LC.C36A and encode the amino acid sequences shown in SEQ ID NO: FIX-L4b-0012LC.C36A (also called FIX-L4b-0061LC): 182.

Example 13

Development of pTT-FVII-L4b-0052$V_H$.C91Y-CH1-HPC4 Expression Construct

The human FVII DNA sequence (including the signal-peptide encoding sequence) was PCR amplified from human FVII DNA sequences using forward primer 751 and reverse primer 752. Forward primer 751 inserts a 5'end HinDIII restriction enzyme site and reverse primer 752 inserts a 17 amino acid long glycine-serine linker (L4b: GGGGSGGGGSGGGGSGS SEQ ID NO:192) containing a 3'end BamHI restriction enzyme site for cloning purposes. The FVII-L4b PCR fragment was inserted into the HinDIII+BamHI sites of pTT-hTF.1-219-L4b-0012LC i.e. replacing hTF.1-219 DNA sequences and resulting in the FVII-L4b-0012LC expresssion construct designated pTT-FVII-L4b-0012LC. The 0052$V_H$ C91Y-CH1-HPC4 encoding DNA sequence was PCR amplified using pTT-0052$V_H$.C91Y-CH1-HPC4 vector as template and using forward primer 1236 containing a 5'end BamHI restriction enzyme site and using reverse primer 1095 containing a stop codon and an EcoRI site for cloning purposes. The resulting PCR fragment was inseted into the BamHI+EcoRI site of pTT-FVII-L4b-0012LC ie replacing the 0012LC sequence and resulting in the expression vector designated pTT-FVII-L4b-0052$V_H$.C91Y-CH1-HPC4. The FVII-L4b-0052$V_H$.C91Y-CH1-HPC4 amino acid is shown in SEQ ID NO: FVII-L4b-0052VH.C91Y-CH1-HPC4 (also called FVII-L4b-0062VH-CH1-HPC4): 180.

Example 14

Transient Transfection of HEK293-6E Cells

All mAb, Fab, and fusion proteins were expressed in HEK293-6E suspension cells by transient transfecting expression plasmids into cells. Individual plasmids combinations underlying the resulting specific protein compounds are shown in Table 5. HEK293-6E cells were grown in Freestyle HEK293 medium (GIBCO, cat. no. 12338-018) supplemented with 1% P/S (GIBCO cat. no. 15140-122), 0.1% pluronic (GIBCO, cat. no. 24040-032) and 25 ug/mL Geneticin (GIBCO, cat. no. 10131-019) and cells were transfected at a cell density of approximately 1 mill/mL using 293fectin (Invitrogen, cat. no. 12347-019) according to the instructions of the manufacturer. In brief, for each liter of HEK293-6E cells, the transfection was performed by diluting a total of 1 mg of DNA into 30 mL Optimem (dilution A) and by diluting 1 mL 293fectin into 30 mL Optimem (GIBCO, cat. no. 51985-026, dilution B). Dilution A and B were mixed and incubated at room temperature for 30 minutes. The transfection mix was hereafter added to the HEK293-6E cells and cells were incubated at 37° C. in a humified incubator with orbital rotation (125 rpm). Five to seven days post-tranfection, cells were removed by centrifugation and the resulting cell culture supernatants were sterile-filtrated prior to purification. For all transient transfection experiments using co-transfection of 2 expression plasmids, the plasmids were cotransfected in a 1:1 (ug:ug) plasmid ratio using a total DNA amount of 1 mg for each liter of HEK293-6E cells to be transfected.

TABLE 4

Primer numbers and sequences.

| Primer No. | Primer sequence (5' to 3') |
|---|---|
| 339 | act gga tgg tgg gaa gat gga tac agt (SEQ ID NO: 199) |
| 341 | aga tcc agg ggc tag cgg ata gac aga (SEQ ID NO: 200) |
| 347 | cct gta gga cca gag ggc tcc aag gac act (SEQ ID NO: 201) |
| 348 | gga gct ggt ggt ggc atc tca gga cct ttg (SEQ ID NO: 202) |
| 448 | ttt aaa aag ctt gcc gcc acc atg gag acc cct gcc tgg ccc cgg gtc (SEQ ID NO: 203) |
| 467 | gga acc tcc ccc gcc tga tcc ccc gcc acc aga ccc gcc acc tcc ttc tct aaa ttc ccc ttt ctc ctg gcc cat (SEQ ID NO: 204) |
| 484 | gaa ttt agc ggc cgc gaa ttc gga tcc gga acc tcc ccc gcc tga tcc (SEQ ID NO: 205) |
| 485 | aaa ttt gaa ttc tta ctt gcc gtc gat cag tct ggg gtc cac ctg gtc ctc aca ctc tcc cct gtt gaa gct ctt tgt gac (SEQ ID NO: 206) |
| 486 | a cgg atc tct agc aag ctt cgt acg gtg gc (SEQ ID NO: 207) |
| 487 | aaa ttt gaa ttc tta ctt gcc gtc gat cag tct ggg gtc cac ctg gtc ctc ttt gga ctc aac tct ctt gtc cac ctt ggt (SEQ ID NO: 208) |
| 488 | aaa ttt gaa ttc tta ttt gga ctc aac tct ctt gtc cac ctt ggt (SEQ ID NO: 209) |
| 489 | acg gat ctc tag c aag ctt gct agc ac caa (SEQ ID NO: 210) |
| 490 | aaa ttt aag ctt gcc gcc acc atg gat ttt ggg ctg att ttt ttt att gtt gct (SEQ ID NO: 211) |
| 491 | aaa ttt gct agc tgc aga gac agt gac cag agt ccc ttg gcc cca (SEQ ID NO: 212) |
| 492 | aaa ttt aag ctt gcc gcc acc atg aag tca cag acc cag gtc ttc gta ttt (SEQ ID NO: 213) |
| 493 | aaa ttt aag ctt gcc gcc acc atg aag ttg cct gtt ggg ctg ttg gtg ctg (SEQ ID NO: 214) |
| 494 | aaa ttt cgt acg ttc tat ttc cag ctt ggt ccc ccc tc (SEQ ID NO: 215) |
| 495 | aaa ttt cgt acg ttt tat ttc cag ctt ggt ccc ccc tcc gaa (SEQ ID NO: 216) |
| 546 | aaa ttt aag ctt gcc gcc acc atg aac ttg ggg ctc agc ttg att ttc ctt gtc (SEQ ID NO: 217) |
| 547 | aaa ttt gct agc tga gga gac ggt gac tga ggt tcc ttg acc (SEQ ID NO: 218) |
| 548 | aaa ttt aag ctt gcc gcc acc atg gat tca cag gcc cag gtt ctt ata ttg ctg (SEQ ID NO: 219) |
| 549 | aaa ttt cgt acg ttt cag ctc cag ctt ggt ccc agc acc gaa (SEQ ID NO: 220) |
| 551 | aaa ttt aaa ttt gga tcc gat gtt gtg atg acc caa act cca ctc tcc (SEQ ID NO: 221) |
| 572 | aaa ttt aag ctt gcc gcc acc atg gat ttt ggg ctg att ttt ttt att gtt gct (SEQ ID NO: 222) |

TABLE 4-continued

| Primer numbers and sequences. | |
|---|---|
| Primer No. | Primer sequence (5' to 3') |
| 576 | aaa ttt aag ctt gcc gcc acc atg aac ttg ggg ctc agc ttg att ttc ctt (SEQ ID NO: 223) |
| 598 | gga aac acc tat ttt cat tgg gcc ctg cag aaa cca ggc cag tct (SEQ ID NO: 224) |
| 599 | aga ctg gcc tgg ttt ctg cag ggc cca atg aaa ata ggt gtt tcc (SEQ ID NO: 225) |
| 610 | gctctaga cta aca ctc att cct gtt gaa gct ctt g (SEQ ID NO: 226) |
| 613 | aaaaa tctagaata gac aga tgg ggg tgt cgt ttt ggc (SEQ ID NO: 227) |
| 614 | aaaaa tctaga ctt gac cag gca tcc tag agt ca (SEQ ID NO: 228) |
| 615 | aaaaa tctaga agg ggc cag tgg ata gac tga tgg (SEQ ID NO: 229) |
| 616 | aaaaa tctaga agg gac caa ggg ata gac aga tgg (SEQ ID NO: 230) |
| 617 | aaa ttt aag ctt gcc gcc acc atg gaa tgg acc tgg gtc ttt ctc ttc ct (SEQ ID NO: 231) |
| 618 | aaa ttt gct agc tga gga gac ggt gac cgt ggt ccc tgc (SEQ ID NO: 232) |
| 619 | aaa ttt aag ctt gcc gcc acc atg atg tcc tct gct cag ttc ctt ggt (SEQ ID NO: 233) |
| 620 | aaa ttt cgt acg ttt cat ctc cag ttt ggt ccc ccc tcc (SEQ ID NO: 234) |
| 627 | aaa ttt aag ctt gcc gcc acc atg ggt tgg agc tgt atc atc ttc ttt ct (SEQ ID NO: 235) |
| 628 | aaa ttt gct agc tgc aga gac agt gac cag agt ccc ttg (SEQ ID NO: 236) |
| 682 | gat agc agt acg ata aac tat aac cca tct cta aag gat aaa ttc (SEQ ID NO: 237) |
| 683 | gaa ttt atc ctt tag aga tgg gtt ata gtt tat cgt act gct atc (SEQ ID NO: 238) |
| 684 | tct gag gac tct gcc gtc tat tac tgt gca aga ggg tac tac ggt (SEQ ID NO: 239) |
| 685 | acc gta gta ccc tct tgc aca gta ata gac ggc aga gtc ctc aga (SEQ ID NO: 240) |
| 688 | gat agc agt acg ata aac tat gcg cca tct cta aag gat aaa ttc (SEQ ID NO: 241) |
| 689 | gaa ttt atc ctt tag aga tgg cgc ata gtt tat cgt act gct atc (SEQ ID NO: 242) |
| 698 | ttt aaa gaa ttc tca gca tgg ggg acc ata ttt gga ctc aac tct ctt (SEQ ID NO: 243) |
| 751 | ttt aaa aag ctt gcc gcc acc atg gtc tcc cag gcc ctc agg ctc ctc (SEQ ID NO: 244) |
| 752 | ttt aaa gga tcc gga acc tcc ccc gcc tga tcc ccc gcc acc aga ccc gcc acc tcc ggg aaa tgg ggc tcg cag gag gac tcc tgg (SEQ ID NO: 245) |
| 753 | ttt aaa aag ctt gcc gcc acc atg cag cgc gtg aac atg atc atg gca g (SEQ ID NO: 246) |
| 754 | ttt aaa gga tcc gga acc tcc ccc gcc tga tcc ccc gcc acc aga ccc gcc acc tcc agt gag ctt tgt ttt ttc ctt aat cca gtt gac ata (SEQ ID NO: 247) |
| 1055 | aaa ttt gga tcc gat gtt gtg atg acc caa act cca ctc tcc (SEQ ID NO: 248) |
| 1056 | aaa ttt gaa ttc cta aca ctc tcc cct gtt gaa gct ctt tgt (SEQ ID NO: 249) |
| 1095 | Aaatgatttgccctcccatatgtccttc (SEQ ID NO: 250) |
| 1236 | aaa ttt ggatcc cag gtc cag ctg cag cag tct gga gct (SEQ ID NO: 251) |

TABLE 5

Overview of plasmid combination underlying the expression of protein ID 0061 (SEQ40 + 41), 0023 (SEQ34 + 35), 0051 (SEQ36 + 37), 0062 (SEQ42 + 39), 0084 (SEQ171 + SEQ167), 0074 (SEQ176 + 177), 0003 (SEQ175 + 174), 0004 (SEQ178 + 179), 0135 (SEQ169 + SEQ173), 0145 (SEQ32 + 173) and protein ID 5001 (SEQ180 + 39).

| Protein ID | LC plasmid | HC plasmid | Protein name |
|---|---|---|---|
| 0061 | pTT-0012LC.C36A | pTT-0012HC.T60N | antiTLT-1 0061mab: $(0012HC.T60N)_2$; $(0012LC.C36A)_2$ |

TABLE 5-continued

Overview of plasmid combination underlying the expression of protein ID 0061 (SEQ40 + 41), 0023 (SEQ34 + 35), 0051 (SEQ36 + 37), 0062 (SEQ42 + 39), 0084 (SEQ171 + SEQ167), 0074 (SEQ176 + 177), 0003 (SEQ175 + 174), 0004 (SEQ178 + 179), 0135 (SEQ169 + SEQ173), 0145 (SEQ32 + 173) and protein ID 5001 (SEQ180 + 39).

| Protein ID | LC plasmid | HC plasmid | Protein name |
|---|---|---|---|
| 0023 | pTT-0023LC | pTT-0023HC | antiTLT-1 0023mab: $(0023HC)_2$; $(0023LC)_2$ |
| 0051 | pTT-0051LC | pTT-0051HC | antiTLT-1 0051mab: $(0051HC)_2$; $(0051LC)_2$ |
| 0062 | pTT-0052LC | pTT-0052HC.C91Y | antiTLT-1 0062mab: $(0052HC.C91Y)_2$; $(0052LC)_2$ |
| 0084 | pTT-0012LC.C36A-HPC4 | pTT-0012VH.T60N-YGPPC | antiTLT-1 0084Fab-YGPPC: (0012VH.T60N-CH1-YGPPC); (0012LC.C36A-HPC4) |
| 0074 | pTT-0051LC-HPC4 | pTT-0051VH-CH1-YGPPC | antiTLT-1 0074Fab-YGPPC: (0051LC-HPC4); (0051VH-CH1-YGPPC) |
| 0003 | pTT-0052LC-HPC4 | pTT-0052VH.C91Y-CH1-YGPPC | antiTLT-1 0003Fab-YGPPC (0052LC-HPC4); (0052VH.C91Y-CH1-YGPPC) |
| 0004 | pTT-0023LC-HPC4 | pTT-0023VH-CH1-YGPPC | antiTLT-1 0004Fab-YGPPC (0023LC-HPC4); (0023VH-CH1-YGPPC) |
| 0135 | pTT-FIX-L4b-0012LC | pTT-0012VH-CH1-HPC4 | FIX-antiTLT-1 Fab: (FIX-L4b-0012LC); (0012VH-CH1-HPC4) |
| 0145 | pTT-FIX-L4b-0012LC | pTT-0012HC | FIX-antiTLT-1 mAb: $(FIX-L4b-0012LC)_2$; $(0012HC)_2$ |
| 5001 | pTT-0052LC | pTT-FVII-L4b-0052$V_H$.C91Y-CH1-HPC4 | FVII-antiTLT-1 Fab: (0052LC); (FVII-L4b-0052$V_H$.C91Y-CH1-HPC4) |

Example 15

Purification and Characterization of Recombinantly Expressed Anti-TLT-1 Fabs (Fab0084, Fab0074, Fab0003 and Fab0004)

Purification of the anti-TLT-1 Fabs (0084, 0074, 0003 and 0004) was conducted using affinity chromatography based on the resin kappaSelect (GE Healthcare, cat. no. 17-5458-01). The four Fabs contain a single free cysteine residue, each included in the sequence. The purification was conducted using an ÄktaExplorer chromatography system (GE Healthcare, cat. no. 18-1112-41). The buffer systems used for the purification step was an equilibration/wash buffer composed of 10 mM NaPhosphate, pH 7.5, 150 mM NaCl and an elution buffer composed of 20 mM Formic acid, pH 3.0. No adjustments of the cleared cell supernatant were conducted prior to application on a pre-equilibrated column packed with the kappaSelect resin. The column was washed with 5 column volumes of equilibration/wash buffer. The protein was eluted isocratically in approximately 4 column volumes of elution buffer. The eluate was adjusted to pH 7 using 0.5 M NaPhosphate, pH 9.0. The molecular mass of the eluted protein was analysed using SDS-PAGE/Coomassie NuPage 4-12% Bis-Tris gels (Invitrogen, cat. no. NP0321BOX) and Liquid Chromatography Electrospray Ionisation Time-of-Flight Mass Spectrometry method setup on an Agilent 6210 instrument and a desalting column MassPREP (Waters, cat. no. USRM10008656). A pure and homogenous protein with an expected molecular mass was observed. A size-exclusion high-performance liquid chromatographic (SEC-HPLC) analysis setup on an Agilent LC 1100/1200 system and using a BIOSep-SEC-53000 300×7.8 mm column (Phenomenex, cat. no. 00H-2146-K0) and a running buffer composed of 200 mM NaPhosphate pH 6.9, 300 mM NaCl and 10% isopropanol was also conducted. Here, the protein eluted as a single symmetric peak at a retention time of approximately 9.1 min at a flow rate of 1 ml/min. To measure final protein concentration, a NanoDrop spectrophotometer (Thermo Scientific) was used together with an extinction coefficient of 1.29.

Example 16

Purification and Characterization of Recombinantly Expressed FIX-Anti-TLT-1 Fab Fusion Protein (FIX-Fab0135)

Purification of FIX-Fab0135 was conducted using an affinity chromatography method based on an anti-HPC4 resin (Roche, cat. no. 11815024001). The purification was conducted using an ÄktaExplorer chromatography system (GE Healthcare, cat. no. 18-1112-41). The buffer systems used for the purification step was an equilibration buffer composed of 20 mM Hepes, pH 7.5, 1.0 mM $CaCl_2$, 100 mM NaCl and 0.005% (v/v) Tween-80, a wash buffer composed of 20 mM Hepes, pH 7.5, 1.0 mM $CaCl_2$, 1.0 M NaCl and 0.005% (v/v) Tween-80, and an elution buffer composed of 20 mM Hepes, pH 7.5, 5.0 mM EDTA and 100 mM NaCl. Cell supernatants were adjusted with 1 mM $CaCl_2$ final concentration and a pH of 7.5 and applied onto a pre-equilibrated anti-HPC4 column. The column was washed with 5 column volumes of equilibration buffer, 5 column volumes of wash buffer and last with 5 column volumes of equilibration buffer. The protein was eluted isocratically in approximately 4 column volumes of elution buffer. The protein was analyzed using SDS-PAGE/Coomassie and Matrix Assisted Laser Desorption Ionisation Time-of-Flight Mass Spectrometry (MALDI-TOF MS) setup on a Microflex system (Bruker Daltonics), showing that a pure and homogenous protein with a molecular mass of 106 kDa was obtained. Since the theoretical mass of the amino acid sequence for the FIX-Fab0135 construct was 95.9 kDa, the expressed protein contained post-translational modifications. To measure the final protein concentrations, a Nano- Drop spectrophotometer (Thermo Scientific) was used together with extinction coefficient of 1.29.

Example 17 pcDNA3.1(+)-hTLT-1 ECD-HPC4 ala Mutant Plasmids

Forty hTLT-1 ECD-HPC4 Ala mutant expression constructs were designed according to Table 6. The expression constructs were developed by external contractor GENEART AG (Im Gewerbepark B35, 93059 Regensburg, Germany) and all 40 expression constructs were made based on the expression vector designated pcDNA3.1(+). Aliquots of DNA for each of the 40 hTLT-1 ECD-HPC4 pcDNA3.1 (+) expression construct were transfected into HEK293-6E suspension cells in order to transiently express each hTLT-1 ECD-HPC4 Ala mutant protein (Table 6). Transient transfection and culturing of HEK293-6E cells were performed as described in example 14.

TABLE 6

| wt | Wild-type |
|---|---|
| 1 | L22A |
| 2 | V25A |
| 3 | Q27A |
| 4 | V30A |
| 5 | L35A |
| 6 | H39A |
| 7 | R41A |
| 8 | L42A |
| 9 | Q43A |
| 10 | K46A |
| 11 | Q48A |
| 12 | F54A |
| 13 | L55A |
| 14 | P56A |
| 15 | E57A |
| 16 | Q60A |
| 17 | D68A |
| 18 | R69A |
| 19 | R70A |
| 20 | R75A |
| 21 | L82A |
| 22 | L86A |
| 23 | E90A |
| 24 | M91A |
| 25 | T93A |
| 26 | Q95A |
| 27 | E96A |
| 28 | E97A |
| 29 | D107A |
| 30 | R110A |
| 31 | H116A |
| 32 | R117A |
| 33 | S119A |
| 34 | P125A |
| 35 | E126A |
| 36 | E128A |
| 37 | E130A |
| 38 | S136A |
| 39 | N140A |
| 40 | K159A |

Example 18

Purification and Characterisation of Monoclonal Anti-TLT-1 Antibodies (mAbOO12, mAbOO23, mAbOO51, mAbOO61, mAbOO62)

Purification of the recombinantly expressed monoclonal anti-TLT-1 antibodies described in Table 5 was conducted by a 2-step process composed of affinity chromatography using a Protein A MabSelect SuRe resin (GE Healthcare, cat. no. 17-5438-01) and gel filtration chromatography using a 26/60 Superdex 200 PrepGrade column (GE Healthcare, cat no. 17-1071-01). Purifications were conducted using an Äkta-Explorer chromatography system (GE Healthcare, cat. no. 18-1112-41). The buffer systems used for the affinity purification step was an equilibration buffer composed of 20 mM NaPhosphate pH 7.2, 150 mM NaCl, an elution buffer composed of 10 mM Formic acid pH 3.5 and an pH-adjustment buffer composed of 0.5 M NaPhosphate pH 9.0. Cell supernatants were applied directly without any adjustments onto a pre-equilibrated MabSelect SuRe column. The column was washed with 15 column volumes of equilibration buffer and the monoclonal antibodies were eluted isocratically in approximately 2-5 column volume of elution buffer. The pooled fractions were adjusted to neutral pH using the described pH-adjustment buffer immediately after elution. The protein was further purified and buffer exchanged using said gel filtration column. The running buffer used for size exclusion chromatography was a 25 mM His pH 6.5, 135 mM NaCl. The flow rate used was 2.5 ml/min and the monoclonal anti-TLT-1 antibodies eluted as single peaks at approximately 0.4 column volumes. Based on analyses of fractions over the entire peak using the previously described SEC-HPLC method (as described in example 2), pools were prepared which contained pure antibody protein eluting as symmetric peaks at approximately 8.5 min. and with a minimum content of earlier eluting high-molecular weight protein.

The purified antibodies were characterized using the previously described SDS-PAGE/Coomassie (as described in example 2) and SEC-HPLC methods, showing that all antibody protein preparations produced were highly homogenous. All antibodies displayed expected heavy chain components of approximately 50 kDa and light chain components of approximately 25 kDa when using reducing conditions prior to running the SDS-PAGE/Coomassie analyses. Intact molecular mass determinations were performed using a Liquid Chromatography Electrospray Ionisation Time-of-Flight Mass Spectrometry method setup on an Agilent 6210 instrument and a desalting column MassPREP (Waters, cat. no. USRM10008656). The buffer system used was an equilibration buffer composed of 0.1% Formic acid in LC-MS graded-$H_2O$ and an elution buffer composed of 0.1% Formic acid in LC-MS graded-ACN. All antibodies displayed intact molecular masses of 147.2-148.6 kDa, which is approximately 2.7-3.1 kDa above the theoretical masses of the amino acid sequences for each of the antibodies. Thus, all the recombinantly expressed anti-TLT-1 antibodies displayed post-translational modifications corresponding to expected HC N-glycosylations. Final purities of 95-99% were obtained for the six antibodies. To verify the N-terminal sequence of the cloned and purified anti-TLT-1 antibodies, EDMAN degradations were performed using an automated sequenator system (Applied Biosystems 494 Protein Sequencer). 10-20 degradation cycles were conducted for each antibody. Here, expected light and heavy chain sequences were confirmed for the six cloned anti-TLT-1 antibodies. To measure the final protein concentrations, a NanoDrop spectrophotometer (Thermo Scientific) was used together with specific extinction coefficients for each of the six antibodies ranging from 1.34-1.51.

Example 19 mAb Binding and Competition of Different mABs for Binding to TLT-1

Materials:

TABLE 7

| Reagents | |
|---|---|
| Reagent | Source |
| TLT-1-His | Example 1 |
| mAb0061 | Example 18 |
| mAb0023 | Example 18 |
| mAb0051 | Example 18 |
| mAb0062 | Example 18 |
| Fab0074 | Example 15 |
| Fab0084 | Example 15 |
| Fab0003 | Example 15 |
| Fab0004 | Example 15 |
| All other reagents | Biacore<br>Human Antibody Capture Kit (BR-1008-39)<br>Anti-His mAb (R&D # MAB050) |

Method: The mAbs of interest were either immobilized directly to a CM5 chip or by capture via a human Fc capture mAb immobilized to a CM5 chip, while TLT-1-His was immobilized by capture via an anti-His mAb CM5 chip for analysis of Fabs. Reagents that were used are shown in Table 7.

mAb direct capture: The TLT-1 mAbs were immobilised to a level of approx 500-1000 RU on a CM5 chip (50 μg/ml diluted in Na-acetate, pH 4.0) using the standard procedure recommended by the supplier. Two-fold dilutions of TLT-1 from 200 nM to 0.2 nM were tested for binding to the mAbs. Running and dilution buffer: 10 mM HEPES, 150 mM, 0.005% p20, pH 7.4. Regeneration was obtained by 10 mM Glycine, pH 1.7. mAb capture via human Fc mAb: Human Fc mAb was immobilised to approx 10.000 RU. The mAb of interest was added (approx 100 nM). Two-fold dilutions of TLT-1 from 200 nM to 0.2 nM were tested. Running and dilution buffer: 10 mM HEPES, 150 mM, 0.005% p20, pH 7.4. Regeneration was obtained in 3 M $MgCl_2$.

TLT-1-His capture via anti-His mAb (R&D #MAB050): The anti-His mAb was immobilised to approx 9.000 RU. The TLT-1-His was added to a level of approx 30-40 RU (10 μg/ml diluted in 10 mM Hepes, 150 mM NaCl, 3 mM EDTA, 0.005% Tween-20) using the standard procedure recommended by the supplier. 8-fold dilutions of Fabs from 3 to 0.047 μg/ml were tested for binding to the TLT-1-His. Running and dilution buffer: 10 mM Hepes, 150 mM NaCl, 3 mM EDTA, 0.005% Tween-20. Regeneration was obtained by 3 M $MgCl_2$.

Determination of kinetic and binding constants ($k_{on}$, $k_{off}$, $K_D$) was obtained assuming a 1:1 interaction of TLT-1 and fibrinogen using the Biacore T100 evaluation software.

Competition: Competitional binding interaction analysis was obtained by Surface Plasmon Resonance in a Biacore T-100 analysing binding of various TLT-1 mAbs to TLT-1 when bound to immobilised mAb0012 (or an alternative mAb). Direct immobilization to a CM5 chip of the mAbs to a level of 5000-10000 RU was achieved in 10 mM sodium acetate pH 4.5-5.0. This was followed by binding of 50 nM TLT-1 and after 2 min of dissociation followed by binding of the three other mAbs to be tested for competition. Running and dilution buffer: 10 mM HEPES, 150 mM, 0.005% p20, pH 7.4. Regeneration was obtained by 10 mM Glycine, pH 1.7.

Results:

TABLE 8

| TLT-1 binding | ka (1/M) | kd (1/s) | $K_D$ (M) TLT-1 | Biacore technique |
|---|---|---|---|---|
| mAb0061 | 9.32E+05 | 0.003499 | 3.75E−09 | capture |
| mAb0023 | 2.87E+05 | 0.00125 | 4.36E−09 | direct |
| mAb0051 | 2.45E+05 | 0.00472 | 19.3E−09 | direct |
| mAb0062 | 3.26E+05 | 0.00134 | 4.12E−09 | direct |
| Fab0074 | 3.35E+06 | 0.00798 | 2.38E−09 | capture |
| Fab0084 | 5.31E+06 | 0.00524 | 0.99E−09 | capture |
| Fab0003 | 5.36E+05 | 0.00279 | 5.20E−09 | capture |
| Fab0004 | 1.15E+06 | 0.00195 | 1.70E−09 | capture |

TABLE 9

SPR analysis. Binding constant for binding to TLT-1. Competition with mAb0012

| mAb ID | Competition with mAb0012 | Competition with mAb0023 | Competition with mAb0051 | Competition with mAb0062 |
|---|---|---|---|---|
| mAb0061 | Yes | No | no | no |
| mAb0023 | | Yes | no | yes |
| mAb0051 | | | yes | no |
| mAb0062 | | | | yes |

Conclusion: Binding constants for mAb0061, mAb0023, mAb0051 and mAb0062 and Fab0074, Fab0084, Fab0003 and Fab0004 were estimated by Biacore analysis (see Table 8). mAb0061 and mAb0051 do not compete with any of the other mAbs for binding (see Table 9). mAb0023 and mAb0062 do compete with each other (see Table 9).

Example 20

Preparation of 20:80 PS:PC Vesicles and Cloning, Expression, Refolding and Relipidation of TLT-1

Relipidated TLT-1 in 20:80 PS:PC vesicles were prepared using Triton X-100 as detergent as described in Smith and Morrissey (2005) 3. Thromb. Haemost., 2, 1155-1162 except that TLT-1 was used instead of TF.

Materials

LB medium Kanamycin (50 mg/ml). Kanamycin Sigma K-0254 1000 mM IPTG (IPTG Sigma 1-6758)

Lysis buffer: 1× Bugbuster (Novagen) in 50 mM Tris-HCl, 100 mM NaCl, 2 mM EDTA, pH 8.0. Add 0.5 mg/ml lysozyme+DNAseI. Add 1× Complete Inhibitor Cocktail (Roche)

IB-Wash buffer 1: 1:10 bugbuster in IB-buffer. Add 50 μg/ml lysozyme+0.5× Complete Inhibitor Coctail (Roche)

IB-Wash buffer 2: 1:10 Bugbuster in IB-buffer

IB-Buffer: 50 mM Tris-HCl, 100 mM NaCl, 2 mM EDTA, pH 8.0

GndHCl buffer: 6M Guanidinium HCl, 50 mM Tris-HCl, 50 mM NaCl, 0.1% Triton X-100 red., pH 8.0

Refolding buffer: 50 mM Tris-HCl, 800 mM Arginine, 0.1% Triton X-100, 5 mM reduced glutathione, 0.5 mM oxidized glutathione pH 8.5

Dialysis buffer: 20 mM Tris-HCl, 0.1% Triton X-100, pH 8.0

DTT:Reduced glutathione (Sigma G4251) Oxidized glutathione Sigma G4376

PC:10 mg/ml L-α-phosphatidylcholine (Egg, chicken) in chloroform (Avanti Polar Lipids Inc.) Catalog No. 840051C. Mw 760.09

PS: 10 mg/ml L-α-phosphatidylserine sodium salt (Brain, porcine) in chloroform. (Avanti Polar Lipids Inc.) Catalog No. 840032C. Mw 812.05

Triton X-100: 10% Triton X-100, hydrogenated, protein grade detergent, sterile filtered.

Calbiochem. Catalog No. 648464 Concentration 159 mM (Mw 628)

HBS buffer: 50 mM HEPES, 100 mM NaCl, pH 7.4

Bio-Beads: Bio-Beads SM2 Adsorbent, 20-50 mesh Bio-Rad Laboratories, Catalog No. 152-3920.

Method

Expression: TLT-1 (hTLT-1.18-188; SEQ ID NO: 149) including extracellular domain, linker and transmembrane domain was cloned into pET24a using primers 1004 (SEQ ID NO: 150) and 1005 (SEQ ID NO: 151) and pTT-hTLT-1 as template. Standard techniques for DNA preparation were employed. Transformation was performed into BL21 (DE3). Overnight Culture: 1×50 ml LB medium in 250 ml flasks (plastic) and 50 μl of 50 mg/ml Kanamycin+1 coloni (transformation) from BL21 plate were mixed. The culture was incubated ON at 37° C., 220 rpm. Starter-culture: 2×500 ml LB medium in 2 L flasks (plastic) with 300 μl of 50 mg/ml Kanamycin was added. 10 ml ON culture TLT-1 lip/pET24a in BL21 (DE3) was added and OD600 followed. Incubated at 37° C., 220 rpm. Induction: 2×500 ml with TLT-1 lip/pET24a~BL21 (DE3) in LB. 25° C.~0.2 mM IPTG was added (100 μl of 1M) to the cell culture when $OD_{600}$ reached between 0.6-0.8. This was incubated for 3 h at 25° C., 220 rpm. The culture was harvested after 3 h and centrifuged for 30 min at 4600 rpm. The supernatant was discarded. The pellet was stored at −20° C. Lysis of Inclusion bodies: The *E. coli* pellet was resuspended in 5 ml lysis buffer/g pellet. MgSO4 was added to 5 mM to support DNAseI activity. Cell suspension was incubated on shaking platform for 20 min at room temperature. The lysate was cleared by centrifugation 20000 g (8500 rpm) for 20 min at 4° C. The pellet was resuspended in 100 ml IB-Wash buffer. Suspension was mixed by gentle vortexing and incubated at RT for 5 min. Suspension was centrifuged at 20000 g for 20 min at 4° C. to collect inclusion bodies. Inclusion bodies were resuspended in 100 ml IB-Wash buffer 2. Sample was centrifuged at 20000 g for 20 min at 4° C. to collect inclusion bodies. The pellet was resuspended in 100 ml water and centrifuged at 20000 g for 20 min at 4° C. to collect inclusion bodies. Refolding: The pellet was resolubilised in x ml GdnHCl buffer (20 ml). The final concentration of TLT-1 (A280 was measured) was 1-2 mg/ml. DTT (400 μl) was added to final concentration of 20 mM. Complete solubilization was ensured by magnetic stirring for ~1-2.5 hrs (1.5 h) at RT. Insolube material was removed by centrifugation at 20000 g for 20 min. A peristaltic pump was used slowly (overnight) to transfer the GdnHCl/protein solution (20 ml) to >20× Refolding buffer (400 ml) at 4° C. The refolding buffer was stirred quickly to ensure rapid dilution. Pump run was obtained at Flow rate 1×, speed 2.5, 4° C. and left overnight at 4° C. Precipitated protein was removed by centrifugation at 20000 g (8500 rpm) in 50 ml tubes for 30 min. The TLT-1 lip was concentrated from 400 ml to 120 ml in Amico-filter 76 mm dia., 10.000 MWCO at 4.5 bar. The protein was checked on an SDS-Page by EtOH-precipitation because of the GdnHCl in the sample. 2×500 μl and 2×25 μl were concentrated in 0.5 ml tubes with 10.000 MWCO. 50 μl sample+9 vol. ice-cold 99% EtOH (450 μl) was mixed and placed at −20° C. for 10 min. The sample wa centrifuged at full speed 13.000 rpm for 5 min. The supernatant was discarded. The pellet was washed with 450 μl ice-cold 96% EtOH+50 μl MQ. Centrifuge again. Let dry (EtOH must be eliminated before SDS-PAGE). 100 μl was resuspended 1× sample buffer PS:PC preparation and relipidation: The exact protocol described in Smith S A & Morrissey J H (2004) "Rapid and efficient incorporation of tissue factor into liposomes". *J. Thromb. Haemost.* 2:1155-1162 was followed for relipidation of TLT-1.

Example 21

Analysis of Fibrinogen Binding to TLT-1 and Binding Competition Between TLT-1 mAbs and Fibrinogen TLT-1 binds fibrinogen as tested by SPR analysis. Furthermore, simultaneous binding of fibrinogen and each of the four mAbs: mAb0012, mAb0023, mAb0051 and mAb0062 was tested by SPR analysis in a Biacore T100 instrument.

Materials used are shown in Table 10.

TABLE 10

| Reagent | Source |
|---|---|
| TLT-1 | Example 2 |
| mAb0012 | Example 18 |
| mAb0023 | Example 18 |
| mAb0051 | Example 18 |
| mAb0062 | Example 18 |
| Fibrinogen | HCI-0150R Haematologic technologies |
| All other reagents | Biacore GE Healthcare |

Method:

Human TLT-1 was immobilised to a level of approx 1000 RU on a CM5 chip (50 μg/ml diluted in Na-acetate, pH 4.0) using the standard procedure recommended by the supplier. Four-fold dilutions of human fibrinogen from 200 nM to 0.2 nM were tested for binding to the immobilized TLT-1. Running and dilution buffer: 10 mM HEPES, 150 mM, 0.005% p20, pH 7.4. Regeneration was obtained by 10 mM Glycine, pH 1.7. Determination of kinetic and binding constants ($k_{on}$, $k_{off}$, $K_D$) was obtained assuming a 1:1 interaction of TLT-1 and fibrinogen using the Biacore T100 evaluation software (Table 11).

Competition of the different mAbs for binding to TLT-1 and fibrinogen simultaneously was tested by immobilisation of each of the mAbs to approximately 10000-15000 RU at a CM5 chip followed by binding of 50 nM TLT-1 followed after 2-3 min dissociation by varying concentrations of the mAbs to be tested for competition. Regeneration of the chip was obtained by 10 mM Glycine, pH 1.7 (Table 12).

Results:

TABLE 11

| TLT-1 binding to fibrinogen | | | |
|---|---|---|---|
| | ka (1/M) | kd (1/s) | $K_D$ (M) |
| TLT-1-fibrinogen Binding | 4171 | $3.92 \times 10^{-4}$ | 9.40E−08 |

TABLE 12

Competition with fibrinogen. The mAb of interest was immobilised to a chip. Addition of TLT-1 was followed by fibrinogen (a sandwich).

| mAb ID | Competition with fibrinogen |
|---|---|
| mAb0012 | no |
| mAb0023 | yes |
| mAb0051 | no |
| mAb0062 | yes |

Conclusion:

TLT-1 (HCl-0150R) binds fibrinogen. mAb0023 and mAb0062 compete with this binding site. mAb0012 and mAb0051 do not compete.

Example 22

Epitope Mapping by Hydrogen Exchange Mass Spectrometry (HX-MS)

The HX-MS technique has been employed to identify the TLT-1 binding epitopes covered by the four monoclonal antibodies mAb0023, mAb0051, mAb0062 and mAb0061.

For the mapping experiments hTLT-1.20-125, hTLT-1.16-162 and hTLT-1.126-162 corresponding to SEQ ID NO 5, 6 and 7, respectively, were used. All proteins were buffer exchanged into PBS pH 7.4 before experiments.

Method: HX-MS Experiments.

Instrumentation and data recording. The HX experiments were automated by a Leap robot (H/D-x PAL; Leap Technologies Inc.) operated by the LeapShell software (Leap Technologies Inc.), which performed initiation of the deuterium exchange reaction, reaction time control, quench reaction, injection onto the UPLC system and digestion time control. The Leap robot was equipped with two temperature controlled stacks maintained at 20° C. for buffer storage and HX reactions and maintained at 2° C. for storage of protein and quench solution, respectively. The Leap robot furthermore contained a cooled Trio VS unit (Leap Technologies Inc.) holding the pepsin-, pre- and analytical columns, and the LC tubing and switching valves at 1° C. The switching valves have been upgraded from HPLC to Microbore UHPLC switch valves (Cheminert, VICI AG). For the inline pepsin digestion, 100 μL quenched sample containing 200 pmol TLT-1 was loaded and passed over a Poroszyme® Immobilized Pepsin Cartridge (2.1×30 mm (Applied Biosystems)) using a isocratic flow rate of 200 μL/min (0.1% formic acid:$CH_3CN$ 95:5). The resulting peptides were trapped and desalted on a VanGuard pre-column BEH C18 1.7 μm (2.1×5 mm (Waters Inc.)). Subsequently, the valves were switched to place the pre-column inline with the analytical column, UPLC-BEH C18 1.7 μm (2.1×100 mm (Waters Inc.)), and the peptides separated using a 9 min gradient of 15-40% B delivered at 150 μL/min from an AQUITY UPLC system (Waters Inc.). The mobile phases consisted of A: 0.1% formic acid and B: 0.1% formic acid in $CH_3CN$. The ESI MS data, and the separate data dependent MS/MS acquisitions (CID) and elevated energy ($MS^E$) experiments were acquired in positive ion mode using a Q-Tof Premier MS (Waters Inc.). Leucine-enkephalin was used as the lock mass ($[M+H]^+$ ion at m/z 556.2771) and data was collected in continuum mode.

Data analysis. Peptic peptides were identified in separate experiments using standard CID MS/MS or $MS^E$ methods (Waters Inc.). $MS^E$ data were processed using BiopharmaLynx 1.2 (version 017). CID data-dependent MS/MS acquisition was analyzed using the MassLynx software and in-house MASCOT database.

HX-MS raw data files were subjected to continuous lockmass-correction. Data analysis, i.e., centroid determination of deuterated peptides and plotting of in-exchange curves, was performed using HX-Express ((Version Beta); Weis et al., J. Am. Soc. Mass Spectrom. 17, 1700 (2006)).

Epitope mapping of mAb0023: Amide hydrogen/deuterium exchange (HX) was initiated by a 30-fold dilution of hTLT-1.20-125 in the presence or absence of mAb0023 into the corresponding deuterated buffer (i.e. PBS prepared in $D_2O$, 96% $D_2O$ final, pH 7.4 (uncorrected value)). All HX reactions were carried out at 20° C. and contained 4 μM hTLT-1.20-125 in the absence or presence of 2.4 μM mAb0023 thus giving a 1.2 fold molar excess of mAb binding sites. At appropriate time intervals ranging from 10 sec to 8 hours, aliquots of the HX reaction were quenched by an equal volume of ice-cold quenching buffer (1.35M TCEP) resulting in a final pH of 2.6 (uncorrected value).

Epitope mapping of mAbs 0051 and 0062: Epitope mapping of mAb0051 and mAb0062 were performed in a separate experiment using hTLT-1.20-125 and carried out similarly to the mapping of mAb0023 as described above.

Epitope mapping of mAb0061: Epitope mapping of mAb0061 was performed in two separate experiments using either the hTLT-1.16-162 protein or the hTLT-1.126-162 peptide.

Experiments were performed similarly as described above for mAb0023. However, the pepsin column was placed at room temperature for experiments using hTLT-1.126-162. This results in an increased pepsin digestion efficacy with minimal additional exchange loss.

Results

Epitope Mapping of mAb0023

The HX time-course of 20 peptides, covering 100% of the primary sequence of TLT-1, were monitored in the presence and absence mAb0023 for 10 sec to 8 hours.

Figure 6:
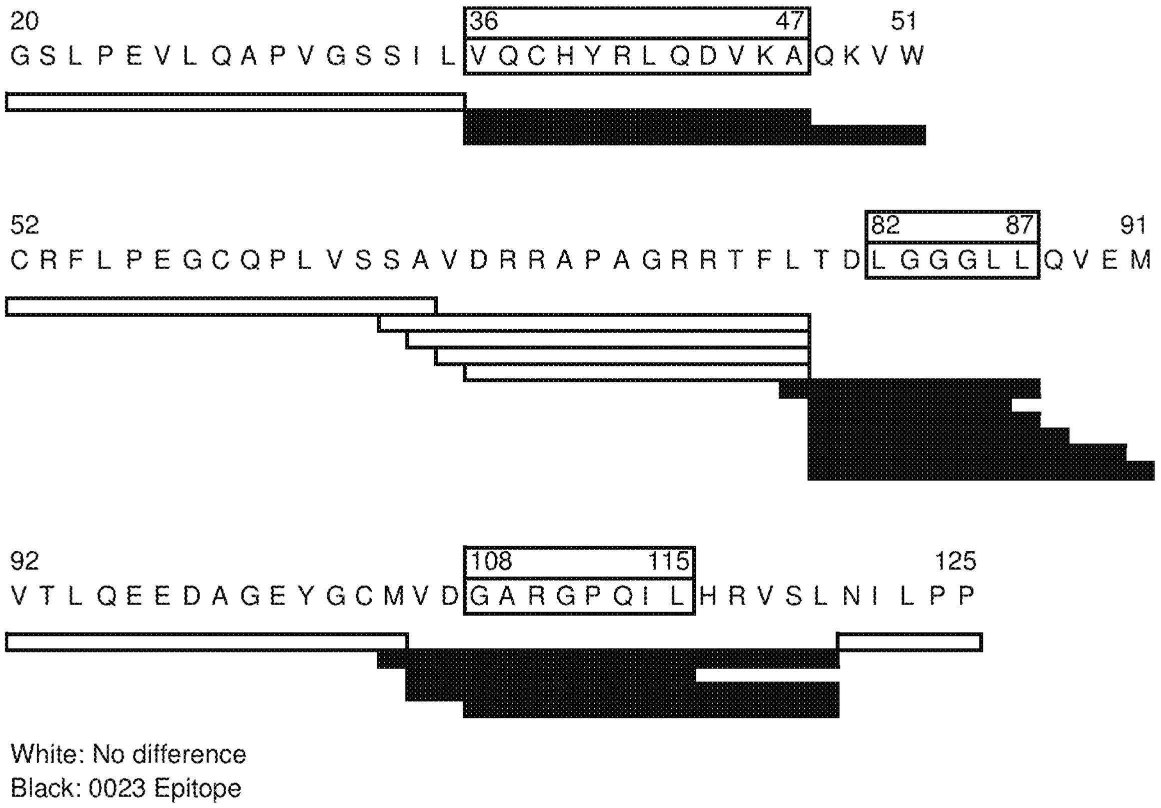
FIG. 6: Sequence coverage of HX analyzed peptides of TLT-1 in the presence and absence of mAb0023. The primary sequence of hTLT-1 is displayed above the HX analyzed peptides (shown as horizontal bars) (SEQ ID NO: 5). Peptides showing similar exchange patterns both in the presence and absence of 0023 are displayed in white whereas peptides showing reduced deuterium incorporation upon 0023 binding are coloured black.

The observed exchange pattern in the presence or absence of mAb0023 can be divided into two different groups: One group of TLT-1 peptides display an exchange pattern that is unaffected by the binding of mAb0023 and another group of TLT-1 peptides that show protection from exchange upon mAb0023 binding. The regions displaying protection upon mAb0023 binding encompass peptides covering TLT-1 residues 36-51, 79-91 and 105-120. By comparing the relative amounts of exchange protection within each peptide the epitope for mAb0023 can be narrowed to residues 36-47, VQCHYRLQDVKA (SEQ ID NO:252) (50%), 82-87, LGGGLL (SEQ ID NO:253) (30%), 108-115, GARGPQIL (SEQ ID NO:254) (20%) with the relative exchange protection for each segment noted in parenthesis. An overview of the peptide map for the 0023 epitope is shown in FIG. 6.

Epitope Mapping of mAb0051

The HX time-course of 22 peptides, covering 100% of the primary sequence of TLT-1, were monitored in the presence and absence mAb0051 for 10 sec to 1000 sec.

Figure 7:
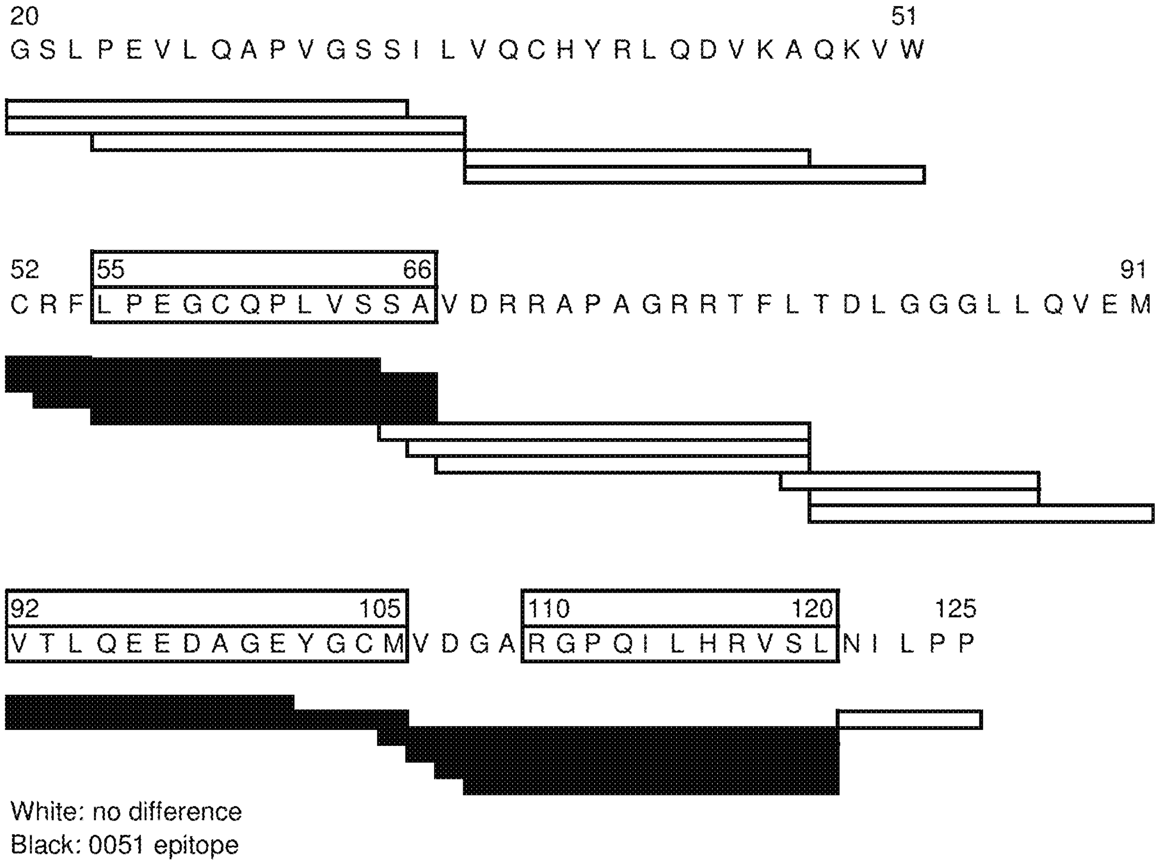
FIG. 7: Sequence coverage of HX analyzed peptides of TLT-1 in the presence and absence of mAb0051. The primary sequence of hTLT-1 is displayed above the HX analyzed peptides (shown as horizontal bars) (SEQ ID NO: 5). Peptides showing similar exchange patterns both in the presence and absence of 0051 are displayed in white whereas peptides showing reduced deuterium incorporation upon 0051 binding are coloured black.

The observed exchange pattern in the presence or absence of mAb0051 can be divided into two different groups: one group of TLT-1 peptides display an exchange pattern that is unaffected by the binding of mAb0051 and a group that is affected. The regions displaying protection upon mAb0051 binding encompass peptides covering residues 52-66, 92-120. By comparing the relative amounts of exchange protection within each peptide the epitope for mAb0051 can be narrowed to residues 55-66, LPEGCQPLVSSA (SEQ ID NO:255) (75%) and 110-120, RGPQILHRVSL (SEQ ID NO:256) (25%) as well as a weak interaction in the 92-105 stretch. An overview of the peptide map for the 0051 epitope is shown in FIG. 7.

Epitope Mapping of mAb0062

The HX time-course of 22 peptides, covering 100% of the primary sequence of TLT-1, were monitored in the presence and absence mAb0062 for 10 sec to 1000 sec.

Figure 8:
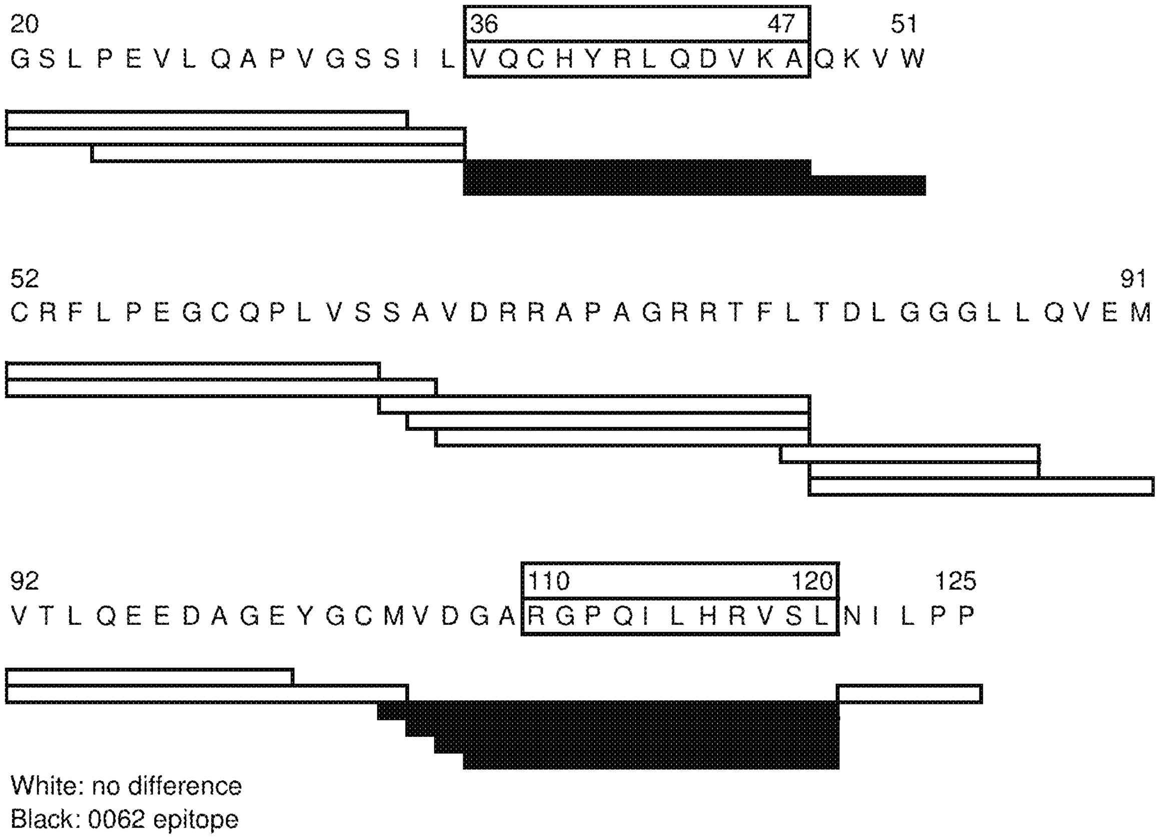
FIG. 8: Sequence coverage of HX analyzed peptides of TLT-1 in the presence and absence of mAb0062. The primary sequence of hTLT-1 is displayed above the HX analyzed peptides (shown as horizontal bars) (SEQ ID NO: 5). Peptides showing similar exchange patterns both in the presence and absence of 0062 are displayed in white whereas peptides showing reduced deuterium incorporation upon 0062 binding are coloured black.

The observed exchange pattern in the presence or absence of mAb0062 can be divided into two different groups: One group of TLT-1 peptides display an exchange pattern that is unaffected by the binding of mAb0062 and another group of TLT-1 peptides that show protection. The regions displaying protection upon mAb0062 binding encompass peptides covering residues 36-51 and 105-120. By comparing the relative amounts of exchange protection within each peptide the epitope for mAb0062 can be narrowed to 36-47, VQCHYRLQDVKA (SEQ ID NO:252) (60%) and 110-120, RGPQILHRVSL (SEQ ID NO:256) (40%). An overview of the peptide map for the 0062 epitope is shown in FIG. 8.

Epitope Mapping of mAb0061

The epitope for mAb0061 was mapped in two separate experiments using either the hTLT-1.16-162 protein or the hTLT-1.126-162.

For hTLT-1.16-162 the HX time-course of 19 peptides, covering 85% of the primary sequence of TLT-1, were monitored in the presence and absence mAb0061 for 10 sec to 8 hours. Due to an O-glycosylation at residue S148, no information could be recorded beyond residue 141.

The observed exchange pattern in the presence or absence of mAb0061 can be divided into two different groups: One group of TLT-1 peptides display an exchange pattern that is unaffected by the binding of mAb0061 and another group of TLT-1 peptides that show protection from exchange upon mAb0061 binding. The regions displaying protection upon mAb0061 binding encompass peptides covering residues 121-141. However, it is important to note that no information is given in this experiment for residue 142 and beyond. By comparing the relative amounts of exchange protection within each peptide the epitope for mAb0061 can be narrowed to begin at residue 130.

In order to gain full information on the mAb0061 epitope, the mapping experiment was repeated using the peptide hTLT-1.126-162. This peptide binds mAb0061 with high affinity and it is not modified by glycosylation. Thus it should be able to give HX-MS information for the entire region.

The HX time-course of 12 peptides, covering the entire 126-162 TLT-1 region were monitored in the presence and absence mAb0061 for 10 sec to 3000 sec.

Figure 9:
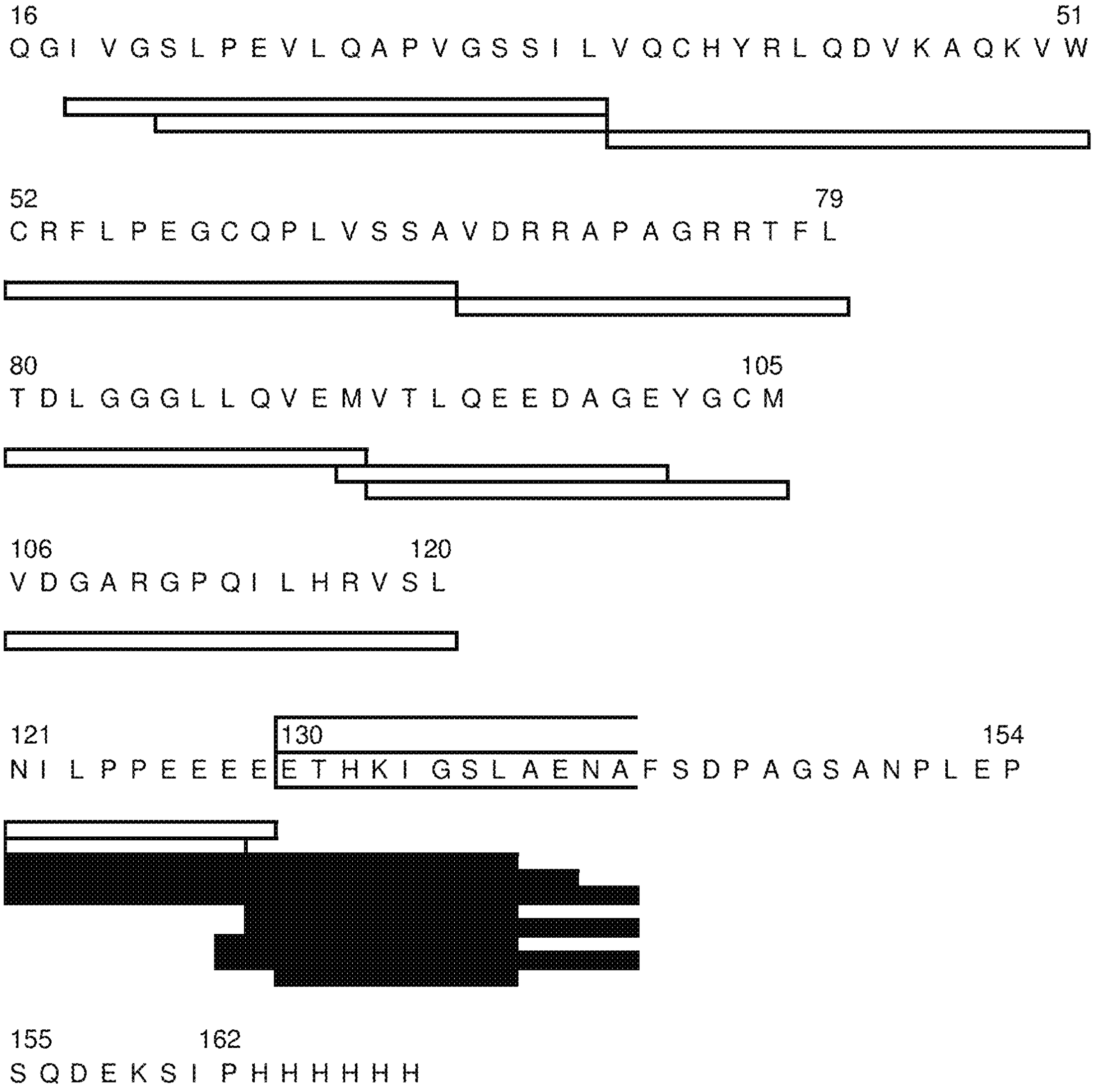
FIG. 9: Sequence coverage of HX analyzed peptides of TLT-1 in the presence and absence of mAb0061 (mAb0012). The primary sequence of hTLT-1 is displayed above the HX analyzed peptides (shown as horizontal bars) (SEQ ID NO: 187). Peptides showing similar exchange patterns both in the presence and absence of 0061 are displayed in white whereas peptides showing reduced deuterium incorporation upon 0061 binding are coloured black.
Figure 10:
FIG. 10: Sequence coverage of HX analyzed peptides of TLT-1 region 126-162. The primary sequence of hTLT-1 is displayed above the HX analyzed peptides (shown as horizontal bars) (SEQ ID NO: 188). All peptides showed reduced deuterium incorporation upon mAb0061 (mAb0012) binding.

All the peptides in this 126-162 region display protection from exchange upon mAb0061 binding. By comparing the relative amounts of exchange protection within each peptide the epitope for mAb0061 can be narrowed to be within residues 130-145, ETHKIGSLAENAFSDP (SEQ ID NO: 257). An overview of the peptide map for the 0061 epitope is shown in FIGS. 9 and 10.

Example 23

Production, Characterization and Binding Analyses of hTLT-1 ECD-HPC4 Ala Mutants hTLT-1 ECD-HPC4 Alanine mutant constructs were designed according to Table 6. The expression constructs were developed by external contractor GENEART AG (Im Gewerbepark B35, 93059 Regensburg, Germany) and all expression constructs were made based on the expression vector designated pcDNA3.1(+). Aliquots of DNA for each of the 40 hTLT-1 ECD-HPC4 pcDNA3.1(+) expression contruct were transfected into HEK293-6E suspension cells in order to transiently express each hTLT-1 ECD-HPC4 Ala mutant protein (Table 6). Transient transfection and culturing of HEK293 6e cells were performed as described in example A.

Seven days post-tranfection, cells were removed by centrifugation and the resulting hTLT-1 ECD-HPC4 Ala mutant protein containing supernatants were sterile-filtrated prior to analyses. The concentration of expressed hTLT-1 ECD-HPC4 Ala mutant protein in the cleared cell supernatant was determined using a combination of RP-HPLC and SDS-PAGE/Coomassie analyses. These ranged from 4-40 μg/mL containing variable degree of dimer formation. As described previously for production of hTLT protein used for immunization experiments, monomer/dimer forms of the expressed protein were observed for all hTLT ECD-HPC4 Ala mutant constructs. The relative concentration of monomer/dimer hTLT-1 ECD-HPC4 protein was estimated by SDS-PAGE/Coomassie and an average Mw for each mutant preparation was calculated.

All binding studies were run at 25° C., and the samples were stored at 15° C. in the sample compartment on a ProteOn Analyzer (BioRad) that measures molecular interactions in real time through surface plasmon resonance. The signal (RU, response units) reported by the ProteOn is directly correlated to the mass on the individual sensor chip surface spots.

Anti-hFc Polyclonal antibody was immobilized onto separate flow cells of a GLM sensor chip using a 1:1 mixture of 0.4 M EDAC [1-ethyl-3-(3-dimethylaminopropyl) carbodiimide hydrochloride] and 0.1 M Sulfo-NHS [N-hydroxysulfosuccinimide]. Each antibody was diluted in 10 mM sodium acetate pH 5.0 to a concentration of 50 μg/ml, and was immobilized to an individual flow cell at 30 μl/min for 240 s. The antibodies were immobilized to flow cells A1-A6 (horizontal direction). After immobilization, the active sites on the flow cell were blocked with 1 M ethanolamine. The final immobilization level of capture antibody typically ranged from approximately 9,000 to 10,000 RU in one experiment. Capture of the anti-TLT-1 antibodies mAb0023, mAb0051, mAb0061 and mAb0062 was conducted by diluting to 0.5 μg/ml into HBS-EP buffer (10 mM HEPES, 150 mM NaCl, 3 mM EDTA, 0.05% surfactant P20, pH 7.4) and injected at 30 μl/min for 60 s in vertical direction, creating interspot reference points with only anti-human Fc antibodies.

The final capture level of test antibodies typically ranged from approximately 200 to 300 RU in one experiment. Binding of wt or Ala mutant hTLT-1 ECD-HPC4 protein was conducted by injecting over parallel flow cells in horizontal direction to allow for comparative analyses of binding to different captured anti-TLT-1 antibodies relative to binding to the interspot references. Each hTLT-1 ECD-HPC4 protein was diluted to 100 nM, based on the calculated average Mw, into HBS-EP buffer and injected at 30 μl/min for 240 s. The GLM chip was regenerated after each injection cycle of analyte via one 18 s injection of 1 M Formic acid followed by a 18s injection of 50 mM NaOH at 100 μl/min. This regeneration step removed the anti-TLT-1 antibody and any bound TLT-1 from the immobilized capture antibody surface, and allowed for the subsequent binding of the next test sample pair. The regeneration procedure did not remove the directly immobilized anti-human-Fc capture antibody from the chip surface.

Data analysis was performed using the ProteOn Manager™ Software. No significant non-specific binding to the interspot control surfaces was observed. Binding curves were processed by double referencing (subtraction of interspot control surface signals as well as blank buffer injections over captured anti-TLT-1 antibodies). This allowed correction for instrument noise, bulk shift and drift during sample injections. Binding signal at 10 s after stop of analyte injection was normalized to level of captured anti-TLT-1 antibody and presented as binding relative to wt hTLT-1 ECD-HPC4 protein.

The following Ala mutations displayed a significant decrease of binding to respective anti-TLT-1 compared to wt hTLT-1 ECD-HPC4 protein. mAb0051: F54A<0.4 wt; M91A<0.2 wt; R117A<0.2 wt; S119A<0.6 wt. mAb0062: R41A<0.2 wt; L42A<0.6 wt; Q43A<0.4 wt; F54A<0.6 wt; M91A<0.4 wt; R110A<0.2 wt; H116A<0.6 wt. mAb0023: L42A<0.2 wt; Q43A<0.2 wt; K46A<0.2 wt; M91A<0.4 wt; R110A<0.2 wt. Since decreased binding could be observed for the hTLT-1 ECD-HPC4 mutant M91A for all 4 anti-TLT-1 antibodies, the residue probably has an important influence on protein stability rather than being part of an actual epitope. mAb0061 did not show a decreased binding to any of the mutated TLT-1 variants tested, indicating that the epitope is not covered by the mutants introduced in the binding study.

Example 24

Crystal Structure Complexes Between Anti-TLT-1 Fab and TLT-1 Stalk Peptides

Expression of anti-TLT-1 Fab, Fab0100 (identical to Fab0061), for crystallization: The anti-TLT-1 Fab fragment, Fab0100, comprising the heavy chain corresponding to SEQ ID NO: 152 and the light chain corresponding SEQ ID NO: 153 was expressed transiently in HEK293 cells according to the generalized procedure.

Purification of anti-TLT-1 Fab, Fab0100, for crystallization: Purification of said Fab was conducted by a two-step process composed of affinity chromatography using the kappaSelect resin (GE Healthcare, cat. no. 17-5458-01) and size-exclusion chromatography. The purification was conducted using an ÄktaExplorer chromatography system (GE Healthcare, cat. no. 18-1112-41). The buffer systems used for the purification step was an equilibration buffer composed of 10 mM NaPhosphate, pH 7.5 and 150 mM NaCl and an elution buffer composed of 20 mM Formic acid, pH 3.0. The supernatant was adjusted with 1 M NaOH to a pH of 7.5 and applied onto a pre-equilibrated kappaSelect column. The column was washed with 5 column volumes of equilibration buffer and the Fab protein was isocratically eluted using approximately 5 column volumes of elution buffer. The Fab protein was analyzed using SDS-PAGE/Coomassie and LC-MS analyses, showing that a pure and homogenous protein with an expected molecular weight of 46.9 kDa was obtained. To measure the protein concentration, a NanoDrop spectrophotometer (Thermo Scientific) was used together with an extinction coefficient of 1.31. The final polish of the Fab protein was conducted using a size-exclusion column (Superdex200).

Preparation of peptides for crystallization: The TLT-1-stalk peptide hTLT-1.126-162 (SEQ ID NO: 7) was prepared by solid phase peptide synthesis. Likewise, a shorter version hTLT-1.129-142 of the stalk peptide corresponding to SEQ ID NO: 8 was prepared.

Preparation, crystallization and structure determination of the Fab0100:TLT-1 complexes: Preparation of Fab0100: hTLT-1.126-162: The complex between Fab0100 and hTLT-1.126-162 was prepared by adding two times molar excess of hTLT-1.126-162 to a solution of Fab0100 followed by isolation of the complex by separating excess hTLT-1.126-162 using preparative size exclusion chromatography. Thus, the Fab0100: hTLT-1.126-162 complex was prepared by mixing Fab (1100 μl, 98 μM) and hTLT-1.126-162 (155 μl, 1391 μM), both in PBS buffer (pH 7.4). The complex was subjected to gel filtration using a Superdex 200 HighLoad 26/60 (GE Healthcare) column eluted with PBS-buffer (pH 7.4) at a flow rate of 1 ml/min. Fractions corresponding to a volume of 3 ml were collected. Fractions containing the desired Fab0100: hTLT-1.126-162 complex were pooled and then concentrated using a centrifugal filter device (Amicon, 10 kDa cut-off) to a protein concentration of 8.6 mg/ml. This preparation was used for crystallization of the Fab0100: hTLT-1.126-162 complex.

Preparation of Fab0100:hTLT-1.129-142: The complex between Fab0100 and the shorter stalk peptide (hTLT-1.129-142) was similarly prepared with the exceptions that the molar ratio between hTLT-1.129-142 and Fab was 1.5:1 and that the gel filtration stop was omitted due to weaker binding of hTLT-1.129-142 compared to that of the longer stalk peptide (hTLT-1.126-162).

Crystallization and data collection of Fab0100:hTLT-1.129-142 and Fab0100:hTLT-1.126-162 complexes: Fab0100:hTLT-1.129-142 and Fab0100:hTLT-1.126-162 complexes were at room temperature crystallized by the sitting drop method. Fab0100:hTLT-1.129-142 was crystallized by adding to the protein solution, in a 1:2 volume ratio (precipitant:protein), a precipitation solution containing 0.04 M potassium dihydrogen phosphate, 16% w/v PEG 8,000 and 20% glycerol, while the Fab0100:hTLT-1.126-162 complex was crystallized by adding to the protein solution, in a 1:1 volume ratio (precipitant:protein), a precipitation solution containing 20% w/v PEG 10,000 and 0.10 M Hepes pH 7.5. A crystal of the Fab0100:hTLT-1.129-142 complex was flash frozen in liquid $N_2$ and during data collection kept at 100 K by a cryogenic $N_2$ gas stream. Crystallographic data were subsequently collected to 2.14 Å resolution using a Rigaku MicroMax-007 HF rotating anode and a marCCD 165 X-ray detector. Space group determination, integration and scaling of the data were made by the XDS software package (Kabsch,W. (1993) *J. Appl. Crystallogr.* 26, 795-800). Cell parameters of the crystal were determined to be 82.10, 64.99, 107.73 Å, 90°, 95.12° and 90°, for a, b, c, $\alpha$, $\beta$ and $\gamma$ respectively, and the space group was determined to be C2. $R_{sym}$ for intensities of the data set was calculated to be 6.5%. Coordinates from a Fab model of the PDB-deposited (Berman, H. M. et al. (2000) *Nucleic Acids Res.* 28, 235-242) 1NGZ structure (Yin, J. et al. *PNAS us* 100, 856-861) was used for structure determination of the anti-TLT-1 Fab molecule. The 1NGZ Fab model was divided into two domains, the variable and the constant domains, which then were used as independent search models in a Molecular replacement run by the PHASER software program (Mccoy, A. J. et al. *Acta Crystallographica Section D Biological Crystallography* 61, 458-464; Mccoy, A. J. et al. *J. Appl. Crystallogr.* 40, 658-674) of the CCP4 suite (Bailey, S. (1994) *Acta Crystallogr. Sect. D-Biol. Crystallogr.* 50, 760-763). The ARP-wARP software package (Evrard, G. X. et al. *Acta Crystallographica Section D* 63, 108-117) was subsequently used for automated model building and phasing. Additional crystallographic refinements, using the REFMAC5 software program (Murshudov, G. N. et al. *Acta*

*Crystallogr. Sect. D-Biol. Crystallogr.* 53, 240-255), followed by computer graphics inspection of the electron density maps, model corrections and building, using the Cour software program (Emsley, P. et al. *Acta Crystallogr. Sect. D-Biol. Crystallogr.* 60, 2126-2132), were applied. The procedure was cycled until no further significant improvements could be made to the model. Final calculated R- and R-free after 3 cycles of manual intervention and following refinements were 0.185 and 0.245, respectively, and the model showed a root-mean-square deviation (RMSD) from ideal bond lengths of 0.022 Å.

A crystal of the Fab0100:hTLT-1.126-162 complex was transferred to a cryo-solution containing 75% of the precipitant solution and 25% of glycerol. The crystal was allowed to soak for about 15 seconds, then flash frozen in liquid $N_2$ and during data collection kept at 100 K by a cryogenic $N_2$ gas stream. Crystallographic data were subsequently collected to 1.85 Å resolution at beam-line BL911-3 (Ursby, T. et al. (2004) AIP Conference Proceedings 705, 1241-1246) at MAX-lab, Lund, Sweden. Space group determination, integration and scaling of the data were made in the XDS software package. Cell parameters for the synchrotron data were determined to be 82.54, 65.32, 108.05 Å, 90°, 95.15° and 90°, for a, b, c, α, β and γ, respectively, and space group was determined to be C2. $R_{sym}$ for intensities of the data set was calculated to be 6.7%. The crystal was isomorphous with the Fab0100:hTLT-1.129-142 crystals and therefore rigid body refinement of the Fab0100:hTLT-1.129-142 complex was used for the original phasing of the Fab0100: hTLT-1.126-162 followed by automated model building and phasing using the ARP-wARP software package. Additional crystallographic refinements, using the REFMAC5 software program, followed by computer graphics inspection of the electron density maps, model corrections and building, using the COOT software program, were applied. The procedure was cycled until no further significant improvements could be made to the model. Final calculated R- and R-free after 13 cycles of manual intervention and following refinements were 0.171 and 0.223, respectively, and the model showed a RMSD from ideal bond lengths of 0.027 Å (Table 11).

Results

As shown in Tables 14 and 15, Anti-TLT-1 effectively binds to the stalk of TLT-1. Using the software program AREAIMOL, of the CCP4 program suite, the average areas excluded in pair-wise interaction between Fab0100 and TLT-1 were calculated to be 764 $Å^2$. The average areas excluded in pair-wise interactions gave for the Fab0100: hTLT-1.126-162 complexe 656 and 871 $Å^2$, for anti-TLT-1 and TLT-1 respectively.

Residues in the TLT-1 peptide (hTLT-1.126-162) making direct contacts to the anti-TLT-1 Fab in the Fab0100: hTLT-1.126-162 complex is defined as the epitope and residues in Fab0100 making direct contacts to hTLT-1.126-162 in the Fab0100: hTLT-1.126-162 complex is defined as the paratope. Epitope and paratope residues were identified by running the CONTACTS software of the CCP4 program suite using a cut-off distance of 4.0 Å between the anti-TLT-1 Fab and the TLT-1 molecule. The results of the contact calculations for the Fab0100:hTLT-1.126-162 complex of the crystal structures are shown in Tables 14 and 15. The resulting TLT-1 epitope for Fab0100 was found to comprise the following residues of SEQ ID NO: 7): Lys 8 (133), Ile 9 (134), Gly 10 (135), Ser 11 (136), Leu 12 (137), Ala 13 (138), Asn 15 (140), Ala 16 (141), Phe 17 (142), Ser 18 (143), Asp 19 (144), Pro 20 (145), Ala 21 (146) where numbers in parenthesis refer to the corresponding residues in SEQ ID NO: 2 (Tables 12 and 13).

The resulting paratope included residues His 31, Asn 33, Tyr 37, His 39, Tyr 54, Phe 60, Ser 96, Thr 97, Val 99 and Tyr 101 of the Fab0100 light chain corresponding to SEQ ID NO: 153 (Table 12), and residues Val 2, Phe 27, Arg 31, Tyr 32, Trp 33, Glu 50, Thr 57, Asn 59, Ser 98, Gly 99, Val 100 and Thr 102 of the Fab0100 heavy chain corresponding to SEQ ID NO: 152 (Table 13). The TLT-1 epitope residues involved in hydrogen-binding are also indicated in Tables 12 and 13.

TABLE 13

Results from the X-ray model refinement to the observed data of the Fab0100:hTLT-1.126-162 complex by the software program refmac5.

```
REMARK   3  REFINEMENT.
REMARK   3   PROGRAM    : REFMAC 5.5.0109
REMARK   3   AUTHORS    : MURSHUDOV, VAGIN, DODSON
REMARK   3
REMARK   3   REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) :  1.85
REMARK   3   RESOLUTION RANGE LOW  (ANGSTROMS) : 34.18
REMARK   3   DATA CUTOFF            (SIGMA(F)): NONE
REMARK   3   COMPLETENESS FOR RANGE        (%): 99.89
REMARK   3   NUMBER OF REFLECTIONS             : 46512
REMARK   3
REMARK   3  FIT TO DATA USED IN REFINEMENT.
REMARK   3   CROSS-VALIDATION METHOD          : THROUGHOUT
REMARK   3   FREE R VALUE TEST SET SELECTION  : RANDOM
REMARK   3   R VALUE     (WORKING + TEST SET) : 0.17330
REMARK   3   R VALUE            (WORKING SET) : 0.17070
REMARK   3   FREE R VALUE:                    : 0.22260
REMARK   3   FREE R VALUE TEST SET SIZE  (%)  : 5.0
REMARK   3   FREE R VALUE TEST SET COUNT      : 2463
REMARK   3
REMARK   3  FIT IN THE HIGHEST RESOLUTION BIN.
REMARK   3   TOTAL NUMBER OF BINS USED           :    20
REMARK   3   BIN RESOLUTION RANGE HIGH           :  1.850
REMARK   3   BIN RESOLUTION RANGE LOW            :  1.898
REMARK   3   REFLECTION IN BIN    (WORKING SET)  :   3409
REMARK   3   BIN COMPLETENESS (WORKING + TEST) (%) :  99.81
REMARK   3   BIN R VALUE           (WORKING SET):  0.266
```

TABLE 13-continued

Results from the X-ray model refinement to the observed data of the Fab0100:hTLT-1.126-162 complex by the software program refmac5.

```
REMARK   3   BIN FREE R VALUE SET COUNT      :   195
REMARK   3   BIN FREE R VALUE                : 0.309
REMARK   3
REMARK   3  NUMBER OF NON-HYDROGEN ATOMS USED IN REFINEMENT.
REMARK   3   ALL ATOMS                : 3993
REMARK   3
REMARK   3  B VALUES.
REMARK   3   FROM WILSON PLOT           (A**2) : NULL
REMARK   3   MEAN B VALUE      (OVERALL, A**2) : 14.967
REMARK   3   OVERALL ANISOTROPIC B VALUE.
REMARK   3    B11 (A**2):   -0.06
REMARK   3    B22 (A**2):    0.23
REMARK   3    B33 (A**2):   -0.24
REMARK   3    B12 (A**2):    0.00
REMARK   3    B13 (A**2):   -0.36
REMARK   3    B23 (A**2):    0.00
REMARK   3
REMARK   3  ESTIMATED OVERALL COORDINATE ERROR.
REMARK   3   ESU BASED ON R VALUE                            (A):  0.116
REMARK   3   ESU BASED ON FREE R VALUE                       (A):  0.123
REMARK   3   ESU BASED ON MAXIMUM LIKELIHOOD                 (A):  0.084
REMARK   3   ESU FOR B VALUES BASED ON MAXIMUM LIKELIHOOD (A**2):  6.165
REMARK   3
REMARK   3  CORRELATION COEFFICIENTS.
REMARK   3   CORRELATION COEFFICIENT FO-FC      :  0.963
REMARK   3   CORRELATION COEFFICIENT FO-FC FREE :  0.939
REMARK   3
REMARK   3  RMS DEVIATIONS FROM IDEAL VALUES        COUNT  RMS  WEIGHT
REMARK   3   BOND LENGTHS REFINED ATOMS        (A):  3538 ; 0.027 ; 0.022
REMARK   3   BOND ANGLES REFINED ATOMS  (DEGREES):  4833 ; 2.132 ; 1.958
REMARK   3   TORSION ANGLES, PERIOD 1   (DEGREES):   473 ; 6.972 ; 5.000
REMARK   3   TORSION ANGLES, PERIOD 2   (DEGREES):   137 ;35.607 ;24.453
REMARK   3   TORSION ANGLES, PERIOD 3   (DEGREES):   583 ;14.216 ;15.000
REMARK   3   TORSION ANGLES, PERIOD 4   (DEGREES):    14 ;23.096 ;15.000
REMARK   3   CHIRAL-CENTER RESTRAINTS      (A**3):   552 ; 0.180 ; 0.200
REMARK   3   GENERAL PLANES REFINED ATOMS   (A):  2664 ; 0.013 ; 0.021
REMARK   3
REMARK   3  ISOTROPIC THERMAL FACTOR RESTRAINTS.   COUNT  RMS  WEIGHT
REMARK   3   MAIN-CHAIN BOND REFINED ATOMS  (A**2): 2262 ; 1.399; 1.500
REMARK   3   MAIN-CHAIN ANGLE REFINED ATOMS (A**2): 3679 ; 2.333 ; 2.000
REMARK   3   SIDE-CHAIN BOND REFINED ATOMS  (A**2): 1276 ; 3.462 ; 3.000
REMARK   3   SIDE-CHAIN ANGLE REFINED ATOMS (A**2): 1139 ; 5.231 ; 4.500
REMARK   3
REMARK   3  NCS RESTRAINTS STATISTICS
REMARK   3   NUMBER OF NCS GROUPS: NULL
REMARK   3
REMARK   3  TWIN DETAILS
REMARK   3   NUMBER OF TWIN DOMAINS :   NULL
REMARK   3
REMARK   3
REMARK   3  TLS DETAILS
REMARK   3   NUMBER OF TLS GROUPS :   2
REMARK   3  ATOM RECORD CONTAINS RESIDUAL B FACTORS ONLY
REMARK   3
REMARK   3  TLS GROUP :   1
REMARK   3   NUMBER OF COMPONENTS GROUP :   3
REMARK   3   COMPONENTS        C SSSEQI  TO C SSSEQI
REMARK   3   RESIDUE RANGE :   L    1    L    109
REMARK   3   RESIDUE RANGE :   H    1    H    113
REMARK   3   RESIDUE RANGE :   P    7    P    21
REMARK   3   ORIGIN FOR THE GROUP (A): -4.1790  48.4400  34.3450
REMARK   3   T TENSOR
REMARK   3     T11:   0.1731 T22:   0.1937
REMARK   3     T33:   0.1093 T12:  -0.0155
REMARK   3     T13:  -0.0164 T23:  -0.0192
REMARK   3   L TENSOR
REMARK   3     L11:   1.9367 L22:   0.4840
REMARK   3     L33:   3.8383 L12:  -0.1522
REMARK   3     L13:  -1.2215 L23:  -0.1172
REMARK   3  S TENSOR
REMARK   3     S11:   0.0447 S12:  -0.2657 S13:   0.0758
REMARK   3     S21:   0.0958 S22:  -0.0414 S23:  -0.0674
REMARK   3     S31:   0.0036 S32:   0.0098 S33:  -0.0032
REMARK   3
REMARK   3  TLS GROUP:   2
REMARK   3   NUMBER OF COMPONENTS GROUP:   2
REMARK   3   COMPONENTS        C SSSEQI  TO C SSSEQI
```

TABLE 13-continued

Results from the X-ray model refinement to the observed data of the Fab0100:hTLT-1.126-162 complex by the software program refmac5.

```
REMARK   3   RESIDUE RANGE:  L  114      L  219
REMARK   3   RESIDUE RANGE:  H  116      H  215
REMARK   3   ORIGIN FOR THE GROUP (A): −24.4360  51.7710   5.9920
REMARK   3   T TENSOR
REMARK   3     T11:   0.0252 T22:   0.0170
REMARK   3     T33:   0.0735 T12:   0.0161
REMARK   3     T13:   0.0018 T23:   0.0048
REMARK   3   L TENSOR
REMARK   3     L11:   2.0324 L22:   1.6905
REMARK   3     L33:   0.8461 L12:   0.7328
REMARK   3     L13:   0.0695 L23:   0.3337
REMARK   3   S TENSOR
REMARK   3     S11: −0.0068 S12:   0.0156 S13:   0.0515
REMARK   3     S21: −0.0127 S22: −0.0101 S23:   0.1316
REMARK   3     S31: −0.0077 S32: −0.0763 S33:   0.0168
REMARK   3
REMARK   3
REMARK   3  BULK SOLVENT MODELLING.
REMARK   3   METHOD USED: MASK
REMARK   3   PARAMETERS FOR MASK CALCULATION
REMARK   3   VDW PROBE RADIUS  :  1.40
REMARK   3   ION PROBE RADIUS   :  0.80
REMARK   3   SHRINKAGE RADIUS  :  0.80
REMARK   3
REMARK   3  OTHER REFINEMENT REMARKS:
REMARK   3  HYDROGENS HAVE BEEN ADDED IN THE RIDING POSITIONS
REMARK   3  U VALUES        : RESIDUAL ONLY
REMARK   3
LINKR         SG  CYS L 139              SG ACYS L 199          SS
LINKR         SG  CYS H 22               SG ACYS H 96           SS
LINKR         SG ACYS H 141              SG ACYS H 197          SS
CISPEP    1 THR L1   7   PRO L  8               0.00
CISPEP    2 VAL L   99   PRO L 100              0.00
CISPEP    3 TYR L 145   PRO L 146               0.00
CISPEP    4 PHE  H 147   PRO H   148            0.00
CISPEP    5 GLU H  149   PRO H   150            0.00
```

TABLE 14 hTLT-1.126-162 "P" (SEQ ID NO 7) interactions with the Fab0100 light chain (SEQ ID NO: 163). A cut-off of 4.0 Å was used. The contacts were identified by the CONTACT computer program of the CCP4 suite. In the last column "***" indicates a strong possibility for a hydrogen bond at this contact (distance < 3.3 Å) as calculated by CONTACT, "*" indicates a weak possibility (distance > 3.3 Å). Blank indicates that the program considered there to be no possibility of a hydrogen bond. Hydrogen-bonds are specific between a donor and an acceptor, are typically strong, and are easily identifiable.

| hTLT-1.126-162 | | | Anti-TLT-1 | | | | |
|---|---|---|---|---|---|---|---|
| Res. Type | Res. # and Chain | Atom name | Res. Type | Res. # and Chain | Atom name | Distance [Å] | Possibly H—bond |
| Ile | 9P | CB | Tyr | 101L | OH | 3.76 | |
| Ile | 9P | CD1 | Ser | 96L | O | 3.58 | |
| | | | Thr | 97L | O | 3.68 | |
| Ile | 9P | CG2 | Val | 99L | CG2 | 3.51 | |
| Ile | 9P | C | Tyr | 101L | OH | 3.95 | |
| Gly | 10P | N | Tyr | 101L | OH | 3.06 | *** |
| Gly | 10P | CA | Tyr | 101L | OH | 3.48 | |
| Gly | 10P | C | Tyr | 101L | OH | 3.67 | |
| Ser | 11P | N | Tyr | 101L | OH | 3.09 | *** |
| Ser | 11P | CB | Ser | 96L | OG | 3.89 | |
| | | | Tyr | 37L | CD1 | 3.94 | |
| | | | Ser | 96L | O | 3.37 | |
| Ser | 11P | OG | Ser | 96L | OG | 2.88 | *** |
| | | | Ser | 96L | CA | 3.76 | |
| | | | Ser | 96L | CB | 3.05 | |
| | | | Ser | 96L | C | 3.33 | |
| | | | Ser | 96L | O | 2.45 | *** |
| | | | Tyr | 101L | CE1 | 3.94 | |
| | | | Tyr | 101L | CZ | 3.59 | |
| | | | Tyr | 101L | OH | 3.37 | * |

TABLE 14-continued hTLT-1.126-162 “P” (SEQ ID NO 7) interactions with the Fab0100 light chain (SEQ ID NO: 163). A cut-off of 4.0 Å was used. The contacts were identified by the CONTACT computer program of the CCP4 suite. In the last column “***” indicates a strong possibility for a hydrogen bond at this contact (distance < 3.3 Å) as calculated by CONTACT, “*” indicates a weak possibility (distance > 3.3 Å). Blank indicates that the program considered there to be no possibility of a hydrogen bond. Hydrogen-bonds are specific between a donor and an acceptor, are typically strong, and are easily identifiable.

| hTLT-1.126-162 | | | Anti-TLT-1 | | | | |
|---|---|---|---|---|---|---|---|
| Res. Type | Res. # and Chain | Atom name | Res. Type | Res. # and Chain | Atom name | Distance [Å] | Possibly H—bond |
| Ser | 11P | O | Tyr | 37L | CE1 | 3.39 | |
| | | | Tyr | 37L | CZ | 3.66 | |
| | | | Tyr | 37L | OH | 3.55 | * |
| Leu | 12P | CG | Asn | 33L | ND2 | 3.41 | |
| | | | Tyr | 37L | OH | 3.86 | |
| Leu | 12P | CD1 | His | 31L | CE1 | 3.73 | |
| | | | His | 31L | NE2 | 3.38 | |
| | | | His | 31L | CD2 | 3.63 | |
| | | | Tyr | 37L | CE2 | 3.65 | |
| | | | Asn | 33L | ND2 | 3.68 | |
| | | | Tyr | 37L | CZ | 3.84 | |
| | | | Tyr | 37L | OH | 3.51 | |
| Leu | 12P | CD2 | His | 31L | CE1 | 3.57 | |
| | | | His | 31L | NE2 | 3.91 | |
| | | | Asn | 33L | ND2 | 3.39 | |
| Phe | 17P | CB | Tyr | 54L | CG | 3.79 | |
| | | | Tyr | 54L | CE1 | 3.70 | |
| | | | Tyr | 54L | CD1 | 3.45 | |
| Phe | 17P | CG | Tyr | 54L | CG | 3.98 | |
| | | | Tyr | 54L | CD1 | 3.63 | |
| Phe | 17P | CD1 | Tyr | 54L | CB | 3.74 | |
| Phe | 17P | CE1 | His | 39L | ND1 | 3.88 | |
| | | | His | 39L | CE1 | 3.32 | |
| | | | His | 39L | NE2 | 3.60 | |
| Phe | 17P | CZ | His | 39L | CE1 | 3.36 | |
| | | | His | 39L | NE2 | 3.66 | |
| | | | Tyr | 37L | CD1 | 3.98 | |
| Phe | 17P | CE2 | Tyr | 37L | CD1 | 3.79 | |
| | | | Tyr | 37L | CE1 | 3.84 | |
| Phe | 17P | O | Phe | 60L | CD1 | 3.84 | |
| | | | Phe | 60L | CE1 | 3.31 | |
| Asp | 19P | N | Phe | 60L | CE1 | 3.88 | |
| Asp | 19P | CA | Phe | 60L | CZ | 3.80 | |
| Asp | 19P | CB | Phe | 60L | CZ | 3.85 | |

TABLE 15 hTLT-1.126-162 “P” (SEQ ID NO 7) interactions with Fab0100 heavy chain (SEQ ID NO: 162). A cut-off of 4.0 Å was used. The contacts were identified by the CONTACT computer program of the CCP4 suite. In the last column “***” indicates a strong possibility for a hydrogen bond at this contact (distance < 3.3 Å) as calculated by CONTACT, “*” indicates a weak possibility (distance > 3.3 Å). Blank indicates that the program considered there to be no possibility of a hydrogen bond. Hydrogen-bonds are specific between a donor and an acceptor, are typically strong, and are easily identifiable.

| hTLT-1.126-162 | | | Anti-TLT-1 | | | | |
|---|---|---|---|---|---|---|---|
| Res. Type | Res. # and Chain | Atom name | Res. Type | Res. # and Chain | Atom name | Distance [Å] | Possibly H—bond |
| Lys | 8P | C | Asn | 59H | OD1 | 3.95 | |
| Lys | 8P | O | Asn | 59H | CG | 3.69 | |
| | | | Asn | 59H | ND2 | 3.78 | * |
| | | | Trp | 33H | CH2 | 3.86 | |
| | | | Asn | 59H | OD1 | 2.85 | *** |
| | | | Thr | 57H | CG2 | 3.45 | |
| Ile | 9P | CA | Trp | 33H | CH2 | 3.91 | |
| | | | Glu | 50H | OE2 | 3.52 | |
| | | | Asn | 59H | OD1 | 3.79 | |
| Ile | 9P | CB | Glu | 50H | OE2 | 3.81 | |
| Ile | 9P | C | Trp | 33H | CZ3 | 4.00 | |
| | | | Trp | 33H | CH2 | 3.65 | |
| | | | Glu | 50H | OE2 | 3.62 | |
| | | | Trp | 33H | CZ2 | 3.87 | |

TABLE 15-continued hTLT-1.126-162 "P" (SEQ ID NO 7) interactions with Fab0100 heavy chain (SEQ ID NO: 162). A cut-off of 4.0 Å was used. The contacts were identified by the CONTACT computer program of the CCP4 suite. In the last column "***" indicates a strong possibility for a hydrogen bond at this contact (distance < 3.3 Å) as calculated by CONTACT, "*" indicates a weak possibility (distance > 3.3 Å). Blank indicates that the program considered there to be no possibility of a hydrogen bond. Hydrogen-bonds are specific between a donor and an acceptor, are typically strong, and are easily identifiable.

| hTLT-1.126-162 | | | Anti-TLT-1 | | | | |
|---|---|---|---|---|---|---|---|
| Res. Type | Res. # and Chain | Atom name | Res. Type | Res. # and Chain | Atom name | Distance [Å] | Possibly H—bond |
| Ile | 9P | O | Trp | 33H | CZ2 | 3.92 | |
| Gly | 10P | N | Glu | 50H | CD | 3.40 | |
| | | | Glu | 50H | OE1 | 3.38 | * |
| | | | Trp | 33H | CZ3 | 3.55 | |
| | | | Trp | 33H | CH2 | 3.68 | |
| | | | Glu | 50H | OE2 | 2.77 | *** |
| | | | Trp | 33H | CE3 | 3.85 | |
| | | | Trp | 33H | CZ2 | 3.99 | |
| Gly | 10P | CA | Glu | 50H | CD | 3.79 | |
| | | | Glu | 50H | OE1 | 3.40 | |
| | | | Trp | 33H | CZ3 | 3.80 | |
| | | | Glu | 50H | OE2 | 3.61 | |
| | | | Trp | 33H | CE2 | 3.75 | |
| | | | Trp | 33H | CD2 | 3.55 | |
| | | | Trp | 33H | CE3 | 3.58 | |
| | | | Trp | 33H | CZ2 | 3.99 | |
| Gly | 10P | C | Val | 100H | CG2 | 3.82 | |
| Gly | 10P | O | Val | 100H | CG2 | 3.86 | |
| Ser | 11P | N | Val | 100H | CG2 | 3.78 | |
| Ser | 11P | CA | Val | 100H | CG2 | 3.78 | |
| Ala | 13P | CB | Trp | 33H | CD1 | 3.60 | |
| | | | Trp | 33H | NE1 | 3.52 | |
| Asn | 15P | CG | Tyr | 32H | CD1 | 3.88 | |
| | | | Tyr | 32H | CE1 | 3.83 | |
| Asn | 15P | ND2 | Arg | 31H | C | 3.94 | |
| | | | Arg | 31H | O | 3.09 | *** |
| | | | Tyr | 32H | CG | 3.98 | |
| | | | Tyr | 32H | CD1 | 3.76 | |
| | | | Tyr | 32H | CE1 | 3.70 | |
| | | | Tyr | 32H | CZ | 3.88 | |
| | | | Arg | 31H | NH1 | 3.93 | * |
| Ala | 16P | O | Val | 100H | CB | 3.86 | |
| | | | Val | 100H | CA | 3.80 | |
| | | | Val | 100H | N | 2.91 | *** |
| | | | Thr | 102H | CG2 | 3.46 | |
| | | | Gly | 99H | CA | 3.74 | |
| | | | Gly | 99H | C | 3.78 | |
| Phe | 17P | CA | Thr | 102H | CG2 | 3.64 | |
| Phe | 17P | CD1 | Val | 100H | O | 3.93 | |
| Phe | 17P | CE1 | Val | 100H | CB | 3.46 | |
| | | | Val | 100H | CG1 | 3.52 | |
| | | | Val | 100H | O | 3.86 | |
| Phe | 17P | CZ | Val | 100H | CB | 3.81 | |
| | | | Val | 100H | CG1 | 3.89 | |
| Phe | 17P | C | Thr | 102H | CG2 | 3.59 | |
| Phe | 17P | O | Thr | 102H | CG2 | 3.79 | |
| Ser | 18P | C | Thr | 102H | CG2 | 3.94 | |
| Ser | 18P | O | Thr | 102H | CB | 3.48 | |
| | | | Thr | 102H | OG1 | 3.64 | * |
| | | | Thr | 102H | CG2 | 3.26 | |
| Pro | 20P | CA | Tyr | 32H | OH | 3.47 | |
| | | | Tyr | 32H | CZ | 3.90 | |
| Pro | 20P | CB | Val | 2H | CG2 | 3.92 | |
| | | | Phe | 27H | CB | 3.93 | |
| | | | Phe | 27H | CD1 | 3.86 | |
| | | | Phe | 27H | CG | 3.78 | |
| Pro | 20P | CG | Thr | 102H | OG1 | 3.88 | |
| | | | Ser | 98H | OG | 3.54 | |
| Pro | 20P | CD | Thr | 102H | CB | 3.95 | |
| | | | Thr | 102H | OG1 | 3.83 | |
| Pro | 20P | C | Val | 2H | CG2 | 3.98 | |
| Pro | 20P | O | Phe | 27H | CB | 3.52 | |
| Ala | 21P | N | Val | 2H | CG2 | 3.51 | |
| Ala | 21P | CA | Val | 2H | CG2 | 3.97 | |
| Ala | 21P | CB | Val | 2H | CG2 | 3.77 | |

Example 25

Epitope Mapping by Peptide Walk

The peptide walking ELISA defined the minimal binding region of the peptide. This was established by coating biotinylated peptides with one residue frameshift in the stalk region of TLT-1 in streptavidin plates followed by binding of the antibody of interest (mAb0061). A secondary antibody was added for detection and binding was measured at 450 nm. Positive control: binding to biotinylated TLT-1.

Materials

10× PBS: 10× GPBS 14200 Gibco

Tween20: Aldrich Cat #27,434-8, Lot #530950-315

Plate: 96-well Streptavidin coated plate Nunc #466014

BSA: A7030-100 g Lot #057K0737

Blocking/Dilute Buffer: 1× PBS pH=7.4

2% BSA 0.5% Tween20

Wash Buffer: 1×PBS+0.5% Tween20

Standard: Biotinylated TLT-1 04/09-08 1 mg/ml mAb: 0197-0000-0061-4A-0.55 mg/ml

Detecting Ab: Goat anti-Human IgG HRP-labeled 1 mg/ml Prod. no. NEF802001EA

TMB Substrate: Ready to use Cat #4390L lot. #70904

Stop Solution: 2M $H_3PO_4$

Dilution of Biotinylated TLT-1

1 mg/ml→6.3 ng/ml (158500× Dilution)

Concentration in well: 0.63 ng

Dilution of Biotinylated Peptides

Approx conc 2-5 mg/ml (2.5 mg/ml)

2.5 mg/ml→10000× Dilution (25 ng/well): 100 µl of each peptide in each well.

Dilution of mAb0061

0.55 mg/ml→100 ng/ml (5500× Dilution)

Concentration in well: 10 ng

Dilution of mAb Goat Anti-Human IgG HRP 1 mg/ml→0.2 µg/ml (5000× Dilution)

Synthesis of Biotinylated Peptides in 96 Well Format

The biotinylated peptides were synthesised using standard solid phase peptide synthesis. Solutions of 0.3M Fmoc-protected amino acids in 0.3 M 1-hydroxybenzotriazole (HOBt) in N-methylpyrrolidinone (NMP) were coupled using diisopropylcarbodiimide (DIC) for 1-4 hours. As solid support the Rink amide LL resin (Merck) was used in a 96 microtiter filterplate (Nunc) and ca. 20 mg resin pr well was used. The synthesis was perfomed using the Multipep RS peptide synthesiser from Intavis, Germany and manufacture protocol was used. The removal of Fmoc was done using 25% piperidin in NMP. All peptides were coupled with biotin at the N-terminal and 8-amino-3,6-dioxaoctanoic acid was used as a spacer between biotin and the peptides. This spacer was also coupled as a Fmoc-protected building block according to the synthesis protocol (IRIS biotech, Germany)

Final Deprotection and Workup

The final deprotection was done using 90% tfrifluoracetic acid (TFA), 5% triisopropylsilan and 5% $H_2O$ for 3 hours. A total of 1 ml TFA was used per well. The TFA was filtered to 96 deep well (Nunc) and the TFA was reduced in volume by evaporation to ca. 100-200 ul per well and diethylether was added to all wells in order to precipitate the peptides. The suspension of peptide in diethylether was transferred to solvinert 96 well filter plate (0.47 um, Millipore) and the peptides were washed twice with diethylether and dried. The peptides were redissolved in 80% DMSO and 20% water giving a stock solution of ca. 1-3 mg/ml.

Biotinylated 20 mer peptides from stalk region of TLT-1 (SEQ ID NO 6)

2-5 mg/ml in 75% DMSO/H2O (biotinylated in N-terminal):

Number of peptide shown at the left:

| | | | |
|---|---|---|---|
| 2 | A 2 | 2619.8 | bio-Oeg-L-N-I-L-P-P-E-E-E-E-E-T-H-K-I-G-S-L-A-E |
| 3 | A 3 | 2620.7 | bio-Oeg-N-I-L-P-P-E-E-E-E-E-T-H-K-I-G-S-L-A-E-N |
| 4 | A 4 | 2577.7 | bio-Oeg-I-L-P-P-E-E-E-E-E-T-H-K-I-G-S-L-A-E-N-A |
| 5 | A 5 | 2611.7 | bio-Oeg-L-P-P-E-E-E-E-E-T-H-K-I-G-S-L-A-E-N-A-F |
| 6 | A 6 | 2585.6 | bio-Oeg-P-P-E-E-E-E-E-T-H-K-I-G-S-L-A-E-N-A-F-S |
| 7 | A 7 | 2603.6 | bio-Oeg-P-E-E-E-E-E-T-H-K-I-G-S-L-A-E-N-A-F-S-D |
| 8 | A 8 | 2603.6 | bio-Oeg-E-E-E-E-E-T-H-K-I-G-S-L-A-E-N-A-F-S-D-P |
| 9 | A 9 | 2545.6 | bio-Oeg-E-E-E-E-T-H-K-I-G-S-L-A-E-N-A-F-S-D-P-A |
| 10 | A10 | 2473.6 | bio-Oeg-E-E-E-T-H-K-I-G-S-L-A-E-N-A-F-S-D-P-A-G |
| 11 | A11 | 2431.6 | bio-Oeg-E-E-T-H-K-I-G-S-L-A-E-N-A-F-S-D-P-A-G-S |
| 12 | A12 | 2373.6 | bio-Oeg-E-T-H-K-I-G-S-L-A-E-N-A-F-S-D-P-A-G-S-A |
| 13 | B 1 | 2358.6 | bio-Oeg-T-H-K-I-G-S-L-A-E-N-A-F-S-D-P-A-G-S-A-N |
| 14 | B 2 | 2354.6 | bio-Oeg-H-K-I-G-S-L-A-E-N-A-F-S-D-P-A-G-S-A-N-P |
| 15 | B 3 | 2330.7 | bio-Oeg-K-I-G-S-L-A-E-N-A-F-S-D-P-A-G-S-A-N-P-L |
| 16 | B 4 | 2331.6 | bio-Oeg-I-G-S-L-A-E-N-A-F-S-D-P-A-G-S-A-N-P-L-E |
| 17 | B 5 | 2315.5 | bio-Oeg-G-S-L-A-E-N-A-F-S-D-P-A-G-S-A-N-P-L-E-P |
| 18 | B 6 | 2345.5 | bio-Oeg-S-L-A-E-N-A-F-S-D-P-A-G-S-A-N-P-L-E-P-S |
| 19 | B 7 | 2386.5 | bio-Oeg-L-A-E-N-A-F-S-D-P-A-G-S-A-N-P-L-E-P-S-Q |
| 20 | B 8 | 2388.4 | bio-Oeg-A-E-N-A-F-S-D-P-A-G-S-A-N-P-L-E-P-S-Q-D |
| 21 | B 9 | 2446.4 | bio-Oeg-E-N-A-F-S-D-P-A-G-S-A-N-P-L-E-P-S-Q-D-E |
| 22 | B10 | 2445.5 | bio-Oeg-N-A-F-S-D-P-A-G-S-A-N-P-L-E-P-S-Q-D-E-K |
| 23 | B11 | 2418.5 | bio-Oeg-A-F-S-D-P-A-G-S-A-N-P-L-E-P-S-Q-D-E-K-S |
| 24 | B12 | 2460.6 | bio-Oeg-F-S-D-P-A-G-S-A-N-P-L-E-P-S-Q-D-E-K-S-I |
| 25 | C 1 | 2410.5 | bio-Oeg-S-D-P-A-G-S-A-N-P-L-E-P-S-Q-D-E-K-S-I-P |
| 26 | C 2 | 2436.6 | bio-Oeg-D-P-A-G-S-A-N-P-L-E-P-S-Q-D-E-K-S-I-P-L |

-continued

| | | | |
|---|---|---|---|
| 27 | C 3 | 2434.7 | bio-Oeg-P-A-G-S-A-N-P-L-E-P-S-Q-D-E-K-S-I-P-L-I |

Biotinylated 16 mer peptides from the stalk region of hTLT-1 (SEQ ID NO 6) 2-5 mg/ml in 75% DMSO/H2O:

| | | | |
|---|---|---|---|
| 29 | C 5 | 2219.3 | bio-Oeg-L-N-I-L-P-P-E-E-E-E-E-T-H-K-I-G |
| 30 | C 6 | 2193.2 | bio-Oeg-N-I-L-P-P-E-E-E-E-E-T-H-K-I-G-S |
| 31 | C 7 | 2192.3 | bio-Oeg-I-L-P-P-E-E-E-E-E-T-H-K-I-G-S-L |
| 32 | C 8 | 2150.2 | bio-Oeg-L-P-P-E-E-E-E-E-T-H-K-I-G-S-L-A |
| 33 | C 9 | 2166.1 | bio-Oeg-P-P-E-E-E-E-E-T-H-K-I-G-S-L-A-E |
| 34 | C10 | 2183.1 | bio-Oeg-P-E-E-E-E-E-T-H-K-I-G-S-L-A-E-N |
| 35 | C11 | 2157.1 | bio-Oeg-E-E-E-E-E-T-H-K-I-G-S-L-A-E-N-A |
| 36 | C12 | 2175.2 | bio-Oeg-E-E-E-E-T-H-K-I-G-S-L-A-E-N-A-F |
| 37 | D 1 | 2133.2 | bio-Oeg-E-E-E-T-H-K-I-G-S-L-A-E-N-A-F-S |
| 38 | D 2 | 2119.2 | bio-Oeg-E-E-T-H-K-I-G-S-L-A-E-N-A-F-S-D |
| 39 | D 3 | 2087.2 | bio-Oeg-E-T-H-K-I-G-S-L-A-E-N-A-F-S-D-P |
| 40 | D 4 | 2029.2 | bio-Oeg-T-H-K-I-G-S-L-A-E-N-A-F-S-D-P-A |
| 41 | D 5 | 1985.2 | bio-Oeg-H-K-I-G-S-L-A-E-N-A-F-S-D-P-A-G |
| 42 | D 6 | 1935.2 | bio-Oeg-K-I-G-S-L-A-E-N-A-F-S-D-P-A-G-S |
| 43 | D 7 | 1878.1 | bio-Oeg-I-G-S-L-A-E-N-A-F-S-D-P-A-G-S-A |
| 44 | D 8 | 1879 | bio-Oeg-G-S-L-A-E-N-A-F-S-D-P-A-G-S-A-N |
| 45 | D 9 | 1919 | bio-Oeg-S-L-A-E-N-A-F-S-D-P-A-G-S-A-N-P |
| 46 | D10 | 1945.1 | bio-Oeg-L-A-E-N-A-F-S-D-P-A-G-S-A-N-P-L |
| 47 | D11 | 1961 | bio-Oeg-A-E-N-A-F-S-D-P-A-G-S-A-N-P-L-E |
| 48 | D12 | 1987 | bio-Oeg-E-N-A-F-S-D-P-A-G-S-A-N-P-L-E-P |
| 49 | E 1 | 1945 | bio-Oeg-N-A-F-S-D-P-A-G-S-A-N-P-L-E-P-S |
| 50 | E 2 | 1959 | bio-Oeg-A-F-S-D-P-A-G-S-A-N-P-L-E-P-S-Q |
| 51 | E 3 | 2003 | bio-Oeg-F-S-D-P-A-G-S-A-N-P-L-E-P-S-Q-D |
| 52 | E 4 | 1984.9 | bio-Oeg-S-D-P-A-G-S-A-N-P-L-E-P-S-Q-D-E |
| 53 | E 5 | 2026 | bio-Oeg-D-P-A-G-S-A-N-P-L-E-P-S-Q-D-E-K |

-continued

| | | | |
|---|---|---|---|
| 54 | E 6 | 1998 | bio-Oeg-P-A-G-S-A-N-P-L-E-P-S-Q-D-E-K-S |
| 55 | E 7 | 2014.1 | bio-Oeg-A-G-S-A-N-P-L-E-P-S-Q-D-E-K-S-I |
| 56 | E 8 | 2040.1 | bio-Oeg-G-S-A-N-P-L-E-P-S-Q-D-E-K-S-I-P |
| 57 | E 9 | 2096.2 | bio-Oeg-S-A-N-P-L-E-P-S-Q-D-E-K-S-I-P-L |
| 58 | E10 | 2122.3 | bio-Oeg-A-N-P-L-E-P-S-Q-D-E-K-S-I-P-L-I |

Method

The epitope mapping involved binding of mAb0061 to two series of biotinylated peptides from the stalk region of TLT-1. The biotinylated peptides were bound to streptavidin plates.

Stalk Peptide:

(SEQ ID NO: 258)
LNILPPEEEEETHKIGSLAENAFSDPAGSANPLEPSQDEKSIPL 1) 20 mer peptide mapping with one residue frameshift (20,1) (see materials)

2) 16 mer peptide mapping with one residue frameshift (16,1) (see materials)

1. Plate was prre-washed 3× with 250 µl wash buffer
2. 100 µl Biotinylated peptide-solution was added (from Masterplate 10000× diluted, one peptide pr well)
3. Incubated at RT for 1 hour or +5° C. over night
4. Washed 3× with wash buffer
5. 100 µl Primary antibody was added (dilution see above)
6. Incubated at RT for 1 hour
7. Washed 3× with wash buffer
8. 100 µl Secondary antibody was added (dilution see above)
9. Incubated at RT for 1 hour
10. Washed 3× with wash buffer
11. 100 µl Substrate/Develop buffer was added (Reaction time 3 min)
12. 100 µl 2M H3PO4 was added
13. Endpoint was read at 450 nm Binding to biotinylated peptide in a well was recorded as "binding" when the absorption at 450 nm was above 3. "No binding" was recorded when signal was below 1. A signal in between was recorded as "weak binding".

Results

The biotinylated peptides were put into wells in the following way:

Row A: peptide 2-12 (20 mers)
Row B: peptide 13-24 (20 mers)
Row C: peptide 25-27 (20 mers)
Row C: peptide 29-36 (16 mers)
Row D: peptide 37-48 (16 mers)
Row E: peptide 49-58 (16 mers)

Result from Triple Determination:

| | 1 | 2 | 3 | 4 | 5 | 6 | 7 | 8 | 9 | 10 | 11 | 12 |
|---|---|---|---|---|---|---|---|---|---|---|---|---|
| A | | <0.1 | <0.1 | <0.1 | >3 | >3 | >3 | >3 | >3 | >3 | >3 | >3 |
| B | >3 | >3 | >3 | >3 | <0.1 | <0.1 | <0.1 | <0.1 | <0.1 | <0.1 | <0.1 | <0.1 |
| C | <0.1 | <0.1 | <0.1 | | <0.1 | <0.1 | <0.1 | <0.1 | <0.1 | <0.1 | <0.1 | >3 |
| D | >3 | >3 | >3 | >3 | >3 | >3 | <0.1 | <0.1 | <0.1 | <0.1 | <0.1 | <0.1 |
| E | <0.1 | <0.1 | <0.1 | <0.1 | <0.1 | <0.1 | <0.1 | <0.1 | <0.1 | <0.1 | | |
| F | | | | | | | | | | | | |
| G | | | | | | | | | | | | |
| H | | | | | | | | | | | | |

In summary, the 20 mer-peptides (5-16) give rise to strong positive signals (<3) corresponding to amino acids: IGS-LAENAF. The 16 mer petides 36-42 give rise to a strong positive signals (<3) corresponding to KIGSLAENAF.

Conclusion

The peptide walking ELISA has defined the minimal binding area of the epitope for binding to mAb0061 as the following stretch of amino acid residues: KIGSLAENAF. This stretch is indeed part of the epitope defined above by the crystal structure: KIGSLA-NAFSDPA.

Example 26

Factor VIIa Polypeptide In Vitro Hydrolysis Assay

Native (wild-type) Factor VIIa and Factor VIIa variant (both hereafter referred to as "Factor VIIa") are assayed in parallel to directly compare their specific activities. The assay is carried out in a microtiter plate (MaxiSorp, Nunc, Denmark). The chromogenic substrate D-Ile-Pro-Arg-p-nitroanilide (S-2288, Chromogenix, Sweden), final concentration 1 mM, is added to Factor VIIa (final concentration 100 nM) in 50 mM Hepes, pH 7.4, containing 0.1 M NaCl, 5 mM $CaCl_2$ and 1 mg/ml bovine serum albumin. The absorbance at 405 nm is measured continuously in a SpectraMax™ 340 plate reader (Molecular Devices, USA). The absorbance developed during a 20-minute incubation, after subtraction of the absorbance in a blank well containing no enzyme, is used to calculate the ratio between the activities of variant and wild-type Factor VIIa:

$$\text{Ratio}=(A_{405\ nm}\ \text{Factor VIIa variant})/(A_{405\ nm}\ \text{Factor VIIa wild-type}).$$

Example 27

Factor VIIa Polypeptide In Vitro Protolysis Assay

Native (wild-type) Factor VIIa and Factor VIIa variant (both hereafter referred to as "Factor VIIa") are assayed in parallel to directly compare their specific activities. The assay is carried out in a microtiter plate (MaxiSorp, Nunc, Denmark). Factor VIIa (10 nM) and Factor X (0.8 microM) in 100 μL 50 mM Hepes, pH 7.4, containing 0.1 M NaCl, 5 mM $CaCl_2$ and 1 mg/ml bovine serum albumin, are incubated for 15 min. Factor X cleavage is then stopped by the addition of 50 μL 50 mM Hepes, pH 7.4, containing 0.1 M NaCl, 20 mM EDTA and 1 mg/ml bovine serum albumin. The amount of Factor Xa generated is measured by addition of the chromogenic substrate Z-D-Arg-Gly-Arg-p-nitroanilide (S-2765, Chromogenix, Sweden), final concentration 0.5 mM. The absorbance at 405 nm is measured continuously in a SpectraMax™ 340 plate reader (Molecular Devices, USA). The absorbance developed during 10 minutes, after subtraction of the absorbance in a blank well containing no FVIIa, is used to calculate the ratio between the proteolytic activities of variant and wild-type Factor VIIa:

$$\text{Ratio}=(A_{405\ nm}\ \text{Factor VIIa variant})/(A_{405\ nm}\ \text{Factor VIIa wild-type}).$$

Example 28

Factor VIIIa Activity Assay: Chromogenic Assay

The FVIII activity (FVIII:C) of the rFVIII compound is evaluated in a chromogenic FVIII assay using Coatest SP reagents (Chromogenix) as follows: rFVIII samples and a FVIII standard (e.g. purified wild-type rFVIII calibrated against the 7th international FVIII standard from NIBSC) are diluted in Coatest assay buffer (50 mM Tris, 150 mM NaCl, 1% BSA, pH 7.3, with preservative). Fifty μl of samples, standards, and buffer negative control are added to 96-well microtiter plates (Nunc) in duplicates. The factor IXa/factor X reagent, the phospholipid reagent and $CaCl_2$ from the Coatest SP kit are mixed 5:1:3 (vol:vol:vol) and 75 μl of this added to the wells. After 15 min incubation at room temperature, 50 μl of the factor Xa substrate 5-2765/thrombin inhibitor I-2581 mix is added and the reagents incubated for 10 minutes at room temperature before 25 μl 1 M citric acid, pH 3, is added. The absorbance at 415 nm is measured on a Spectramax microtiter plate reader (Molecular Devices) with absorbance at 620 nm used as reference wavelength. The value for the negative control is subtracted from all samples and a calibration curve prepared by linear regression of the absorbance values plotted vs. FVIII concentration. Specific activity is calculated by dividing the activity of the samples with the protein concentration determined by HPLC. The concentration of the sample is determined by integrating the area under the peak in the chromatogram corresponding to the light chain and compare with the area of the same peak in a parallel analysis of a wild-type unmodified rFVIII, where the concentration is determined by amino acid analyses.

Example 29

Factor VIIIa Activity Assay: One-Stage Clot Assay

FVIII activity (FVIII:C) of the rFVIII compounds is further evaluated in a one-stage FVIII clot assay as follows: rFVIII samples and a FVIII standard (e.g. purified wild-type rFVIII calibrated against the 7th international FVIII standard from NIBSC) are diluted in HBS/BSA buffer (20 mM hepes, 150 mM NaCl, pH 7.4 with 1% BSA) to approximately 10 U/ml, followed by 10-fold dilution in FVIII-deficient plasma containing VWF (Dade Behring). Samples are subsequently diluted in HBS/BSA buffer. The APTT clot time is measured using an ACL300R or an ACL5000 instrument (Instrumentation Laboratory) using the single factor program. FVIII-deficient plasma with VWF (Dade Behring) is used as assay plasma and SynthASil, (HemosIL™, Instrumentation Laboratory) as aPTT reagent. In the clot instrument, the diluted sample or standard is mixed with FVIII-deficient plasma and aPTT reagents at 37° C. Calcium chloride is added and time until clot formation is determined by measuring turbidity. The FVIII:C in the sample is calculated based on a standard curve of the clot formation times of the dilutions of the FVIII standard.

Example 30

Factor Xa Polypeptide In Vitro Protolysis Assay

Preactivated native (wild-type) Factor Xa and preactivated Factor Xa variant (both hereafter referred to as "Factor Xa") are assayed in parallel to directly compare their specific activities. The assay is carried out in a microtiter plate (MaxiSorp, Nunc, Denmark). Factor Xa (10 nM) and Prothrombin (0.8 microM) in 100 μL 50 mM Hepes, pH 7.4, containing 0.1 M NaCl, 5 mM $CaCl_2$ and 1 mg/ml bovine serum albumin, are incubated for 15 min. Prothrombin cleavage is then stopped by the addition of 50 μL 50 mM Hepes, pH 7.4, containing 0.1 M NaCl, 20 mM EDTA and 1 mg/ml bovine serum albumin. The amount of Thrombin generated is measured by addition of the chromogenic substrate H-D-Phenylalanyl-L-pipecolyl-L-Arg-p-nitroanilide (S-2738, Chromogenix, Sweden), final concentration 0.5 mM. The absorbance at 405 nm is measured continuously in a SpectraMax™ 340 plate reader (Molecular Devices, USA). The absorbance developed during 10 minutes, after subtraction of the absorbance in a blank well containing no FXa, is used to calculate the ratio between the proteolytic activities of variant and wild-type Factor FXa:

$$\text{Ratio}=(A_{405\ nm}\ \text{Factor Xa variant})/(A_{405\ nm}\ \text{Factor Xa wild-type}).$$

Example 31

Chemical Conjugation of an Anti-TLT-1 Antibody (Fragment) with a Coagulation Factor A compound of the general formula

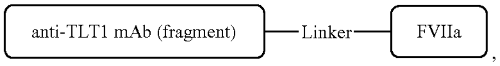

, wherein "anti-TLT-1 mAb (fragment)" may be a full size mAb against TLT-1 or a fragment or an analogue intellectually derived thereof such as but not limited to, a FAB-fragment or a sc-FAB with none, one or more point mutations, the linker may be a water soluble polymer such as but not limited to e.g. PEG, polysialic acid, or hydroxyethyl starch, and FVIIa is any molecule with a sequence similarity of >50% to native FVIIa with any retained activity of FVIIa may, for example, be prepared in a two step procedure.

During the first step, a linker, with two different reactive groups RS1 and RS2 may be attached to the anti-TLT-1 mAb (fragment). The reaction may be run with low site selectivity or in a selective way, such that RS1 only reacts at one or few position of the anti TLT-1 mAb (fragment). As a non-exclusive example, RS1 could be an aldehyde and react by reductive amination only with N-termini of the anti TLT-1 mAb (fragment) by reductive amination, known to a person trained in the art. Another non-exclusive example RS1 could be a maleimide group, which may react with a free thiol on the anti-TLT-1 mAb (fragment).

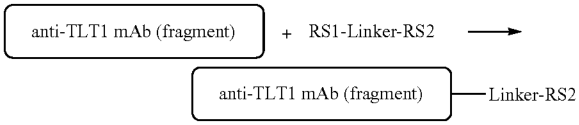

During the second step, the reactive group RS2 may be reacted with low site selectivity or site selectivity with a FVIIa molecule. As a non-exclusive example, a site selective reaction at FVIIa may be obtained when RS2 is a sialic acid derivative, which can react in the presence of a suitable enzyme such as but not limited to ST3Gal-III with N-linked glycans, which do not end exclusively with sialic acids.

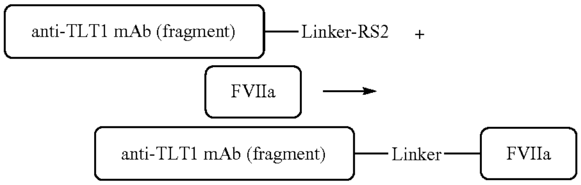

The order of attachment of the linker to the two proteins, namely the anti-TLT-1 mAb (fragment) and the FVIIa molecule may be switched, thereby attaching the RS1-Linker-RS2 molecule first to the FVIIa molecule and then to the anti TLT-1 mAb (fragment).

Example 32

Conjugation of Anti TLT-1-FAB Fragment (Fab0084) to FVIIa for Production of FVIIa-Fab1029

-continued
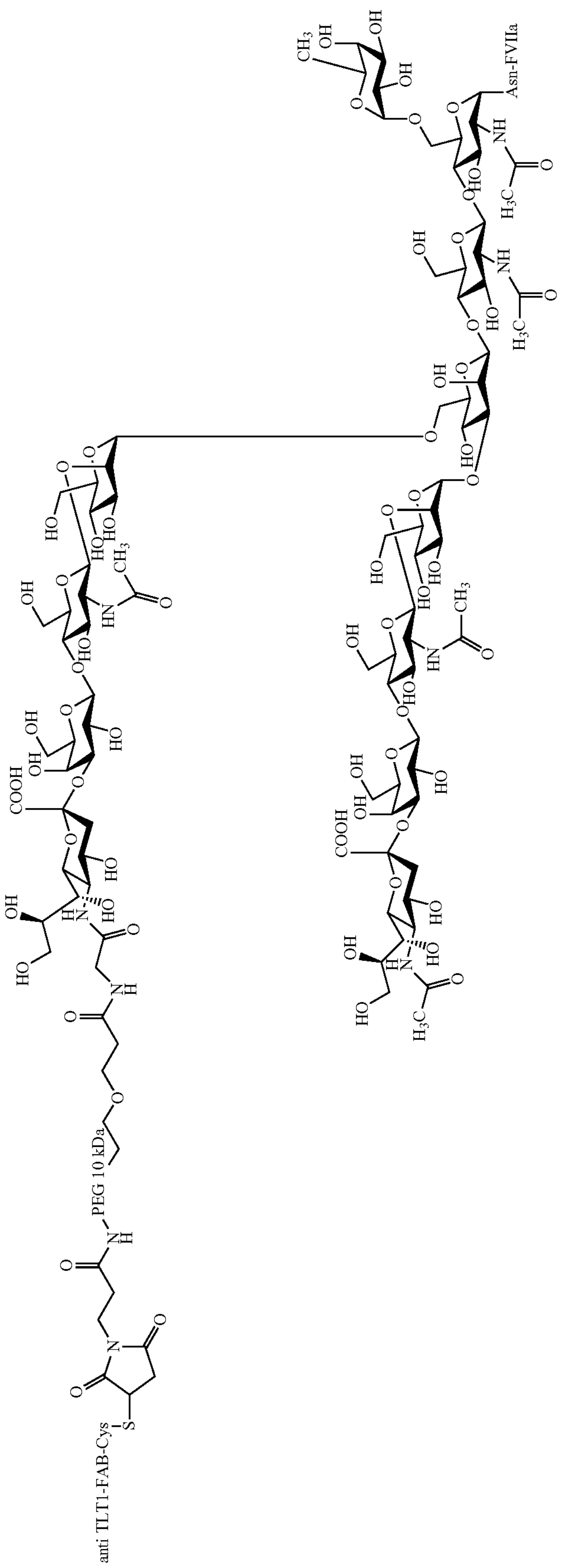

Step 1: 3-(2,5-Dioxo-2,5-dihydropyrrol-1-yl)propionic acid 2,5-dioxopyrrolidiny-1-yl ester

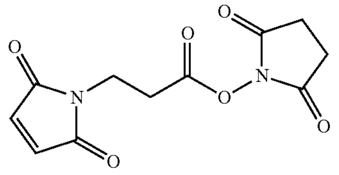 [SMILES: O=C(CCN1C(=O)C=CC1=O)ON1C(=O)CCC1=O]

3-Maleimidopropionic acid (1.0 g, 5.9 mmol) was dissolved in tetrahydrofuran (20 ml). 2-Succinimido-1,1,3,3-tetramethyluronium tetrafluoroborate (TSTU, 2.14 g, 7.1 mmol) and ethyldiisopropylamine (1.24 ml, 7.1 mmol) were added subsequently. N,N-Dimethylformamide (5 ml) was added. The reaction mixture was stirred at room temperature, while it was turning sluggish. The mixture was stirred for 2 min. N,N-Dimethylformamide (5 ml) was added. The mixture was stirred for 2.5 h at room temperature. It was diluted with dichloromethane (150 ml) and was washed subsequently with a 10% aqueous solution of sodium hydrogensulphate (150 ml), a saturated aqueous solution of sodium hydrogencarbonate (150 ml) and water (150 ml). It was dried over magnesium sulphate. The solvent was removed in vacuo. The crude product was recrystallized from ethyl acetate to give 1.20 g of 3-(2,5-dioxo-2,5-dihydropyrrol-1-yl)propionic acid 2,5-dioxopyrrolidiny-1-yl ester.

MS: m/z=289, required for $[M+Na]^+$: 289

$^1$H-NMR ($CDCl_3$) δ 2.82 (m, 4H); 3.02 (t, 2H); 3.94 (t, 2H), 6.73 (s, 2H).

Step 2: N-((3-(ω-(3-(2,5-dioxo-2,5-dihydropyrrol-1-yl)propionylamino)10 kDa PEGyl)propionylamino) acetyl)-$O^2$-[5]cytidylyl-ξ-neuraminic acid (NNC 0129-0000-3259)

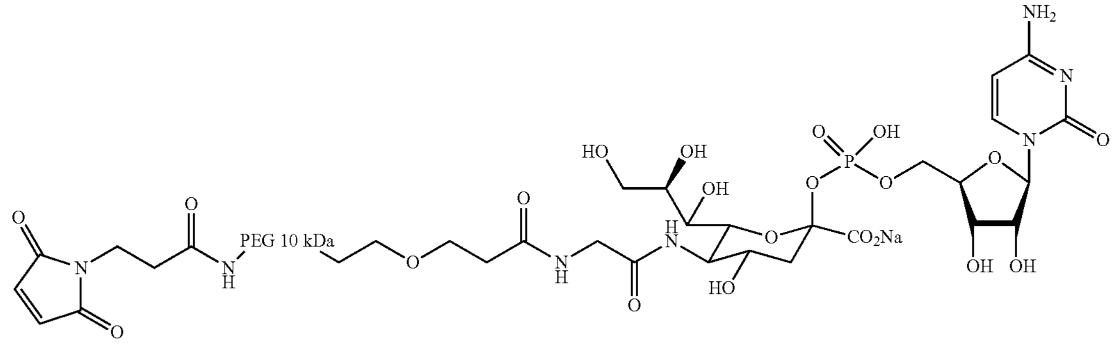

N-((3-(ω-Amino10 kDa PEGyl)propionylamino)acetyl)-$O^2$-[5]cytidylyl-ξ-neuraminic acid (100 mg, 0.009 mmol) was dissolved in a mixture of tetrahydrofuran (2 ml) and dichloromethane (10 ml). A solution of 3-(2,5-dioxo-2,5-dihydropyrrol-1-yl)propionic acid 2,5-dioxopyrrolidiny-1-yl ester (50 mg, 0.18 mmol) in dichloromethane (3 ml) was added. Ethyldiisopropylamine (0.005 ml, 0.028 mmol) was added. The reaction mixture was stirred at room temperature for 16 h. Dichloromethane (2 ml) and ethyldiisopropylamine (0.5 ml) were added. Amionomethylated polystyrene resin (commercially available at e.g. Novabiochem, loading 0.85 mmol/g, 438 mg, 0.372 mmol) was added. The mixture was slowly stirred at room temperature for 1 h. The resin was removed by filtration. The solvent was removed in vacuo with a bath temperature of 25° C. The residue was dissolved in dichloromethane (4 ml). Ether (200 ml) was added. The mixture was left at room temperature for 2 h in order to let the formed precipitation grow old. The precipitation was isolated by filtration and dried in vacuo to give 38 mg of the title compound. The $^1$H-NMR spectrum in DMSO-$d_6$ showed the presence of a maleimide group.

Step 3: Attachment of N-((3-(ω-(3-(2,5-dioxo-2,5-dihydropyrrol-1-yl)propionylamino)10 kDa PEGyl) propionylamino)acetyl)-$O^2$-[5]cytidylyl-ξ-neuraminic acid to an anti-TLT-1 FAB

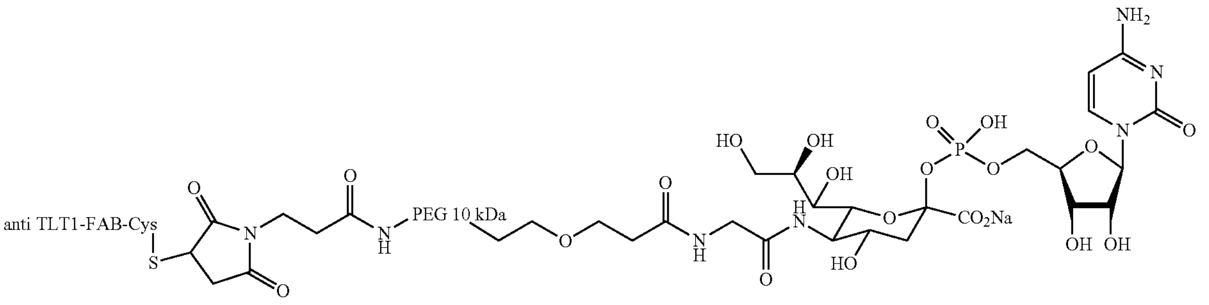

A LC-MS analysis of an anti-TLT-1 FAB fragment with parts of the hinge region wherein an unpaired Cys was incorporated indicated that the unpaired Cys was capped with a cysteine. Therefore, prior reaction with N-((3-(ω-(3-(2,5-dioxo-2,5-dihydropyrrol-1-yl)propionylamino)10 kDa PEGyl)propionylamino)acetyl)-$O^2$-[5]cytidylyl-ξ-neuraminic acid decapping of the unpaired Cys by reaction with tris(2-carboxyethyl)phosphine hydrochloride had to be performed.

A solution of an anti-TLT-1 FAB fragment with parts of the hinge region wherein an unpaired Cys was incorporated (1 mg) in a buffer of 20 mM HEPES, 5.0 mM EDTA, 100 mM NaCl, which had been adjusted to pH 7.5 was placed in amicon ultracentrifugation device with a cut off of 10 kDa. The buffer was changed to a buffer composed of 20 mM imidazole, 10 mM $CaCl_2$, 0.02% Tween 80, 1 M glycerol, which had been adjusted to pH 7.35 by repeated ultracentrifugation at 4000 rpm. After the buffer was changed, a solution of the protein in the buffer composed of 20 mM imidazole, 10 mM $CaCl_2$, 0.02% Tween 80, 1 M glycerol, which had been adjusted to pH 7.35 (4 ml) was obtained. A 1 mg/ml solution of tris(2-carboxyethyl)phosphine hydrochloride (0.40 ml) was added. The reaction mixture was shaken at 300 rpm at 20° C. for 1 h. The reaction mixture was placed in an ultracentrifugation device with a cut off of 10 kDa and was concentrated by ultracentrifugation at 4000 rpm for 7 min, leaving a solution of 0.700 ml behind. This was applied to a PD-10 column (Amersham Bioscience), which had been equilibrated with a buffer of 25 mM HEPES, which had been adjusted to pH 7.00. The protein was eluted from the column using a buffer of 25 mM HEPES, which had been adjusted to pH 7.00 (3.2 ml). This solution was concentrated by ultracentrifugation at 4000 rpm in an Amicon ultracentrifugation device with a cut off of 10 kDa for 7 min to yield a solution of 0.750 ml. The solution was placed in a vial and buffer of 25 mM HEPES, which had been adjusted to pH 7.00 (0.360 ml) was added. A 1 mg/ml solution of N-((3-(ω-(3-(2,5-dioxo-2,5-dihydropyrrol-1-yl) propionylamino)10 kDa PEGyl)-propionylamino)acetyl)-$O^2$-[5]cytidylyl-ξ-neuraminic acid (0.89 ml) was added. The reaction mixture was gently shaken at 300 rpm at 20° C. for 3.5 h. It was placed in an Amicon ultracentrifugation device with a cut off of 10 kDa and concentrated by ultracentrifugation at 4000 rpm for 10 min to a volume of 0.120 ml. The solution was subjected to a size exclusion chromatography on a Superose 75 10/300 GL column (GE Healthcare) at a flow of 0.50 ml/min, utilizing a buffer composed of 25 mM TRIS, 150 mM NaCl, which had been adjusted to pH 8.00 as eluent. Fractions were pooled on the basis of the UV-trace at 280 nm of the chromatogram. The pool (0.148 mg, 1.4 ml), containing the desired compound as judged by SDS-PAGE and which were devoid of free PEG reagent as judged by SDS-PAGE utilizing a PEG-specific staining method (described in Kurfürst, M. M. *Analyt. Biochem.* 1992, 200, 244-248.) was used in the following step.

Step 4: Immobilized sialidase. (*C. Perfingens* type VI-A immobilized on agarose, Sigma: N-5254, 0.6-1.8 U/ml gel, 0.180 ml) was washed with water (2×0.50 ml) and subsequently with a buffer of 25 mM MES, 20 mM $CaCl_2$, 100 mM NaCl, which had been adjusted to pH 6.1 (3×0.50 ml). A solution of FVIIa (0.50 mg) in a buffer composed of 25 mM Gly-Gly, 10 mM $CaCl_2$, which had been adjusted to pH 6.0 was added to the immobilized sialidase. The reaction mixture was left at room temperature, while it was mixed carefully every 20 min. After 3 h, the immobilized resin was removed by filtration through a Pierce spin column by centrifugation at 2000 rpm for 2 min.

The product mixture of the attachment of N-((3-(ω-(3-(2,5-dioxo-2,5-dihydropyrrol-1-yl)propionylamino)10 kDa PEGyl)propionylamino)acetyl)-$O^2$-[5]cytidylyl-ξ-neuraminic acid to an anti TLT-1 FAB as described in a preceding step was placed in an Amicon ultracentrifugation device with a cut off of 10 kDa. The buffer was changed by repeated ultracentrifugation to a buffer composed of 25 mM MES, 20 mM $CaCl_2$, 100 mM NaCl, which had been adjusted to pH 6.1.

To this solution, a part of the solution of the FVIIa derivative (0.092 ml) was added. The buffer was changed into a buffer composed of 25 mM MES, 20 mM $CaCl_2$, 100 mM NaCl, which had been adjusted to pH 6.1 and a total volume of (0.20 ml). A solution of ST3-Gal-III (0.015 ml) was added. The reaction mixture is gently shaken at 32° C. for 25 min and thereafter left at 32° C. for 16 h. A 10 mg/ml solution of CMP-N-acetylneuraminic acid (CMP NeuNAc, 0.70 mg, 0.070 ml) in a buffer of 25 mM MES, 20 mM $CaCl_2$, 100 mM NaCl, which had been adjusted to pH 6.1 was added. The reaction mixture was gently shaken at 32° C. for 15 min and thereafter left at 32° C. for 1 h. The reaction mixture was subjected to a size exclusion chromatography on a Superdex 200 10/300 GL column (GE Healthcare) with a flow of 0.5 ml/min utilizing a buffer of 10 mM Histidine, 20 mM $CaCl_2$, 150 mM NaCl which had been adjusted to pH 6.1 as eluent. The fractions containing the desired product as judged by SDS-PAGE on a TRIS-Acetate gel were pooled. Using a molar absorption of 11.22 at 280 nm on a Nandrop® apparatus, a yield of 0.022 mg was found. The result of a SDS-PAGE analysis was in accordance with the expectation for the desired product. The product was named FVIIa-Fab1029.

Example 33

Conjugation of an Anti-TLT-1-FAB Fragment (Fab0084) to FVIII, FVIII-Fab3002

Tween 80, 1 M glycerol which had been adjusted to pH 7.35 (4 ml) was added, so that the total volume of the reaction mixture was at this time 4.7 ml. A 1 M solution of TCEP (0.54 ml) in a buffer of imidazole, 10 mM $CaCl_2$, 0.02% Tween 80, 1 M glycerol which had been adjusted to pH 7.35 was added. The reaction mixture was shaken at 300 rpm for 1 h. The mixture was divided into two parts each of which was applied to a PD-10 column (GE Healthtech) which had

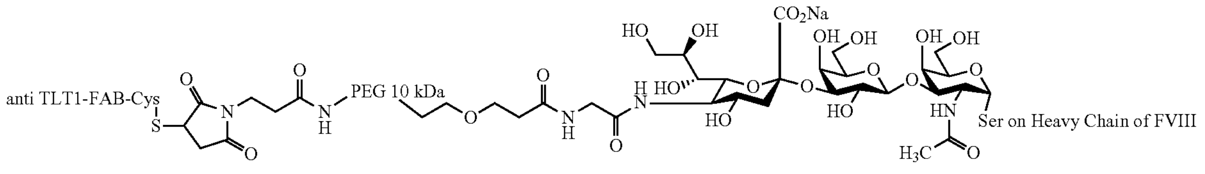

Step 1: Attachment of N-((3-(ω-(3-(2,5-dioxo-2,5-dihydropyrrol-1-yl)propionylamino)10 kDa PEGyl) propionylamino)acetyl)-$O^2$-[5]cytidylyl-ξ-neuraminic acid to an anti TLT-1 FAB fragment been equilibrated with a buffer of 25 mM HEPES with a pH 7.0. The eluates were combined (7 ml in total) and were concentrated to 1 ml by ultracentrifugation at 4000 rpm for at 20° C. for 6-8 min in an Amicon ultracentrifugation device with a cut off of 10 kDa.

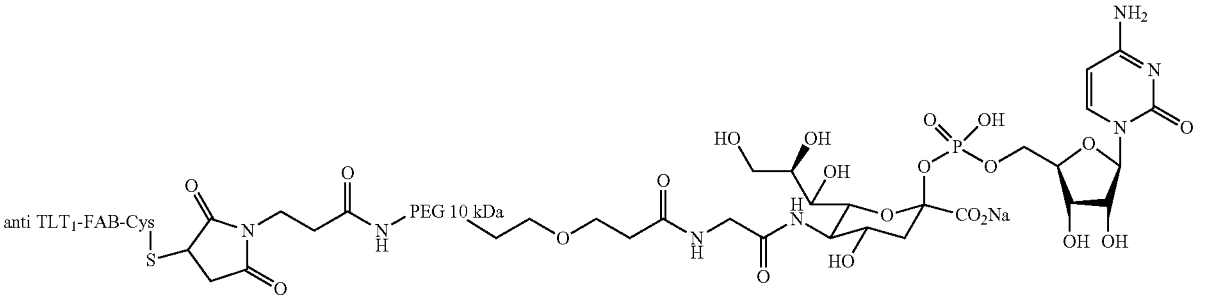

A LC-MS analysis of an anti-TLT-1 FAB fragment with parts of the hinge region wherein an unpaired Cys was incorporated indicated that the unpaired Cys may be capped with a cysteine. Therefore, prior reaction with N-((3-(ω-(3-(2,5-dioxo-2,5-dihydropyrrol-1-yl)propionylamino)10 kDa PEGyl)propionylamino)acetyl)-$O^2$-[5]cytidylyl-ξ-neuraminic acid decapping of the unpaired Cys by reaction with tris(2-carboxyethyl)phosphine hydrochloride (TCEP) had to be performed.

Said TLT-1-FAB-fragment (1.35 mg, 27.4 nmol) in a 0.27 mg/ml solution in a buffer composed of 20 mM HEPES, 5 mM EDTA, 100 mM NaCl which had been adjusted to pH 7.5 was placed in an Amicon ultracentrifugation device with a cut off of 10 kDa. It was subjected to ultracentrifugation at 4000 rpm at 20° C. for 10 min. Buffer composed of 20 mM imidazole, 10 mM $CaCl_2$, 0.02% Tween 80, 1 M glycerol which had been adjusted to pH 7.35 (4 ml) was added. The mixture was subjected to ultracentrifugation at 4000 rpm at 20° C. for 8 min. Buffer composed of 20 mM imidazole, 10 mM $CaCl_2$, 0.02% Tween 80, 1 M glycerol which had been adjusted to pH 7.35 (4 ml) was added. The mixture was subjected to ultracentrifugation at 4000 rpm at 20° C. for 8 min. Buffer composed of 20 mM imidazole, 10 mM $CaCl_2$, 0.02% Tween 80, 1 M glycerol which had been adjusted to pH 7.35 (3 ml) was added. The mixture was subjected to ultracentrifugation at 4000 rpm at 20° C. for 10 min. The mixture was placed in a reaction vial. Buffer composed of 20 mM imidazole, 10 mM $CaCl_2$, 0.02%

The solution was placed in a reaction vial. A buffer of 25 mM HEPES which had been adjusted to pH 7.0 (0.50 ml) was added to obtain a total volume of 1.5 ml. A freshly prepared 1 mg/ml solution of N-((3-(ω-(3-(2,5-dioxo-2,5-dihydropyrrol-1-yl)propionylamino)10 kDa PEGyl)propionylamino)acetyl)-$O^2$-[5]cytidylyl-ξ-neuraminic acid (1.2 ml, 1.2 mg, 109 nmol) in a buffer of 25 mM HEPES which had been adjusted to pH 7.0 was added. The reaction mixture was gently shaken at 300 rpm at 20° C. for 3.2 h. It was concentrated to a volume of 0.30 ml by ultracentrifugation at 4000 rpm at 19° C. for 11 min in an Amicon ultracentrifugation device with a cut off of 10 kDa. It was applied to a size exclusion chromatography on a Superdex 75 10/300 GL column (GE Healthtech) at a flow of 0.50 ml/min utilizing a buffer of 25 mM TRIS, 150 mM NaCl which had been adjusted to pH 8.0 as eluent. The fraction containing the desired product in an acceptable purity as judged by SDS-PAGE analysis in the presence of N-methylmaleimide (NEM) and which were devoid of unreacted N-((3-(ω-(3-(2,5-dioxo-2,5-dihydropyrrol-1-yl)propionylamino)10 kDa PEGyl)propionylamino)acetyl)-$O^2$-[5]cytidylyl-ξ-neuraminic acid as judged by SDS-PAGE in combination with a PEG-sensitive staining ((described in Kurfürst, M. M. *Analyt. Biochem.* 1992, 200, 244-248.)) was used in the following step. The SDS-PAGE analysis under reducing conditions was in compliance with the expected result for the desired product. The SDS-PAGE analysis under non-reducing conditions showed some material, in which one chain of the anti-TLT-1-FAB fragment had been lost. However, it remained unsolved, whether this finding was due to problems in the analysis or whether a chain had really been lost either during the described reaction or even earlier. Using a molar absorbance of 10.44 at 280 nm on a Nanodrop® apparatus, a concentration of 0.1 mg/ml was found giving a yield of 0.287 mg.

Step 2: The solution of the product of the attachment of N-((3-(ω-(3-(2,5-dioxo-2,5-dihydropyrrol-1-yl)propionylamino)10 kDa PEGyl)propionylamino)acetyl)-$O^2$-[5] cytidylyl-ξ-neuraminic acid to an anti TLT-1 FAB fragment as described in the preceding example and a solution of B-domain deleted FVIII which had a residual B-domain sequence of SFSQNSRHPSQNPPVLKRHQR (SEQ ID NO: 259) at the C-terminus of the heavy chain (0.780 mg, 5.64 mmol) in a buffer composed of 20 mM imidazole, 10 mM $CaCl_2$, 150 mM NaCl, 0.02% Tween80 and 1 M glycerol which had been adjusted to pH 7.35 (0.018 ml) were mixed and placed in an Amicon ultracentrifugation device with a cut off of 10 kDa. The solution was subjected to a buffer change to 20 mM histidine, 10 mM $CaCl_2$, 20% glycerol, 0.02% Tween 80, 500 mM NaCl which had been adjusted to pH 6.05 by repeating ultracentrifugation and addition of the buffer. A total volume of 0.40 ml was obtained. A 0.4 mg/ml (242 U/mg, 98 U/ml, 0.0055 ml) solution of sialidase from A. Urifaciens and a 2.5 mg/ml solution of ST3Gal-III (0.033 ml) were added subsequently. The reaction mixture was gently shaken for 15 min at 300 rpm at 32° C., left for 2 h at 32° C. during which it was occasional shaken carefully, and finally left at 32° C. for 18 h. The reaction mixture was diluted with water (0.030 ml). It was subjected to a size exclusion chromatography using a Superose 6 10/300 GL column (GE Healthcare) and utilizing a buffer of 10 mM Histidine, 1.7 mM $CaCl_2$, 0.01% Tween80, 0.3 M NaCl, 8.8 mM sucrose which had been adjusted to pH 7 at a flow of 0.50 ml/min. The fractions containing the desired product as judged by SDS-PAGE analysis were pooled. The pool was subjected to a buffer change using an Amicon ultracentrifugation device with a cut off of 10 kDa to a buffer composed of 20 mM histidine, 10 mM $CaCl_2$, 1 M glycerol, 0.02% Tween 80, 500 mM NaCl which had been adjusted to pH 6.07. A total volume of 0.250 ml was obtained. Using a molar absorption of 14.6 at 280 nm on a Nanodrop apparatus, a concentration of 0.59 mg/ml was found, corresponding to a yield of 0.148 mg. A 10 mg/ml solution of CMP-N-acetylneuraminic acid (CMP NeuNAc, 0.26 mg, 0.026 ml) in a buffer of 20 mM histidine, 10 mM $CaCl_2$, 20% glycerol, 0.02% Tween 80, 500 mM NaCl which had been adjusted to pH 6.05 and a solution of ST3Gal-III (0.015 ml) was added. The reaction mixture was shaken gently at 300 rpm at 32° C. for 15 min and then left at 32° C. for another 45 min. The reaction mixture was diluted with water (0.10 ml). It was subjected to a size exclusion chromatography using Superose 6 10/300 GL column (GE Healthcare) and utilizing a buffer of 10 mM Histidine, 1.7 mM $CaCl_2$, 0.01% Tween80, 0.3 M NaCl, 8.8 mM sucrose which had been adjusted to pH 7 at a flow of 0.50 ml/min. The fractions containing the desired product as judged by SDS-PAGE analysis were pooled giving and concentrated by ultracentrifugation in an Amicon ultracentrifugation device to a total volume of approximately 0.275 ml. Using a molar absorption at 280 nm of 14.6 on a Nanodrop® apparatus, a concentration of 0.180 ml/ml was found corresponding to a yield of 0.0495 mg. The SDS-PAGE analysis of the product under reduced conditions is in accordance with the expectation for the desired product. The SDS-PAGE analysis under non-reduced conditions shows changing amounts of a band which corresponds to a product where the FAB-fragment has lost one chain. The appearance of a band corresponding to a may be due to the presence of such compound in the product or may be due to decomposition during denaturizing prior SDS-PAGE analysis.

Example 34

Binding to TLT-1

TABLE 16

| Reagents | |
|---|---|
| Reagent | Source |
| TLT-1 | Example 2 |
| FVIIa-Fab1029 | Example 32 |
| FIX-Fab0135 | Example 16 |
| All other reagents | Biacore |

Method:

TLT-1 was immobilized directly to a CM5 chip to a level of approx 2000 RU (50 ug/ml diluted in Na-acetate, pH 4.0) using the standard procedure recommended by the supplier and reagents provided in Table 16. Two-fold dilutions of FVIIa-Fab1029 and FIX-Fab0135 from 20 nM to 0.3 nM were tested for binding to TLT-1. Running and dilution buffer: 10 mM HEPES, 150 mM, 0.005% p20, pH 7.4. Regeneration was obtained by 10 mM Glycine, pH 1.7. Determination of kinetic and binding constants ($k_{on}$, $k_{off}$, $K_D$) was obtained assuming a 1:1 interaction of TLT-1 and FVIIa-Fab1029 or FIX-Fab0135 using the Biacore T100 evaluation software.

Result:

TABLE 17

| TLT-1 binding | ka (1/M) | kd (1/s) | $K_D$ (M) TLT-1 |
|---|---|---|---|
| FVIIa-Fab1029 | 3.97E+05 | 0.007259 | 1.83E−08 |
| FIX-Fab0135 | 4.28E+05 | 8.71E−04 | 2.04E−09 |

Conclusion:

Binding constants for FVIIa-Fab1029 and FIX-Fab0135 binding to TLT-1 was estimated by biacore analysis and binding to TLT-1 was confirmed (Table 17).

Example 35

FVIIa-Fab1029 Promotes Fibrin Clot Formation in Hemophilia-Like Whole Blood

Figure 11A:
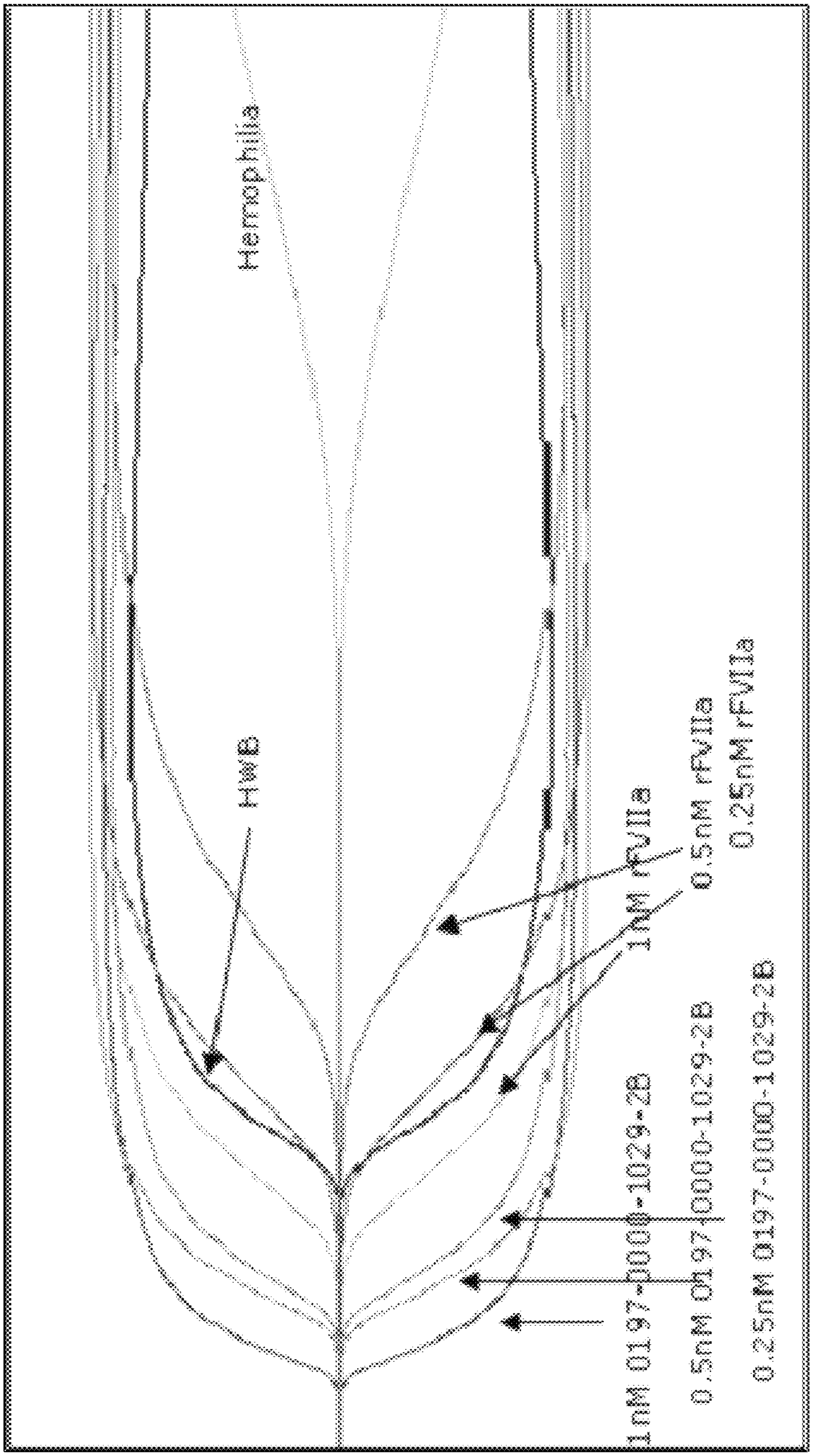
FIG. 11A: Effect of FVIIa-Fab1029 on TF-induced fibrin clot formation in human whole blood (HWB) from a normal donor measured by thromb-elastography (TEG). Clot formation in re-calcified HWB (curve HWB) is induced by 0.03 pM TF (Innovin®). The curve "Hemophilia" shows the delayed and inadequate clot formation when HWB is supplemented with 10 μg/ml anti-FVIII antibody. Other curves show the curves obtained when the hemophilia-like condition induced by the FVIII antibody is reverted by various concentrations (0; 0.25; 0.5; 1.0 nM) of either FVIIa-Fab1029 or rFVIIa as indicated. The FVIII bypassing activity of FVIIa-Fab1029 is shown to be more potent than that of rFVIIa.
Figure 11B:
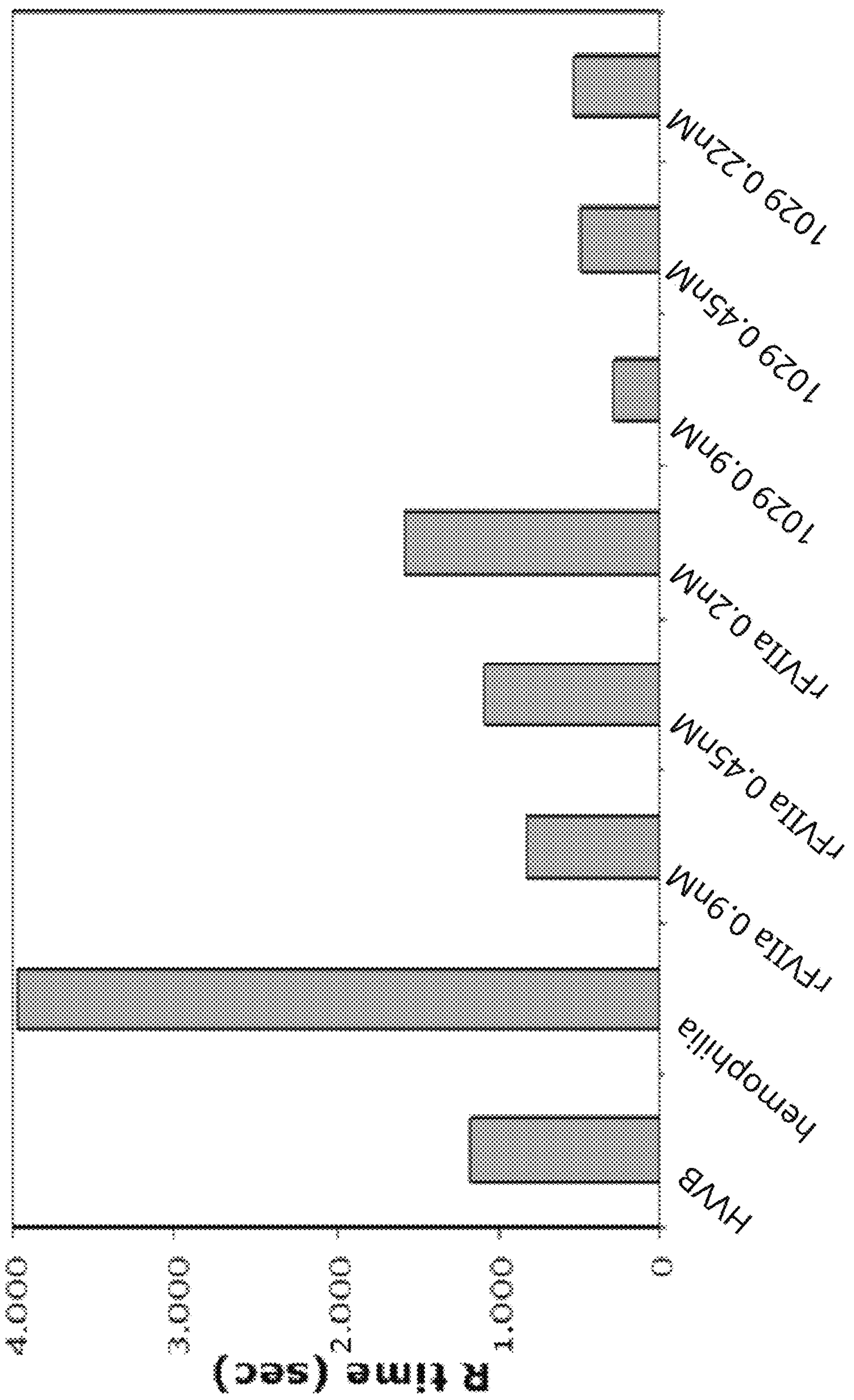
FIG. 11B: Effect of FVIIa-Fab1029 on TF-induced fibrin clot formation in human whole blood (HWB) from a normal donor measured by thromb-elastography (TEG). R-time determined from the TEG traces of the experiment shown in FIG. 11A.

The TEG traces obtained with normal HWB (NWB), “hemophilia” blood, and “hemophilia” blood supplemented with (0; 0.25; 0.5; 1.0; nM) of FVIIa-Fab1029 or rFVIIa are shown in FIG. 11A. Shown in FIG. 11B are the R-time values obtained for the depicted TEG traces. FIG. 11B, in addition to R-time values for the FVIIa-Fab1029 or rFVIIa protein, also includes R-time values for equivalent concentrations of rFVIIa. All data are obtained from one representative donor. The FVIIa-Fab1029 is observed to efficiently normalize clotting of hemophilia-like HWB. In addition the results show that the known pro-coagulant effect of rFVIIa is further potentiated by conjugation of rFVIIa to a FAb fragment of an antibody against TLT-1. Thus, the example with the FVIIa-Fab1029 protein demonstrates that targeting of rFVIIa to TLT-1 on platelets further potentiates the FVIII bypassing activity of rFVIIa.

Example 36

FIX-Fab0135 has FVIII-Bypassing Activity and Promotes Fibrin Clot Formation in Hemophilia A-Like Whole Blood Citrated-stabilized human whole blood (HWB) is drawn from normal donors. Clot formation is measured by thrombelastography (5000 series TEG analyzer, Haemoscope Corporation, Niles, Ill., USA). Hemophilia A-like conditions are obtained by incubation of normal citrate-stabilized human whole blood (HWB) with 10 μg/ml anti-FVIII antibody (Sheep anti-Human Factor VIII; Hematologic Technologies Inc) for 30 min at room temp. Various concentrations (0.1; 0.2; 1.0; 5.0; 10 nM) of the FIX-Fab0135 are added to hemophilia A-like citrated HWB. Clotting is initiated when 340 μl of normal or premixed HWB is transferred to a thrombelastograph cup containing 20 μl 0.2 M $CaCl_2$ with 0.03 pM lipidated TF (Innovin®, Dade Behring GmbH (Marburg, Germany). The TEG trace is followed continuously for up to 120 min. TEG traces obtained with normal HWB (HWB), "hemophilia" blood, and "hemophilia" blood supplemented with (0.1; 0.2; 1.0; 5.0; 10 nM) of FIX-Fab0135 are shown in FIG. 12. Also shown for comparison are the TEG traces obtained when FIX-Fab0135 is replaced by 1 nM rFVIIa or 10 nM rFIX. All data are obtained from one representative donor.

Surprisingly the results show that fusion of FIX to a FAb fragment of an antibody against TLT-1 produces a protein with FVIII bypassing activity. The FIX-Fab0135 is observed to efficiently normalize clotting of hemophilia A-like HWB. FIX dependent propagation of the coagulation requires assembly of a FIXa/FVIIIa complex on the surface of activated platelets, and the resulting FX activation (tenase) activity is prevented by inhibitory FVIII antibodies. The present example with FIX-Fab0135 demonstrates that targeting of FIX to TLT-1 on the surface of platelets generates a FIX containing complex with pro-coagulant activity even when FVIII is blocked by an inhibitory antibody.

Example 37

FIX-Fab0135 Fusion Protein Targeted to TLT-1 Enriched Phospholipid Vesiches Markedly Promotes FX Activation Induced by FVIIa in Absence of FVIII Methods: TLT-1 enriched phospholipid vesicles, prepared as described in Example 20 are applied in the experiment shown in FIG. 13 to mimic TLT-1 on the surface of activated platelets. Various concentrations (0.05-100 nM) rFVIIa is incubated at room temperature for 15 min i) in Hepes buffer (50 mM Hepes, 0.1 M NaCl, 5 mM $CaCl_2$, 1 mg/ml BSA pH 7.4) or in Hepes buffer with ii) 10 nM FIX, iii) 10 nM FIXa or iv) 10 nM FIX-Fab0135. This is then mixed with 100 nM FX (Enzyme Research Laboratories, UK) and TLT-1 enriched phospholipid vesicles at 1:4,000 dilution in absence or presence of 5 nM FVIII and incubated for 3 min. The reaction is stopped by addition of an equal volume stop buffer (50 mM Hepes, 0.1 M NaCl, 20 mM EDTA, 1 mg/ml BSA pH 7.5). The amount of FXa generated in the samples is then determined in a chromogenic assay by transferring 50 μl of the mixture to a microtiter plate well and adding 25 μl Chromozyme X (final 0.42 mg/ml) to the well. The absorbance at 405 nm is measured continuously in a microplate Spectramax photometer (Molecular Devices, Sunnyvale Calif., USA).

FVIIa is capable of activating FIX (Østerud and Rappaport, 1977) and the resulting FIXa is then designated to combine with FVIIIa and form the proteolytic component of the so-called tenase complex. Formation of this complex takes place on the surface of activated platelets. The tenase complex is responsible for a massive FX activation that plays a key role in the propagation phase of the coagulation process. Inability to form an active tenase complex is the central diathesis in both hemophilia A and B patients.

In the present example, TLT-1 enriched phospholipid vesicles are applied to mimic the surface of activated platelets. This system is used to test whether targeting of FIX to TLT-1 on such vesicles by means of the FIX-Fab0135 can promote FX activation in analogy with the tenase complex on activated platelets. Furthermore it is of interest to examine whether the presence of FVIII is obligatory or not for this activity.

FIG. 13 shows: 1) that very little FXa is generated at all FVIIa concentrations tested in absence and presence of 5 nM FVIII under the conditions of the experiment without FIX derivatives added (○); 2) that this is the case also when 10 nM FIX is present in the reaction mixture (□); 3) that a marked FX activation is observed when 10 nM FIX is replaced by 10 nM FIXa, however, only in the presence of FVIII (■); 4) that targeting of FIX to TLT-1 enriched phospholipid vesicles by means of the FIX-Fab0135 provides a complex which is activated by FVIIa in a concentration dependent manner; 5) that the resulting activated tenase-like complex markedly promotes FX activation both in presence and in absence of FVIII.

These results, as well as those of example 36, suggest that the FIX-Fab0135 FIX fusion protein provides a FVIII bypassing agent which markedly promotes FVIIa-mediated FXa activation by a mechanism which involves FVIIa activation of FIX targeted to TLT-1 and formation of a complex with a considerable FVIII-independent tenase-like activity.

Example 38

TLT-1 Expression on Human Platelets

TLT-1 has been reported to only be expressed on activated platelets (Washington et al. (2004) Blood. 2004 Aug. 15; 104(4):1042-7). To verify this and estimate the specific copy number of TLT-1 on the platelet surface we used the "Platelet calibrator kit" from Biocytex (Marseille, France) in which platelets are stained by no wash indirect immunoflurescence with specific monoclonal antibodies and analyzed by quantitative flow cytometry. The expression level of the tested antigen is determined using calibration beads with a definite number of binding sites for the detecting antibody. According to manufacturers instruction platelets in citrated human whole blood were activated by different concentrations (0.3-30 μM) of protease activated receptor (PAR)-1 activating peptide with amino acid sequence SFLLRN. The samples were diluted 1:4 in a saline buffer provided in the kit before labeled with TLT-1 binding antibodies. The TLT-1 binding antibodies used were either mAb0123 (IgG1 subtype of the mAb0023 antibody) or mAb0136 (IgG1 subtype of the mAb0012 antibody). After 15 min incubation with either of the TLT-1 antibodies (10 μg/ml) followed by 15 min incubation with FITC labeled detecting antibody (provided by the manufacturer) the samples were diluted 1:50 before immediately flow cytometry analysis. The absolute number of TLT-1 on the platelet surface was obtained by using the bead derived standard curve.

Unactivated platelets show no expression of TLT-1 with none of the two antibodies used. However, when the platelets were activated with SFLLRN an increased TLT-1 expression was observed with a maximal expression of 9685±1696 and 12981±2083 surface molecules detected by mAb0123 and mAb0136 respectively (FIG. 14). Maximal platelet TLT-1 expression was achieved by double stimulation by SFLLRN (30 μM) and Convulxin (100 ng/ml).

Example 39

Conjugation of Anti TLT-1-FAB Fragment (Fab0084) to FVIIa Via a 3 kDa PEG Linker, FVIIa-Fab1001

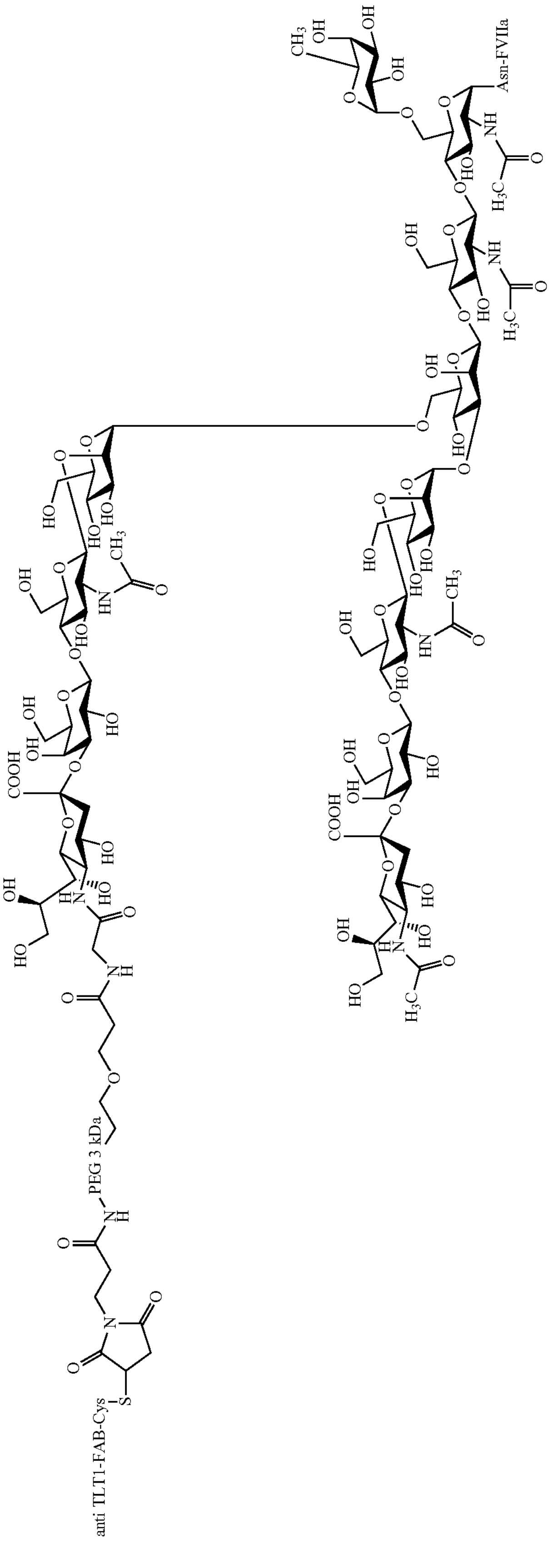

Step 1: N-((3-(ω-(Fluorenylmethoxycarbonylamino)3 kDa PEGyl)propionylamino)acetyl)-$O^2$-[5]cytidylyl-ξ-neuraminic acid

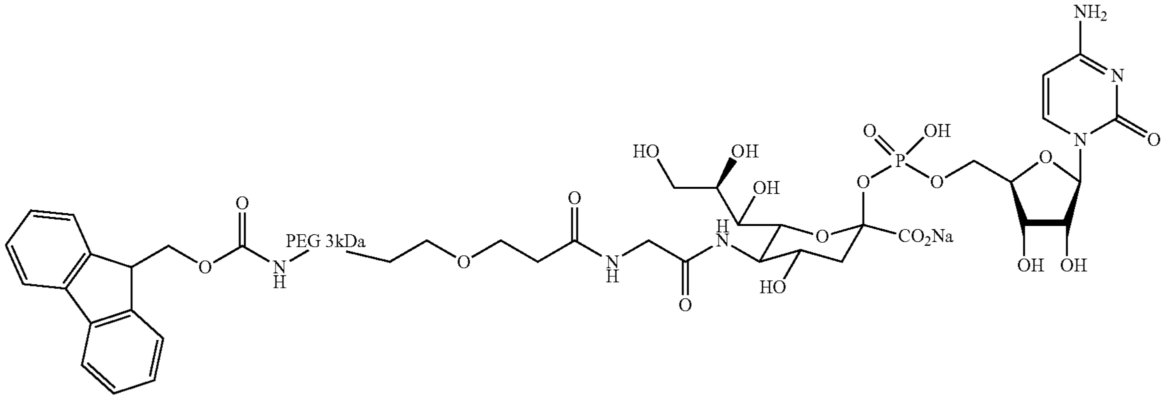

3-(ω-(Fluorenylmethoxycarbonlyamino)3 kDa PEGyl) propionic acid pyrrolidin-2,5-dion-1-ylester (purchased at Rapp Polymere GmbH, 1 g, 0.292 mmol) was dissolved in tetrahydrofuran (80 ml). A solution of cytidine-5'-monophospho-N-glycylneuraminic acid disodium salt (0.276 g, 0.438 mmol) in a buffer (20 ml) composed of 50 mM TRIS, which had been adjusted to pH 8.9 was added. The reaction mixture was stirred at room temperature for 16 h. The THF was removed in vacuo, having a bath temperature of 25° C. The remaining mixture was diluted with water up to 60 ml and was filtered through a 0.45 μm filter. The solution was divided into three parts each of which was subjected to an HPLC chromatography on a C4 column, using a flow of 20 ml/min and a gradient of 0-60% acetonitrile in an aqueous buffer of 50 mM ammonium hydrogencarbonate over 50 min after it had washed with an aqueous buffer of 50 mM ammonium hydrogencarbonate for 10 min. Fractions were combined, having no cytidine-5'-monophospho-N-glycylneuraminic acid and having an absorption at 214 nm greater than 15-20% of the maximum absorption. The combined fractions were freeze dried to give 532 mg of N-((3-(ω-(fluorenylmethoxycarbonylamino)3 kDa PEGyl)propionylamino)acetyl)-$O^2$-[5]cytidylyl-ξ-neuraminic acid. The $^1H$-NMR spectrum was in accordance with the expectation.

Step 2: N-((3-(ω-Amino3 kDa PEGyl)propionylamino)acetyl)-$O^2$-[5]cytidylyl-ξ-neuraminic acid

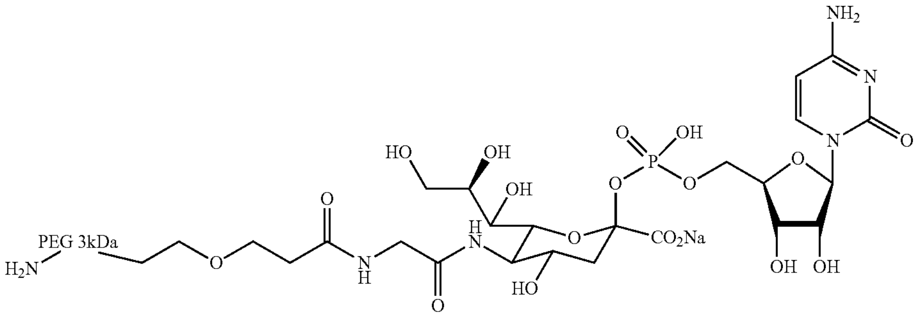

N-((3-(ω-(Fluorenylmethoxycarbonylamino)3 kDa PEGyl)propionylamino)acetyl)-$O^2$-[5]cytidylyl-ξ-neuraminic acid (532 mg, 0.135 mmol) was dissolved in N,N-dimethylformamide (9 ml). Piperidine (2.25 ml) was added. The reaction mixture was stirred for 20 min at room temperature. Ether (150 ml) was added. The mixture was left at room temperature for 1 h. The formed precipitate was isolated by decantation and centrifugation. It was dissolved in dichloromethane (10 ml). Ethyldiisopropylamine (2.4 ml) was added. The mixture was stirred for 2 min. Ether (150 ml) was added. The mixture was left for 1.5 h in order to let the precipitate grow old. The precipitate was isolated by decantation and filtration. It was dried in vacuo with a bath temperature of 25° C. to give 343 mg of N-((3-(ω-amino3 kDa PEGyl)propionylamino)acetyl)-$O^2$-[5]cytidylyl-ξ-neuraminic acid. The $^1H$-NMR was in accordance with the expectation.

Step 3: N-((3-(ω-(3-(2,5-dioxo-2,5-dihydropyrrol-1-yl)propionylamino)3 kDa PEGyl)propionylamino) acetyl)-$O^2$-[5]cytidylyl-ξ-neuraminic acid (NNC 0129-0000-3259)

A solution of an anti-TLT-1 FAB fragment with parts of the hinge region wherein an unpaired Cys was incorporated (10 mg) in a phosphate buffer was placed in amicon ultracentrifugation device with a cut off of 10 kDa. The buffer was changed to a buffer composed of 100 mM HEPES

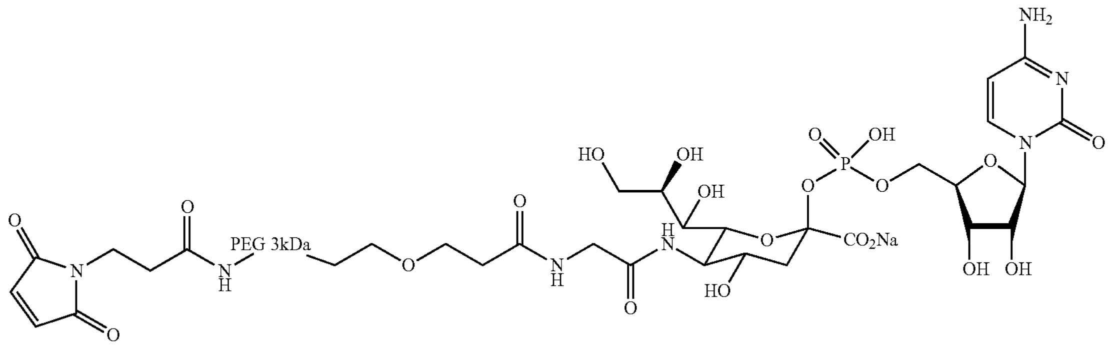

N-((3-(ω-Amino3 kDa PEGyl)propionylamino)acetyl)-$O^2$-[5]cytidylyl-ξ-neuraminic acid (343 mg, 0.009 mmol) was dissolved in a mixture of dichloromethane (15 ml). Ethyldiisopropylamine (0.05 ml, 0.028 mmol) was added. 3-(2,5-Dioxo-2,5-dihydropyrrol-1-yl)propionic acid 2,5-dioxopyrrolidiny-1-yl ester (492 mg, 1.85 mmol) was added as a solid. The reaction mixture was stirred at room temperature for 16 h. Dichloromethane (140 ml) was added. Amionomethylated polystyrene resin (commercially available at e.g. Novabiochem, loading 0.85 mmol/g, 4.3 g, 3.69 mmol) was added. The mixture was slowly stirred at room temperature for 1 h. The resin was removed by filtration. The solvent was removed in vacuo with a bath temperature of 25° C. Amberlyst 15 resin (2 g) was added. The reaction mixture was slowly stirred for 20 min. The resin was removed by filtration. The solvent was removed in vacuo with a bath temperature of 25° C. The residue was dissolved in dichloromethane (10 ml). Ether (200 ml) was added. The mixture was left at room temperature for 6 h in order to let the formed precipitate grow old. The precipitate was isolated by decantation and centrifugation. It was dried in vacuo to give 180 mg of the title compound. The $^1$H-NMR spectrum in DMSO-$d_6$ showed the presence of a maleimide group.

Step 4: Attachment of N-((3-(ω-(3-(2,5-dioxo-2,5-dihydropyrrol-1-yl)propionylamino)3 kDa PEGyl) propionylamino)acetyl)-$O^2$-[5]cytidylyl-ξ-neuraminic acid to an anti TLT-1 FAB which had been adjusted to pH 7.3, by repeated ultracentrifugation at 4000 rpm. After the buffer was changed, a solution of the protein in the buffer composed of 100 mM HEPES which had been adjusted to pH 7.3, (36 ml) was obtained. A 1 mg/ml solution of tris(2-carboxyethyl)phosphine hydrochloride (4 ml) was added. The reaction mixture was shaken at 300 rpm at 20° C. for 15 min and left at 20° C. for 45 min. The reaction mixture was placed in an ultracentrifugation device with a cut off of 10 kDa. The buffer was changed to a buffer composed of 25 mM HEPES which had been adjusted to pH 7.0 by repeated ultracentrifugation at 4000 rpm to give a solution of 13.2 ml. A 1 mg/ml solution of N-((3-(ω-(3-(2,5-dioxo-2,5-dihydropyrrol-1-yl)propionylamino)3 kDa PEGyl)propionylamino) acetyl)-$O^2$-[5]cytidylyl-ξ-neuraminic acid (6.4 ml) was added. The reaction mixture was gently shaken at 300 rpm at 20° C. for 15 min and left at 20° C. for 16 h. It was placed in an Amicon ultracentrifugation device with a cut off of 10 kDa and concentrated by ultracentrifugation at 4000 rpm for 10 min to a volume<5 ml. The solution was subjected to a size exclusion chromatography on a Superose 75 16/60 GL column (GE Healthcare) at a flow of 1 ml/min, utilizing a buffer composed of 25 mM TRIS, 150 mM NaCl, which had been adjusted to pH 8.00 as eluent. Fractions were pooled on the basis of the UV-trace at 280 nm of the chromatogram. The pool (9.9 mg, 13.7 ml), containing the desired compound as judged by SDS-PAGE and which were devoid of free PEG reagent as judged by SDS-PAGE utilizing a

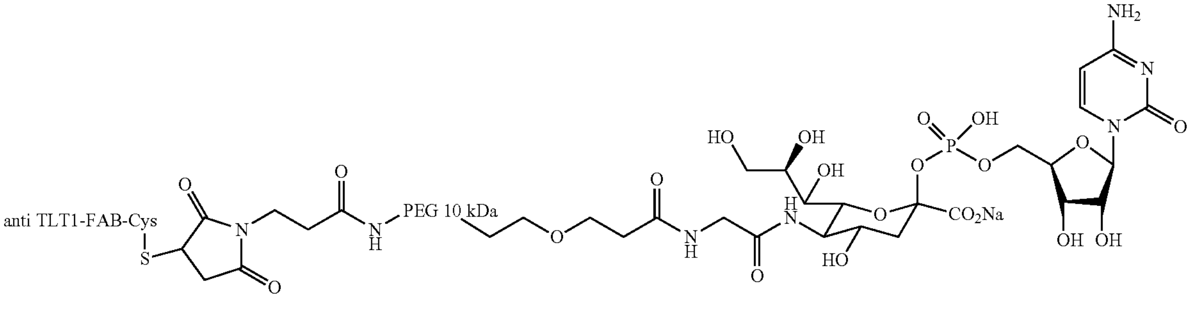

PEG-specific staining method (described in Kurfürst, M. M. *Analyt. Biochem.* 1992, 200, 244-248.) was used in the following step.

Step 5: Immobilized sialidase. (*C. Perfingens* type VI-A immobilized on agarose, Sigma: N-5254, 0.6-1.8 U/ml gel, 1.52 ml) was washed with water (3×9 ml) and subsequently with a buffer of 20 mM HEPES, 10 mM $CaCl_2$, 0.005% Tween80, 100 mM NaCl, which had been adjusted to pH 7.5 (3×9 ml). A solution of FVIIa (8.9 mg) in a buffer (6.59 ml) composed of 25 mM Gly-Gly, 10 mM $CaCl_2$ which had been adjusted to pH 6.0 was placed in an Amicon ultracentrifugation device with a cut off of 10 kDa. The buffer was changed to a buffer of 20 mM HEPES, 10 mM $CaCl_2$, 0.005% Tween80, 100 mM NaCl, which had been adjusted to pH 7.5 be repeated centrifugation at 4000 rpm to give a final volume of 6.5 ml. This solution was added to the immobilized sialidase. The reaction mixture was rolled at room temperature for 3.5 h.

The product of the attachment of N-((3-(ω-(3-(2,5-dioxo-2,5-dihydropyrrol-1-yl)propionylamino)3 kDa PEGyl)propionylamino)acetyl)-$O^2$-[5]cytidylyl-ξ-neuraminic acid to an anti TLT-1 FAB (10 mg) obtained as described in a preceding step in a buffer (13. 5 ml) consisiting of 25 mM TRIS, 150 mM NaCl, which had been adjusted to pH 8.00 was placed in an Amicon ultracentrifugation device with a cut off of 10 kDa. Buffer composed of 20 mM histidine, 10 mM $CaCl_2$, 20% glycerol, 0.02% Tween 80, 500 mM NaCl which had been adjusted to pH 6.0 was added. An ultracentrifugation at 4000 rpm for 2 min was applied. Another portion of buffer composed of 20 mM histidine, 10 mM $CaCl_2$, 20% glycerol, 0.02% Tween 80, 500 mM NaCl which had been adjusted to pH 6.0 was added. An ultracentrifugation at 4000 rpm for 10 min was applied. The reaction product of the reaction with the immobilized sialidase was added, by filtration to remove the immobilized sialidase. Another portion of buffer composed of 20 mM histidine, 10 mM $CaCl_2$, 20% glycerol, 0.02% Tween 80, 500 mM NaCl which had been adjusted to pH 6.0 was added. An ultracentrifugation at 4000 rpm for 10 min was applied to obtain a total volume of 9 ml. A solution of ST3Gal-III (500 μl) was added. The reaction mixture is gently shaken at 32° C. for 15 min and thereafter left at 32° C. for 16 h. A 10 mg/ml solution of CMP-N-acetylneuraminic acid (CMP NeuNAc, 0.70 mg, 0.89 ml) in a buffer of 20 mM histidine, 10 mM $CaCl_2$, 20% glycerol, 0.02% Tween 80, 500 mM NaCl which had been adjusted to pH 6.0 was added was added. The reaction mixture was gently shaken at 32° C. for 15 min and thereafter left at 32° C. for 1 h. The reaction mixture was subjected to a size exclusion chromatography on a Superdex 200 26/60 GL column (GE Healthcare) with a flow of 2 ml/min utilizing a buffer of 10 mM Histidine, 10 mM $CaCl_2$, 0.01% Tween 80, 200 mM NaCl which had been adjusted to pH 6 as eluent. The fractions containing the desired product as judged by SDS-PAGE on a TRIS-Acetate gel were pooled. Using a molar absorption of 12.86 at 280 nm on a Nandrop® apparatus, a yield of 3.2 mg was found. The result of a SDS-PAGE analysis was in accordance with the expectation for the desired product.

Example 40

Conjugation of Anti TLT-1-FAB Fragment (Fab0084) to FVIIa 407C Via 3 kDa PEG Linker, FVIIa-Fab9015

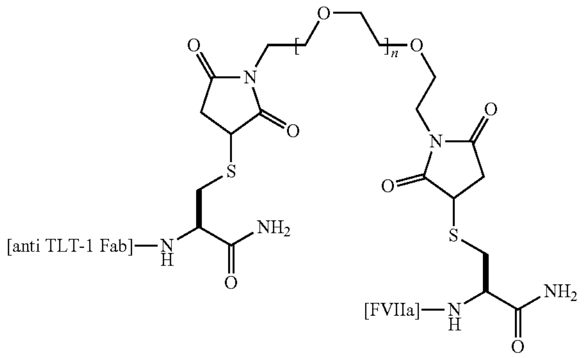

FVIIa 407C (5 mg, 0.55 mg/ml, 9 ml) in 20 mM HEPES, 100 mM NaCl, 10 mM CaCl2, pH 7.0 was mixed with solutions of glutathione (reduced, 40 mM, 125 microliter, in HEPES buffer), glutathione (oxidised, 1.6 mM, 125 microliter, in HEPES buffer), para-aminobenzamidine (0.5 M, 500 microliter, in HEPES buffer), and glutaredoxin (Grx2, EC 1.20.4.1, 96 micromolar, 200 microliter). The volume was adjusted to 10.0 ml, pH was 7.0.

The resulting mixture was incubated at 32 degrees Celsius for 5 h.

EDTA in water (800 microliter, 0.25 M, pH 7.0) was added. The solution was diluted with desalted water until the conductivity was reduced to 8.3 mS/cm (20 ml).

The solution was injected on a pre-conditioned HiTrap Q FF column (pre-conditioned in Buffer A, 5 ml column volume).

Buffer A: 50 mM HEPES, 100 mM NaCl, 1 mM EDTA, 0.01% Tween-80, pH 7.0

Buffer B: 50 mM HEPES, 100 mM NaCl, 10 mM CaCl2, 0.01% Tween-80, pH 7.0

The immobilised protein was washed with Buffer A (5 CV) using a Äkta purifier 100 chromatography station. The protein was eluded with buffer B (10 CV) at 2 ml/min. Elution of the protein of interest was done by monitoring the absorbance at 280 nm.

Seven fractions were pooled. Protein concentration in the combined pool was estimated to be 0.49 mg/ml (abs. 280 nm), volume 7.5 ml, 3.8 mg FVIIa (77.6 nmol).

A solution of bis-maleimide polyethylene glycol linker (3 kDa, Rapp Polymere Gmbh, Tubingen, Germany, prod. no. 11300-45, lot no. 1210.764, 70 mg, 23 micromol) in 20 mM HEPES, 100 mM NaCl, 10 mM $CaCl_2$, pH 7.0 (3.5 ml) was added. The resulting mixture was incubated at room temperature for 1 h.

A solution of EDTA in water (250 mM, 900 microliter) was added to the mixture. pH was adjusted to 7.0. The resulting mixture was diluted with water until the conductivity was 8.3 mS/cm reaching a volume of 17 ml.

The solution was injected on a pre-conditioned HiTrap Q FF column (pre-conditioned in Buffer A, 5 ml column volume).

Buffer A: 50 mM HEPES, 100 mM NaCl, 1 mM EDTA, 0.01% Tween-80, pH 7.0

Buffer B: 50 mM HEPES, 100 mM NaCl, 10 mM CaCl2, 0.01% Tween-80, pH 7.0

The immobilised protein was washed with Buffer A (5 CV) using a Äkta purifier 100 chromatography station. The protein was eluded with buffer B (10 CV) at 2 ml/min. Elution of the protein of interest was done by monitoring the absorbance at 280 nm.

The fractions of interest were pooled resulting in a total volume of 12 ml. The protein concentration was measured (Abs. at 280 nm) to 0.30 mg/ml, 3.6 mg of protein in total.

A solution of antibody fragment, Fab protein ID 0084 (6.7 mg, 3.21 mg/ml) in HEPES buffer (20 mM HEPES, 1.0 mM CaCl2, 100 mM NaCl, 0.005% (v/v) Tween-80, pH 7.5) was mixed with a solution of tris(3-sulfonatephenyl)phosphine hydrate sodium salt (techn. grade 85% pure, 10 mg/ml, 5 ml, same buffer). The resulting mixture was incubated for 2 h at room temperature. The mixture was placed in an Amicon Ultracentrifugal filter device (Millipore corp., MWCO 10 kDa) and the buffer was exchanged by repetitive additions of buffer (20 mM HEPES, 1.0 mM CaCl2, 100 mM NaCl, 0.005% (v/v) Tween-80, pH 7.5) followed by centrifugation.

The buffer exchanged sample of antibody fragment was mixed with the linker conjugated FVIIa sample and the resulting solution was bufferexchanged into a buffer (50 mM HEPES, 100 mM NaCl, 35 mM $CaCl_2$, 50 mM benzamidine, 0.01% Tween-80, pH 7.5) and subsequently concentrated to 7 ml. The mixture was incubated over night at room temperature. The resulting mixture was analysed using SDS-PAGE gel electrophoresis.

Water (8.5 ml), EDTA solution (5.5 ml, 0.25 M), and sodium hydroxide (1 M) was added to the mixture until pH was 7.2 and the conductivity measured to 11.0 mS/cm, total volume: 21 ml The solution was injected on a pre-conditioned HiTrap Q FF column (pre-conditioned in Buffer A, 5 ml column volume).

Buffer A: 50 mM HEPES, 100 mM NaCl, 1 mM EDTA, 0.01% Tween-80, pH 7.0

Buffer B: 50 mM HEPES, 100 mM NaCl, 10 mM CaCl2, 0.01% Tween-80, pH 7.0

The immobilised protein was washed with Buffer A (5 CV) using a Äkta purifier 100 chromatography station. The protein was eluded with buffer B (10 CV) at 2 ml/min. The selected fractions were concentrated in an Amicon Ultracentrifugal filter device (Millipore corp., MWCO 10 kDa) and the buffer was exchanged by repetitive additions of buffer (20 mM HEPES, 1.0 mM CaCl2, 100 mM NaCl, 0.005% (v/v) Tween-80, pH 7.5) followed by centrifugation. The concentrated sample (5 ml) was injected on a pre-conditioned Superdex Hiload 16/60 column (GE Healthcare, pre-conditioned in the applied buffer).

Buffer: 10 mM L-Histidine, 10 mM CaCl2, 100 mM NaCl, 0.01% Tween80, pH 6.0

The protein was purified by elution at a flow of 0.8 ml/min over 2 CV.

Fractions were selected based on analysis by SDS PAGE gel electrophoresis (4-12% Bis-Tris acetate, MES running buffer).

The pool of selected fractions was concentrated using an Amicon Ultracentrifugal filter device (Millipore corp., MWCO 10 kDa) to a total volume: 2.25 ml. The amount of protein was measured (abs. 280 nm) to be 1.2 mg (protein conjugate).

Analysis by SDS PAGE gel electrophoresis (4-12% Bis-Tris acetate) and (HPC4) Western Blotting against 1. Primary—ProteinC-tag Antibody (HPC4) pAb, Rabbit, cot no: A00637 (40 ug). was dissolved in 80 ul milliQ water to concentration of 0.5 mg/ml. Diluted 1:1000 during the blot.
2. Secondary—Goat anti-Rabbit IgG antibody (H&L) (HRP), pAb, cat. No A00098, Lot No 11B000259. Diluted 1:1000 during the blot.

Example 41

Synthesis of 2-[2-[4-[2-(3-hydroxy-6-oxo-xanthen-9-yl)benzoyl]piperazin-1-yl]-2-oxo-ethoxy]acetic acid

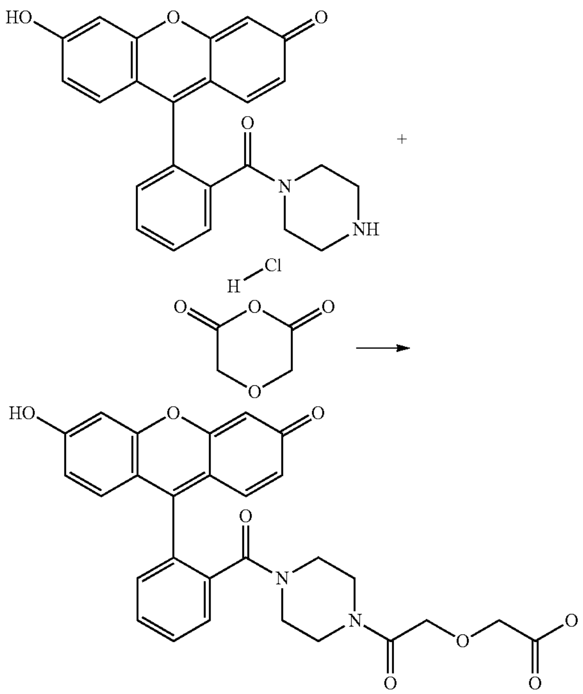

| Name | Dens [g/ml] | Mw [g/mol] | Mol Ratio | N [mmol] | W [g] | V [ml] |
|---|---|---|---|---|---|---|
| 1 | | 436.899 | 1 | 121.31 | 53 | |
| 2 | | 116.074 | 1 | 121.31 | 14.081 | |
| Product: C28H24N2O8 | | 516.512 | | | | |

6-hydroxy-9-[2-(piperazin-4-ium-1-carbonyl)phenyl]xanthen-3-one (prepared as described in Chang et al., *J. Am. Chem. Soc.,* 2007, 129, 8400) was suspended in a mixture of sat. aq. sodium bicarbonate (50 ml) and tetrahydrofuran (50 ml). The mixture was stirred for 10 minutes. Diglycolic anhydride is added. After 3 h, additional diglyoclic anydride (500 mg) was added. The mixture is stirred for 20 h. The mixture was acidified with fuming hydrochloric acid to pH 1. Dichloromethane (100 ml) and hydrochloric acid (1 M, 100 ml) were added. Brine (100 ml) and solid sodium chloride was added. A massive amount of solid was observed. The solid was isolated by filtration, washed with water, and dried under vacuum for several days. LC-MS: 517.1641 $[M+H]^+$.

Example 42

Synthesis of fluorescent cytidyl monophosphate neuraminic acid derivative, (2R,5R,6R)-2-[[(2R,3S,4R,5R)-5-(4-amino-2-oxo-pyrimidin-1-yl)-3,4-dihydroxy-tetrahydrofuran-2-yl]methoxy-hydroxy-phosphoryl]oxy-4-hydroxy-5-[[2-[[5-[2-[2-[[2-[2-[4-[2-(3-hydroxy-6-oxo-xanthen-9-yl)benzoyl]piperazin-1-yl]-2-oxo-ethoxy]acetyl]amino]ethyldisulfanyl]ethylamino]-5-oxo-pentanoyl]amino]acetyl]amino]-6-[(2R)-1,2,3-trihydroxypropyl]tetrahydropyran-2-carboxylic acid

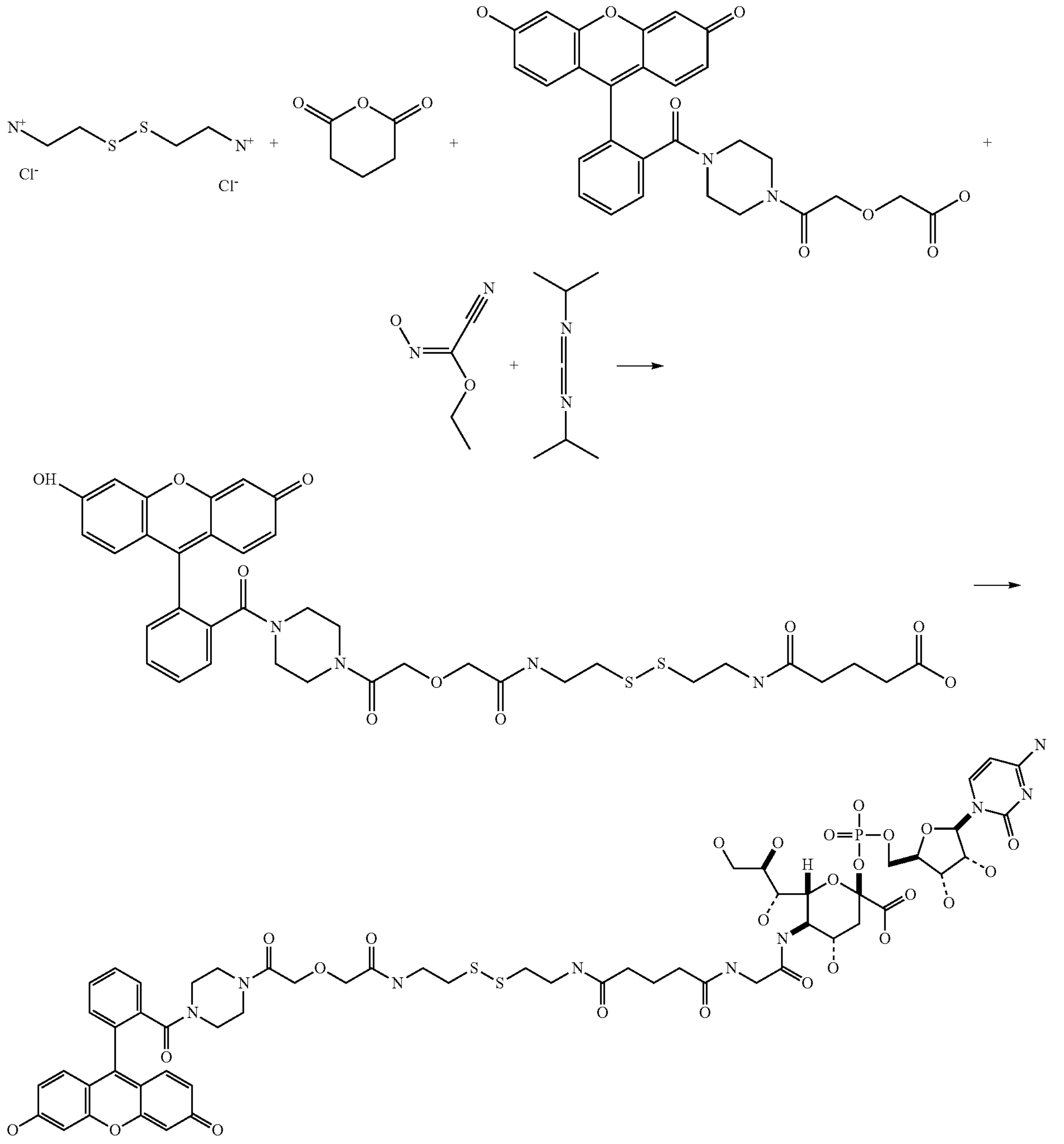

| Name | Dens [g/ml] | Mw [g/mol] | Mol Ratio | n [mmol] | W [g] | V [ml] |
|---|---|---|---|---|---|---|
| Cysteamine dihydrochloride | | 225.204 | 1 | 8.881 | 2 | |
| Glutaric anhydride | | 114.102 | 1 | 8.881 | 1.013 | |
| Fluorescent | | 516.512 | 0.218 | 1.936 | 1 | |
| Oxyma Pure | | 114.105 | 0.3 | 2.664 | 0.304 | |
| diisopropylcarbodiimide | 0.815 | 126.203 | 0.5 | 4.44 | 0.56 | 0.688 |
| Product: C37H40N4O10S2 | | 764.88 | | | | |
| Product: C57H70N9O25PS2 | | 1376.341 | | | | |

Cystamine dihydrochloride was dissolved in 1 M NaOH (aq.), 50 ml. The solution was extracted with DCM (5×30 ml). The combined org. phases were dried ($Na_2SO_4$), filtered, and concentrated in vacuo.

The diamine was dissolved in acetonitril (30 ml). A solution was added dropwise solution of anhydride in acetonitril (30 ml) to the solution. The resulting mixture was stirred for 15 minutes. The formed solid was allowed to settle for 1 h. The solvent was decanted off.

2-[2-[4-[2-(3-hydroxy-6-oxo-xanthen-9-yl)benzoyl]piperazin-1-yl]-2-oxo-ethoxy]acetic acid, Oxyma, and DIC were mixed in DMF (25 ml). The mixture was stirred for 1 h.

The formed amino acid was dissolved in sat. aq. sodium bicarbonate (25 ml). The resulting mixture was stirred over night. DCM (50 ml) and aq. sodium hydroxide (50 ml) were added. The phases were separated. The organic phase was extracted with aq. sodium hydroxide (3×50 ml). The combined aqueous extracts were acidified by addition of hydrochloric acid (fuming) causing extensive precipitation. The mixture was filtered. The isolated slurry was redissolved in DMF and concentrated in vacuo.

The crude isolated compound and Oxyma were dissolved in DMF (20 ml). DIC (1.5 ml) was added. The mixture was stirred for 2 h. A solution of GSC in sat. aq. sodium bicarbonate (10 ml) was added. The mixture was stirred over night. DCM (50 ml) was added. The phases were separated. The org. phase was extracted with sat. aq. sodium bicarbonate (2×5 ml). The combined aqueous phases were purified using reversed phase HPLC (0-50% MeCN in water, 50 mM NH4HCO3, 5 cm column). LC-MS: 688.6752 $[M+H]^{2+}$. Analytical HPLC and LC-MS indicated that the compound was not pure. It was, however, used as is.

Example 43

Conjugation of Anti TLT-1-FAB Fragment (Fab0084) to FVIII, FVIII-Fab0247

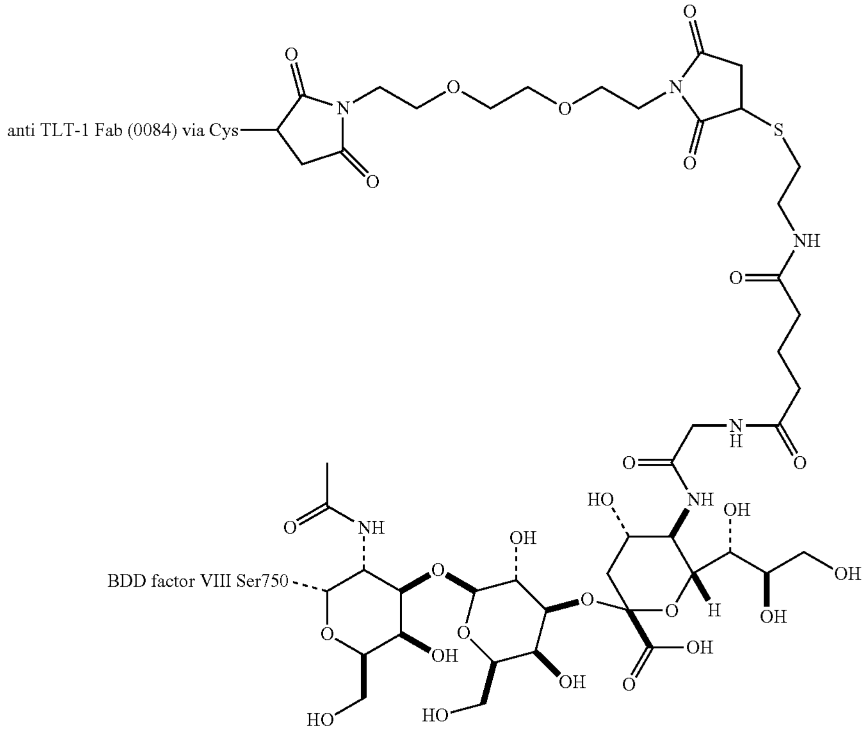

B-domain deleted factor VIII (turoctocoq alpha, Novo Nordisk A/S, 1.92 ml, 4.2 mg/ml) in imidazol buffer (20 mM Imidazol, 10 mM $CaCl_2$, 0.02% Tween 80, 150 mM NaCl, 1 M glycerol, pH 7.3) and sialidase (recombinant, *Arthrobactor Ureafaciens* sialidase, 3.2 U) were mixed and left for 1 hour at ambient temperature. The sample was diluted to 25 ml with buffer.

The solution was injected on a pre-conditioned monoQ column (pre-conditioned in Buffer A, 5 ml column volume).

Buffer A: 20 mM Imidazol, 10 mM $CaCl_2$, 0.02% Tween 80, 25 mM NaCl, 1M glycerol, pH 7.3

Buffer B: 20 mM Imidazol, 10 mM $CaCl_2$, 0.02% Tween 80, 1M NaCl, 1 M glycerol, pH7.3.

The immobilised protein was washaed with Buffer A (5 CV) using a Äkta purifier 100 chromatography station. The protein was eluded with a gradient of buffer B (2 CV eq+5 wash out unbound sample+2 CV 0-20% B+10 CV 20% B+10 CV 100% B) at 1 ml/min. Elution of the protein of interest was done by monitoring the absorbance at 280 nm.

The isolated N,O-asialo BDD-FVIII (0.98 mg/ml, 5 mg) was mixed with Fluorescent cytidyl monophosphate neuraminic acid derivative and recombinant sialyltransferase (His-ST3Gal1). The resulting mixture was incubated over night at room temperature in the dark.

The sample was diluted to 40 ml with buffer A: 20 mM Imidazol, 10 mM $CaCl_2$, 0.02% Tween 80, 25 mM NaCl, 1M glycerol, pH 7.3.

The solution was injected on a pre-conditioned monoQ column (pre-conditioned in Buffer A, 5 ml column volume).

Buffer A: 20 mM Imidazol, 10 mM $CaCl_2$, 0.02% Tween 80, 25 mM NaCl, 1M glycerol, pH 7.3.

Buffer B: 20 mM Imidazol, 10 mM $CaCl_2$, 0.02% Tween 80, 1M NaCl, 1 M glycerol, pH 7.3.

The immobilised protein was washed with Buffer A (5 CV) using a Äkta purifier 100 chromatography station. The protein was eluded with a gradient of buffer B (2 CV eq+5 wash out unbound sample+2 CV 0-20% B+10 CV 20% B+10 CV 100% B) at 1 ml/min. Elution of the protein of interest was done by monitoring the absorbance at 280 nm.

The selected fractions were pooled and incubated with cytidylmonophosphate N-acetylneuraminic acid and sialyltranferase (ST3GalIII) for 30 minutes. The mixture was diluted to 35 ml with buffer A.

The solution was injected on a pre-conditioned monoQ column (pre-conditioned in Buffer A, 5 ml column volume).

Buffer A: 20 mM Imidazol, 10 mM $CaCl_2$, 0.02% Tween 80, 25 mM NaCl, 1M glycerol, pH 7.3.

Buffer B: 20 mM Imidazol, 10 mM $CaCl_2$, 0.02% Tween 80, 1M NaCl, 1 M glycerol, pH 7.3.

The immobilised protein was washed with Buffer A (5 CV) using a Äkta purifier 100 chromatography station. The protein was eluded with a gradient of buffer B (2 CV eq+5 wash out unbound sample+2 CV 0-20% B+10 CV 20% B+10 CV 100% B) at 1 ml/min. Elution of the protein of interest was done by monitoring the absorbance at 280 nm.

The selected fractions were pooled and evaluted by SDS PAGE gel electrophoresis (4-12% Bis-Tris acetate, reduced and non-reduced).

The isolated fractions were mixed with buffer (15 ml) containing tris(carboxyethyl)phosphine, TCEP (20 mM Imidazol, 10 mM $CaCl_2$, 0.02% Tween 80, 25 mM NaCl, 1M glycerol, pH 7.3, 0.7 mM TCEP). The resulting mixture was incubated for 20 minutes. The solution was injected on a pre-conditioned monoQ column (5/50 GL, pre-conditioned in Buffer A with TCEP).

Buffer A1: 20 mM Imidazol, 10 mM $CaCl_2$, 0.02% Tween 80, 25 mM NaCl, 1M glycerol, pH 7.3, 0.7 mM TCEP).

Buffer A2: 20 mM Imidazol, 10 mM $CaCl_2$, 0.02% Tween 80, 25 mM NaCl, 1M glycerol, pH 7.3).

Buffer B1: 20 mM Imidazol, 10 mM $CaCl_2$, 0.02% Tween 80, 1 M NaCl, 1M glycerol, pH 7.3).

10 CV eq i A1, 5 wash out unbound sample i A1, 30CV in 100% A1, 10 CV in 100% A2, 15 CV 100% B1

The immobilised protein was washed with Buffer A1 (45 CV) followed by Buffer A2 (10 CV) using a Äkta purifier 100 chromatography station. The protein was eluded with buffer B (15 CV 100% B) at 1 ml/min. Elution of the protein of interest was done by monitoring the absorbance at 280 nm.

The selected fractions were pooled and analysed by SDS-PAGE (Tris-acetate).

The isolated factor VIII compound was diluted with Buffer A and injected on a pre-conditioned monoQ column (5/50 GL, pre-conditioned in Buffer A).

A flow of Buffer A containing 4.8 mM BM(PEG)2 (1,8-Bismaleimidodiethyleneglycol, Pierce/Thermo scientific) was maintained for 100 minutes.

The protein was washed and eluded using the following protocol: 10 CV A1, 25CV in buffer A2 (bismaleimide) at 0.25 ml/min(100 min), 10CV buffer A1, 10CV 100% B1.

Anti-TLT-1 antibody fragment, 0084, was buffer exchanged using an Amicon Ultracentrifugal filter device MWCO 30 kDa into HEPES buffer (20 mM HEPES+1 mM $CaCl_2$, 100 mM NaCl+0.005% Tween80, pH: 7.50). Concentration measured to be: 3.44 mg/ml, 2 mg): Tris(3-sulfonatephenyl)phosphine hydrate sodium salt (Alfa Aesar, technical grade 85%) was added to a resulting concentration of 12.5 mM. The resulting mixture was incubated at room temperature for 2 h. The antibody fragment was was buffer exchanged using an Amicon Ultracentrifugal filter device MWCO 30 kDa into imidazol buffer (20 mM Imidazol, 10 mM $CaCl_2$, 0.02% Tween 80, 25 mM NaCl, 1M glycerol, pH 7.3).

The solutions of factor VIII and antibody fragment were mixed and concentrated to 2 ml. The resulting solution was incubated over night at room temperature.

The solution was injected on a pre-conditioned monoQ column (pre-conditioned in Buffer A, 5 ml column volume).

Buffer A: 20 mM Imidazol, 10 mM $CaCl_2$, 0.02% Tween 80, 25 mM NaCl, 1M glycerol, pH 7.3.

Buffer B: 20 mM Imidazol, 10 mM $CaCl_2$, 0.02% Tween 80, 1M NaCl, 1 M glycerol, pH 7.3.

The immobilised protein was washed with Buffer A (5 CV) using a Äkta purifier 100 chromatography station. The protein was eluded with a gradient of buffer B (2 CV eq+5 wash out unbound sample+2 CV 0-20% B+10 CV 20% B+10 CV 100% B) at 1 ml/min. Elution of the protein of interest was done by monitoring the absorbance at 280 nm.

The selected fractions were pooled and concentrated. The protein was injected on a pre-conditioned Superdex 200 16/60 PG column (pre-conditioned in Buffer A).

Buffer A: Histidine (1.5 g, 1.5 mg/ml), CaCl2*H2O (376 mg, 0.37 mg/ml), NaCl (18 g, 18 mg/ml), Sucrose (3 g, 3 mg/ml), Tween 80 (100 mg, 0.1 mg/ml), Diluted to 1000 ml with MQ, adjust to pH 7.0.

Fractions were selected based on analysis by SDS-PAGE and anti-HPC4 Western blotting.

Example 44

Conjugation of Anti TLT-1-FAB Fragment (Fab0084) to FIX

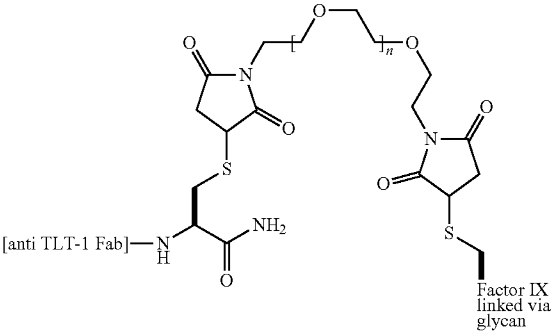

Factor IX (50 microliter), Sialyltransferase3 (10 microliter), Fluorescent cytidyl monophosphate neuraminic acid derivative; tip of a spatula) are mixed. The mixture is incubated at 32 degrees Celsius for 24 hours.

The end concentrations are: Factor IX: 0.33 mg/ml, ST3Gal3: 0.08 mg/ml

Analysed by SDS-PAGE (fluorescense respons and coomassie blue stained).

Factor IX and an antibody fragment are conjugated using the methods described herein, i.e, reduction mediated by a phosphine or glutathion, coupling to a linker entity, and conjugation followed by purification and analysis.

Example 45

FVIIa-Fab9015 is Superior to rFVIIa in Reducing Tail-Bleeding in Transient Haemophilic Mice Humanized TLT-1 knock-out/knock-in (KOKI) mice were made transiently haemophilic by administration of a monoclonal FVIII-antibody. Five minutes before induction of tail-bleeding, the mice were pre-treated with 20, 5 or 0.8 nmol/kg FVIIa-Fab9015 (3.625 ml/kg), 20 nmol/kg rFVIIa or vehicle. Tail-bleeding was induced by transection 4 mm from the tail-tip, and the resulting bleeding was observed for 30 minutes. Platelet counts were obtained initially and 30, 60 and 120 minutes after induction of tail-bleeding.

In order to be able to show superiority of FVIIa-Fab9015, we used a dose of rFVIIa (20 nmol/kg~1 mg/kg) that was not expected to have significant effect on the bleeding.

TLT-1-FAb-FVIIa dose-dependently reduced blood loss and bleeding time, reaching statistical significance at 20 and 5 nmol/kg. Moreover 20 nmol/kg FVIIa-Fab9015 was significantly more efficacious compared to 20 nmol/kg rFVIIa (FIG. 15).

No significantly changes in platelet count was observed within 2 hours of treatment in any of the treatment groups (FIG. 16).

In conclusion, FVIIa-Fab9015 was superior to rFVIIa in reducing haemophilic tail-bleeding in TLT-1 KOKI mice. No signs of adverse effects, eg. decrease in platelet counts, were observed.

Example 46

Enhancement of Thrombin Generation by Localization of rFVIIa to the Surface of Activated Platelets Through Binding to Surface Expressed TLT-1 Under Haemophilia A Like Conditions FVIIa-Fab9015 was tested in a thrombin generation assay. In brief, human platelet rich plasma (PRP) obtained by centrifugation of citrated human whole blood at 220 g for 20 min. The upper phase containing platelets was collected and the remaining sample was centrifuged at 2500 g for 10 min to obtain platelet poor plasma (PPP) used to adjust the platelet concentration to be used at a final concentration of 150000 plts/μl. The PRP was made haemophilic by 30 min incubation with a sheep anti-human FVIII polyclonal antibody (0.1 mg/ml) (HTI #Z0429). Platelets were activated with either protease activated recertor-1 activation peptide (SFLLRN; Bachem #H-2936) or a combination of the peptide and the GPVI activating snake venom Convulxin (Pentapharm #119-02). Generated thrombin was measured using a fluorogenic method from Thrombinoscope®. PRP, FluCa reagent and compound were mixed and added to 96-well Nunc Microwell round bottom well plates. The reaction was started by the addition of platelet activator and the fluorescent signal from the substrate was detected in a ThermoFisher Fluoroskan plate reader (Fisher Scientific). The thrombin concentration was calculated using a Thrombin calibrator provided by Thrombinoscope according to their instructions.

The results showed an increased potency of FVIIa-Fab9015 compared to rFVIIa (FIG. 17A). Furthermore the results revealed that this increase in potency was dependent on the activation stage of the platelets. FIG. 18 shows the increased thrombin generation capacity when the platelets were activated with SFLLRN (10 μM) and that full potential was reached when the platelets were activated with a combination of SFLLRN (30 μM) and Convulxin (100 ng/ml). When activating the platelets with this combination of activators FVIIa-Fab9015 showed an approximately four times increased potency, measured as peak thrombin generation, compared to rFVIIa at the two concentrations tested (5 and 25 nM) (FIGS. 17A and 17B, respectively). This increase in thrombin generation capacity was completely dependent on FVIIa-Fab9015 binding to TLT-1 on the surface of the activated platelet since pre-incubation with soluble TLT-1 fully reversed the enhancement (FIG. 19).

Example 47

Enhancement of Thrombin Generation by Localization of rFIX to the Surface of Activated Platelets Through Binding to Surface Expressed TLT-1 Under Haemophilia B Like Conditions FIX-Fab0155 was tested in a thrombin generation assay and compared to rFIX (Benefix®). Human platelets were isolated from fresh citrate stabilized whole blood. One part ACD-solution (2.5% tri-sodium citrate, 1.5% citric acid and 2% D-glucose) was added to five parts of blood before centrifugation at 220 g for 20 min to obtain platelet rich plasma. The upper phase was collected and transferred to a new cone shaped tube and spun at 500 g for 15 min. The plasma was removed and the pellet was dissolved in Hepes-buffer (10 mM Hepes, 137 mM NaCl, 2.7 mM KCl, 1.7 mM MgCl2, 5 mM D-glucose, 0.4 mM $NaH_2PO_4$; pH 6.5) supplemented with prostaglandin E1 (5 μg/ml). After a second centrifugation at 500 g for 15 min the supernatant was discarded and the washed platelets were dissolved in factor IX deficient plasma (Geroge King Bio-medical, Inc.) and the platelet concentration was adjusted to 300000 plts/µl. In the thrombin generation assay when agonists, factor IX variants and FluCa reagent (Thrombinoscope®) were added to 96-well Nunc Microwell round bottom well plates together with the factor IX deficient plasma containing platelets the final platelet concentration was 150000 plts/µl. The platelets were activated with a combination of protease activated recertor-1 activation peptide (SFLLRN; Bachem #H-2936) and the GPVI activating snake venom Convulxin (Pentapharm #119-02). Generated thrombin was measured by a fluorogenic method from Thrombinoscope® in which the fluorescent signal from the thrombin cleaved substrate was detected in a ThermoFisher Fluoroskan plate reader (Fisher Scientific). The thrombin concentration was calculated using a thrombin calibrator provided by Thrombinoscope® according to their instructions.

The results showed an increased potency at 1 nM of FIX-Fab0155 compared to rFIX (FIG. 20) when the platelets were activated with a combination of SFLLRN (30 µM) and Convulxin (100 ng/ml). Furthermore the results revealed that this increase in potency was dependent on expression of TLT-1 on the platelets since soluble TLT-1 (100 nM) antagonised the enhanced effect.

Example 48

Purification and Characterization of Wild-Type FVIIa (SEQ ID NO: 156), FVIIa 407C (SEQ ID NO: 181) and FVIIa-Fab5001 (SEQ ID NO: 180)

Purification of FVIIa proteins were conducted using a capture affinity chromatography method based on the anti-FVIIa F1A2-Sepharose 4B resin, which is a resin (base affinity gel from GE Healthcare) with a coupled antibody, developed at Novo Nordisk, that binds specifically the FVIIa Gla domain (for details see reference Jurlander B, Thim L, Klausen N K, Persson E, Kjalke M, Rexen P, Jorgensen T B, Østergaard P B, Erhardtsen E, Bjørn S E (2001) Recombinant activated factor VII (rFVIIa): characterization, manufacturing, and clinical development. Semin Thromb Hemost. 27:373-84). The purification was conducted using an Äkta-Explorer chromatography system (GE Healthcare, cat. no. 18-1112-41). The buffer systems used for the purification step were an equilibration buffer composed of 10 mM Histidine, pH 6.0, 5 mM $CaCl_2$, 25 mM NaCl and 0.01% (v/v) Tween-80, a wash buffer composed of 10 mM Histidine, pH 6.0, 5 mM $CaCl_2$, 1.0 M NaCl and 0.01% (v/v) Tween-80, and an elution buffer composed of 50 mM Histidine, pH 6.0, 15 mM EDTA. Cell supernatants were adjusted with 5 mM $CaCl_2$ final concentration and applied onto a pre-equilibrated anti-HPC4 column. The column was washed with 5-10 column volumes of equilibration buffer, 5-10 column volumes of wash buffer and last with 5-10 column volumes of equilibration buffer. The FVIIa proteins were eluted isocratically in approximately 5 column volumes of elution buffer.

Further purifications of capture eluates with low purities of the FVIIa variants (<90% based on a SEC-HPLC method setup on an Agilent 1100/2100 system and using a TSK G3000$SW_{XL}$ column (From Tosho) and a PBS running buffer) were conducted using 1) an anion-exchange chromatography (AIEC) based on a Poros HQ50 resin (from Applied Biosystems) and 2) preparative gel filtrations using pre-packed Superdex200 columns (from GE Healthcare).

The buffer systems used for the AIEC purification step was an equilibration buffer composed of 10 mM Hepes, pH 5.9 and 150 mM NaCl, a wash buffer composed of 10 mM Hepes, pH 5.9 and 50 mM NaCl, and an elution buffer composed of 10 mM Hepes, pH 5.9, 50 NaCl and 30 mM $CaCl_2$. The capture eluate was diluted 1:6 (v:v) before applying it onto a pre-equilibrated Poros HQ50 column. The column was washed with 5-10 column volumes of equilibration buffer and 5-10 column volumes of wash buffer before eluting the FVIIa proteins isocratically in approximately 2-5 column volumes of elution buffer.

The buffer systems used for the gel filtration steps was a running buffer composed of 10 mM Histidine, pH 6.0, 10 mM $CaCl_2$, 100 mM NaCl and 0.01% Tween 80. The FVIIa proteins were collected as symmetric peaks in approx 0.02-0.08 column volumes. Activations of the purified FVIIa preparations were conducted using a resin composed of plasma-derived FXa (from Enzyme Research Lab.) coupled to activated CNBr-Sepharose 4 FF bead (from GE Healthcare).

The FVIIa proteins were analyzed using SDS-PAGE/Coomassie and intact molecular mass determinations performed using a Liquid Chromatography Electrospray Ionisation Time-of-Flight Mass Spectrometry method setup on an Agilent 6210 instrument and a desalting column MassPREP (from Waters) with an equilibration buffer composed of 0.1% Formic acid in LC-MS graded-H2O and an elution buffer composed of 0.1% Formic acid in LC-MS graded-ACN. All FVIIa variants and wild-type purified displayed intact molecular masses of ~50 kDa. Based on intact-mass SDS-PAGE/Coomassie and LC-MS analyses using reductive conditions, chain identifications of FVIIa-Fab5001 fusion were performed.

Based on SEC-HPLC analyses, all FVIIa preparations displayed a purity of >90-99% and appeared highly homogenous.

Example 49

Autoactivation of FVII-Fab5001 Using a Proteolytic Assay in the Presence of Soluble Tissue Factor Autoactivation was determined as the ability to activate FX in the presence of soluble Tissue Factor (sTF). The protein was diluted in 50 mM HEPES (pH 7.4), 100 mM NaCl, 10 mM $CaCl_2$, 1 mg/mL BSA, and 0.1% (w/v) PEG8000. The kinetic parameters for FX activation were determined by pre-incubating 5 pM of the FVII-Fab5001 (n=2) with 100 nM sTF and 25 pM PC:PS phospholipids (Haematologic technologies) for 10 min. 30 nM FX was then added in a total reaction volume of 100 µL in a 96-well plate and the reaction allowed to incubate for 20 min at room temperature. After incubation, the reaction was quenched by adding 50 µL stop buffer (50 mM HEPES (pH 7.4), 100 mM NaCl, 80 mM EDTA) followed by the addition of 50 µL 2 mM S-2765. Finally, the absorbance increase was measured continuously at 405 nM in a Spectramax 190 microplate reader. The $k_{cat}/K_m$ values were determined by fitting the data to a revised form of the Michaelis Menten equation ($[S]<K_m$) using linear regression. The amount of FXa generated was estimated from a FXa standard curve.

The zymogen fusion protein FVII-Fab5001 showed 38% proteolytic activity relative to that of wtFVIIa, being a result of autoactivation of the protein in the presence of sTF, see FIG. 21).

Example 50

Lack of Anti-Aggregatory Effect of Anti-TLT-1 Antibodies, mAb0023, mAb0051, mAb0061 and mAb0062

The anti-aggregatory effect of anti-TLT-1 antibodies was tested in human platelet rich plasma (PRP). The PRP was obtained by a 200 g centrifugation for 15 min of heparin stabilized human whole blood. The upper phase containing platelets was collected and the remaining sample was centrifuged at 1500 g for 10 min to obtain platelet poor plasma (PPP) which was used as a reference sample in the aggregation measurements. The PRP was incubated 3 min at 37° C. in the Platelet Aggregation Profiler (PAP-8) instrument (Bio/Data Corporation, Horsham, Pa.). A stable baseline was recorded before the addition of anti-TLT-1 antibodies (10 nM) or irrelevant control antibody (10 nM) to the PRP. The platelets were activated 3 min after the addition of the antibodies with protease activated receptor-1 (PAR-1) activating peptide SFLLRN (1 or 10 μM) (Bachem).

The results showed no inhibitory effect of the antibodies (10 nM) (mAb0023, mAb0051, mAb0061 and mAb0062) compared to irrelevant control antibody. Platelet aggregation was initiated with either a high (10 μM) or an intermediate (1 μM) concentration of SFLLRN. The data shows that the antibodies did not inhibit aggregation at neither of the SFLLRN concentrations. In conclusion, these data shows that the antibodies do not induce nor inhibit platelet function measured as aggregation.

Example 51

Effect of FIX-mAb0145 on TF-Induced Fibrin Clot Formation in Human Whole Blood (HWB) from a Normal Donor Measured by Thromb-Elastography (TEG)

Figure 23:
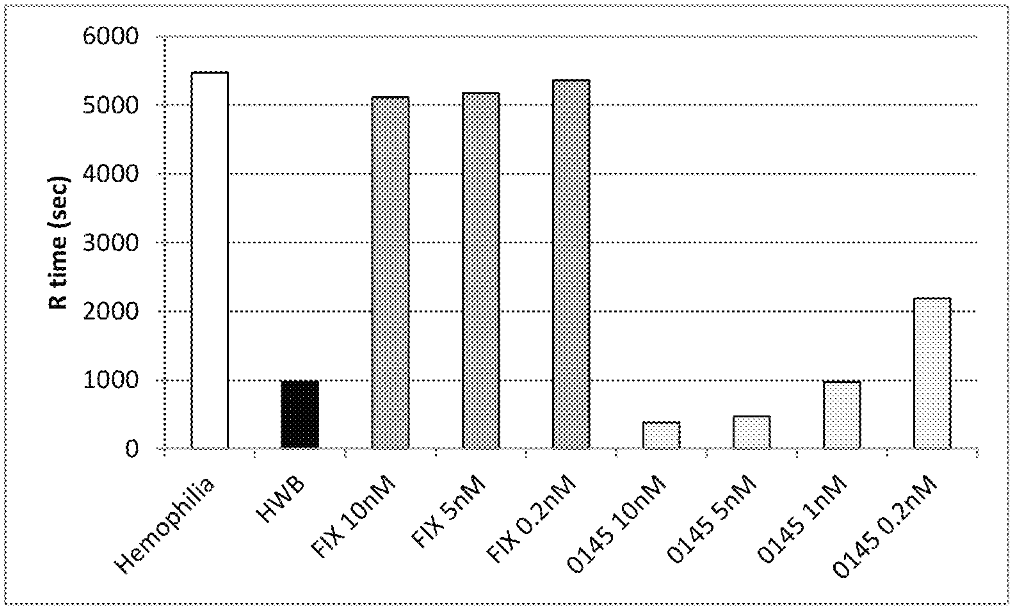

Citrated-stabilized human whole blood (HWB) is drawn from normal donors. Hemophilia-like conditions are obtained by incubation of HWB with 10 μg/ml anti-FVIII antibody (Sheep anti-Human Factor VIII; Hematologic Technologies Inc) for 30 min at room temp. Clot formation is measured by thrombelastography (5000 series TEG analyzer, Haemoscope Corporation, Niles, Ill., USA). Various concentrations (0; 0.2; 1.0; 5.0 and 10 nM) of FIX-mAb0145 or (0; 0.2; 5.0 and 10 nM) of rFIX (Novo Nordisk A/S) are added to "hemophilia-like" citrated HWB. Clotting in is initiated when 340 μl of normal or "hemophilia-like" HWB is transferred to a thrombelastograph cup containing 20 μl 0.2 M $CaCl_2$ with 0.03 pM lipidated TF (Innovin®, Dade Behring GmbH (Marburg, Germany). The TEG trace is followed continuously for up to 120 min. The following TEG variables are recorded: R time (clotting time i.e. the time from initiation of coagulation until an amplitude of 2 mm was obtained), α-angle (clot development measured as the angle between the R value and the inflection point of the TEG trace), K (speed of clot kinetics to reach a certain level of clot strength, amplitude=20 mm), and MA (maximal amplitude of the TEG trace reflecting the maximal mechanical strength of the clot). FIG. 23 shows R time values determined from individual TEG traces.

The R time obtained from TEG traces with normal HWB and "hemophilia" blood supplemented with various concentrations of FIX-mAb0145 or rFIX are shown in FIG. 23. HWB from a normal donor showed a R time of 980 sec which was prolonged to 5475 sec when the blood was made "haemophilia like" by the addition of a FVIII neutralizing antibody. FIX-mAb0145 shortened R-time clotting in a concentration dependent manner in contrast to rFIX which was without a significant effect when added as a control at equivalent concentratons. All data are obtained from one representative donor.

FIX-mAb0145 is observed to normalize clotting of "hemophilia-like HWB" in a concentration dependent manner. Thus surprisingly the results show that conjugation of rFIX to an antibody against TLT-1, which target rFIX to the surface of activated platelets, provides it with a FVIII-independent by-passing activity resulting in improved procoagulant activity.

Example 52

Enhancement of Thrombin Generation by Localization of rFVIIa to the Surface of Activated Platelets Through Binding to Surface Expressed TLT-1 Under Haemophilia A Like Conditions FVIIa-Fab9015, FVIIa-Fab1029 and FVIIa-Fab1001 at 25 nM were tested in a thrombin generation assay. In brief, human platelet rich plasma (PRP) was obtained by centrifugation of citrated human whole blood at 220 g for 20 min. The upper phase containing platelets was collected and the remaining sample was centrifuged at 2500 g for 10 min to obtain platelet poor plasma (PPP) used to adjust the platelet concentration to a final concentration of 150000 plts/μl. The PRP was made haemophilic by 30 min incubation with a sheep anti-human FVIII polyclonal antibody (0.1 mg/ml) (HTI #Z0429). Platelets were activated with a combination of protease activated recertor-1 (PAR-1) activation peptide (30 μM) (SFLLRN; Bachem #H-2936) and the GPVI activating snake venom Convulxin (100 ng/ml) (Pentapharm #119-02). Generated thrombin was measured using a fluorogenic method from Thrombinoscope® in which PRP, FluCa reagent and test compound were mixed and added to 96-well Nunc Microwell round bottom well plates (Nunc #268152). The reaction was started by the addition of platelet activators and the fluorescent signal from the substrate was detected in a ThermoFisher Fluoroskan plate reader (Fisher Scientific). The thrombin concentration was calculated using a Thrombin calibrator provided by Thrombinoscope® according to their instructions.

The results showed an increased potency of all three proteins, FVIIa-Fab9015, FVIIa-Fab1029 and FVIIa-Fab1001, compared to rFVIIa. FVIIa-Fab9015 and FVIIa-Fab1001 (25 nM) showed an approximately four times increased potency whereas FVIIa-Fab1029 (25 nM) had approximately a twofold increased potency measured as peak thrombin generation, compared to rFVIIa (25 nM) (FIG. 24).

Example 53

Purification and Characterization of Recombinantly Expressed FIX (SEQ ID 161), FIX-Anti-TLT-1 Fab and Mab Fusion Protein (FIX-Fab0155 and FIX-Mab0145)

Purification of said FIX proteins were conducted using a capture affinity chromatography method based on the anti-FIX A3B6-Sepharose 4 FF resin, which is a resin (base affinity gel from GE Healthcare) with a coupled antibody, developed at Novo Nordisk, that binds specifically to the FIX Gla domain (see refererence Østergaard et al. (2011), Blood 118: 2333-41). The purification was conducted using an ÄktaExplorer chromatography system (GE Healthcare, cat. no. 18-1112-41). The buffer systems used for the purification step were an equilibration buffer composed of 20 mM Tris, 1 mM $CaCl_2$, 100 mM NaCl, 0.01% (v/v) Tween 80 pH 7.5, a wash buffer composed of 20 mM Tris, 1 mM $CaCl_2$, 2.0 M NaCl, 0.01% (v/v) Tween 80 pH 7.5 and an elution buffer composed of 20 mM Tris, 20 mM EDTA, 50 mM NaCl, 0.01% (v/v) Tween 80 pH 7.5. Cell supernatants were adjusted with 5 mM $CaCl_2$ final concentration and applied onto a pre-equilibrated A3B6-Seph 4 FF column. The column was washed with 5-10 column volumes of equilibration buffer, 5-10 column volumes of wash buffer and last with 5-10 column volumes of equilibration buffer. The FIX fusion proteins were eluted isocratically in approximately 5 column volumes of elution buffer.

The FIX proteins were analyzed using SDS-PAGE/Coomassie and intact molecular mass determinations performed using a Liquid Chromatography Electrospray Ionisation Time-of-Flight Mass Spectrometry method setup on an Agilent 6210 instrument and a desalting column MassPREP (from Waters) with an equilibration buffer composed of 0.1% Formic acid in LC-MS graded-H2O and an elution buffer composed of 0.1% Formic acid in LC-MS graded-ACN. Based on intact-mass SDS-PAGE/Coomassie and LC-MS analyses using reductive conditions, chain identifications of the FIX proteins were performed. Based on SEC-HPLC analyses, all FIX fusion protein preparations displayed a purity of >85-99% and appeared highly homogenous.

Example 54

Production of Recombinant Expression of FVIIa Wild-Type (SEQ ID NO: 157) and FVIIa-407C (SEQ ID NO:181)

Said variant and wild-type FVIIa were produced as described in patent Ser. No. 02/077,218 and Jurlander et al. (2001), Semin Thromb Hemost. 27:373-84. More specifically, the FVIIa molecules were expressed in adherent BHK cell lines. The growth medium employed was a DMEM/F12 medium variant with 5 mg/L vitamin K1 and 10% fetal bovine serum (2% during production). Briefly, the cells were propagated in vented T-175 flasks, 2-layer and 10-layer cell factories incubated at 37° C. and 5% CO2. At confluency, cells were dissociated using TrypLE™ Express (GIBCO cat. no. 12604-013) prior to passaging to the next step. The production phase was performed as a repeated batch culture in a 15 L bioreactor with microcarriers (5 g/L, Cytodex 3, GE Life Sciences). pH was controlled at an upper limit of 7.2 by adding CO2 and at a lower limit of 6.8 by adding $Na_2CO_3$. Dissolved oxygen concentration was kept above 50% of saturation in air by sparging with oxygen. Temperature was maintained at 36.5° C. Agitation was at 50-70 rpm. Harvesting/medium exchanges were performed to maintain a glutamine concentration above 1 mM. One hour before a medium exchange, agitation was stopped to allow microcarriers (with cells attached) to settle at the bottom of the reactor. Thereafter, approximately 80% of the volume was harvested before filling up with fresh medium to 100% working volume. Cell harvests were withdrawn and clarified by a filter train consisting of two disposable capsule filters (3 μm Clarigard, Opticap XL10, Millipore, cat. no. K030A10HH1; 0.22 μm Durapore, Opticap XL10, Millipore, cat. no. KVGLS10HH1) prior to purification.

Example 55

Enhancement of Thrombin Generation by Localization of rFVIIa to the Surface of Activated Platelets Through Binding to Surface Expressed TLT-1 Under Haemophilia A Like Conditions A FVIIa-Fab5001 was tested in a thrombin generation assay and compared to rFVIIa in factor VIII deficient plasma containing washed human platelets. To isolate human platelets, one part ACD-solution (2.5% tri-sodium citrate, 1.5% citric acid and 2% D-glucose) was added to five parts of blood before centrifugation at 220 g for 20 min to obtain platelet rich plasma. The upper phase was collected and transferred to a new cone shaped tube and spun at 500 g for 15 min. The plasma was removed and the pellet was dissolved in Hepes-buffer (10 mM Hepes, 137 mM NaCl, 2.7 mM KCl, 1.7 mM $MgCl_2$, 5 mM D-glucose, 0.4 mM $NaH_2PO_4$; pH 6.5) supplemented with prostaglandin E1 (5 μg/ml). After a second centrifugation at 500 g for 15 min the supernatant was discarded and the washed platelets were dissolved in factor VIII deficient plasma (Geroge King Bio-medical, Inc.) and the platelet concentration was adjusted to 300000 plts/μl. In the thrombin generation assay when agonists, factor IX variants and FluCa reagent (Thrombinoscope®) were added to 96-well Nunc Microwell round bottom well plates together with the factor IX deficient plasma containing platelets the final platelet concentration was 150000 plts/μl. The platelets were activated with a combination of protease activated recertor-1 activation peptide (SFLLRN; Bachem #H-2936) and the GPVI activating snake venom Convulxin (Pentapharm #119-02). Generated thrombin was measured by a fluorogenic method from Thrombinoscope® in which the fluorescent signal from the thrombin cleaved substrate was detected in a ThermoFisher Fluoroskan plate reader (Fisher Scientific). The thrombin concentration was calculated using a thrombin calibrator provided by Thrombinoscope® according to their instructions. The results showed an increased potency of the FVIIa-Fab5001 compared to wild-type rFVIIa (FIG. 25). Furthermore the results revealed that this increase in potency was dependent on platelet activation. Activating the platelets with a combination of SFLLRN (30 μM) and Convulxin (100 ng/ml), FVIIa-Fab5001 (25 nM) showed an approximately four times increased potency, measured as peak thrombin generation, compared to wild-type rFVIIa (25 nM).

Example 56

SPR-Analysis of FVIIa-Fab1001 and FVIIa-Fab5001 Binding to TLT1

SPR-analysis of FVIIa-Fab1001 binding to TLT1. FVIIa-Fab1001 binds TLT-1 as tested by SPR analysis in a Biacore T200 instrument.

Materials used are shown in Table 18.

TABLE 18

| Reagent | Source |
|---|---|
| His tagged human TLT1 | Example 1 |
| FVIIa-Fab1001 | Example 39 |

TABLE 18-continued

| Reagent | Source |
|---|---|
| Anti 6X his mAb | R&D #MAB050 0.5 mg/ml in PBS |
| All other reagents | Biacore GE Healthcare |

Method: An anti 6×his antibody was immobilised to a level of approx 9000 RU on a CM5 chip (0.5 mg/ml diluted in Na-acetate, pH 5.0) using the standard procedure recommended by the supplier. Human his-tagged TLT-1 in a concentration of 100 ng/ml was used as ligand. FVIIa-Fab1001 in two-fold dilutions from 29.29 nM to 0.45 nM was used as analytes. The running and dilution buffer was made from: 10 mM HEPES, 150 mM NaCl, 3 mM EDTA, 0.005% p20, pH 7.4. Regeneration was obtained by 3 M $MgCl_2$. The experiment was run at 25 degree Celsius. Determination of kinetic and binding constants ($k_{on}$, $k_{off}$, $K_D$) was obtained assuming a 1:1 interaction of TLT1 and FVIIa-Fab1001 using the Biacore T200 evaluation software (Table 19).

TABLE 19

| FVIIa-Fab1001 binding to TLT-1 | | | |
|---|---|---|---|
| | Ka (1/Ms) | kd (1/s) | KD (M) |
| FVIIa-Fab1001 binding to TLT-1 | 8.01E+05 | 3.19E−03 | 3.99E−09 |

Conclusion: Binding constants for FVIIa-Fab1001 binding to TLT-1 was estimated by SPR-analysis and binding to TLT-1 was confirmed.

SPR-analysis of FVIIa-Fab5001 binding to TLT1. FVIIa-Fab5001 binds TLT-1 as tested by SPR analysis in a Biacore T200 instrument.

Materials used are shown in Table 20.

TABLE 20

| Reagent | Source |
|---|---|
| His tagged human TLT1 | Example 1 |
| FVIIa-Fab5001 | Example 48 |

TABLE 20-continued

| Reagent | Source |
|---|---|
| Anti 6X his mAb | R&D #MAB050 0.5 mg/ml in PBS |
| All other reagents | Biacore GE Healthcare |

Method: An anti 6×his antibody was immobilised to a level of approx 9000 RU on a CM5 chip (0.5 mg/ml diluted in Na-acetate, pH 5.0) using the standard procedure recommended by the supplier. Human his-tagged TLT-1 in a concentration of 100 ng/ml was used as ligand. FVIIa-Fab5001 in two-fold dilutions from 15.77 nM to 0.49 nM was used as analytes. The running and dilution buffer was made from: 10 mM HEPES, 150 mM NaCl, 3 mM EDTA, 0.005% p20, pH 7.4. Regeneration was obtained by 3 M MgCl2. The experiment was run at 25 degree Celsius. Determination of kinetic and binding constants ($k_{on}$, $k_{off}$, $K_D$) was obtained assuming a 1:1 interaction of TLT1 and FVII-fab using the Biacore T200 evaluation software (Table 21).

TABLE 21

| FVIIa-Fab5001 binding to TLT-1 | | | |
|---|---|---|---|
| | ka (1/Ms) | kd (1/s) | KD (M) |
| FVIIa-Fab5001 binding to TLT-1 | 2.384E+05 | 0.001696 | 7.11E−09 |

Conclusion: Binding constants for FVIIa-Fab5001 binding to TLT-1 was estimated by SPR-analysis and binding to TLT-1 was confirmed.

Example 57

Recombinant Production of Human FVIII

The production of the human Factor VIII variants as used herein has been described in patent number WO2009108806, example 1.

The invention claimed is:

1. A procoagulant protein comprising:

a polypeptide attached to a monoclonal antibody or fragment thereof, wherein the amino acid sequence of the polypeptide is at least 90% identical to SEQ ID NO: 157 and has activity to catalyze the conversion of factor IX to factor IXa and/or catalyze the conversion of factor X to factor Xa, and wherein the procoagulant protein is capable of binding to a TREM-like transcript 1 (TLT-1) comprising SEQ ID NO: 2 at an epitope therein comprising K133, I134, G135, S136, L137, A138, N140, A141, F142, S143, D144, P145, and A146.

2. The procoagulant protein according to claim 1, wherein the heavy chain of the monoclonal antibody or fragment thereof comprises:

(i) a CDR1 sequence comprising amino acids 49 to 53 (RYWMT) of SEQ ID NO: 40;

(ii) a CDR2 sequence comprising amino acids 68 to 84 (EINPDSSTINYNPSLKD) of SEQ ID NO: 40; and (iii) a CDR3 sequence comprising amino acids 117 to 121 (GVFTS) of SEQ ID NO: 40; and wherein the light chain of the monoclonal antibody or fragment thereof comprises:

(iv) a CDR1 sequence comprising amino acids 43 to 58 (RSSQSLVHRNGNTYFH) of SEQ ID NO: 41;

(v) a CDR2 sequence comprising amino acids 74 to 80 (KVSNRFS) of SEQ ID NO: 41; and (vi) a CDR3 sequence comprising amino acids 113 to 121 (SQSTHVPYT) of SEQ ID NO: 41.

3. The procoagulant protein according to claim 1, wherein the monoclonal antibody or fragment thereof is a humanized monoclonal antibody or fragment thereof.

4. The procoagulant protein according to claim 1, wherein the fragment is a Fab fragment.

5. The procoagulant protein according to claim 2, wherein the monoclonal antibody or fragment thereof is a humanized monoclonal antibody or fragment thereof.

6. The procoagulant protein according to claim 2, wherein the fragment is a Fab fragment.

* * * * *